US010669304B2

(12) United States Patent
Indermuhle et al.

(10) Patent No.: US 10,669,304 B2
(45) Date of Patent: Jun. 2, 2020

(54) METHODS AND DEVICES FOR DE NOVO OLIGONUCLEIC ACID ASSEMBLY

(71) Applicant: TWIST BIOSCIENCE CORPORATION, San Francisco, CA (US)

(72) Inventors: Pierre F. Indermuhle, Berkeley, CA (US); Eugene P. Marsh, El Granada, CA (US); Andres Fernandez, San Francisco, CA (US); William Banyai, San Francisco, CA (US); Bill J. Peck, Santa Clara, CA (US)

(73) Assignee: TWIST BIOSCIENCE CORPORATION, San Francisco, CA (US)

(*) Notice: Subject to any disclaimer, the term of this patent is extended or adjusted under 35 U.S.C. 154(b) by 976 days.

(21) Appl. No.: 15/015,059

(22) Filed: Feb. 3, 2016

(65) Prior Publication Data
US 2016/0229884 A1 Aug. 11, 2016

Related U.S. Application Data

(60) Provisional application No. 62/112,083, filed on Feb. 4, 2015.

(51) Int. Cl.
*C07H 21/04* (2006.01)
*B01J 19/00* (2006.01)
*C07H 1/00* (2006.01)
*C12P 19/34* (2006.01)
*C23C 16/455* (2006.01)

(52) U.S. Cl.
CPC .......... *C07H 21/04* (2013.01); *B01J 19/0046* (2013.01); *C07H 1/00* (2013.01); *C12P 19/34* (2013.01); *C23C 16/455* (2013.01); *B01J 2219/0059* (2013.01); *B01J 2219/00527* (2013.01); *B01J 2219/00596* (2013.01)

(58) Field of Classification Search
CPC ...................................................... C07H 21/04
See application file for complete search history.

(56) References Cited

U.S. PATENT DOCUMENTS

| 3,549,368 A | 12/1970 | Robert et al. |
| 3,920,714 A | 11/1975 | Streck |
| 4,123,661 A | 10/1978 | Wolf et al. |
| 4,415,732 A | 11/1983 | Caruthers et al. |
| 4,613,398 A | 9/1986 | Chiong et al. |
| 4,726,877 A | 2/1988 | Fryd et al. |
| 4,808,511 A | 2/1989 | Holmes |
| 4,837,401 A | 6/1989 | Hirose et al. |
| 4,863,557 A | 9/1989 | Kokaku et al. |
| 4,981,797 A | 1/1991 | Jessee et al. |
| 4,988,617 A | 1/1991 | Landegren et al. |
| 5,102,797 A | 4/1992 | Tucker et al. |
| 5,118,605 A | 6/1992 | Urdea |
| 5,137,814 A | 8/1992 | Rashtchian et al. |
| 5,143,854 A | 9/1992 | Pirrung et al. |
| 5,242,794 A | 9/1993 | Whiteley et al. |
| 5,242,974 A | 9/1993 | Holmes |
| 5,288,514 A | 2/1994 | Ellman |
| 5,299,491 A | 4/1994 | Kawada |
| 5,384,261 A | 1/1995 | Winkler et al. |
| 5,387,541 A | 2/1995 | Hodge et al. |
| 5,395,753 A | 3/1995 | Prakash |
| 5,431,720 A | 7/1995 | Nagai et al. |
| 5,445,934 A | 8/1995 | Fodor et al. |
| 5,449,754 A | 9/1995 | Nishioka |
| 5,459,039 A | 10/1995 | Modrich et al. |
| 5,474,796 A | 12/1995 | Brennan |
| 5,476,930 A | 12/1995 | Letsinger et al. |
| 5,487,993 A | 1/1996 | Herrnstadt et al. |
| 5,494,810 A | 2/1996 | Barany et al. |
| 5,501,893 A | 3/1996 | Laermer et al. |
| 5,508,169 A | 4/1996 | Deugau et al. |
| 5,510,270 A | 4/1996 | Fodor et al. |
| 5,514,789 A | 5/1996 | Kempe |
| 5,527,681 A | 6/1996 | Holmes |
| 5,530,516 A | 6/1996 | Sheets |
| 5,556,750 A | 9/1996 | Modrich et al. |
| 5,586,211 A | 12/1996 | Dumitrou et al. |
| 5,641,658 A | 6/1997 | Adams et al. |
| 5,677,195 A | 10/1997 | Winkler et al. |
| 5,679,522 A | 10/1997 | Modrich et al. |
| 5,688,642 A | 11/1997 | Chrisey et al. |

(Continued)

FOREIGN PATENT DOCUMENTS

| CN | 1771336 A | 5/2006 |
| CN | 102159726 A | 8/2011 |

(Continued)

OTHER PUBLICATIONS

Assembly manual for the POSaM: The ISB Piezoelelctric Oligonucleotide Synthesizer and Microarrayer, The Institute for Systems Biology, May 28, 2004 (50 pages).
Eroshenko et al.: Gene Assembly from Chip-Synthesized Oligonucleotides; Current Protocols in Chemical biology 4: 1-17 (2012).
International Application No. PCT/US2017/026232 International Preliminary Report on Patentability dated Feb. 26, 2019.
International Application No. PCT/US2017/045105 International Preliminary Report on Patentability dated Feb. 5, 2019.
International Application No. PCT/US2018/050511 International Search Report and Written Opinion dated Jan. 11, 2019.
International Application No. PCT/US2019/012218 International Search Report and Written Opinion dated Mar. 21, 2019.

(Continued)

Primary Examiner — Jezia Riley
(74) Attorney, Agent, or Firm — Wilson Sonsini Goodrich & Rosati

(57) ABSTRACT

Methods and devices are provided herein for surfaces for de novo nucleic acid synthesis which provide for low error rates. In addition, methods and devices are provided herein for increased nucleic acid mass yield resulting from de novo nucleic acid synthesis.

20 Claims, 27 Drawing Sheets
Specification includes a Sequence Listing.

(56) References Cited

U.S. PATENT DOCUMENTS

| | | |
|---|---|---|
| 5,700,637 A | 12/1997 | Southern |
| 5,700,642 A | 12/1997 | Monforte et al. |
| 5,702,894 A | 12/1997 | Modrich et al. |
| 5,707,806 A | 1/1998 | Shuber |
| 5,712,124 A | 1/1998 | Walker |
| 5,739,386 A | 4/1998 | Holmes |
| 5,750,672 A | 5/1998 | Kempe |
| 5,780,613 A | 7/1998 | Letsinger et al. |
| 5,830,655 A | 11/1998 | Monforte et al. |
| 5,830,662 A | 11/1998 | Soares et al. |
| 5,834,252 A | 11/1998 | Stemmer et al. |
| 5,843,669 A | 12/1998 | Kaiser et al. |
| 5,843,767 A | 12/1998 | Beattie |
| 5,846,717 A | 12/1998 | Brow et al. |
| 5,854,033 A | 12/1998 | Lizardi |
| 5,858,754 A | 1/1999 | Modrich et al. |
| 5,861,482 A | 1/1999 | Modrich et al. |
| 5,863,801 A | 1/1999 | Southgate et al. |
| 5,869,245 A | 2/1999 | Yeung |
| 5,877,280 A | 3/1999 | Wetmur |
| 5,882,496 A | 3/1999 | Northrup et al. |
| 5,922,539 A | 7/1999 | Modrich et al. |
| 5,922,593 A | 7/1999 | Livingston |
| 5,928,907 A | 7/1999 | Woudenberg et al. |
| 5,962,272 A | 10/1999 | Chenchik et al. |
| 5,976,842 A | 11/1999 | Wurst |
| 5,976,846 A | 11/1999 | Passmore et al. |
| 5,989,872 A | 11/1999 | Luo et al. |
| 5,994,069 A | 11/1999 | Hall et al. |
| 6,001,567 A | 12/1999 | Brow et al. |
| 6,008,031 A | 12/1999 | Modrich et al. |
| 6,013,440 A | 1/2000 | Lipshutz et al. |
| 6,015,674 A | 1/2000 | Woudenberg et al. |
| 6,027,898 A | 2/2000 | Gjerde et al. |
| 6,028,189 A | 2/2000 | Blanchard |
| 6,028,198 A | 2/2000 | Liu et al. |
| 6,040,138 A | 3/2000 | Lockhart et al. |
| 6,077,674 A | 6/2000 | Schleifer et al. |
| 6,090,543 A | 7/2000 | Prudent et al. |
| 6,090,606 A | 7/2000 | Kaiser et al. |
| 6,103,474 A | 8/2000 | Dellinger et al. |
| 6,107,038 A | 8/2000 | Choudhary et al. |
| 6,110,682 A | 8/2000 | Dellinger et al. |
| 6,114,115 A | 9/2000 | Wagner, Jr. |
| 6,130,045 A | 10/2000 | Wurst et al. |
| 6,132,997 A | 10/2000 | Shannon |
| 6,136,568 A | 10/2000 | Hiatt et al. |
| 6,171,797 B1 | 1/2001 | Perbost |
| 6,180,351 B1 | 1/2001 | Cattell |
| 6,201,112 B1 | 3/2001 | Ach |
| 6,218,118 B1 | 4/2001 | Sampson et al. |
| 6,221,653 B1 | 4/2001 | Caren et al. |
| 6,222,030 B1 | 4/2001 | Dellinger et al. |
| 6,232,072 B1 | 5/2001 | Fisher |
| 6,235,483 B1 | 5/2001 | Wolber et al. |
| 6,242,266 B1 | 6/2001 | Schleifer et al. |
| 6,251,588 B1 | 6/2001 | Shannon et al. |
| 6,251,595 B1 | 6/2001 | Gordon et al. |
| 6,251,685 B1 | 6/2001 | Dorsel et al. |
| 6,258,454 B1 | 7/2001 | Lefkowitz et al. |
| 6,262,490 B1 | 7/2001 | Hsu et al. |
| 6,274,725 B1 | 8/2001 | Sanghvi et al. |
| 6,284,465 B1 | 9/2001 | Wolber |
| 6,287,776 B1 | 9/2001 | Hefti |
| 6,287,824 B1 | 9/2001 | Lizardi |
| 6,297,017 B1 | 10/2001 | Schmidt et al. |
| 6,300,137 B1 | 10/2001 | Earhart et al. |
| 6,306,599 B1 | 10/2001 | Perbost |
| 6,309,822 B1 | 10/2001 | Fodor et al. |
| 6,309,828 B1 | 10/2001 | Schleifer et al. |
| 6,312,911 B1 | 11/2001 | Bancroft et al. |
| 6,319,674 B1 | 11/2001 | Fulcrand et al. |
| 6,323,043 B1 | 11/2001 | Caren et al. |
| 6,329,210 B1 | 12/2001 | Schleifer |
| 6,346,423 B1 | 2/2002 | Schembri |
| 6,365,355 B1 | 4/2002 | McCutchen-Maloney |
| 6,372,483 B2 | 4/2002 | Schleifer et al. |
| 6,375,903 B1 | 4/2002 | Cerrina et al. |
| 6,376,285 B1 | 4/2002 | Joyner et al. |
| 6,384,210 B1 | 5/2002 | Blanchard |
| 6,387,636 B1 | 5/2002 | Perbost et al. |
| 6,399,394 B1 | 6/2002 | Dahm et al. |
| 6,399,516 B1 | 6/2002 | Ayon |
| 6,403,314 B1 | 6/2002 | Lange et al. |
| 6,406,849 B1 | 6/2002 | Dorsel et al. |
| 6,406,851 B1 | 6/2002 | Bass |
| 6,408,308 B1 | 6/2002 | Maslyn et al. |
| 6,419,883 B1 | 7/2002 | Blanchard |
| 6,428,957 B1 | 8/2002 | Delenstarr |
| 6,440,669 B1 | 8/2002 | Bass et al. |
| 6,444,268 B2 | 9/2002 | Lefkowitz et al. |
| 6,446,642 B1 | 9/2002 | Caren et al. |
| 6,446,682 B1 | 9/2002 | Viken |
| 6,451,998 B1 | 9/2002 | Perbost |
| 6,458,526 B1 | 10/2002 | Schembri et al. |
| 6,458,535 B1 | 10/2002 | Hall et al. |
| 6,458,583 B1 | 10/2002 | Bruhn et al. |
| 6,461,812 B2 | 10/2002 | Barth et al. |
| 6,461,816 B1 | 10/2002 | Wolber et al. |
| 6,469,156 B1 | 10/2002 | Schafer et al. |
| 6,472,147 B1 | 10/2002 | Janda et al. |
| 6,492,107 B1 | 12/2002 | Kauffman et al. |
| 6,518,056 B2 | 2/2003 | Schembri et al. |
| 6,521,427 B1 | 2/2003 | Evans |
| 6,521,453 B1 | 2/2003 | Crameri et al. |
| 6,555,357 B1 | 4/2003 | Kaiser et al. |
| 6,558,908 B2 | 5/2003 | Wolber et al. |
| 6,562,611 B1 | 5/2003 | Kaiser et al. |
| 6,566,495 B1 | 5/2003 | Fodor et al. |
| 6,582,908 B2 | 6/2003 | Fodor et al. |
| 6,582,938 B1 | 6/2003 | Su et al. |
| 6,586,211 B1 | 7/2003 | Staehler et al. |
| 6,587,579 B1 | 7/2003 | Bass |
| 6,589,739 B2 | 7/2003 | Fisher |
| 6,599,693 B1 | 7/2003 | Webb |
| 6,602,472 B1 | 8/2003 | Zimmermann et al. |
| 6,610,978 B2 | 8/2003 | Yin et al. |
| 6,613,513 B1 | 9/2003 | Parce et al. |
| 6,613,523 B2 | 9/2003 | Fischer |
| 6,613,560 B1 | 9/2003 | Tso et al. |
| 6,613,893 B1 | 9/2003 | Webb |
| 6,621,076 B1 | 9/2003 | Van et al. |
| 6,630,581 B2 | 10/2003 | Dellinger et al. |
| 6,632,641 B1 | 10/2003 | Brennan et al. |
| 6,635,226 B1 | 10/2003 | Tso et al. |
| 6,642,373 B2 | 11/2003 | Manoharan et al. |
| 6,649,348 B2 | 11/2003 | Bass et al. |
| 6,660,338 B1 | 12/2003 | Hargreaves |
| 6,664,112 B2 | 12/2003 | Mulligan et al. |
| 6,670,127 B2 | 12/2003 | Evans |
| 6,670,461 B1 | 12/2003 | Wengel et al. |
| 6,673,552 B2 | 1/2004 | Frey |
| 6,682,702 B2 | 1/2004 | Barth et al. |
| 6,689,319 B1 | 2/2004 | Fisher et al. |
| 6,692,917 B2 | 2/2004 | Neri et al. |
| 6,702,256 B2 | 3/2004 | Killeen et al. |
| 6,706,471 B1 | 3/2004 | Brow et al. |
| 6,706,875 B1 | 3/2004 | Goldberg et al. |
| 6,709,852 B1 | 3/2004 | Bloom et al. |
| 6,709,854 B2 | 3/2004 | Donahue et al. |
| 6,713,262 B2 | 3/2004 | Gillibolian et al. |
| 6,716,629 B2 | 4/2004 | Hess et al. |
| 6,716,634 B1 | 4/2004 | Myerson |
| 6,723,509 B2 | 4/2004 | Ach |
| 6,728,129 B2 | 4/2004 | Lindsey et al. |
| 6,743,585 B2 | 6/2004 | Dellinger et al. |
| 6,753,145 B2 | 6/2004 | Holcomb et al. |
| 6,768,005 B2 | 7/2004 | Mellor et al. |
| 6,770,748 B2 | 8/2004 | Imanishi et al. |
| 6,770,892 B2 | 8/2004 | Corson et al. |
| 6,773,676 B2 | 8/2004 | Schembri |
| 6,773,888 B2 | 8/2004 | Li et al. |
| 6,780,982 B2 | 8/2004 | Lyamichev et al. |
| 6,787,308 B2 | 9/2004 | Balasubramanian et al. |

(56) References Cited

U.S. PATENT DOCUMENTS

| | | |
|---|---|---|
| 6,789,965 B2 | 9/2004 | Barth et al. |
| 6,790,620 B2 | 9/2004 | Bass et al. |
| 6,794,499 B2 | 9/2004 | Wengel et al. |
| 6,796,634 B2 | 9/2004 | Caren et al. |
| 6,800,439 B1 | 10/2004 | McGall et al. |
| 6,814,846 B1 | 11/2004 | Berndt |
| 6,815,218 B1 | 11/2004 | Jacobson et al. |
| 6,824,866 B1 | 11/2004 | Glazer et al. |
| 6,830,890 B2 | 12/2004 | Lockhart et al. |
| 6,833,246 B2 | 12/2004 | Balasubramanian |
| 6,833,450 B1 | 12/2004 | McGall et al. |
| 6,835,938 B2 | 12/2004 | Ghosh et al. |
| 6,838,888 B2 | 1/2005 | Peck |
| 6,841,131 B2 | 1/2005 | Zimmermann et al. |
| 6,845,968 B2 | 1/2005 | Killeen et al. |
| 6,846,454 B2 | 1/2005 | Peck |
| 6,846,922 B1 | 1/2005 | Manoharan et al. |
| 6,852,850 B2 | 2/2005 | Myerson et al. |
| 6,858,720 B2 | 2/2005 | Myerson et al. |
| 6,879,915 B2 | 4/2005 | Cattell |
| 6,880,576 B2 | 4/2005 | Karp et al. |
| 6,884,580 B2 | 4/2005 | Caren et al. |
| 6,887,715 B2 | 5/2005 | Schembri |
| 6,890,723 B2 | 5/2005 | Perbost et al. |
| 6,890,760 B1 | 5/2005 | Webb |
| 6,893,816 B1 | 5/2005 | Beattie |
| 6,897,023 B2 | 5/2005 | Fu et al. |
| 6,900,047 B2 | 5/2005 | Bass |
| 6,900,048 B2 | 5/2005 | Perbost |
| 6,911,611 B2 | 6/2005 | Wong et al. |
| 6,914,229 B2 | 7/2005 | Corson et al. |
| 6,916,113 B2 | 7/2005 | Van et al. |
| 6,916,633 B1 | 7/2005 | Shannon |
| 6,919,181 B2 | 7/2005 | Hargreaves |
| 6,927,029 B2 | 8/2005 | Lefkowitz et al. |
| 6,929,951 B2 | 8/2005 | Corson et al. |
| 6,936,472 B2 | 8/2005 | Earhart et al. |
| 6,938,476 B2 | 9/2005 | Chesk |
| 6,939,673 B2 | 9/2005 | Bass et al. |
| 6,943,036 B2 | 9/2005 | Bass |
| 6,946,285 B2 | 9/2005 | Bass |
| 6,950,756 B2 | 9/2005 | Kincaid |
| 6,951,719 B1 | 10/2005 | Dupret et al. |
| 6,958,119 B2 | 10/2005 | Yin et al. |
| 6,960,464 B2 | 11/2005 | Jessee et al. |
| 6,969,488 B2 | 11/2005 | Bridgham et al. |
| 6,976,384 B2 | 12/2005 | Hobbs et al. |
| 6,977,223 B2 | 12/2005 | George et al. |
| 6,987,263 B2 | 1/2006 | Hobbs et al. |
| 6,989,267 B2 | 1/2006 | Kim et al. |
| 6,991,922 B2 | 1/2006 | Dupret et al. |
| 7,008,037 B2 | 3/2006 | Caren et al. |
| 7,025,324 B1 | 4/2006 | Slocum et al. |
| 7,026,124 B2 | 4/2006 | Barth et al. |
| 7,027,930 B2 | 4/2006 | Cattell |
| 7,028,536 B2 | 4/2006 | Karp et al. |
| 7,029,854 B2 | 4/2006 | Collins et al. |
| 7,034,290 B2 | 4/2006 | Lu et al. |
| 7,041,445 B2 | 5/2006 | Chenchik et al. |
| 7,045,289 B2 | 5/2006 | Allawi et al. |
| 7,051,574 B2 | 5/2006 | Peck |
| 7,052,841 B2 | 5/2006 | Delenstarr |
| 7,062,385 B2 | 6/2006 | White et al. |
| 7,064,197 B1 | 6/2006 | Rabbani et al. |
| 7,070,932 B2 | 7/2006 | Leproust et al. |
| 7,075,161 B2 | 7/2006 | Barth |
| 7,078,167 B2 | 7/2006 | Delenstarr et al. |
| 7,078,505 B2 | 7/2006 | Bass et al. |
| 7,094,537 B2 | 8/2006 | Leproust et al. |
| 7,097,974 B1 | 8/2006 | Staehler et al. |
| 7,101,508 B2 | 9/2006 | Thompson et al. |
| 7,101,986 B2 | 9/2006 | Dellinger et al. |
| 7,105,295 B2 | 9/2006 | Bass et al. |
| 7,115,423 B1 | 10/2006 | Mitchell |
| 7,122,303 B2 | 10/2006 | Delenstarr et al. |
| 7,122,364 B1 | 10/2006 | Lyamichev et al. |
| 7,125,488 B2 | 10/2006 | Li |
| 7,125,523 B2 | 10/2006 | Sillman |
| 7,128,876 B2 | 10/2006 | Yin et al. |
| 7,129,075 B2 | 10/2006 | Gerard et al. |
| 7,135,565 B2 | 11/2006 | Dellinger et al. |
| 7,138,062 B2 | 11/2006 | Yin et al. |
| 7,141,368 B2 | 11/2006 | Fisher et al. |
| 7,141,807 B2 | 11/2006 | Joyce et al. |
| 7,147,362 B2 | 12/2006 | Caren et al. |
| 7,150,982 B2 | 12/2006 | Allawi et al. |
| 7,153,689 B2 | 12/2006 | Tolosko et al. |
| 7,163,660 B2 | 1/2007 | Lehmann |
| 7,166,258 B2 | 1/2007 | Bass et al. |
| 7,179,659 B2 | 2/2007 | Stolowitz et al. |
| 7,183,406 B2 | 2/2007 | Belshaw et al. |
| 7,192,710 B2 | 3/2007 | Gellibolian et al. |
| 7,193,077 B2 | 3/2007 | Dellinger et al. |
| 7,198,939 B2 | 4/2007 | Dorsel et al. |
| 7,202,264 B2 | 4/2007 | Ravikumar et al. |
| 7,202,358 B2 | 4/2007 | Hargreaves |
| 7,205,128 B2 | 4/2007 | Ilsley et al. |
| 7,205,400 B2 | 4/2007 | Webb |
| 7,206,439 B2 | 4/2007 | Zhou et al. |
| 7,208,322 B2 | 4/2007 | Stolowitz et al. |
| 7,217,522 B2 | 5/2007 | Brenner |
| 7,220,573 B2 | 5/2007 | Shea et al. |
| 7,221,785 B2 | 5/2007 | Curry et al. |
| 7,226,862 B2 | 6/2007 | Staehler et al. |
| 7,227,017 B2 | 6/2007 | Mellor et al. |
| 7,229,497 B2 | 6/2007 | Stott et al. |
| 7,247,337 B1 | 7/2007 | Leproust et al. |
| 7,247,497 B2 | 7/2007 | Dahm et al. |
| 7,252,938 B2 | 8/2007 | Leproust et al. |
| 7,269,518 B2 | 9/2007 | Corson |
| 7,271,258 B2 | 9/2007 | Dellinger et al. |
| 7,276,336 B1 | 10/2007 | Webb et al. |
| 7,276,378 B2 | 10/2007 | Myerson |
| 7,276,599 B2 | 10/2007 | Moore et al. |
| 7,282,183 B2 | 10/2007 | Peck |
| 7,282,332 B2 | 10/2007 | Caren et al. |
| 7,282,705 B2 | 10/2007 | Brennen |
| 7,291,471 B2 | 11/2007 | Sampson et al. |
| 7,302,348 B2 | 11/2007 | Ghosh et al. |
| 7,306,917 B2 | 12/2007 | Prudent et al. |
| 7,314,599 B2 | 1/2008 | Roitman et al. |
| 7,323,320 B2 | 1/2008 | Oleinikov |
| 7,344,831 B2 | 3/2008 | Wolber et al. |
| 7,348,144 B2 | 3/2008 | Minor |
| 7,351,379 B2 | 4/2008 | Schleifer |
| 7,353,116 B2 | 4/2008 | Webb et al. |
| 7,361,906 B2 | 4/2008 | Ghosh et al. |
| 7,364,896 B2 | 4/2008 | Schembri |
| 7,368,550 B2 | 5/2008 | Dellinger et al. |
| 7,371,348 B2 | 5/2008 | Schleifer et al. |
| 7,371,519 B2 | 5/2008 | Wolber et al. |
| 7,371,580 B2 | 5/2008 | Yakhini et al. |
| 7,372,982 B2 | 5/2008 | Le |
| 7,384,746 B2 | 6/2008 | Lyamichev et al. |
| 7,385,050 B2 | 6/2008 | Dellinger et al. |
| 7,390,457 B2 | 6/2008 | Schembri |
| 7,393,665 B2 | 7/2008 | Brenner |
| 7,396,676 B2 | 7/2008 | Robotti et al. |
| 7,399,844 B2 | 7/2008 | Sampson et al. |
| 7,402,279 B2 | 7/2008 | Schembri |
| 7,411,061 B2 | 8/2008 | Myerson et al. |
| 7,413,709 B2 | 8/2008 | Roitman et al. |
| 7,417,139 B2 | 8/2008 | Dellinger et al. |
| 7,422,911 B2 | 9/2008 | Schembri |
| 7,427,679 B2 | 9/2008 | Dellinger et al. |
| 7,432,048 B2 | 10/2008 | Neri et al. |
| 7,435,810 B2 | 10/2008 | Myerson et al. |
| 7,439,272 B2 | 10/2008 | Xu |
| 7,476,709 B2 | 1/2009 | Moody et al. |
| 7,482,118 B2 | 1/2009 | Allawi et al. |
| 7,488,607 B2 | 2/2009 | Tom-Moy et al. |
| 7,504,213 B2 | 3/2009 | Sana et al. |
| 7,514,369 B2 | 4/2009 | Li et al. |
| 7,517,979 B2 | 4/2009 | Wolber |

(56) References Cited

U.S. PATENT DOCUMENTS

| | | |
|---|---|---|
| 7,524,942 B2 | 4/2009 | Wang et al. |
| 7,524,950 B2 | 4/2009 | Dellinger et al. |
| 7,527,928 B2 | 5/2009 | Neri et al. |
| 7,531,303 B2 | 5/2009 | Dorsel et al. |
| 7,534,561 B2 | 5/2009 | Sana et al. |
| 7,534,563 B2 | 5/2009 | Hargreaves |
| 7,537,936 B2 | 5/2009 | Dahm et al. |
| 7,541,145 B2 | 6/2009 | Prudent et al. |
| 7,544,473 B2 | 6/2009 | Brenner |
| 7,556,919 B2 | 7/2009 | Chenchik et al. |
| 7,563,600 B2 | 7/2009 | Oleinikov |
| 7,572,585 B2 | 8/2009 | Wang |
| 7,572,907 B2 | 8/2009 | Dellinger et al. |
| 7,572,908 B2 | 8/2009 | Dellinger et al. |
| 7,585,970 B2 | 9/2009 | Dellinger et al. |
| 7,588,889 B2 | 9/2009 | Wolber et al. |
| 7,595,350 B2 | 9/2009 | Xu |
| 7,604,941 B2 | 10/2009 | Jacobson |
| 7,604,996 B1 | 10/2009 | Stuelpnagel et al. |
| 7,608,396 B2 | 10/2009 | Delenstarr |
| 7,618,777 B2 | 11/2009 | Myerson et al. |
| 7,629,120 B2 | 12/2009 | Bennett et al. |
| 7,635,772 B2 | 12/2009 | McCormac |
| 7,648,832 B2 | 1/2010 | Jessee et al. |
| 7,651,762 B2 | 1/2010 | Xu et al. |
| 7,659,069 B2 | 2/2010 | Belyaev et al. |
| 7,678,542 B2 | 3/2010 | Lyamichev et al. |
| 7,682,809 B2 | 3/2010 | Sampson |
| 7,709,197 B2 | 5/2010 | Drmanac |
| 7,718,365 B2 | 5/2010 | Wang |
| 7,718,786 B2 | 5/2010 | Dupret et al. |
| 7,723,077 B2 | 5/2010 | Young et al. |
| 7,737,088 B1 | 6/2010 | Staehler et al. |
| 7,737,089 B2 | 6/2010 | Guimil et al. |
| 7,741,463 B2 | 6/2010 | Gormley et al. |
| 7,749,701 B2 | 7/2010 | Leproust et al. |
| 7,759,471 B2 | 7/2010 | Dellinger et al. |
| 7,776,021 B2 | 8/2010 | Borenstein et al. |
| 7,776,532 B2 | 8/2010 | Gibson et al. |
| 7,790,369 B2 | 9/2010 | Stahler et al. |
| 7,790,387 B2 | 9/2010 | Dellinger et al. |
| 7,807,356 B2 | 10/2010 | Sampson et al. |
| 7,807,806 B2 | 10/2010 | Allawi et al. |
| 7,811,753 B2 | 10/2010 | Eshoo |
| 7,816,079 B2 | 10/2010 | Fischer |
| 7,820,387 B2 | 10/2010 | Neri et al. |
| 7,829,314 B2 | 11/2010 | Prudent et al. |
| 7,855,281 B2 | 12/2010 | Dellinger et al. |
| 7,862,999 B2 | 1/2011 | Zheng et al. |
| 7,867,782 B2 | 1/2011 | Barth |
| 7,875,463 B2 | 1/2011 | Adaskin et al. |
| 7,879,541 B2 | 2/2011 | Kincaid |
| 7,879,580 B2 | 2/2011 | Carr et al. |
| 7,894,998 B2 | 2/2011 | Kincaid |
| 7,919,239 B2 | 4/2011 | Wang |
| 7,919,308 B2 | 4/2011 | Schleifer |
| 7,927,797 B2 | 4/2011 | Nobile et al. |
| 7,927,838 B2 | 4/2011 | Shannon |
| 7,932,025 B2 | 4/2011 | Carr et al. |
| 7,932,070 B2 | 4/2011 | Hogrefe et al. |
| 7,935,800 B2 | 5/2011 | Allawi et al. |
| 7,939,645 B2 | 5/2011 | Borns |
| 7,943,046 B2 | 5/2011 | Martosella et al. |
| 7,943,358 B2 | 5/2011 | Hogrefe et al. |
| 7,960,157 B2 | 6/2011 | Borns |
| 7,977,119 B2 | 7/2011 | Kronick et al. |
| 7,979,215 B2 | 7/2011 | Sampas |
| 7,998,437 B2 | 8/2011 | Berndt et al. |
| 7,999,087 B2 | 8/2011 | Dellinger et al. |
| 8,021,842 B2 | 9/2011 | Brenner |
| 8,021,844 B2 | 9/2011 | Wang |
| 8,034,917 B2 | 10/2011 | Yamada |
| 8,036,835 B2 | 10/2011 | Sampas et al. |
| 8,048,664 B2 | 11/2011 | Guan et al. |
| 8,053,191 B2 | 11/2011 | Blake |
| 8,058,001 B2 | 11/2011 | Crameri et al. |
| 8,058,004 B2 | 11/2011 | Oleinikov |
| 8,058,055 B2 | 11/2011 | Barrett et al. |
| 8,063,184 B2 | 11/2011 | Allawi et al. |
| 8,067,556 B2 | 11/2011 | Hogrefe et al. |
| 8,073,626 B2 | 12/2011 | Troup et al. |
| 8,076,064 B2 | 12/2011 | Wang |
| 8,076,152 B2 | 12/2011 | Robotti |
| 8,097,711 B2 | 1/2012 | Timar et al. |
| 8,137,936 B2 | 3/2012 | Macevicz |
| 8,148,068 B2 | 4/2012 | Brenner |
| 8,154,729 B2 | 4/2012 | Baldo et al. |
| 8,168,385 B2 | 5/2012 | Brenner |
| 8,168,388 B2 | 5/2012 | Gormley et al. |
| 8,173,368 B2 | 5/2012 | Staehler et al. |
| 8,182,991 B1 | 5/2012 | Kaiser et al. |
| 8,194,244 B2 | 6/2012 | Wang et al. |
| 8,198,071 B2 | 6/2012 | Goshoo et al. |
| 8,202,983 B2 | 6/2012 | Dellinger et al. |
| 8,202,985 B2 | 6/2012 | Dellinger et al. |
| 8,206,952 B2 | 6/2012 | Carr et al. |
| 8,213,015 B2 | 7/2012 | Kraiczek et al. |
| 8,242,258 B2 | 8/2012 | Dellinger et al. |
| 8,247,221 B2 | 8/2012 | Fawcett |
| 8,263,335 B2 | 9/2012 | Carr et al. |
| 8,268,605 B2 | 9/2012 | Sorge et al. |
| 8,283,148 B2 | 10/2012 | Sorge et al. |
| 8,288,093 B2 | 10/2012 | Hall et al. |
| 8,298,767 B2 | 10/2012 | Brenner et al. |
| 8,304,273 B2 | 11/2012 | Stellacci et al. |
| 8,309,307 B2 | 11/2012 | Barrett et al. |
| 8,309,706 B2 | 11/2012 | Dellinger et al. |
| 8,309,710 B2 | 11/2012 | Sierzchala et al. |
| 8,314,220 B2 | 11/2012 | Mullinax et al. |
| 8,318,433 B2 | 11/2012 | Brenner |
| 8,318,479 B2 | 11/2012 | Domansky et al. |
| 8,357,489 B2 | 1/2013 | Chua et al. |
| 8,357,490 B2 | 1/2013 | Froehlich et al. |
| 8,367,016 B2 | 2/2013 | Quan et al. |
| 8,367,335 B2 | 2/2013 | Staehler et al. |
| 8,380,441 B2 | 2/2013 | Webb et al. |
| 8,383,338 B2 | 2/2013 | Kitzman et al. |
| 8,415,138 B2 | 4/2013 | Leproust |
| 8,435,736 B2 | 5/2013 | Gibson et al. |
| 8,445,205 B2 | 5/2013 | Brenner |
| 8,445,206 B2 | 5/2013 | Bergmann et al. |
| 8,470,996 B2 | 6/2013 | Brenner |
| 8,476,018 B2 | 7/2013 | Brenner |
| 8,476,598 B1 | 7/2013 | Pralle et al. |
| 8,481,292 B2 | 7/2013 | Casbon et al. |
| 8,481,309 B2 | 7/2013 | Zhang et al. |
| 8,491,561 B2 | 7/2013 | Borenstein et al. |
| 8,497,069 B2 | 7/2013 | Hutchison, III et al. |
| 8,500,979 B2 | 8/2013 | Elibol et al. |
| 8,501,454 B2 | 8/2013 | Liu et al. |
| 8,507,226 B2 | 8/2013 | Carr et al. |
| 8,507,239 B2 | 8/2013 | Lubys et al. |
| 8,507,272 B2 | 8/2013 | Zhang et al. |
| 8,530,197 B2 | 9/2013 | Li et al. |
| 8,552,174 B2 | 10/2013 | Dellinger et al. |
| 8,563,478 B2 | 10/2013 | Gormley et al. |
| 8,569,046 B2 | 10/2013 | Love et al. |
| 8,577,621 B2 | 11/2013 | Troup et al. |
| 8,586,310 B2 | 11/2013 | Mitra et al. |
| 8,614,092 B2 | 12/2013 | Zhang et al. |
| 8,642,755 B2 | 2/2014 | Sierzchala et al. |
| 8,664,164 B2 | 3/2014 | Ericsson et al. |
| 8,669,053 B2 | 3/2014 | Stuelpnagel et al. |
| 8,679,756 B1 | 3/2014 | Brenner et al. |
| 8,685,642 B2 | 4/2014 | Sampas |
| 8,685,676 B2 | 4/2014 | Hogrefe et al. |
| 8,685,678 B2 | 4/2014 | Casbon et al. |
| 8,715,933 B2 | 5/2014 | Oliver |
| 8,715,967 B2 | 5/2014 | Casbon et al. |
| 8,716,467 B2 | 5/2014 | Jacobson |
| 8,722,368 B2 | 5/2014 | Casbon et al. |
| 8,722,585 B2 | 5/2014 | Wang |
| 8,728,766 B2 | 5/2014 | Casbon et al. |
| 8,741,606 B2 | 6/2014 | Casbon et al. |

(56) References Cited

U.S. PATENT DOCUMENTS

| | | |
|---|---|---|
| 8,808,896 B2 | 8/2014 | Choo et al. |
| 8,808,986 B2 | 8/2014 | Jacobson et al. |
| 8,815,600 B2 | 8/2014 | Liu et al. |
| 8,889,851 B2 | 11/2014 | Leproust et al. |
| 8,932,994 B2 | 1/2015 | Gormley et al. |
| 8,962,532 B2 | 2/2015 | Shapiro et al. |
| 8,968,999 B2 | 3/2015 | Gibson et al. |
| 8,980,563 B2 | 3/2015 | Zheng et al. |
| 9,018,365 B2 | 4/2015 | Brenner |
| 9,023,601 B2 | 5/2015 | Oleinikov |
| 9,051,666 B2 | 6/2015 | Oleinikov |
| 9,073,962 B2 | 7/2015 | Fracchia et al. |
| 9,074,204 B2 | 7/2015 | Anderson et al. |
| 9,085,797 B2 | 7/2015 | Gebeyehu et al. |
| 9,133,510 B2 | 9/2015 | Andersen et al. |
| 9,139,874 B2 | 9/2015 | Myers et al. |
| 9,150,853 B2 | 10/2015 | Hudson et al. |
| 9,187,777 B2 | 11/2015 | Jacobson et al. |
| 9,194,001 B2 | 11/2015 | Brenner |
| 9,216,414 B2 | 12/2015 | Chu |
| 9,217,144 B2 | 12/2015 | Jacobson et al. |
| 9,279,149 B2 | 3/2016 | Efcavitch et al. |
| 9,286,439 B2 | 3/2016 | Shapiro et al. |
| 9,295,965 B2 | 3/2016 | Jacobson et al. |
| 9,315,861 B2 | 4/2016 | Hendricks et al. |
| 9,328,378 B2 | 5/2016 | Earnshaw et al. |
| 9,347,091 B2 | 5/2016 | Bergmann et al. |
| 9,375,748 B2 | 6/2016 | Harumoto et al. |
| 9,376,677 B2 | 6/2016 | Mir |
| 9,376,678 B2 | 6/2016 | Gormley et al. |
| 9,384,320 B2 | 7/2016 | Church |
| 9,384,920 B1 | 7/2016 | Bakulich |
| 9,388,407 B2 | 7/2016 | Jacobson |
| 9,394,333 B2 | 7/2016 | Wada et al. |
| 9,403,141 B2 | 8/2016 | Banyai et al. |
| 9,409,139 B2 | 8/2016 | Banyai et al. |
| 9,410,149 B2 | 8/2016 | Brenner et al. |
| 9,410,173 B2 | 8/2016 | Betts et al. |
| 9,416,411 B2 | 8/2016 | Stuelpnagel et al. |
| 9,422,600 B2 | 8/2016 | Ramu et al. |
| 9,487,824 B2 | 11/2016 | Kutyavin et al. |
| 9,523,122 B2 | 12/2016 | Zheng et al. |
| 9,528,148 B2 | 12/2016 | Zheng et al. |
| 9,534,251 B2 | 1/2017 | Young et al. |
| 9,555,388 B2 | 1/2017 | Banyai et al. |
| 9,568,839 B2 | 2/2017 | Stahler et al. |
| 9,580,746 B2 | 2/2017 | Leproust et al. |
| 9,670,529 B2 | 6/2017 | Osborne et al. |
| 9,670,536 B2 | 6/2017 | Casbon et al. |
| 9,677,067 B2 | 6/2017 | Toro |
| 9,695,211 B2 | 7/2017 | Wada et al. |
| 9,718,060 B2 | 8/2017 | Venter et al. |
| 9,745,573 B2 | 8/2017 | Stuelpnagel et al. |
| 9,745,619 B2 | 8/2017 | Rabbani et al. |
| 9,765,387 B2 | 9/2017 | Rabbani et al. |
| 9,771,576 B2 | 9/2017 | Gibson et al. |
| 9,833,761 B2 | 12/2017 | Banyai |
| 9,834,774 B2 | 12/2017 | Carstens |
| 9,839,894 B2 | 12/2017 | Banyai |
| 9,879,283 B2 | 1/2018 | Ravinder et al. |
| 9,889,423 B2 | 2/2018 | Banyai |
| 9,895,673 B2 * | 2/2018 | Peck .................. B01J 19/0046 |
| 9,925,510 B2 | 3/2018 | Jacobson et al. |
| 9,932,576 B2 | 4/2018 | Raymond et al. |
| 9,981,239 B2 | 5/2018 | Banyai |
| 2001/0018512 A1 | 8/2001 | Blanchard |
| 2001/0039014 A1 | 11/2001 | Bass et al. |
| 2001/0055761 A1 | 12/2001 | Kanemoto et al. |
| 2002/0012930 A1 | 1/2002 | Rothberg et al. |
| 2002/0025561 A1 | 2/2002 | Hodgson |
| 2002/0076716 A1 | 6/2002 | Sabanayagam et al. |
| 2002/0081582 A1 | 6/2002 | Gao et al. |
| 2002/0094533 A1 | 7/2002 | Hess et al. |
| 2002/0095073 A1 | 7/2002 | Jacobs et al. |
| 2002/0119459 A1 | 8/2002 | Griffiths et al. |
| 2002/0132308 A1 | 9/2002 | Liu et al. |
| 2002/0155439 A1 | 10/2002 | Rodriguez et al. |
| 2002/0160536 A1 | 10/2002 | Regnier et al. |
| 2002/0164824 A1 | 11/2002 | Xiao et al. |
| 2003/0008411 A1 | 1/2003 | Van Dam et al. |
| 2003/0022207 A1 | 1/2003 | Balasubramanian et al. |
| 2003/0022317 A1 | 1/2003 | Jack et al. |
| 2003/0044781 A1 | 3/2003 | Korlach et al. |
| 2003/0058629 A1 | 3/2003 | Hirai et al. |
| 2003/0064398 A1 | 4/2003 | Barnes |
| 2003/0068633 A1 | 4/2003 | Belshaw et al. |
| 2003/0082719 A1 | 5/2003 | Schumacher et al. |
| 2003/0100102 A1 | 5/2003 | Rothberg et al. |
| 2003/0108903 A1 | 6/2003 | Wang et al. |
| 2003/0120035 A1 | 6/2003 | Gao et al. |
| 2003/0138782 A1 | 7/2003 | Evans |
| 2003/0143605 A1 | 7/2003 | Lok et al. |
| 2003/0148291 A1 | 8/2003 | Robotti |
| 2003/0148344 A1 | 8/2003 | Rothberg et al. |
| 2003/0171325 A1 | 9/2003 | Gascoyne et al. |
| 2003/0186226 A1 | 10/2003 | Brennan et al. |
| 2003/0228602 A1 | 12/2003 | Parker et al. |
| 2003/0228620 A1 | 12/2003 | Du |
| 2004/0043509 A1 | 3/2004 | Stahler et al. |
| 2004/0053362 A1 | 3/2004 | De et al. |
| 2004/0086892 A1 | 5/2004 | Crothers et al. |
| 2004/0087008 A1 | 5/2004 | Schembri |
| 2004/0106130 A1 | 6/2004 | Besemer et al. |
| 2004/0106728 A1 | 6/2004 | McGall et al. |
| 2004/0110133 A1 | 6/2004 | Xu et al. |
| 2004/0175710 A1 | 9/2004 | Haushalter |
| 2004/0175734 A1 | 9/2004 | Stahler et al. |
| 2004/0191810 A1 | 9/2004 | Yamamoto |
| 2004/0219663 A1 | 11/2004 | Page et al. |
| 2004/0236027 A1 | 11/2004 | Maeji et al. |
| 2004/0248161 A1 | 12/2004 | Rothberg et al. |
| 2004/0259146 A1 | 12/2004 | Friend et al. |
| 2005/0022895 A1 | 2/2005 | Barth et al. |
| 2005/0049796 A1 | 3/2005 | Webb et al. |
| 2005/0053968 A1 | 3/2005 | Bharadwaj et al. |
| 2005/0079510 A1 | 4/2005 | Berka et al. |
| 2005/0100932 A1 | 5/2005 | Lapidus et al. |
| 2005/0112608 A1 | 5/2005 | Grossman et al. |
| 2005/0112636 A1 | 5/2005 | Hurt et al. |
| 2005/0112679 A1 | 5/2005 | Myerson et al. |
| 2005/0124022 A1 | 6/2005 | Srinivasan et al. |
| 2005/0137805 A1 | 6/2005 | Lewin et al. |
| 2005/0208513 A1 | 9/2005 | Agbo et al. |
| 2005/0227235 A1 | 10/2005 | Carr et al. |
| 2005/0255477 A1 | 11/2005 | Carr et al. |
| 2005/0266045 A1 | 12/2005 | Canham et al. |
| 2005/0277125 A1 | 12/2005 | Benn et al. |
| 2005/0282158 A1 | 12/2005 | Landegren |
| 2006/0003381 A1 | 1/2006 | Gilmore et al. |
| 2006/0012784 A1 | 1/2006 | Ulmer |
| 2006/0012793 A1 | 1/2006 | Harris |
| 2006/0019084 A1 | 1/2006 | Pearson |
| 2006/0024678 A1 | 2/2006 | Buzby |
| 2006/0024711 A1 | 2/2006 | Lapidus et al. |
| 2006/0024721 A1 | 2/2006 | Pedersen |
| 2006/0076482 A1 | 4/2006 | Hobbs et al. |
| 2006/0078909 A1 | 4/2006 | Srinivasan et al. |
| 2006/0078927 A1 | 4/2006 | Peck et al. |
| 2006/0078937 A1 | 4/2006 | Korlach et al. |
| 2006/0127920 A1 | 6/2006 | Church et al. |
| 2006/0134638 A1 | 6/2006 | Mulligan et al. |
| 2006/0160138 A1 | 7/2006 | Church |
| 2006/0171855 A1 | 8/2006 | Yin et al. |
| 2006/0202330 A1 | 9/2006 | Reinhardt et al. |
| 2006/0203236 A1 | 9/2006 | Ji et al. |
| 2006/0203237 A1 | 9/2006 | Ji et al. |
| 2006/0207923 A1 | 9/2006 | Li |
| 2006/0219637 A1 | 10/2006 | Killeen et al. |
| 2007/0031857 A1 | 2/2007 | Makarov et al. |
| 2007/0031877 A1 | 2/2007 | Stahler et al. |
| 2007/0043516 A1 | 2/2007 | Gustafsson et al. |
| 2007/0054127 A1 | 3/2007 | Hergenrother et al. |
| 2007/0059692 A1 | 3/2007 | Gao et al. |
| 2007/0087349 A1 | 4/2007 | Staehler et al. |

(56) References Cited

U.S. PATENT DOCUMENTS

| | | |
|---|---|---|
| 2007/0099208 A1 | 5/2007 | Drmanac et al. |
| 2007/0122817 A1 | 5/2007 | Church et al. |
| 2007/0141557 A1 | 6/2007 | Raab et al. |
| 2007/0196854 A1 | 8/2007 | Stahler et al. |
| 2007/0207482 A1 | 9/2007 | Church et al. |
| 2007/0207487 A1 | 9/2007 | Emig et al. |
| 2007/0231800 A1 | 10/2007 | Roberts et al. |
| 2007/0238104 A1 | 10/2007 | Barrett et al. |
| 2007/0238106 A1 | 10/2007 | Barrett et al. |
| 2007/0238108 A1 | 10/2007 | Barrett et al. |
| 2007/0259344 A1 | 11/2007 | Leproust et al. |
| 2007/0259345 A1 | 11/2007 | Sampas |
| 2007/0259346 A1 | 11/2007 | Gordon et al. |
| 2007/0259347 A1 | 11/2007 | Gordon et al. |
| 2007/0269870 A1 | 11/2007 | Church et al. |
| 2008/0085514 A1 | 4/2008 | Peck et al. |
| 2008/0087545 A1 | 4/2008 | Jensen et al. |
| 2008/0161200 A1 | 7/2008 | Yu et al. |
| 2008/0182296 A1 | 7/2008 | Chanda et al. |
| 2008/0214412 A1 | 9/2008 | Stahler et al. |
| 2008/0227160 A1 | 9/2008 | Kool |
| 2008/0233616 A1 | 9/2008 | Liss |
| 2008/0287320 A1 | 11/2008 | Baynes et al. |
| 2008/0308884 A1 | 12/2008 | Kalvesten |
| 2008/0311628 A1 | 12/2008 | Shoemaker |
| 2009/0036664 A1 | 2/2009 | Peter |
| 2009/0053704 A1 | 2/2009 | Novoradovskaya et al. |
| 2009/0062129 A1 | 3/2009 | McKernan et al. |
| 2009/0087840 A1 | 4/2009 | Baynes et al. |
| 2009/0088679 A1 | 4/2009 | Wood et al. |
| 2009/0105094 A1 | 4/2009 | Heiner et al. |
| 2009/0170802 A1 | 7/2009 | Stahler et al. |
| 2009/0176280 A1 | 7/2009 | Hutchison, III et al. |
| 2009/0181861 A1 | 7/2009 | Li et al. |
| 2009/0194483 A1 | 8/2009 | Robotti et al. |
| 2009/0230044 A1 | 9/2009 | Bek |
| 2009/0238722 A1 | 9/2009 | Mora-Fillat et al. |
| 2009/0239759 A1 | 9/2009 | Balch |
| 2009/0263802 A1 | 10/2009 | Drmanac |
| 2009/0285825 A1 | 11/2009 | Kini et al. |
| 2009/0324546 A1 | 12/2009 | Notka et al. |
| 2010/0004143 A1 | 1/2010 | Shibahara |
| 2010/0047805 A1 | 2/2010 | Wang |
| 2010/0051967 A1 | 3/2010 | Bradley et al. |
| 2010/0069250 A1 | 3/2010 | White, III et al. |
| 2010/0090341 A1 | 4/2010 | Wan et al. |
| 2010/0099103 A1 | 4/2010 | Hsieh et al. |
| 2010/0160463 A1 | 6/2010 | Wang et al. |
| 2010/0167950 A1 | 7/2010 | Juang et al. |
| 2010/0173364 A1 | 7/2010 | Evans, Jr. et al. |
| 2010/0216648 A1 | 8/2010 | Staehler et al. |
| 2010/0256017 A1 | 10/2010 | Larman et al. |
| 2010/0258487 A1 | 10/2010 | Zelechonok et al. |
| 2010/0286290 A1 | 11/2010 | Lohmann et al. |
| 2010/0292102 A1 | 11/2010 | Nouri |
| 2010/0300882 A1 | 12/2010 | Zhang et al. |
| 2011/0009607 A1 | 1/2011 | Komiyama et al. |
| 2011/0082055 A1 | 4/2011 | Fox et al. |
| 2011/0114244 A1 | 5/2011 | Yoo et al. |
| 2011/0114549 A1 | 5/2011 | Yin et al. |
| 2011/0124049 A1 | 5/2011 | Li et al. |
| 2011/0124055 A1 | 5/2011 | Carr et al. |
| 2011/0126929 A1 | 6/2011 | Velasquez-Garcia et al. |
| 2011/0171651 A1 | 7/2011 | Richmond |
| 2011/0172127 A1 | 7/2011 | Jacobson et al. |
| 2011/0201057 A1 | 8/2011 | Carr et al. |
| 2011/0217738 A1 | 9/2011 | Jacobson |
| 2011/0230653 A1 | 9/2011 | Novoradovskaya et al. |
| 2011/0254107 A1 | 10/2011 | Bulovic et al. |
| 2011/0287435 A1 | 11/2011 | Grunenwald et al. |
| 2012/0003713 A1 | 1/2012 | Hansen et al. |
| 2012/0021932 A1 | 1/2012 | Mershin et al. |
| 2012/0027786 A1 | 2/2012 | Gupta et al. |
| 2012/0028843 A1 | 2/2012 | Ramu et al. |
| 2012/0032366 A1 | 2/2012 | Ivniski et al. |
| 2012/0046175 A1 | 2/2012 | Rodesch et al. |
| 2012/0050411 A1 | 3/2012 | Mabritto et al. |
| 2012/0094847 A1 | 4/2012 | Warthmann et al. |
| 2012/0129704 A1 | 5/2012 | Gunderson et al. |
| 2012/0149602 A1 | 6/2012 | Friend et al. |
| 2012/0164127 A1 | 6/2012 | Short et al. |
| 2012/0164633 A1 | 6/2012 | Laffler |
| 2012/0164691 A1 | 6/2012 | Eshoo et al. |
| 2012/0184724 A1 | 7/2012 | Sierzchala et al. |
| 2012/0220497 A1 | 8/2012 | Jacobson et al. |
| 2012/0231968 A1 | 9/2012 | Bruhn et al. |
| 2012/0238737 A1 | 9/2012 | Dellinger et al. |
| 2012/0258487 A1 | 10/2012 | Chang et al. |
| 2012/0264653 A1 | 10/2012 | Carr et al. |
| 2012/0270750 A1 | 10/2012 | Oleinikov |
| 2012/0270754 A1 | 10/2012 | Blake |
| 2012/0283140 A1 | 11/2012 | Chu |
| 2012/0288476 A1 | 11/2012 | Hartmann et al. |
| 2012/0289691 A1 | 11/2012 | Dellinger et al. |
| 2012/0315670 A1 | 12/2012 | Jacobson et al. |
| 2012/0322681 A1 | 12/2012 | Kung et al. |
| 2013/0005585 A1 | 1/2013 | Anderson et al. |
| 2013/0005612 A1 | 1/2013 | Carr et al. |
| 2013/0017642 A1 | 1/2013 | Milgrew et al. |
| 2013/0017977 A1 | 1/2013 | Oleinikov |
| 2013/0017978 A1 | 1/2013 | Kavanagh et al. |
| 2013/0035261 A1 | 2/2013 | Sierzchala et al. |
| 2013/0040836 A1 | 2/2013 | Himmler et al. |
| 2013/0045483 A1 | 2/2013 | Treusch et al. |
| 2013/0053252 A1 | 2/2013 | Xie et al. |
| 2013/0059296 A1 | 3/2013 | Jacobson et al. |
| 2013/0059761 A1 | 3/2013 | Jacobson et al. |
| 2013/0065017 A1 | 3/2013 | Sieber |
| 2013/0109595 A1 | 5/2013 | Routenberg |
| 2013/0109596 A1 | 5/2013 | Peterson et al. |
| 2013/0123129 A1 | 5/2013 | Zeiner et al. |
| 2013/0130321 A1 | 5/2013 | Staehler et al. |
| 2013/0137161 A1 | 5/2013 | Zhang et al. |
| 2013/0137173 A1 | 5/2013 | Zhang et al. |
| 2013/0137174 A1 | 5/2013 | Zhang et al. |
| 2013/0137861 A1 | 5/2013 | Leproust et al. |
| 2013/0164308 A1 | 6/2013 | Foletti et al. |
| 2013/0225421 A1 | 8/2013 | Li et al. |
| 2013/0244884 A1 | 9/2013 | Jacobson et al. |
| 2013/0252849 A1 | 9/2013 | Hudson et al. |
| 2013/0261027 A1 | 10/2013 | Li et al. |
| 2013/0281308 A1 | 10/2013 | Kung et al. |
| 2013/0296192 A1 | 11/2013 | Jacobson et al. |
| 2013/0296194 A1 | 11/2013 | Jacobson et al. |
| 2013/0298265 A1 | 11/2013 | Cunnac et al. |
| 2013/0309725 A1 | 11/2013 | Jacobson et al. |
| 2013/0323722 A1 | 12/2013 | Carr et al. |
| 2013/0323725 A1 | 12/2013 | Peter et al. |
| 2013/0330778 A1 | 12/2013 | Zeiner et al. |
| 2014/0011226 A1 | 1/2014 | Bernick et al. |
| 2014/0018441 A1 | 1/2014 | Fracchia et al. |
| 2014/0031240 A1 | 1/2014 | Behlke et al. |
| 2014/0038240 A1 | 2/2014 | Temme et al. |
| 2014/0106394 A1 | 4/2014 | Ko et al. |
| 2014/0141982 A1 | 5/2014 | Jacobson et al. |
| 2014/0170665 A1 | 6/2014 | Hiddessen et al. |
| 2014/0178992 A1 | 6/2014 | Nakashima et al. |
| 2014/0274729 A1 | 9/2014 | Kurn et al. |
| 2014/0274741 A1 | 9/2014 | Hunter et al. |
| 2014/0303000 A1 | 10/2014 | Armour et al. |
| 2014/0309119 A1 | 10/2014 | Jacobson et al. |
| 2014/0309142 A1 | 10/2014 | Tian |
| 2015/0010953 A1 | 1/2015 | Lindstrom et al. |
| 2015/0012723 A1 | 1/2015 | Park et al. |
| 2015/0031089 A1 | 1/2015 | Lindstrom |
| 2015/0038373 A1 | 2/2015 | Banyai et al. |
| 2015/0056609 A1 | 2/2015 | Daum et al. |
| 2015/0057625 A1 | 2/2015 | Coulthard |
| 2015/0065357 A1 | 3/2015 | Fox |
| 2015/0065393 A1 | 3/2015 | Jacobson |
| 2015/0099870 A1 | 4/2015 | Bennett et al. |
| 2015/0120265 A1 | 4/2015 | Amirav-Drory |
| 2015/0159152 A1 | 6/2015 | Allen et al. |
| 2015/0183853 A1 | 7/2015 | Sharma et al. |

(56) References Cited

U.S. PATENT DOCUMENTS

| | | |
|---|---|---|
| 2015/0191719 A1 | 7/2015 | Hudson et al. |
| 2015/0196917 A1 | 7/2015 | Kay et al. |
| 2015/0203839 A1 | 7/2015 | Jacobson et al. |
| 2015/0211047 A1 | 7/2015 | Borns |
| 2015/0225782 A1 | 8/2015 | Walder et al. |
| 2015/0240232 A1 | 8/2015 | Zamore et al. |
| 2015/0240280 A1 | 8/2015 | Gibson et al. |
| 2015/0261664 A1 | 9/2015 | Goldman et al. |
| 2015/0269313 A1 | 9/2015 | Church |
| 2015/0293102 A1 | 10/2015 | Shim |
| 2015/0307875 A1 | 10/2015 | Happe et al. |
| 2015/0321191 A1 | 11/2015 | Kendall et al. |
| 2015/0322504 A1 | 11/2015 | Lao et al. |
| 2015/0344927 A1 | 12/2015 | Sampson et al. |
| 2015/0353921 A9 | 12/2015 | Tian |
| 2015/0353994 A1 | 12/2015 | Myers et al. |
| 2015/0361420 A1 | 12/2015 | Hudson et al. |
| 2015/0361422 A1 | 12/2015 | Sampson et al. |
| 2015/0361423 A1 | 12/2015 | Sampson et al. |
| 2015/0368687 A1 | 12/2015 | Saaem et al. |
| 2015/0376602 A1 | 12/2015 | Jacobson et al. |
| 2016/0001247 A1 | 1/2016 | Oleinikov |
| 2016/0002621 A1 | 1/2016 | Nelson et al. |
| 2016/0002622 A1 | 1/2016 | Nelson et al. |
| 2016/0010045 A1 | 1/2016 | Cohen et al. |
| 2016/0017394 A1 | 1/2016 | Liang et al. |
| 2016/0017425 A1 | 1/2016 | Ruvolo et al. |
| 2016/0019341 A1 | 1/2016 | Harris et al. |
| 2016/0024138 A1 | 1/2016 | Gebeyehu et al. |
| 2016/0024576 A1 | 1/2016 | Chee |
| 2016/0026753 A1 | 1/2016 | Krishnaswami et al. |
| 2016/0026758 A1 | 1/2016 | Jabara et al. |
| 2016/0032396 A1 | 2/2016 | Diehn et al. |
| 2016/0046973 A1 | 2/2016 | Efcavitch et al. |
| 2016/0046974 A1 | 2/2016 | Efcavitch et al. |
| 2016/0082472 A1 | 3/2016 | Perego et al. |
| 2016/0089651 A1 | 3/2016 | Banyai |
| 2016/0090592 A1 | 3/2016 | Banyai |
| 2016/0096160 A1 | 4/2016 | Banyai et al. |
| 2016/0097051 A1 | 4/2016 | Jacobson et al. |
| 2016/0102322 A1 | 4/2016 | Ravinder et al. |
| 2016/0108466 A1 | 4/2016 | Nazarenko et al. |
| 2016/0122755 A1 | 5/2016 | Hall et al. |
| 2016/0122800 A1 | 5/2016 | Bernick et al. |
| 2016/0152972 A1 | 6/2016 | Stapleton et al. |
| 2016/0168611 A1 | 6/2016 | Efcavitch et al. |
| 2016/0184788 A1 | 6/2016 | Hall et al. |
| 2016/0200759 A1 | 7/2016 | Srivastava et al. |
| 2016/0215283 A1 | 7/2016 | Braman et al. |
| 2016/0230175 A1 | 8/2016 | Carstens |
| 2016/0230221 A1 | 8/2016 | Bergmann et al. |
| 2016/0251651 A1 | 9/2016 | Banyai et al. |
| 2016/0256846 A1 | 9/2016 | Smith et al. |
| 2016/0264958 A1 | 9/2016 | Toro et al. |
| 2016/0289758 A1 | 10/2016 | Akeson et al. |
| 2016/0289839 A1 | 10/2016 | Harumoto et al. |
| 2016/0303535 A1 | 10/2016 | Banyai et al. |
| 2016/0304862 A1 | 10/2016 | Igawa et al. |
| 2016/0304946 A1 | 10/2016 | Betts et al. |
| 2016/0310426 A1 | 10/2016 | Wu |
| 2016/0310927 A1 | 10/2016 | Banyai et al. |
| 2016/0333340 A1 | 11/2016 | Wu |
| 2016/0339409 A1 | 11/2016 | Banyai et al. |
| 2016/0340672 A1 | 11/2016 | Banyai et al. |
| 2016/0348098 A1 | 12/2016 | Stuelpnagel et al. |
| 2016/0354752 A1 | 12/2016 | Banyai et al. |
| 2016/0355880 A1 | 12/2016 | Gormley et al. |
| 2017/0017436 A1 | 1/2017 | Church |
| 2017/0066844 A1 | 3/2017 | Glanville |
| 2017/0067099 A1 | 3/2017 | Zheng et al. |
| 2017/0073731 A1 | 3/2017 | Zheng et al. |
| 2017/0081660 A1 | 3/2017 | Cox et al. |
| 2017/0081716 A1 | 3/2017 | Peck |
| 2017/0088887 A1 | 3/2017 | Makarov et al. |
| 2017/0095785 A1 | 4/2017 | Banyai et al. |
| 2017/0096706 A1 | 4/2017 | Behlke et al. |
| 2017/0114404 A1 | 4/2017 | Behlke et al. |
| 2017/0141793 A1 | 5/2017 | Strauss et al. |
| 2017/0147748 A1 | 5/2017 | Staehler et al. |
| 2017/0151546 A1 | 6/2017 | Peck et al. |
| 2017/0159044 A1 | 6/2017 | Toro et al. |
| 2017/0175110 A1 | 6/2017 | Jacobson et al. |
| 2017/0218537 A1 | 8/2017 | Olivares |
| 2017/0233764 A1 | 8/2017 | Young et al. |
| 2017/0249345 A1 | 8/2017 | Malik et al. |
| 2017/0253644 A1 | 9/2017 | Steyaert et al. |
| 2017/0320061 A1 | 11/2017 | Venter et al. |
| 2017/0327819 A1 | 11/2017 | Banyai |
| 2017/0355984 A1 | 12/2017 | Evans et al. |
| 2017/0357752 A1 | 12/2017 | Diggans |
| 2017/0362589 A1 | 12/2017 | Banyai |
| 2018/0029001 A1 | 2/2018 | Banyai |
| 2018/0051278 A1 | 2/2018 | Cox |
| 2018/0051280 A1 | 2/2018 | Gibson et al. |
| 2018/0068060 A1 | 3/2018 | Ceze et al. |
| 2018/0101487 A1 | 4/2018 | Peck |
| 2018/0104664 A1 | 4/2018 | Fernandez |
| 2018/0126355 A1 | 5/2018 | Peck |
| 2018/0142289 A1 | 5/2018 | Zeitoun |
| 2018/0171509 A1 | 6/2018 | Cox |
| 2018/0236425 A1 | 8/2018 | Banyai et al. |
| 2018/0326388 A1 | 11/2018 | Banyai et al. |
| 2019/0060345 A1 | 2/2019 | Harrison et al. |
| 2019/0118154 A1 | 4/2019 | Marsh et al. |
| 2019/0240636 A1 | 8/2019 | Peck et al. |

FOREIGN PATENT DOCUMENTS

| | | |
|---|---|---|
| CN | 103907117 A | 7/2014 |
| CN | 104734848 A | 6/2015 |
| DE | 10260805 A1 | 7/2004 |
| EP | 0090789 A1 | 10/1983 |
| EP | 0126621 B1 | 11/1984 |
| EP | 0753057 A1 | 1/1997 |
| EP | 1314783 A1 | 5/2003 |
| EP | 1363125 A2 | 11/2003 |
| EP | 1546387 A2 | 6/2005 |
| EP | 1153127 B1 | 7/2006 |
| EP | 1728860 A1 | 12/2006 |
| EP | 1072010 B1 | 4/2010 |
| EP | 2175021 A2 | 4/2010 |
| EP | 2330216 A1 | 6/2011 |
| EP | 1343802 B1 | 5/2012 |
| EP | 2504449 A1 | 10/2012 |
| EP | 2751729 A1 | 7/2014 |
| EP | 2872629 A1 | 5/2015 |
| EP | 2928500 A1 | 10/2015 |
| EP | 2971034 A1 | 1/2016 |
| EP | 3030682 A2 | 6/2016 |
| EP | 3044228 A4 | 4/2017 |
| EP | 2994509 B1 | 6/2017 |
| EP | 3204518 A1 | 8/2017 |
| JP | 2002538790 A | 11/2002 |
| JP | 2006503586 A | 2/2006 |
| JP | 2009294195 A | 12/2009 |
| WO | WO-9015070 A1 | 12/1990 |
| WO | WO-9210092 A1 | 6/1992 |
| WO | WO-9210588 A1 | 6/1992 |
| WO | WO-9309668 A1 | 5/1993 |
| WO | WO-9525116 A1 | 9/1995 |
| WO | WO-9526397 A1 | 10/1995 |
| WO | WO-9615861 A1 | 5/1996 |
| WO | WO-9710365 A1 | 3/1997 |
| WO | WO-9822541 A2 | 5/1998 |
| WO | WO-9841531 A2 | 9/1998 |
| WO | WO-9942813 A1 | 8/1999 |
| WO | WO-0013017 A2 | 3/2000 |
| WO | WO-0018957 A1 | 4/2000 |
| WO | WO-0042559 A1 | 7/2000 |
| WO | WO-0042560 A2 | 7/2000 |
| WO | WO-0042561 A2 | 7/2000 |
| WO | WO-0049142 A1 | 8/2000 |
| WO | WO-0156216 A2 | 8/2001 |
| WO | WO-0210443 A1 | 2/2002 |

(56) References Cited

FOREIGN PATENT DOCUMENTS

| | | |
|---|---|---|
| WO | WO-0156216 A3 | 3/2002 |
| WO | WO-0220537 A2 | 3/2002 |
| WO | WO-0224597 A2 | 3/2002 |
| WO | WO-0227638 A1 | 4/2002 |
| WO | WO-0233669 A1 | 4/2002 |
| WO | WO-02072791 A2 | 9/2002 |
| WO | WO-03040410 A1 | 5/2003 |
| WO | WO-03046223 A1 | 6/2003 |
| WO | WO-03054232 A2 | 7/2003 |
| WO | WO-03064026 A1 | 8/2003 |
| WO | WO-03064027 A2 | 8/2003 |
| WO | WO-03064699 A2 | 8/2003 |
| WO | WO-03065038 A2 | 8/2003 |
| WO | WO-03066212 A2 | 8/2003 |
| WO | WO-03089605 A2 | 10/2003 |
| WO | WO-03100012 A2 | 12/2003 |
| WO | WO-2004024886 A2 | 3/2004 |
| WO | WO-2004029220 A2 | 4/2004 |
| WO | WO-2004029586 A1 | 4/2004 |
| WO | WO-2004031351 A2 | 4/2004 |
| WO | WO-2004031399 A2 | 4/2004 |
| WO | WO-2004059556 A2 | 7/2004 |
| WO | WO-2005014850 A2 | 2/2005 |
| WO | WO-2005051970 A2 | 6/2005 |
| WO | WO-2005059096 A2 | 6/2005 |
| WO | WO-2005059097 A2 | 6/2005 |
| WO | WO-2006023144 | 3/2006 |
| WO | WO-2006076679 A1 | 7/2006 |
| WO | WO-2006116476 A1 | 11/2006 |
| WO | WO-2007120627 A2 | 10/2007 |
| WO | WO-2007137242 A2 | 11/2007 |
| WO | WO-2008006078 A2 | 1/2008 |
| WO | WO-2008027558 A2 | 3/2008 |
| WO | WO-2008045380 | 4/2008 |
| WO | WO-2008054543 A2 | 5/2008 |
| WO | WO-2008063134 A1 | 5/2008 |
| WO | WO-2008063135 A1 | 5/2008 |
| WO | WO-2008109176 A2 | 9/2008 |
| WO | WO-2010025310 A2 | 3/2010 |
| WO | WO-2010025566 A1 | 3/2010 |
| WO | WO-2010027512 A2 | 3/2010 |
| WO | WO-2010089412 A1 | 8/2010 |
| WO | WO-2010141433 A2 | 12/2010 |
| WO | WO-2010141433 A3 | 4/2011 |
| WO | WO-2011053957 A2 | 5/2011 |
| WO | WO-2011056872 A2 | 5/2011 |
| WO | WO-2011066185 A1 | 6/2011 |
| WO | WO-2011066186 A1 | 6/2011 |
| WO | WO-2011085075 A2 | 7/2011 |
| WO | WO-2011103468 A2 | 8/2011 |
| WO | WO-2011109031 A1 | 9/2011 |
| WO | WO-2011143556 A1 | 11/2011 |
| WO | WO-2011150168 A1 | 12/2011 |
| WO | WO-2011161413 A2 | 12/2011 |
| WO | WO-2012013913 A1 | 2/2012 |
| WO | WO-2012061832 A1 | 5/2012 |
| WO | WO-2012078312 A2 | 6/2012 |
| WO | WO-2012149171 A1 | 11/2012 |
| WO | WO-2012154201 A1 | 11/2012 |
| WO | WO-2013030827 A1 | 3/2013 |
| WO | WO-2013032850 A2 | 3/2013 |
| WO | WO-2013036668 A1 | 3/2013 |
| WO | WO-2013101896 A1 | 7/2013 |
| WO | WO-2013177220 A1 | 11/2013 |
| WO | WO-2014004393 A1 | 1/2014 |
| WO | WO-2014008447 A1 | 1/2014 |
| WO | WO-2014035693 A2 | 3/2014 |
| WO | WO-2014088693 A1 | 6/2014 |
| WO | WO-2014089160 A1 | 6/2014 |
| WO | WO-2014093330 A1 | 6/2014 |
| WO | WO-2014093694 A1 | 6/2014 |
| WO | WO-2014151696 A1 | 9/2014 |
| WO | WO-2014160004 A1 | 10/2014 |
| WO | WO-2014160059 A1 | 10/2014 |
| WO | WO-2015021280 A1 | 2/2015 |
| WO | WO-2015040075 A1 | 3/2015 |
| WO | WO-2015054292 A1 | 4/2015 |
| WO | WO-2015081142 A1 | 6/2015 |
| WO | WO-2015090879 A1 | 6/2015 |
| WO | WO-2015120403 A1 | 8/2015 |
| WO | WO-2015160004 A1 | 10/2015 |
| WO | WO-2015175832 A1 | 11/2015 |
| WO | WO-2016007604 A1 | 1/2016 |
| WO | WO-2016011080 A2 | 1/2016 |
| WO | WO-2016022557 A1 | 2/2016 |
| WO | WO-2016053883 A1 | 4/2016 |
| WO | WO-2016055956 A1 | 4/2016 |
| WO | WO-2016065056 A1 | 4/2016 |
| WO | WO-2016126882 A1 | 8/2016 |
| WO | WO-2016126987 A1 | 8/2016 |
| WO | WO-2016130868 A2 | 8/2016 |
| WO | WO-2016161244 A2 | 10/2016 |
| WO | WO-2016172377 A1 | 10/2016 |
| WO | WO-2016173719 A1 | 11/2016 |
| WO | WO-2016183100 A1 | 11/2016 |
| WO | WO-2017049231 A1 | 3/2017 |
| WO | WO-2017053450 A1 | 3/2017 |
| WO | WO-2017059399 A1 | 4/2017 |
| WO | WO-2017095958 A1 | 6/2017 |
| WO | WO-2017118761 A1 | 7/2017 |
| WO | WO-2017158103 A1 | 9/2017 |
| WO | WO-2017214574 A1 | 12/2017 |
| WO | WO-2018026920 A1 | 2/2018 |
| WO | WO-2018038772 A1 | 3/2018 |
| WO | WO-2018057526 A2 | 3/2018 |
| WO | WO-2018094263 A1 | 5/2018 |
| WO | WO-2018112426 A1 | 6/2018 |
| WO | WO-2018156792 A1 | 8/2018 |
| WO | WO-2018170164 A1 | 9/2018 |

OTHER PUBLICATIONS

Jacobus et al. Optimal cloning of PCR fragments by homologous recombination in *Escherichia soli*. PLoS One 10(3):e0119221 (2015).

Lee: Covalent End-Immobilization of Oligonucleotides onto Solid Surfaces; Thesis, Massachusetts Institute of Technology, Aug. 2001 (315 pages).

Light source unit for printable patterning VUV-Aligner / USHIO Inc., Link here: https://www.ushio.co.jp/en/products/1005.html, published Apr. 25, 2016, printed from the internet on Aug. 2, 2016, 3 pages.

Douthwaite et al.: Affinity maturation of a novel antagonistic human monoclonal antibody with a long VH CDR3 targeting the Class a GPCR formyl-peptide receptor 1; mAbs, vol. 7, Iss. 1, pp. 152-166 (Jan. 1, 2015).

Jo et al.: Engineering therapeutic antibodies targeting G-protein-coupled receptors; Experimental & Molecular Medicine; 48; 9 pages (2016).

Lausted et al.: POSaM: a fast, flexible, open-source, inkjet oligonucleotide synthesizer and microarrayer; Genome Biology 2004, 5:R58.

Martinez-Torrecuadrada et al.: Targeting the Extracellular Domain of Fibroblast Growth Factor Receptor 3 with Human Single-Chain Fv Antibodies Inhibits Bladder Carcinoma Cell Line Proliferation; Clinical Cancer Research; vol. 11; pp. 6282-6290 (2005).

PCT/IL2012/000326 International Preliminary Report on Patentability dated Dec. 5, 2013.

PCT/IL2012/000326 International Search Report dated Jan. 29, 2013.

PCT/US2016/064270 International Preliminary Report on Patentability dated Jun. 14, 2018.

PCT/US2018/037152 International Search Report and Written Opinion dated Aug. 28, 2018.

PCT/US2018/037161 International Search Report and Written Opinion dated Oct. 22, 2018.

PCT/US2018/037161 Invitation to Pay Additional Fees dated Aug. 27, 2018.

PCT/US2018/056783 International Search Report and Written Opinion of the International Searching Authority dated Dec. 20, 2018.

(56) References Cited

OTHER PUBLICATIONS

Puigbo. Optimizer: a web server for optimizing the codon usage of DNA sequences. Nucleic Acid Research, 35(14):126-131, 2007.
Sharan et al. Recombineering: a homologous recombination-based method of genetic engineering. Nat Profile 4(2):1-37 (originally pp. 206-223) (2009).
U.S. Appl. No. 15/860,445 Final Office Action dated Dec. 13, 2018.
U.S. Appl. No. 15/187,714 Office Action dated Apr. 4, 2019.
U.S. Appl. No. 14/241,874 Final Office Action dated Jan. 28, 2019.
U.S. Appl. No. 14/241,874 Office Action dated Jul. 14, 2016.
U.S. Appl. No. 14/241,874 Office Action dated May 4, 2018.
U.S. Appl. No. 14/885,965 Office Action dated Aug. 28, 2018.
U.S. Appl. No. 15/156,134 Office Action dated Apr. 4, 2019.
U.S. Appl. No. 15/187,714 Restriction Requirement dated Sep. 17, 2018.
U.S. Appl. No. 15/268,422 Final Office Action dated Mar. 1, 2019.
U.S. Appl. No. 15/268,422 Restriction Requirement dated Oct. 4, 2018.
U.S. Appl. No. 15/377,547 Final Office Action dated Feb. 8, 2019.
U.S. Appl. No. 15/433,909 Non-Final Office Action dated Feb. 8, 2019.
U.S. Appl. No. 15/433,909 Restriction Requirement dated Sep. 17, 2018.
U.S. Appl. No. 15/602,991 Final Office Action dated Dec. 13, 2018.
U.S. Appl. No. 15/729,564 Final Office Action dated Dec. 13, 2018.
U.S. Appl. No. 15/151,316 Final Office Action dated Feb. 21, 2019.
U.S. Appl. No. 15/816,995 Restriction Requirement dated Apr. 4, 2019.
Wu, et al. "Sequence-Specific Capture of Protein-DNA Complexes for Mass Spectrometric Protein Identification" PLoS ONE. Oct. 20, 2011, vol. 6, No. 10.
Zhou, et al. "Establishment and application of a loop-mediated isothermal amplification (LAMP) system for detection of cry1Ac transgenic sugarcane" Scientific Reports May 9, 2014, vol. 4, No. 4912.
Abudayyeh et al., C2c2 is a single-component programmable RNA-guided RNA-targeting CRISPR effector. Science, available on line, Jun. 13, 2016, at: http://zlab.mit.edu/assets/reprints/Abudayyeh_OO_Science_2016.pdf, 17 pages.
Crick. On protein synthesis. Symp Soc Exp Biol12:138-163,1958.
Doudna et al. Genome editing. The new frontier of genome engineering with CRISPR-Cas9. Science 346(6213):1258096-1 through 1258096-9, 2014.
Genomics 101. An Introduction to the Genomic Workflow. 2016 edition, 64 pages. Available at: http://www.frontlinegenomics.com/magazine/6757/genomics-101/.
Hughes et al. Principles of early drug discovery. Br J Pharmacol 162(2):1239-1249, 2011.
Liu et al., Comparison of Next-Generation Sequencing Systems. Journal of Biomedicine and Biotechnology, 11 pages, 2012.
PCT Patent Application No. PCT/US2016/028699 International Search Report and Written Opinion dated Jul. 29, 2016.
PCT Patent Application No. PCT/US2016/031674 International Search Report and Written Opinion dated Aug. 11, 2016.
Pirrung. How to make a DNA chip. Angew. Chem. Int. Ed., 41:1276-1289, 2002.
Poster. Reimagine Genome Scale Research. 2016, 1 page. Available at http://www2.twistbioscience.com/Oligo_Pools_CRISPR_poster.
Powers et al. Optimal strategies for the chemical and enzymatic synthesis of bihelical deoxyribonucleic acids. J Am Chem Soc., 97(4):875-884, 1975.
Taylor et al., Impact of surface chemistry and blocking strategies on DNA microarrays. Nucleic Acids Research, 31(16):e87, 19 pages, 2003.
U.S. Appl. No. 14/885,965 Office Action dated Jul. 7, 2016.
U.S. Appl. No. 14/452,429 Notice of Allowance dated Jun. 7, 2016.
U.S. Appl. No. 14/885,962 Office Action dated Sep. 8, 2016.
U.S. Appl. No. 14/885,963 Notice of Allowance dated May 24, 2016.

Acevedo-Rocha et al. Directed evolution of stereoselective enzymes based on genetic selection as opposed to screening systems. J. Biotechnol. 191:3-10 (2014).
Arand et al. Structure of Rhodococcus erythropolis limonene-1,2-epoxide hydrolase reveals a novel active site. EMBO J. 22:2583-2592 (2003).
Bethge et al., "Reverse synthesis and 3'-modification of RNA." Jan. 1, 2011, pp. 64-64, XP055353420. Retrieved from the Internet: URL:http://www.is3na.org/assets/events/Category%202-Medicinal%20Chemistry%20of%20Oligonucleotides%20%2864-108%29.pdf.
Binkowski et al., Correcting errors in synthetic DNA through consensus shuffling. Nucleic Acids Research, 33(6):e55, 8 pages, 2005.
Bonini and Mondino, Adoptive T-cell therapy for cancer: The era of engineered T cells. European Journal of Immunology, 45:2457-2469, 2015.
Borovkov et al., High-quality gene assembly directly from unpurified mixtures of microassay-synthesized oligonucleotides. Nucleic Acid Research, 38(19):e180, 10 pages, 2010.
CeGaT. Tech Note available at https://www.cegat.de/web/wp-content/uploads/2018/06/Twist-Exome-Tech-Note.pdf (4 pgs.) (2018).
Chilamakuri et al. Performance comparison of four exome capture systems for deep sequencing. BMC Genomics 15(1):449 (2014).
Co-pending U.S. Appl. No. 15/902,855, filed Feb. 22, 2018.
Co-pending U.S. Appl. No. 15/921,479, filed Mar. 14, 2018.
Co-pending U.S. Appl. No. 15/921,537, filed Mar. 14, 2018.
Co-pending U.S. Appl. No. 16/006,581, filed Jun. 12, 2018.
Cruse et al. Atlas of Immunology, Third Edition. Boca Raton: CRC Press (pp. 282-283) (2010).
De Silva et al. New Trends of Digital Data Storage in DNA. BioMed Res Int. 2016:8072463 (2016).
Dillon et al. Exome sequencing has higher diagnostic yield compared to simulated disease-specific panels in children with suspected monogenic disorders. Eur J Hum Genet 26(5):644-651 (2018).
Dormitzer et al., Synthetic generation of influenza vaccine viruses for rapid response to pandemics. Sci Translational Medicine, 5(185):185ra68, 14 pages, 2013.
Dvorsky. Living Bacteria Can Now Store Data. GIZMODO internet publication. Retrieved from https://gizmodo.com/living-bacteria-can-now-store-data-1781773517 (4 pgs) (Jun. 10, 2016).
Gao et al. A method for the generation of combinatorial antibody libraries using pIX phage display. PNAS 99(20):12612-12616 (2002).
Gibson et al. Creation of a Bacterial Cell Controlled by a Chemically Synthesized Genome. Science 329(5989):52-56 (2010).
Goldfeder et al. Medical implications of technical accuracy in genome sequencing. Genome Med 8(1):24 (2016).
Han et al. Linking T-cell receptor sequence to functional phenotype at the single-cell level. Nat Biotechnol 32(7):684-692 (2014).
Imgur: The magic of the internet. Uploaded May 10, 2012, 2 pages, retrieved from: https://imgur.com/mEWuW.
Jager et al. Simultaneous Humoral and Cellular: Immune Response against Cancer—Testis Antigen NY-ES0-1: Definition of Human Histocompatibility LeukocyteAntigen (HLA)-A2—binding Peptide Epitopes. J. Exp. Med. 187(2):265-270 (1998).
Koike-Yusa et al., Genome-wide recessive genetic screening in mammalian cells with a lentiviral CRISPR-guide RNA library. Nature Biotechnology, 32:267-273, 2014 (with three pages of supplemental "Online Methods").
Li et al., Beating bias in the directed evolution of proteins: Combining high-fidelity on-chip solid-phase gene synthesis with efficient gene assembly for combinatorial library construction. First published Nov. 24, 2017, 2 pages. retrieved from: https://doi.org/10.1002/cbic.201700540.
Li et al. Beating Bias in the Directed Evolution of Proteins: Combining High-Fidelity on-Chip Solid-Phase Gene Synthesis with Efficient Gene Assembly for Combinatorial Library Construction. ChemBioChem 19:221-228 (2018).
Link Technologies. "Product Guide 2010." Nov. 27, 2009, 136 pages. XP055353191. Retrieved from the Internet: URL:http://www.linktech.co.uk/documents/517/517.pdf.

(56) References Cited

OTHER PUBLICATIONS

Meynert et al. Quantifying single nucleotide variant detection sensitivity in exome sequencing. BMC Bioinformatics 14:195 (2013).
Meynert et al. Variant detection sensitivity and biases in whole genome and exome sequencing. BMC Bioinformatics 15:247 (2014).
Morin et al., Profiling the HeLa S3 transcriptome using randomly primed cDNA and massively parallel short-read sequencing. Biotechniques, 45:81-94, 2008.
Morris and Stauss, Optimizing T-cell receptor gene therapy for hematologic malignancies. Blood, 127(26):3305-3311, 2016.
Mulligan. Commercial Gene Synthesis Technology PowerPoint presentation. BlueHeron® Biotechnology. Apr. 5, 2006 (48 pgs).
Organick et al., Random access in large-scale DNA data storage. Nature Biotechnology, Advance Online Publication, 8 pages, 2018.
PCT/US2016/016459 International Preliminary Report on Patentability dated Aug. 17, 2017.
PCT/US2016/016636 International Preliminary Report on Patentability dated Aug. 17, 2017.
PCT/US2016/028699 International Preliminary Report on Patentability dated Nov. 2, 2017.
PCT/US2016/031674 International Preliminary Report on Patentability dated Nov. 23, 2017.
PCT/US2016/052336 International Preliminary Report on Patentability dated Mar. 29, 2018.
PCT/US2016/052916 International Preliminary Report on Patentability dated Apr. 5, 2018.
PCT/US2017/026232 International Search Report and Written Opinion dated Aug. 28, 2017.
PCT/US2017/036868 International Search Report and Written Opinion dated Aug. 11, 2017.
PCT/US2017/045105 International Search Report and Written Opinion dated Oct. 20, 2017.
PCT/US2017/052305 International Search Report and Written Opinion dated Feb. 2, 2018.
PCT/US2017/062391 International Search Report and Written Opinion dated Mar. 28, 2018.
PCT/US2017/066847 International Search Report and Written Opinion dated May 4, 2018.
PCT/US2018/022487 International Search Report and Written Opinion dated Aug. 1, 2018.
PCT/US2018/022493 International Search Report and Written Opinion dated Aug. 1, 2018.
PCT/US2018/19268 International Search Report and Written Opinion dated Jun. 26, 2018.
PCT/US2018/19268 Invitation to Pay Additional Fees and, where applicable, protest fee dated May 2, 2018.
PCT/US2018/22487 Invitation to Pay Additional Fees and, where applicable, protest fee dated May 31, 2018.
PCT/US2018/22493 Invitation to Pay Additional Fees and, where applicable, protest fee dated May 31, 2018.
Plesa et al., Multiplexed gene synthesis in emulsions for exploring protein functional landscapes. Science, 10.1126/science.aao5167, 10 pages, 2018.
Rogozin et al., Origin and evolution of spliceosomal introns. Biology Direct, 7:11, 2012.
Schmitt et al., New strategies in engineering T-cell receptor gene-modified T cells to more effectively target malignancies. Clinical Cancer Research, 21(23):5191-5197, 2015.
Sharpe et al., Genetically modified T cells in cancer therapy: opportunities and challenges. Disease Models and Mechanisms, 8:337-350, 2015.
Skerra. Phosphorothioate primers improve the amplification of DNA sequences by DNA polymerases with proofreading activity. Nucleic Acids Res. Jul. 25, 1992; 20(14):3551-4.
Srivannavit et al., Design and fabrication of microwell array chips for a solution-based, photogenerated acid-catalyzed parallel oligonucleotide DNA synthesis. Sensors and Actuators A, 116:150-160, 2004.
Srivastava et al., "RNA synthesis: phosphoramidites for RNA synthesis in the reverse direction. Highly efficient synthesis and application to convenient introduction of ligands, chromophores and modifications of synthetic RNA at the 3'-end", Nucleic Acids Symposium Series, 52(1):103-104, 2008.
Sullivan et al. Library construction and evaluation for site saturation mutagenesis. Enzyme Microb. Technol. 53:70-77 (2013).
Sun et al. Structure-Guided Triple-Code Saturation Mutagenesis: Efficient Tuning of the Stereoselectivity of an Epoxide Hydrolase. ACS Catal. 6:1590-1597 (2016).
Twist Bioscience | White Paper. DNA-Based Digital Storage. Retrieved from the internet, Twistbioscience.com, Mar. 27, 2018, 5 pages.
U.S. Appl. No. 14/885,962 Notice of Allowance dated Nov. 8, 2017 and Sep. 29, 2017.
U.S. Appl. No. 14/885,965 Office Action dated Aug. 30, 2017.
U.S. Appl. No. 14/885,965 Office Action dated Jan. 4, 2018.
U.S. Appl. No. 15/135,434 Notice of Allowance dated Feb. 9, 2018.
U.S. Appl. No. 15/135,434 Office Action dated Nov. 30, 2017.
U.S. Appl. No. 15/135,434 Restriction Requirement dated Jul. 12, 2017.
U.S. Appl. No. 15/151,316 Office Action dated Jun. 7, 2018.
U.S. Appl. No. 15/233,835 Notice of Allowance dated Oct. 4, 2017.
U.S. Appl. No. 15/233,835 Office Action dated Jul. 26, 2017.
U.S. Appl. No. 15/377,547 Office Action dated Jul. 27, 2018.
U.S. Appl. No. 15/377,547 Office Action dated Nov. 30, 2017.
U.S. Appl. No. 15/602,991 Notice of Allowance dated Oct. 25, 2017.
U.S. Appl. No. 15/602,991 Office Action dated May 31, 2018.
U.S. Appl. No. 15/602,991 Office Action dated Sep. 21, 2017.
U.S. Appl. No. 15/603,013 Office Action dated Jan. 30, 2018.
U.S. Appl. No. 15/603,013 Office Action dated Jul. 10, 2018.
U.S. Appl. No. 15/603,013 Office Action dated Oct. 20, 2017.
U.S. Appl. No. 15/682,100 Office Action dated Jan. 2, 2018.
U.S. Appl. No. 15/682,100 Restriction Requirement dated Nov. 8, 2017.
U.S. Appl. No. 15/729,564 Office Action dated Jan. 8, 2018.
U.S. Appl. No. 15/729,564 Office Action dated Jun. 6, 2018.
U.S. Appl. No. 15/860,445 Office Action dated May 30, 2018.
Van Der Werf et al. Limonene-1,2-epoxide hydrolase from Rhodococcus erythropolis DCL14 belongs to a novel class of epoxide hydrolases. J. Bacteriol. 180:5052-5057 (1998).
Wagner et al., Nucleotides, Part LXV, Synthesis of 2'-Deoxyribonucleoside 5'-Phosphoramidites: New Building Blocks for the Inverse (5'-3')-Oiigonucleotide Approach. Helvetica Chimica Acta, 83(8):2023-2035, 2000.
Warr et al. Exome Sequencing: current and future perspectives. G3: (Bethesda) 5(8):1543-1550 (2015).
Wiedenheft et al., RNA-guided genetic silencing systems in bacteria and archaea. Nature, 482:331-338, 2012.
Xu et al., Design of 240,000 orthogonal 25mer DNA barcode probes. PNAS, 106(7):2289-2294, 2009.
Zheng et al. Manipulating the Stereoselectivity of Limonene Epoxide Hydrolase by Directed Evolution Based on Iterative Saturation Mutagenesis. J. Am. Chem. Soc. 132:15744-15751 (2010).
Adessi, et al., Solid phase DNA amplification: characterisation of primer attachment and amplification mechanisms. Nucleic Acids Res. Oct. 15, 2000;28(20):E87.
Alexeyev, et al., Gene synthesis, bacterial expression and purification of the Rickettsia prowazekii ATP/ADP translocase, Biochimica et Biophysics Acta, vol. 1419, 299-306 (1999).
Al-Housseiny et al., Control of interfacial instabilities using flow geometry. Nature Physics, 8:747-750 (2012); Published online at: DOI:10.1038/NPHYS2396.
Amblard, Francois et al., A magnetic manipulator for studying local rheology and micromechanical properties of biological systems, Rev. Sci.Instrum., vol. 67, No. 3, 818-827, Mar. 1996.
Arkles, et al. The Role of Polarity in the Structure of Silanes Employed in Surface Modification. Silanes and Other Coupling Agents. 2009; 5:51-64.
Assi, Fabiano et al., Massive-parallel adhesion and reactivity-measurements using simple and inexpensive magnetic tweezers, J. Appl. Phys., vol. 92, No. 9, 5584-5586, Nov. 1, 2002.

(56) References Cited

OTHER PUBLICATIONS

Au, Lo-Chun et al. Gene synthesis by a LCR-based approach : high level production of Leptin-L54 using synthetic gene in *Escherichia coli*, Biochemical and Biophysical Reasearch Communications, vol. 248, 200-203, 1998.
Baedeker, Mathias et al., Overexression of a designed 2.2kb gene of eukaryotic phenylalanine ammonialyase in *Escherichia coli*. FEBS Letters, vol. 457, 57-60 (1999).
Barbee, et al. Magnetic Assembly of High-Density DNA Arrays for Genomic Analyses. Anal Chem. Mar. 15, 2008; 80(6): 2149-2154.
Beaucage, et al. Advances in the synthesis of oligonucleotides by the phosphoramidite approach. Tetrahedron. 1992, 48:2223-2311.
Beaucage, et al. Deoxynucleoside phosphoramidites—A new class of key intermediates for deoxypolynucleotide synthesis. Tetrahedron Lett. 1981, 22(20):1859-1862.
Beaulieu, et al., "PCR candidate region mismatch scanning adaptation to quantitative, highthroughput genotyping", Nucleic Acids Research, vol. 29, No. 5, 1114-1124 (2001).
Beigelman, et al. Base-modified phosphoramidite analogs of pyrimidine ribonucleosides for RNA structure-activity studies. Methods Enzymol. 2000;317:39-65.
Biswas, et al., "Identification and characterization of a thermostable MutS homolog from Thennus aquaticus", The Journal of Biological Chemistry, vol. 271, No. 9, 5040-5048 (Mar. 1, 1996).
Biswas, et al., "Interaction of MutS/crotein with the major and minor grooves of a heteroduplex DNA", The Journal of Biological Chemistry, vol. 272, No. 20, 13355-13364 (May 1, 1997).
Bjornson, Keith P. et al., "Differential and simultaneous adenosine Di- and Tri~hosphate binding by MutS", The Journal of Biological Chemistry, vol. 278, No. 20, 18557-18562 (May 16, 2003).
Blanchard, et al. High-Density Oligonucleotide Arrays. Biosens. & Bioelectronics. 1996; 11:687-690.
Blanchard, in:*Genetic Engineering, Principles and Methods*, vol. 20, Ed. J. Sedlow, New York: Plenum Press, p. 111-124, 1979.
Butler, et al. In situ synthesis of oligonucleotide arrays by using surface tension. J Am Chem Soc. Sep. 19, 2001;123(37):8887-94.
Carr, et al. Protein-mediated error correction for de novo DNA synthesis. Nucleic Acids Res. Nov. 23, 2004;32(20):e162.
Caruthers, Gene synthesis machines: DNA chemistry and its uses. Science. Oct. 18, 1985;230(4723):281-5.
Caruthers, Chemical synthesis of deoxyoligonucleotides by the phosphoramidite method. In Methods in Enzymology, Chapter 15, 154:287-313 1987.
Casmiro, Danilo R. et al., "PCR-based gene synthesis and protein NMR spectroscopy", Structure, vol. 5, •No. 11, 1407-1412 1997.
Cello, et al. Chemical synthesis of poliovirus cDNA: generation of infectious virus in the absence of natural template. Science. Aug. 9, 2002;297(5583):1016-8.
Chalmers, et al. Scaling up the ligase chain reaction-based approach to gene synthesis. Biotechniques. Feb. 2001;30(2):249-52.
Chan, et al. Natural and engineered nicking endonucleases—from cleavage mechanism to engineering of strand-specificity. Nucleic Acids Res. Jan. 2011; 39(1): 1-18.
Chen, et al. Chemical modification of gene silencing oligonucleotides for drug discovery and development. Drug Discov Today. Apr. 15, 2005;10(8):587-93.
Cheng, et al. High throughput parallel synthesis of oligonucleotides with 1536 channel synthesizer. Nucleic Acids Res. Sep. 15, 2002;30(18):e93.
Cho, et al. Capillary passive valve in microfluidic systems. NSTI-Nanotech. 2004; 1:263-266.
Chrisey et al., Fabrication of patterned DNA surfaces. Nucleic Acids Research, 24(15):3040-3047 (1996).
Chung et al., One-step preparation of competent *Escherichia coli*: Transformation and storage of bacterial cells in the same solution. Proc Natl Acad Sci U S A. Apr. 1989;86(7):2172-2175.
Cleary, et al. Production of complex nucleic acid libraries using highly parallel in situ oligonucleotide synthesis. Nat Methods. Dec. 2004;1(3):241-8. Epub Nov. 18, 2004.

Cutler, David J. ef al., "High-throughput variation detection and genotyping using microarrays", Genome Research, vol. 11, 1913-19 (2001 ).
Dahl, et al. Circle-to-circle amplification for precise and sensitive DNA analysis. Proc Natl Acad Sci U S A. Mar. 30, 2004;101(13):4548-53. Epub Mar. 15, 2004.
De Mesmaeker, et al. Backbone modifications in oligonucleotides and peptide nucleic acid systems. Curr Opin Struct Biol. Jun. 1995;5(3):343-55.
Deamer, David W. et al., "Characterization of nucleic acids by nanopore analysis", Ace. Cham. Res., vol. 35, No. 10, 817-825 (2002).
Deaven, The Human Genome Project: Recombinant clones for mapping and sequencing DNA. Los Alamos Science, 20:218-249, 1992.
Deng et al., Targeted bisulfite sequencing reveals changes in DNA methylation associated with nuclear reprogramming. Nature Biotechnology, 27:352-360 (2009)—http://www.nature.com/nbt/journal/v27/n4/abs/nbt.1530.html.
Dietrich, Rudiger.et al., "Gene assembly based on blunt-ended double-stranded DNA-modules", Biotechnology Techniques, vol. 12, No. 1, 49-54 (Jan. 1998).
Dower et al., High efficiency transformation of *E.coli* by high voltage electroporation. Nucleic Acids Res. 16(13):6127-45 (1988).
Dressman, et al. Transforming single DNA molecules into fluorescent magnetic particles for detection and enumeration of genetic variations. Proc Natl Acad Sci U S A. Jul. 22, 2003;100(15):8817-22. Epub Jul. 11, 2003.
Drmanac, et al. Human genome sequencing using unchained base reads on self-assembling DNA nanoarrays. Science. 2010, 327(5961):78-81.
Duffy, et al. Rapid Prototyping of Microfluidic Systems in Poly(dimethylsiloxane). Anal Chem. Dec. 1, 1998;70(23):4974-84. doi: 10.1021/ac980656z.
Duggan, et al. Expression profiling using cDNA microarrays. Nat Genet. Jan. 1999;21(1 Suppl):10-4.
Eadie, et al. Guanine modification during chemical DNA synthesis. Nucleic Acids Res. Oct. 26, 1987;15(20):8333-49.
Ellis, et al. DNA assembly for synthetic biology: from parts to pathways and beyond. Integr Biol (Camb). Feb. 2011;3(2):109-18. doi: 10.1039/c0ib00070a. Epub Jan. 19, 2011.
El-Sagheer, et al. Biocompatible artificial DNA linker that is read through by DNA polymerases and is functional in *Escherichia coli*. Proc Natl Acad Sci U S A. Jul. 12, 2011;108(28):11338-43. doi: 10.1073/pnas.1101519108. Epub Jun. 27, 2011.
Elsner et al., 172 nm excimer VUV-triggered photodegradation and micropatterning of aminosilane films, Thin Solid Films, 517:6772-6776 (2009).
Engler, et al. A one pot, one step, precision cloning method with high throughput capability. PLoS One. 2008;3(11):e3647. doi: 10.1371/journal.pone.0003647.
Engler, et al. Golden gate shuffling: a one-pot DNA shuffling method based on type lls restriction enzymes. PLoS One. 2009;4(5):e5553. doi: 10.1371/journal.pone.0005553. Epub May 14, 2009.
Evans et al., DNA Repair Enzymes. Current Protocols in Molecular Biology. 84:III:3.9:3.9.1-3.9.12—http://www.ncbi.nlm.nih.gov/pubmed/18972391 (Published online Oct. 1, 2008) Abstract only provided.
Fahy, et al. Self-sustained sequence replication (3SR): an isothermal transcription-based amplification system alternative to PCR. PCR Methods Appl. Aug. 1991;1(1):25-33.
Fedoryak, Olesya D. et al., "Brominated hydroxyquinoline as a photolabile protecting group with sensitivity to multiphoton excitation", Org. Lett., vol. 4, No. 2 , 3419-3422 (2002).
Ferretti et al., Total synthesis of a gene for bovine rhodopsin. PNAS, 83:599-603 (1986).
Fodor, et al. Light-directed, spatially addressable parallel chemical synthesis. Science. Feb. 15, 1991;251(4995):767-73.
Foldesi, et al. The synthesis of deuterionucleosides. Nucleosides Nucleotides Nucleic Acids. Oct.-Dec. 2000;19(10-12):1615-56.

(56) References Cited

OTHER PUBLICATIONS

Frandsen, et al. Efficient four fragment cloning for the construction of vectors for targeted gene replacement in filamentous fungi. BMC Molecular Biology, 2008, 9:70.

Frandsen. Experimental setup. Dec. 7, 2010, 3 pages. http://www.rasmusfrandsen.dk/experimental_setup.htm.

Frandsen. The USER Friendly technology. USER cloning. Oct. 7, 2010, 2 pages. http://www.rasmusfrandsen.dk/user_cloning.htm.

Galneder. et al., Microelectrophoresis of a bilayer-coated silica bead in an optical trap: application to enzymology. Biophysical Journal, vol. 80, No. 5, 2298-2309 (May 2001).

Gao, et al. A flexible light-directed DNA chip synthesis gated by deprotection using solution photogenerated acids. Nucleic Acids Res. Nov. 15, 2001;29(22):4744-50.

Gao, et al. Thermodynamically balanced inside-out (TBIO) PCR-based gene synthesis: a novel method of primer design for high-fidelity assembly of longer gene sequences. Nucleic Acids Res. Nov. 15, 2003;31(22):e143.

Garaj, et al. Graphene as a subnanometre trans-electrode membrane. Nature. Sep. 9, 2010;467(7312):190-3. doi: 10.1038/nature09379.

Garbow, Norbert et al., "Optical tweezing electroghoresis of isolated, highly charged colloidal spheres", Colloids and Surfaces A: Physiochem. Eng. Aspec s, vol. 195, 227-241 (2001).

Geu-Flores, et al. USER fusion: a rapid and efficient method for simultaneous fusion and cloning of multiple PCR products. Nucleic Acids Res. 2007;35(7):e55. Epub Mar. 27, 2007.

Gibson, et al. Complete chemical synthesis, assembly, and cloning of a Mycoplasma genitalium genome. Science. Feb. 29, 2008;319(5867):1215-20. doi: 10.1126/science.1151721. Epub Jan. 24, 2008.

Gosse, Charlie et al. "Magnetic tweezers: micromanipulation and force measurement at the molecular level", Biophysical Journal, vol. 8, 3314-3329 (Jun. 2002).

Grovenor. Microelectronic materials. CRC Press. 1989; 113-123.

Haber, Charbel et al., Magnetic tweezers for DNA micromanipulation, Rev. Sci. Instrum., vol. 71, No. 12, 4561-4570 (Dec. 2000).

Hanahan and Cold Spring Harbor Laboratory, Studies on transformation of *Escherichia coli* with plasmids. J. Mol. Biol. 166:557-580 (1983).

Hanahan et al., Plasmid transformation of *Escherichia coli* and other bacteria. Methods Enzymol, vol. 204, p. 63-113 (1991).

Harada, et al. Unexpected substrate specificity of T4 DNA ligase revealed by in vitro selection. Nucleic Acids Res. May 25, 1993;21(10):2287-91.

Heckers Karl H. et al., "Error analysis of chemically synthesized polynucleotides", BioTechniques, vol. 24, No. 2, 255-260 (1998).

Herzer et al.: Fabrication of patterned silane based self-assembled monolayers by photolithography and surface reactions on silicon-oxide substrates Chem. Commun., 46:5634-5652 (2010).

Hosu, Basarab G. et al., Magnetic tweezers for intracellular applications•, Rev. Sci. Instrum., vol. 74, No. 9, 4158-4163 (Sep. 2003).

Huang, Hayden et al., "Three-dimensional cellular deformation analysis with a two-photon magnetic manipulator workstation", Biophysical Journal, vol. 82, No. 4, 2211•2223 (Apr. 2002).

Hughes, et al. Expression profiling using microarrays fabricated by an ink-jet oligonucleotide synthesizer. Nat Biotechnol. Apr. 2001;19(4):342-7.

Hutchison, et al. Cell-free cloning using phi29 DNA polymerase. Proc Natl Acad Sci U S A. Nov. 29, 2005;102(48):17332-6.

Jacobs and Schar, DNA glycosylases: In DNA repair and beyond. Chromosome, 121:1-20 (2012)—http://www.ncbi.nlm.nih.gov/pmc/articles/PMC3260424/.

Jeffrey M. Calvert, Lithographically patterned self-assembled films. In:*Organic Thin Films and Surfaces: Directions for the Nineties*, vol. 20, p. 109, ed. By Abraham Ulman, San Diego: Academic Press, 1995.

Ke, Song-Hua et al., "Influence of neighboring base pairs on the stability of single base bulges and base pairs in a DNA fragment", Biochemistry, Vo. 34, 4593-4600 (1995).

Kelley, Shana, et al. Single-base mismatch detection based on charge transduction through DNA, Nucleic Acids Research, vol. 27, No. 24, 4830-4837 (1999).

Kim, Yang-Gyun et al., "Chimeric restriction endonuclease", Proc. Natl. Acad. Sci. USA, vol. 91, 883-887 (Feb. 1994).

Kim, Yang-Gyun, "The interaction between Z-ONA and the Zab domain of double-stranded RNA adenosine deaminase characterized using fusion nucleases", The Journal of Biological Chemistry, vol. 274, No. 27, 19081-19086 (1999).

Kim, Yan~Gyun et al., "Site specific cleavage of DNA-RNA hybrids by zinc finger/Fok I cleavage domain fusions" Gene, vol. 203, 43-49 (1997).

Kodumal, et al. Total synthesis of long DNA sequences: synthesis of a contiguous 32-kb polyketide synthase gene cluster. Proc Natl Acad Sci U S A. Nov. 2, 2004;101(44):15573-8. Epub Oct. 20, 2004.

Kong et al., Parallel gene synthesis in a microfluidic device. Nucleic Acids Res., 35(8):e61 (2007).

Kong. Microfluidic Gene Synthesis. MIT Thesis. Submitted to the program in Media Arts and Sciences, School of Architecture and Planning, in partial fulfillment of the requirements for the degree of Doctor of Philosophy in Media Arts and Sciences at the Massachusetts Institute of Technology. 143 pages Jun. 2008.

Kopp, Martin U. et al., "Chemical amplification: continuous-flow PCR on a chip", Science, vol. 280, 1046-1048 (May 15, 1998).

Kosuri, et al. A scalable gene synthesis by selective amplification of DNA pools from high-fidelity microchips. Nature Biotechnology. 2010; 28:1295-1299.

Lagally, E.T. et al., "Single-molecule DNA amplification and analysis in an integrated microfluidic device" Anal. Chem., vol. 73, No. , 565-570 (Feb. 1, 2001).

Lahue, R.S. et. al., "DNA mismatch correction in a defined system", Science, vol. 425; No. 4914, 160-164 (Jul. 14, 1989).

Lambrinakos, A. et al., "Reactivity of potassium permanganate and tetraethylammonium chloride with mismatched bases and a simple mu ation detection protoco",Nucleic Acids Research, vol. 27, No. 8, 1866-1874 (1999).

Landegren, et al. A ligase-mediated gene detection technique. Science. Aug. 26, 1988;241(4869):1077-80.

Lang, Matthew J. et al., "An automated two-dimensional optical force clamp for single molecule studies", Biophysical Journal, vol. 83, 491• 501 (Jul. 2002).

Lashkari, et al. An automated multiplex oligonucleotide synthesizer: development of high-throughput, low-cost DNA synthesis. Proc Natl Acad Sci U S A. Aug. 15, 1995;92(17):7912-5.

Leamon, et al. A massively parallel PicoTiterPlate based platform for discrete picoliter-scale polymerase chain reactions. Electrophoresis. Nov. 2003;24(21):3769-77.

Lee, Covalent end-immobilization of oligonucleotides onto solid surfaces. Thesis submitted to the Department of Chemical Engineering in Partial Fulfillment of the Requirements for the Degree of Doctor of Philosopy in Chemical Engineering at the Massachusetts Institute of Technology. Aug. 2001, 315 pages.

Lee, C.S. et al., "Microelectromagnets for the control of magnetic nanoparticles", Appl. Phys. Lett., vol. 79, No. 20, 3308-3310, 2001.

Lee, et al. A microfluidic oligonucleotide synthesizer. Nucleic Acids Research 2010 vol. 38(8):2514-2521. DOI: 10.1093/nar/gkq092.

Leproust, et al. Agilent's Microarray Platform: How High-Fidelity DNA Synthesis Maximizes the Dynamic Range of Gene Expression Measurements. 2008; 1-12. http://www.miltenyibiotec.com/~/media/Files/Navigation/Genomic%20Services/Agilent_DNA_Microarray_Platform.ashx.

Leproust, et al. Synthesis of high-quality libraries of long (150mer) oligonucleotides by a novel depurination controlled process. Nucleic Acids Research. 2010; 38(8):2522-2540.

Lesnikowski, et al. Nucleic acids and nucleosides containing carboranes. J. Organometallic Chem. 1999; 581:156-169.

Leumann. DNA analogues: from supramolecular principles to biological properties. Bioorg Med Chem. Apr. 2002;10(4):841-54.

Levene, et al. Zero-mode waveguides for single-molecule analysis at high concentrations. Science. Jan. 31, 2003;299(5607):682-6.

Lipshutz, Robert J. et al., "High density synthetic oligonucleotide arrays", Nature Genetics Supplement, vol. 21, Jan. 20-24, 1999.

(56) References Cited

OTHER PUBLICATIONS

Lishanski, Alia et al., "Mutation detection by mismatch binding protein, MutS, in amplified DNA: application to the cystic fibrosis gene", Proc. Natl. Acad. Sci. USA, vol. 91, 2674-2678 (Mar. 1994).
Liu, et al. Enhanced Signals and Fast Nucleic Acid Hybridization by Microfluidic Chaotic Mixing. Angew. Chem. Int. Ed. 2006; 45:3618-3623.
Lizardi, et al. Mutation detection and single-molecule counting using isothermal rolling-circle amplification. Nat Genet. Jul. 1998;19(3):225-32.
Li, Lin et al., "Functional domains in Fok I restriction endonuclease", Proc. Natl. Acad. Sci. USA, vol. 89, 4275-4279 (May 1992).
Lu, A.-Lien et al., "Methyl-directed repair of DNA base-pair mismatches in vitro",Proc. Natl. Acad. Sci. USA, vol. 80, 4639-4643 (Aug. 1983).
Lund, et al. A validated system for ligation-free uracilexcision based assembly of expression vectors for mammalian cell engineering. DTU Systems of Biology. 2011. 1 page. http://www.lepublicsystemepco.com/files/modules/gestion_rubriques/REF-B036-Lund_Anne%20Mathilde.pdf.
Ma, et al. DNA synthesis, assembly and application in synthetic biology. Current Opinion in Chemical Biology. 2012; 16:260-267.
Ma et al., Versatile surface functionalization of cyclic olefin copolymer (COC) with sputtered SiO2 thin film for potential BioMEMS applications. Journal of Materials Chemistry, DOI: 10.1039/b904663a, 11 pages (2009).
Margulies, et al. Genome sequencing in open microfabricated high-density picolitre reactors. Nature. Sep. 15, 2005;437(7057):376-80.
Matteucci, et al. Synthesis of deoxyoligonucleotides on a polymer support. J. Am. Chem. Soc. 1981; 103(11):3185-3191.
McGall, et al. Light-directed synthesis of high-density oligonucleotide arrays using semiconductor photoresists. Proc Natl Acad Sci U S A. Nov. 26, 1996;93(24):13555-60.
McGall, et al. The Efficiency of Light-Directed Synthesis of DNA Arrays on Glass Substrates. J. Am. Chem. Soc. 1997; 119(22):5081-5090.
Mendel-Hartvig. Padlock probes and rolling circle amplification. New possibilities for sensitive gene detection. Comprehensive Summaries of Uppsala Dissrtations from the Faculty of Medicine 1175. Uppsala University. 2002, 39 pages. http://www.diva-portal.org/smash/get/diva2:161926/FULLTEXT01.pdf.
Mitra, et al. In situ localized amplification and contact replication of many individual DNA molecules. Nucleic Acids Res. Dec. 15, 1999;27(24):e34.
Muller, Caroline et al. "Protection and labelling of thymidine by a fluorescent photolabile group", Helvetica Chimica Acta, vol. 84, 3735-3741 (2001).
Nakatani, Kazuhiko et al., "Recognition of a single guanine bulge by 2-Acylamino-1,8-naphthyridine", J. Am. Chem. Soc., vol. 122, 2172-2177 (2000).
Nour-Eldin, et al. USER Cloning and USER Fusion: The Ideal Cloning Techniques for Small and Big Laboratories. Plant Secondary Metabolism Engineering. Methods in Molecular Biology vol. 643, 2010, pp. 185-200.
Ochman, et al. Genetic applications of an inverse polymerase chain reaction. Genetics. Nov. 1998;120(3):621-3.
Pan, et al. An approach for global scanning of single nucleotide variations. Proc Natl Acad Sci U S A. Jul. 9, 2002;99(14):9346-51.
Pankiewicz. Fluorinated nucleosides. Carbohydr Res. Jul. 10, 2000;327(1-2):87-105.
PCT Patent Application No. PCT/US14/049834 International Preliminary Report on Patentability dated Feb. 18, 2016.
PCT Patent Application No. PCT/US2015/043605 International Search Report and Written Opinion dated Jan. 6, 2016.
PCT Patent Application No. PCT/US2015/043605 Invitation to Pay Additional Fees dated Oct. 28, 2015.
PCT/US2014/049834 International Search Report and Written Opinion dated Mar. 19, 2015.
PCT/US2014/049834, Invitation to Pay Additional Fees and, where applicable, protest fee, dated Jan. 5, 2015.
Pease, et al. Light-generated oligonucleotide arrays for rapid DNA sequence analysis. Proc Natl Acad Sci U S A. May 24, 1994;91(11):5022-6.
Peisajovich, et al. BBF RFC 28: A method for combinatorial multi-part assembly based on the type-IIs restriction enzyme aarl. Sep. 16, 2009.
Pellois, et al. "Individually addressable parallel peptide synthesis on microchips", Nature Biotechnology, vol. 20, 922-926 (Sep. 2002).
Petersen, et al. LNA: a versatile tool for therapeutics and genomics. Trends Biotechnol. Feb. 2003;21(2):74-81.
Pierce, et al. Linear-after-the-exponential polymerase chain reaction and allied technologies. Real-time detection strategies for rapid, reliable diagnosis from single cells. Methods Mol Med. 2007;132:65-85.
Pon. Solid-phase supports for oligonucleotide synthesis. Methods Mol Biol. 1993;20:465-96.
Eisen, Jonathan A., "A phylogenomic study of the MutS family of proteins", Nucleic Acids Research, vol. 26, No. 18, 4291-4300 (1998).
Hoover et al., "DNAWorks: an automated method for designing oligonucleotides for PCR-based gene synthesis", Nucleic Acids Research, vol. 30, No. 10, e43, 7 page (2002).
Jackson, Brian A. et al., "Recognition of DNA base mismatches by a rhodium intercalator", J. Am. Chem. Soc., vol. 19, 12986•12987 (1997).
Prodromou, et al. Recursive PCR: a novel technique for total gene synthesis. Protein Eng. Dec. 1992;5(8):827-9.
Quan, et al. Parallel on-chip gene synthesis and application to optimization of protein expression. Nature Biotechnology. 2011; 29:449-452.
RF Electric discharge type excimer lamp. Products Catalog. Excimer lamp light source "flat excimer" (2.0 MB/PDf).—http://www.hamamatsu.com/jp/en/product/category/1001/3026/index.html, 2 pages, downloaded on Dec. 28, 2015.
Richmond, et al. Amplification and assembly of chip-eluted DNA (AACED): a method for high-throughput gene synthesis. Nucleic Acids Res. Sep. 24, 2004;32(17):5011-8. Print 2004.
Roche. Restriction Enzymes FAQS and Ordering Guide. Roche Applied Science. Access Jan. 12, 2015, 37 pages. http://www.roche-diagnostics.ch/content/dam/corporate/roche-dia_ch/documents/broschueren/applied_science/biochemical-reagents-custom-biotech/cloning/04520599990_EN_EA_Restriction-Enzymes-FAQS-and-Ordering-Guide.pdf.
Ruminy, et al., "Long-range identification of hepatocyte nuclear factor-3 (FoxA) high and low-affinity binding Sites wit a chimeric nuclease", J. Mol. Bioi., vol. 310, 523-535 (2001).
Saboulard, et al. High-throughput site-directed mutagenesis using oligonucleotides synthesized on DNA chips. Biotechniques. Sep. 2005;39(3):363-8.
Sacconi, L. et al., Three-dimendional magneto-optic trap for micro-object manipulation•, Optics Letters, vol. 26, No. 17, 1359-1361 (Sep. 1, 2001).
Saiki et al., Analysis of enzymatically amplified beta-globin and HLA-DQ alpha DNA with allele-specific oligonucleotide probes Nature 324:163-166 (1986).
Sandhu, et al. Dual asymmetric PCR: one-step construction of synthetic genes. Biotechniques. Jan. 1992;12(1):14-6.
Schaller, et al. Studies on Polynucleotides. XXV.1 The Stepwise Synthesis of Specific Deoxyribopolynucleotides (5). Further Studies on the Synthesis of Internucleotide Bond by the Carbodiimide Method. The Synthesis of Suitably Protected Dinucleotides as Intermediates in the Synthesis of Higher Oligonucleotides. J. Am. Chem. Soc. 1963; 85(23):3828-3835.
Schmalzing, Dieter et al., "Microchip electrophoresis: a method for high-speed SNP detection", Nucleic Acids Research, vol. 28, No. 9, i-vi (2000).
Sierzchala, Agnieszka B. et al., "Solid-phase oligodeoxynucleotide synthesis: a two-step cycle using peroxy anion eprotection", J. Am. Chem. Soc., vol. 125, No. 44, 13427-13441 (2003).

(56) References Cited

OTHER PUBLICATIONS

Singh-Gasson, Sangeet et al., Maskless fabrication of lijht-directed olxyonucleotide microarrays using a digital micromirror array, Nature Biotechnology, vol. 17, 974-978 (Oct. 1999).
Smith, et al. Generating a synthetic genome by whole genome assembly: phiX174 bacteriophage from synthetic oligonucleotides. Proc Natl Acad Sci U S A. Dec. 23, 2003;100(26):15440-5.
Smith, et al. Generation of cohesive ends on PCR products by UDG-mediated excision of dU, and application for cloning into restriction digest-linearized vectors. PCR Methods Appl. May 1993;2(4):328-32.
Smith, Jane et al., "Mutation detection with MutH, MutL, and MutS mismatch repair proteins", Proc. Natl. Acad. Sci. USA, vol. 93, 4374-4379 (Apr. 1996).
Smith Jane et al., "Removal of Polymerase-Produced mutant sequences from PCR products", Proc. Natl. Acad. Sci. USA, vol. 94, 6847-6850 (Jun. 1997).
Smith, Steven B. et al., "Direct mechanical measurements of the elasticity of single DNA molecules using magnetic beads", Science, vol. 258, 1122-1126 (Nov. 13, 1992).
Soni, et al. Progress toward ultrafast DNA sequencing using solid-state nanopores. Clin Chem. Nov. 2007;53(11):1996-2001. Epub Sep. 21, 2007.
Southern, et al. Analyzing and comparing nucleic acid sequences by hybridization to arrays of oligonucleotides: evaluation using experimental models. Genomics. Aug. 1992;13(4):1008-17.
Sproat, et al. An efficient method for the isolation and purification of oligoribonucleotides. Nucleosides & Nucleotides. 1995; 14(1&2):255-273.
Steel, The Flow-Thru Chip A Three-dimensional biochip platform. In: Schena, Microarray Biochip Technology, Chapter 5, Natick, MA: Eaton Publishing, 2000, 33 pages.
Stemmer, et al. Single-step assembly of a gene and entire plasmid from large numbers of oligodeoxyribonucleotides. Gene. Oct. 16, 1995;164(1):49-53.
Stryer. "DNA Probes and genes can be synthesized by automated solid-phase methods." Biochemistry, 3rd edition, New York: W.H. Freeman and Company, 1988; 123-125.
Stutz, et al. Novel fluoride-labile nucleobase-protecting groups for the synthesis of 3'(2')-O-amino-acylated RNA sequences. Helv. Chim. Acta. 2000; 83(9):2477-2503.
Takahashi, Cell-free cloning using multiply-primed rolling circle amplification with modified RNA primers. Biotechniques. Jul. 2009;47(1):609-15. doi: 10.2144/000113155.
Tanase, M. et al., "Magnetic trapping of multicomponent nanowires", The Johns Hopkins University, Baltimore, Maryland, p. 1-3 (Jun. 25, 2001).
Tian, et al. Accurate multiplex gene synthesis from programmable DNA microchips. Nature. Dec. 23, 2004;432(7020):1050-4.
Unger, et al. Monolithic microfabricated valves and pumps by multilayer soft lithography. Science. Apr. 7, 2000;288(5463):113-6.
U.S. Appl. No. 14/452,429 Office Action dated Apr. 9, 2015.
PCT Patent Application No. PCT/US2016/016459 International Search Report and Written Opinion dated Apr. 13, 2016.
U.S. Appl. No. 14/452,429 Office Action dated Oct. 21, 2015.
U.S. Appl. No. 14/885,962 Restriction Requirement dated Mar. 1, 2016.
U.S. Appl. No. 14/885,963 Office Action dated Feb. 5, 2016.
U.S. Appl. No. 14/885,965 Office Action dated Feb. 18, 2016.
Vaijayanthi, et al. Recent advances in oligonucleotide synthesis and their applications. Indian J Biochem Biophys. Dec. 2003;40(6):377-91.
Van Den Brulle, et al. A novel solid phase technology for high-throughput gene synthesis. Biotechniques. 2008; 45(3):340-343.
Vargeese, et al. Efficient activation of nucleoside phosphoramidites with 4,5- dicyanoimidazole during oligonucleotide synthesis. Nucleic Acids Res. Feb. 15. 1998;26(4):1046-50.
Verma, et al. Modified oligonucleotides: synthesis and strategy for users. Annu Rev Biochem. 1998;67:99-134.
Vincent, et al. Helicase-dependent isothermal DNA amplification. EMBO Rep. Aug. 2004;5(8):795-800.
Visscher et al., "Construction of multiple-beam optical traps with nanometer-resolution position sensing", IEEE Journal of Selected Topics in Quantum Electronics, vol. 2, No. 4, 1066-1076 (Dec. 1996.
Voldmans Joel et al., "Holding forces of single-particle dielectrophoretic traps." Biophysical Journal, vol. 80, No. 1, 531-541 (Jan. 2001).
Vos, et al. AFLP: A new technique for DNA fingerprinting. Nucleic Acids Res. Nov. 11, 1995;23(21):4407-14.
Wah, David A. et al., "Structure of Fok I has implications for DNA cleavage", Proc. Natl. Acad. Sci. USA, vol. 95, 10564-10569 (Sep. 1998).
Wah, David A. et al., "Structure of the multimodular endonuclease Fok I bound to DNA", Nature, vol. 388, 97-100 ( Jul. 1997).
Walker, et al. Strand displacement amplification—an isothermal, in vitro DNA amplification technique. Nucleic Acids Res. Apr. 11, 1992;20(7):1691-6.
Weber, et al. A modular cloning system for standardized assembly of multigene constructs. PLoS One. Feb. 18, 2011;6(2):e16765. doi: 10.1371/journal.pone.0016765.
Welz, et al. 5-(Benzylmercapto)-1H-tetrazole as activator for 2'-O-TBDMS phosphoramidite building blocks in RNA synthesis. Tetrahedron Lett. 2002; 43(5):795-797.
Westin et al., Anchored multiplex amplification on a microelectronic chip array Nature Biotechnology, 18:199-202 (2000) (abstract only).
Whitehouse, Adrian et al. "Analysis of the mismatch and insertion/deletion binding properties of Thermus thermophilus, HB8, MutS", Biochemical and Biophysical Research Communications, vol. 233, 834-837 (1997).
Wirtz, Denis, "Direct measurement of the transport properties of a single DNA molecule", Physical Review Letters, vol. 75, No. 12, 2436-2439 (Sep. 18, 1995).
Withers-Martinez, Chrislaine et al., "PCR-based gene synthesis as an efficient approach for expression of the A+ T-rich malaria genome", Protein Engineering, vol. 12, No. 12, 1113-1120 (1999).
Wood, Richard D. et al., "Human DNA repair genes", Science, vol. 291, 1284-1289 (Feb. 16, 2001).
Wosnick, et al. Rapid construction of large synthetic genes: total chemical synthesis of two different versions of the bovine prochymosin gene. Gene. 1987;60(1):115-27.
Wu, et al. RNA-mediated gene assembly from DNA arrays. Angew Chem Int Ed Engl. May 7, 2012;51(19):4628-32. doi: 10.1002/anie. 201109058.
Wu, et al. Specificity of the nick-closing activity of bacteriophage T4 DNA ligase. Gene. 1989;76(2):245-54.
Wu, Xing-Zheng et al., "An improvement of the on-line electrophoretic concentration method for capillary electrophoresis of proteins involving an experimental factors affecting he concentration effect", Analytical Sciences, vol. 16, 329-331 (Mar. 2000).
Xiong, et al. A simple, rapid, high-fidelity and cost-effective PCR-based two-step DNA synthesis method for long gene sequences. Nucleic Acids Res. Jul. 7, 2004;32(12):e98.
Xiong, et al. Non-polymerase-cycling-assembly-based chemical gene synthesis: Strategies, methods, and progress. Biotechnology Advances. 2008; 26(2):121-134.
Yang, et al "Purification, cloning, and characterization of the CEL I nuclease", Biochemistry, vol. 39, No. 13, 3533-351 (2000).
Youil, Rima et al., "Detection of 51 of 51 known mouse P.Giobin promoter mutations with T4 Endonuclease VII. The EMC Method", Genomics, vol. 32, 431-435 (1996).
Young, et al. Two-step total gene synthesis method. Nucleic Acids Res. Apr. 15, 2004;32(7):e59.
Zheleznaya, et al. Nicking endonucleases. Biochemistry (Mosc). Dec. 2009;74(13):1457-66.
Arkles, Hydrophobicity, Hydrophilicity. Reprinted with permission from the Oct. 2006 issue of Paint & Coatings Industry magazine, Retrieved from the internet on Mar. 19, 2016, 10 pages.
Droege and Hill, The Genome Sequencer FLXTM System-Longer reads, more applications, straight forward bioinformatics and more complete data sets Journal of Biotechnology, 136:3-10, 2008.

(56) References Cited

OTHER PUBLICATIONS

Fullwood et al., Next-generation DNA sequencing of paired-end tags [PET] for transcriptome and genome analysis Genome Research, 19:521-532, 2009.
Karagiannis and Ei-Osta, RNA interference and potential therapeutic applications of short interfering RNAs Cancer Gene Therapy, 12:787-795, 2005.
Kinde et al., Detection and quantification of rare mutations with massively parallel sequencing PNAS, 108(23):9530-9535, 2011.
Kosuri et al., A scalable gene synthesis platform using high-fidelity DNA microchips Nat. Biotechnol., 28(12):1295-1299, 2010.
Mahato et al., Modulation of gene expression by antisense and antigene oligodeoxynucleotides and small interfering RNA. Expert Opin. Drug Delivery, 2(1):3-28, 2005.
Matzas et al., Next generation gene synthesis by targeted retrieval of bead-immobilized, sequence verified DNA clones from a high throughput pyrosequencing device. Nat. Biotechnol., 28(12):1291-1294, 2010.
Mei et al., Cell-free protein synthesis in microfluidic array devices Biotechnol. Prog. 23(6):1305-1311, 2007.
Meyers and Friedland, Knowledge-based simulation of genetic regulation in bacteriophage lambda Nucl. Acids Research, 12(1):1-16, 1984.
Nishikura, A short primer on RNAi: RNA-directed RNA polymerase acts as a key catalyst Cell, 107:415-418, 2001.
PCT Patent Application No. PCT/US2016/016636 International Search Report and Written Opinion dated May 2, 2016.
Reimagine SequenceSpace, Reimagine Research, Twist Bioscience, Product Brochure, Published Apr. 6, 2016 online at: www2.twistbioscience.com/TB_Product_Brochure_04.2016, 8 pages.
Tsai et al., Dimeric CRISPR RNA-guided FokI nucleases for highly specific genome editing Nat. Biotechnol., 32(6):569-576, 2014.
Yehezkel et al., De novo DNA synthesis using single molecule PCR Nucleic Acids Research, 36(17):e107, 2008.
Zhou et al., Microfluidic PicoArray synthesis of oligodeoxynucleotides and simultaneous assembling of multiple DNA sequences Nucleic Acids Research, 32(18):5409-5417, 2004.
Saaem et al., In situ synthesis of DNA microarray on functionalized cyclic olefin copolymer substrate ACS Applied Materials & Interfaces, 2(2):491-497, 2010.
Andoni and Indyk, Near-Optimal Hashing Algorithms for Approximate Nearest Neighbor in High Dimensions, Communications of the ACM, 51(1):117-122, Jan. 2008.
ATDBio, "Nucleic Acid Structure," Nucleic Acids Book, 9 pages, published on Jan. 22, 2005. from: http://www.atdbio.com/content/5/Nucleic-acid-structure.
ATDBio, "Solid-Phase Oligonucleotide Synthesis," Nucleic Acids Book, 20 pages, Published on Jul. 31, 2011. from: http://www.atdbio.com/content/17/Solid-phase-oligonucleotide-synthesis.
Barton et al., A desk electrohydrodynamic jet printing system. Mechatronics, 20:611-616, 2010.
Blanchard, et al., "High-Density Oligonucleotide Arrays," Biosensors & Bioelectronics, 11(617):687-690, 1996.
Blawat et al., Forward error correction for DNA data storage. Procedia Computer Science, 80:1011-1022, 2016.
Bornholt et al., A DNA-Based Archival Storage System, in International Conference on Architectural Support for Programming Languages and Operating Systems (ASPLOS), Apr. 2-6, 2016, Atlanta, GA, 2016, 637-649.
Brunet, Aims and methods of biosteganography. Journal of Biotechnology, 226:56-64, 2016.
Buermans et al., "Next Generation sequencing technology: Advances and applications," Biochimica et Biophysica Acta (BBA)—Molecular Basis of Disease, 1842:1931-1941, 2014.
Cardelli, Two-Domain DNA Strand Displacement, Electron. Proc. Theor. Comput. Sci., 26:47-61, 2010.
Carlson, "Time for New DNA Synthesis and Sequencing Cost Curves," 2014. [Online]. Available: http://www.synthesis.cc/synthesis/2014/02/time_for_new_cost_curves_2014. [Accessed: May 25, 2017], 10 pages.
Caruthers, The Chemical Synthesis of DNA/RNA: Our Gift to Science. J. Biol. Chem., 288(2):1420-1427, 2013.
Chen et al., Programmable chemical controllers made from DNA, Nat. Nanotechnol., 8(10):755-762, 2013.
Church et al., Next-generation digital information storage in DNA. Science, 337:6102, 1628-1629, 2012.
Cleary et al., "Production of complex nucleic acid libraries using highly parallel n s tu oligonucleotide synthesis," Nature Methods, 1(13):241-248, 2004.
Cohen et al., Human population: The next half century. Science, 302:1172-1175, 2003.
Elsik et al., The Genome sequence of taurine cattle: A window of ruminant biology and evolution. Science, 324:522-528, 2009.
Erlich and Zielinski, DNA fountain enables a robust and efficient storage architecture. Science, 355(6328):950-054, 2017.
European Patent Application No. 14834665.3 extended European Search Report dated Apr. 28, 2017.
Finger et al., The wonders of Flap Endonucleases: Structure, function, mechanism and regulation. Subcell Biochem., 62:301-326, 2012.
Fodor et al. "Light-Directed, Spatially Addressable Parallel Chemical Synthesis," Science, 251(4995):767-773, 1991.
Fogg et al., Structural basis for uracil recognition by archaeal family B DNA polymerases. Nature Structural Biology, 9(12):922-927, 2002.
GeneArt Seamless Cloning and Assembly Kits. Life Technologies Synthetic Biology. 8 pages, available online Jun. 15, 2012.
Gibson Assembly. Product Listing. Application Overview. 2 pages, available online Dec. 16, 2014.
Goldman et al., Towards practical, high-capacity, low-maintenance information storage in synthesized DNA, Nature, 494(7435):77-80, 2013.
Grass, et al., Robust chemical preservation of digital information on DNA in silica with error-correcting codes, Angew. Chemie—Int. Ed., 54(8):2552-2555, 2015.
Greagg et al., A read-ahead function in archaeal DNA polymerases detects promutagenic template-strand uracil. Proc. Nat. Acad. Sci. USA, 96:9045-9050, 1999.
Gu et al., Depletion of abundant sequences by hybridization (DASH): using Cas9 to remove unwanted high-abundance species in sequencing libraries and molecular counting applications. Genome Biology, 17:41, 13 pages, 2016.
In-Fusion Cloning: Accuracy, Not Background. Cloning & Competent Cells, ClonTech Laboratories, 3 pages, available online Jul. 6, 2014.
Jinek et al., A Programmable dual-RNA-guided DNA endonuclease in adaptive bacterial immunity. Science, 337:816-821, 2012.
Kim et al., High-resolution patterns of quantum dots formed by electrohydrodynamic jet printing for light-emitting diodes. Nano Letters, 15:969-973, 2015.
Kosuri and Church, "Large-scale de novo DNA synthesis: technologies and applications," Nature Methods, 11:499-507, 2014. Available at: http://www.nature.com/nmeth/journal/v11/n5/full/nmeth.2918.html.
Krayden, Inc., A Guide to Silane Solutions. Silane coupling agents. 7 pages. Published on May 31, 2005 at: http://krayden.com/pdf/xia_silane_chemistry.pdf.
Lausted et al., "POSaM: a fast, flexible, open-source, inkjet oligonucleotide synthesizer and microarrayer," Genome Biology, 5:R58, 17 pages, 2004. available at https://www.ncbi.nlm.gov/pmc/articles/PMC507883/.
Leproust et al., "Synthesis of high-quality libraries of long (150mer) oligonucleotides by a novel depurination controlled process," Nucleic Acids Research, 35(8):2522-2540, 2010.
Lewontin and Harti, Population genetics in forensic DNA typing. Science, 254:1745-1750, 1991.
Limbachiya et al., Natural data storage: A review on sending information from now to then via Nature. ACM Journal on Emerging Technologies in Computing Systems, V(N):Article A, May 19, 2015, 17 pages.
Liu et al., Rational design of CXCR4 specific antibodies with elongated CDRs. JACS, 136:10557-10560, 2014.

(56) References Cited

OTHER PUBLICATIONS

McBride & Caruthers, "An investigation of several deoxynucleoside phosphoramidites useful for synthesizing deoxyoligonucleotides." Tetrahedron Lett. 24: 245-248, 1983.
Milo and Phillips, Numbers here reflect the number of protein coding genes and excludes tRNA and non-coding RNA. Cell Biology by the Numbers, p. 286, 2015.
Neiman M.S,. Negentropy principle in information processing systems. Radiotekhnika, 1966, N°11, p. 2-9.
Neiman M.S., On the bases of the theory of information retrieval. Radiotekhnika, 1967, N° 5, p. 2-10.
Neiman M.S., On the molecular memory systems and the directed mutations. Radiotekhnika, 1965, No. 6, pp. 1-8.
Neiman M.S., On the relationships between the reliability, performance and degree of microminiaturization at the molecular-atomic level. Radiotekhnika, 1965, No. 1, pp. 1-9.
Neiman M.S., Some fundamental issues of microminiaturization. Radiotekhnika, 1964, No. 1, pp. 3-12.
Organick et al., Scaling up DNA data storage and random access retrieval, bioRxiv, preprint first posted online Mar. 7, 2017, 14 pages.
PCT Patent Application No. PCT/US2015/043605 International Preliminary Report on Patentability dated Feb. 16, 2017.
PCT Patent Application No. PCT/US2016/052336 International Search Report and Written Opinion dated Dec. 7, 2016.
PCT Patent Application No. PCT/US2016/052916 International Search Report and Written Opinion dated Dec. 30, 2016.
PCT/US2016/064270 International Search Report and Written Opinion dated Apr. 28, 2017.
Pray. "Discovery of DNA Structure and Function: Watson and Crick," Nature Education, 2008, 6 pages. available at: http://www.nature.com/scitable/topicpage/discovery-of-dna-structure-and-function-watson-397.
Qian and Winfree, Scaling up digital circuit computation with DNA strand displacement cascades. Science, 332(6034):196-1201, 2011.
Qian, et al., Neural network computation with DNA strand displacement cascades, Nature, 475(7356):368-372, 2011.
Quan et al., "Parallel on-chip gene synthesis and application to optimization of protein expression," Nature Biotechnology, 29(5):449-452, 2011.
Rafalski and Morgante, Corn and humans: recombination and linkage disequilibrium in two genomes of similar size. Trends in Genetics, 20(2):103-111, 2004.
Raje and Murma, A Review of electrohydrodynamic-inkjet printing technology. International Journal of Emerging Technology and Advanced Engineering, 4(5):174-183, 2014.
Rastegari, et al., XNOR-Net: ImageNet Classification Using Binary Convolutional Neural Networks, in ECCV 2016, Part IV, LNCS 9908, p. 525-542, 2016.
Sargolzaei et al., Extent of linkage disequilibrium in Holstein cattle in North America. J.Dairy Science, 91:2106-2117, 2007.
Seelig, et al., Enzyme-Free Nucleic Acid Logic Circuits, Science 314(5805):1585-1588, 2006.
Simonyan and Zisserman, Very Deep Convolutional Networks for Large-Scale Image Recognition, Published as a conference paper at Int. Conf. Learn. Represent., pp. 1-14, 2015.
The Hood Laboratory, "Beta Group." Assembly Manual for the POSaM: The ISB Piezoelelctric Oligonucleotide Synthesizer and Microarrayer, Inkjet Microarrayer Manual Version 1.2, 50 pages, May 28, 2004.
The SLIC, Gibson, CPEC and SLiCE assembly methods (and GeneArt Seamless, In-Fusion Cloning). 5 pages, available online Sep. 2, 2010.
U.S. Appl. No. 14/241,874 Office Action dated Feb. 27, 2017.
U.S. Appl. No. 14/885,962 Office Action dated Dec. 16, 2016.
U.S. Appl. No. 14/885,965 Office Action dated Feb. 10, 2017.
U.S. Appl. No. 15/154,879 Notice of Allowance dated Feb. 1, 2017.
U.S. Appl. No. 15/187,721 Notice of Allowance dated Dec. 7, 2016.
U.S. Appl. No. 15/187,721 Office Action dated Oct. 14, 2016.
U.S. Appl. No. 15/233,835 Office Action dated Feb. 8, 2017.
U.S. Appl. No. 15/233,835 Restriction Requirement dated Nov. 4, 2016.
U.S. Appl. No. 15/245,054 Office Action dated Mar. 21, 2017.
U.S. Appl. No. 15/245,054 Office Action dated Oct. 19, 2016.
U.S. Appl. No. 15/377,547 Office Action dated Mar. 24, 2017.
Van Tassell et al., SNP discovery and allele frequency estimation by deep sequencing of reduced representation libraries. Nature Methods, 5:247-252, 2008.
Wan et al., Deep Learning for Content-Based Image Retrieval: A comprehensive study. in Proceedings of the 22nd ACM International Conference on Multimedia—Nov. 3-7, 2014, Orlando, FL, p. 157-166, 2014.
Wijshoff, Herman. Structure and fluid-dynamics in Piezo inkjet printheads. Thesis. Venio, The Netherlands, published 2008, p. 1-185.
Wright and Church, An open-source oligomicroarray standard for human and mouse. Nature Biotechnology, 20:1082-1083, 2002.
Xiong et al., Chemical gene synthesis: Strategies, softwares, error corrections, and applications. FEMS Microbiol. Rev., 32:522-540, 2008.
Yazdi, et al., A Rewritable, Random-Access DNA-Based Storage System, Scientific Reports, 5, Article No. 14138, 27 pages, 2015.
Zhang and Seelig, Dynamic DNA nanotechnology using strand-displacement reactions, Nat. Chem., 3(2):103-113, 2011.
Zhirnov et al., Nucleic acid memory. Nature Materials, 15:366, 2016.
European Patent Application No. 16871446.7 European Search Report dated Apr. 10, 2019.
Galka et al.: QuickLib, a method for building fully synthetic plasmid libraries by seamless cloning of degenerate oligonucleotides. PLOS ONE, 12, e0175146:1-9 (2017).
Galka et al.: QuickLib, a method for building fully synthetic plasmid libraries by seamless cloning of degenerate oligonucleotides. PLOS ONE, 12, e0175146:S1 figure (2017).
Galka et al.: QuickLib, a method for building fully synthetic plasmid libraries by seamless cloning of degenerate oligonucleotides. PLOS ONE, 12, e0175146:S1 Table (2017).
Galka et al.: QuickLib, a method for building fully synthetic plasmid libraries by seamless cloning of degenerate oligonucleotides. PLOS ONE, 12, e0175146:S2 figure (2017).
International Application No. PCT/US2017/052305 International Preliminary Report on Patentability dated Apr. 30, 2019.
International Application No. PCT/US2017/062391 International Preliminary Report on Patentability dated May 21, 2019.
International Application No. PCT/US2018/019268 International Preliminary Report on Patentability dated Sep. 6, 2019.
International Application No. PCT/US2018/057857 International Search Report and Written Opinion dated Mar. 18, 2019.
International Application No. PCT/US2019/032992 International Search Report and Written Opinion dated Oct. 28, 2019.
International Application No. PCT/US2019/032992 Invitation to Pay Additional Fees dated Sep. 6, 2019.
Mazor et al.: Isolation of Full-Length IgG Antibodies from Combinatorial Libraries Expressed in *Escherichia coli*; Antony S. Dimitrov (ed.), Therapeutic Antibodies: Methods and Protocols, vol. 525, Chapter 11, pp. 217-239 (2009).
U.S. Appl. No. 15/151,316 Office Action dated Oct. 4, 2019.
U.S. Appl. No. 15/187,714 Final Office Action dated Sep. 17, 2019.
U.S. Appl. No. 15/268,422 Final Office Action dated Oct. 3, 2019.
U.S. Appl. No. 15/602,991 Office Action dated May 31, 2019.
U.S. Appl. No. 15/603,013 Final Office Action dated Nov. 6, 2019.
U.S. Appl. No. 15/619,322 Office Action dated Aug. 14, 2019.
U.S. Appl. No. 15/709,274 Notice of Allowance dated Apr. 3, 2019.
U.S. Appl. No. 15/729,564 Office Action dated May 30, 2019.
U.S. Appl. No. 15/816,995 Office Action dated Sep. 20, 2019.
U.S. Appl. No. 15/835,243 Restriction Requirement dated Sep. 10, 2019.
U.S. Appl. No. 15/844,395 Restriction Requirement dated May 17, 2019.
U.S. Appl. No. 15/921,479 Office Action dated Nov. 12, 2019.
U.S. Appl. No. 15/921,479 Restriction Requirement dated May 24, 2019.
U.S. Appl. No. 15/960,319 Office Action dated Aug. 16, 2019.

(56) References Cited

OTHER PUBLICATIONS

U.S. Appl. No. 16/006,581 Office Action dated Sep. 25, 2019.
U.S. Appl. No. 16/239,453 Office Action dated Nov. 7, 2019.
U.S. Appl. No. 16/409,608 Office Action dated Sep. 9, 2019.
U.S. Appl. No. 16/530,717 Office Action dated Sep. 6, 2019.
U.S. Appl. No. 15/603,013 Office Action dated Jun. 26, 2019.

* cited by examiner 300
305  310

315
320  325

101

703

103

105
107
109

705

707

709

US 10,669,304 B2

METHODS AND DEVICES FOR DE NOVO OLIGONUCLEIC ACID ASSEMBLY

CROSS REFERENCE

This application claims the benefit of U.S. Provisional Application No. 62/112,083 filed Feb. 4, 2015, which is herein incorporated by reference in its entirety.

SEQUENCE LISTING

The instant application contains a Sequence Listing which has been submitted electronically in ASCII format and is hereby incorporated by reference in its entirety. The ASCII copy, created on Jan. 25, 2016, is named 44854_708_201_SL.txt and is 5,878 bytes in size.

BACKGROUND

Highly efficient chemical gene synthesis with high fidelity and low cost has a central role in biotechnology and medicine, and in basic biomedical research. De novo gene synthesis is a powerful tool for basic biological research and biotechnology applications. While various methods are known for the synthesis of relatively short fragments in a small scale, these techniques suffer from scalability, automation, speed, accuracy, and cost. There is a need for devices for simple, reproducible, scalable, less error-prone and cost-effective methods that guarantee successful synthesis of desired genes and are amenable to automation.

BRIEF SUMMARY

Provided herein are methods for preparing a surface for oligonucleic acid synthesis, comprising: providing a structure comprising a surface, wherein the structure comprises silicon dioxide; depositing a first molecule on the surface at a first region, wherein the first molecule binds to the surface and lacks a reactive group that binds to a nucleoside phosphoramidite; depositing a second molecule on the surface at a second region, wherein the second region comprises a plurality of loci surrounded by the first region, wherein the second molecule binds to the surface and lacks a reactive group that binds to the nucleoside phosphoramidite; and depositing a mixture on the surface at the second region, wherein the mixture comprises the second molecule and a third molecule, wherein the third molecule binds to the surface and nucleoside phosphoramidite, and wherein the mixture comprises a greater amount of the second molecule than the third molecule. Methods are further provided wherein the second molecule and the third molecule both have a higher surface energy than a surface energy of the first molecule, and wherein surface energy is a measurement of water contact angle on a smooth planar surface. Methods are further provided wherein the difference in water contact angle between the first region and the second region is at least 10, 20, 50, or 75 degrees. Methods are further provided wherein the third molecule is a silane. Methods are further provided wherein the third molecule is N-(3-triethoxysilylpropyl)-4-hydroxybutyramide (HAPS), 11-acetoxyundecyltriethoxysilane, n-decyltriethoxysilane, (3-aminopropyl)trimethoxysilane, (3-aminopropyl)triethoxysilane, 3-glycidoxypropyltrimethoxysilane, 3-iodo-propyltrimethoxysilane, or octylchlorosilane. Methods are further provided wherein the third molecule is 3-glycidoxypropyltrimethoxysilane. Methods are further provided wherein the silane is an aminosilane. Methods are further provided wherein the second molecule is propyltrimethoxysilane. Methods are further provided wherein the first molecule is a fluorosilane. Methods are further provided wherein the fluorosilane is (tridecafluoro-1,1,2,2-tetrahydrooctyl)trichlorosilane. Methods are further provided wherein the mixture comprises the second molecule and the third molecule present in a molar ratio of about 100:1 to about 2500:1. Methods are further provided wherein the mixture comprises the second molecule and the third molecule present in a molar ratio of about 2000:1. Methods are further provided wherein the mixture comprises the second molecule and the third molecule present in a molar ratio of 2000:1. Methods are further provided wherein the first molecule lacks a free hydroxyl, amino, or carboxyl group. Methods are further provided wherein the second molecule lacks a free hydroxyl, amino, or carboxyl group. Methods are further provided wherein the mixture is in a gaseous state when deposited on the surface. Methods are further provided wherein the first molecule is in a gaseous state when deposited on the surface. Methods are further provided wherein the surface comprises a layer of silicon oxide. Provided herein is a device for oligonucleic acid synthesis prepared by any one of the methods described herein.

Provide herein are methods for preparing a surface for oligonucleic acid synthesis, comprising: providing a structure comprising a surface, wherein the structure comprises silicon dioxide, and wherein the surface comprises a layer of silicon oxide; coating the surface with a light-sensitive material that binds silicon oxide; exposing predetermined regions of the surface to a light source to remove a portion of the light-sensitive material coated on the surface; depositing a first molecule on the surface, wherein the first molecule binds the surface at the predetermined regions and lacks a reactive group that binds to a nucleoside phosphoramidite; removing a remaining portion of the light-sensitive material coated on the surface to expose loci, wherein each of the loci are surrounded by the predetermined regions comprising the first molecule; depositing a second molecule on the surface at the loci, wherein the second molecule binds to the loci and lacks a reactive group that binds to the nucleoside phosphoramidite; and depositing a mixture on the surface at the loci, the mixture comprises the second molecule and a third molecule, and wherein the third molecule binds to the surface and nucleoside phosphoramidite. Methods are further provided wherein the second molecule and the third molecule both have a higher surface energy than a surface energy of the first molecule, wherein the second molecule and the third molecule both have a higher surface energy than a surface energy of the first molecule, and wherein surface energy is a measurement of water contact angle on a smooth planar surface. Methods are further provided wherein the difference in water contact angle between the first region and the second region is at least 10, 20, 50, or 75 degrees. Methods are further provided wherein the difference in water contact angle between the first region and the second region is at least 50 degrees. Methods are further provided wherein the third molecule is a silane. Methods are further provided wherein the third molecule is N-(3-triethoxysilylpropyl)-4-hydroxybutyramide (HAPS), 11-acetoxyundecyltriethoxysilane, n-decyltriethoxysilane, (3-aminopropyl)trimethoxysilane, (3-aminopropyl)triethoxysilane, 3-glycidoxypropyltrimethoxysilane, 3-iodo-propyltrimethoxysilane, or octylchlorosilane. Methods are further provided wherein the third molecule is 3-glycidoxypropyltrimethoxysilane. Methods are further provided wherein the silane is an aminosilane. Methods are further provided wherein the second molecule is propyltrimethoxysilane. Methods are further provided wherein the first molecule is a fluorosilane. Methods are further provided wherein the fluorosilane is (tridecafluoro-1,1,2,2-tetrahydrooctyl)trichlorosilane. Methods are further provided wherein the mixture comprises the second molecule and the third molecule present in a molar ratio of about 100:1 to about 2500:1. Methods are further provided wherein the mixture comprises the second molecule and the third molecule present in a molar ratio of about 2000:1. Methods are further provided wherein the mixture comprises the second molecule and the third molecule present in a molar ratio of 2000:1. Methods are further provided wherein the first molecule lacks a free hydroxyl, amino, or carboxyl group. Methods are further provided wherein the second molecule lacks a free hydroxyl, amino, or carboxyl group. Methods are further provided wherein the mixture is in a gaseous state when deposited on the surface. Methods are further provided wherein the first molecule is in a gaseous state when deposited on the surface. Methods are further provided wherein the method further comprises applying oxygen plasma to the surface prior to coating the surface with the light-sensitive material that binds silicon oxide. Methods are further provided wherein the method further comprises applying oxygen plasma to the surface after exposing predetermined regions of the surface to light. Provided herein is a device for oligonucleic acid synthesis prepared by any one of the methods described herein.

Provided herein are methods for oligonucleic acid synthesis, comprising: providing predetermined sequences for at least 30,000 non-identical oligonucleic acids; providing a structure comprising a patterned surface, wherein the structure comprises silicon dioxide; wherein the patterned surface is generated by: depositing a first molecule on the surface at a first region, wherein the first molecule binds to the surface and lacks a reactive group that binds to a nucleoside phosphoramidite; and depositing a second molecule on the surface at a second region, wherein the second region comprises a plurality of loci surrounded by the first region, wherein the second molecule binds to the surface and lacks a reactive group that binds to the nucleoside phosphoramidite; and depositing a mixture on the surface at the second region, wherein the mixture comprises the second molecule and a third molecule, wherein the third molecule binds to the surface and nucleoside phosphoramidite, wherein the mixture comprises a greater amount of the second molecule than the third molecule; and synthesizing the at least 30,000 non-identical oligonucleic acids each at least 10 bases in length, wherein the at least 30,000 non-identical oligonucleic acids encode sequences with an aggregate deletion error rate of less than 1 in 1500 bases compared to the predetermined sequences, and wherein each of the at least 30,000 non-identical oligonucleic acids extends from a different locus. Methods are further provided wherein the second molecule and the third molecule both have a higher surface energy than a surface energy of the first molecule, and surface energy is a measurement of water contact angle on a smooth planar surface. Methods are further provided wherein a difference in water contact angle between the first region and the second region is at least 10, 20, 50, or 75 degrees. Methods are further provided wherein the difference in water contact angle between the first region and the second region is at least 50 degrees. Methods are further provided wherein the third molecule is a silane. Methods are further provided wherein the third molecule is N-(3-triethoxysilylpropyl)-4-hydroxybutyramide (HAPS), 11-acetoxyundecyltriethoxysilane, n-decyltriethoxysilane, (3-aminopropyl)trimethoxysilane, (3-aminopropyl)triethoxysilane, 3-glycidoxypropyltrimethoxysilane, 3-iodo-propyltrimethoxysilane, or octylchlorosilane. Methods are further provided wherein the silane is an aminosilane. Methods are further provided wherein the third molecule is 3-glycidoxypropyltrimethoxysilane. Methods are further provided wherein the second molecule is propyltrimethoxysilane. Methods are further provided wherein the first molecule is a fluorosilane. Methods are further provided wherein the fluorosilane is (tridecafluoro-1,1,2,2-tetrahydrooctyl)trichlorosilane. Methods are further provided wherein the mixture comprises the second molecule and the third molecule present in a molar ratio of about 100:1 to about 2500:1. Methods are further provided wherein the mixture comprises the second molecule and the third molecule present in a molar ratio of about 2000:1. Methods are further provided wherein the mixture comprises the second molecule and the third molecule present in a molar ratio of 2000:1. Methods are further provided wherein the first molecule lacks a free hydroxyl, amino, or carboxyl group. Methods are further provided wherein the second molecule lacks a free hydroxyl, amino, or carboxyl group. Methods are further provided wherein the mixture is in a gaseous state when deposited on the surface. Methods are further provided wherein the first molecule is in a gaseous state when deposited on the surface. Methods are further provided wherein each of the at least 30,000 non-identical oligonucleic acids is at least 30 bases in length. Methods are further provided wherein each of the at least 30,000 non-identical oligonucleic acids is 10 bases to 1 kb in length. Methods are further provided wherein each of the at least 30,000 non-identical oligonucleic acids is about 50 to about 120 bases in length. Methods are further provided wherein the aggregate deletion error rate is less than about 1 in 1700 bases compared to the predetermined sequences. Methods are further provided wherein the aggregate deletion error rate is achieved without correcting errors. Methods are further provided wherein the at least 30,000 non-identical oligonucleic acids synthesized encode sequences with an aggregate error rate of less than 1 in 1500 bases compared to the predetermined sequences without correcting errors. Methods are further provided wherein the aggregate error rate is less than 1 in 2000 bases compared to the predetermined sequences. Methods are further provided wherein the aggregate error rate is less than 1 in 3000 bases compared to the predetermined sequences. Methods are further provided wherein the surface comprises a layer of silicon oxide.

Provided herein are methods for nucleic acid synthesis, comprising: providing predetermined sequences for at least 200 preselected nucleic acids; providing a structure comprising a patterned surface, wherein the structure comprises silicon dioxide; wherein the patterned surface is generated by: depositing a first molecule on the surface at a first region, wherein the first molecule binds to the surface and lacks a reactive group that binds to a nucleoside phosphoramidite; and depositing a second molecule on the surface at a second region, wherein the second region comprises a plurality of loci surrounded by the first region, wherein the second molecule binds to the surface and lacks a reactive group that binds to the nucleoside phosphoramidite; and depositing a mixture on the surface at the second region, wherein the mixture comprises the second molecule and a third molecule, wherein the third molecule binds to the surface and nucleoside phosphoramidite, wherein the mixture comprises a greater amount of the second molecule than the third molecule; and synthesizing at least 20,000 non-identical oligonucleic acids each at least 50 bases in length, wherein each of the at least 20,000 non-identical oligonucleic acids extends from a different locus of the patterned surface; releasing the at least 20,000 non-identical oligonucleic acids from the patterned surface; suspending the at least 20,000 non-identical oligonucleic acids in a solution; and subjecting the solution comprising at least 20,000 non-identical oligonucleic acids to a polymerase chain assembly reaction to assemble at least 200 genes, wherein the assembled at least 200 preselected nucleic acids encode sequences with an aggregate deletion error rate of less than 1 in 1500 bases compared to the predetermined sequences. Methods are further provided wherein the second molecule and the third molecule both have a higher surface energy than a surface energy of the first molecule, and wherein surface energy is a measurement of water contact angle on a smooth planar surface. Methods are further provided wherein the difference in water contact angle between the first region and the second region is at least 10, 20, 50, or 75 degrees. Methods are further provided wherein the difference in water contact angle between the first region and the second region is at least 50 degrees. Methods are further provided wherein the third molecule is N-(3-triethoxysilylpropyl)-4-hydroxybutyramide (HAPS), 11-acetoxyundecyltriethoxysilane, n-decyltriethoxysilane, (3-aminopropyl)trimethoxysilane, (3-aminopropyl)triethoxysilane, 3-glycidoxypropyltrimethoxysilane, 3-iodo-propyltrimethoxysilane, or octylchlorosilane. Methods are further provided wherein the third molecule is a silane. Methods are further provided wherein the third molecule is 3-glycidoxypropyltrimethoxysilane. Methods are further provided wherein the silane is an aminosilane. Methods are further provided wherein the second molecule is propyltrimethoxysilane. Methods are further provided wherein the first molecule is a fluorosilane. Methods are further provided wherein the fluorosilane is (tridecafluoro-1,1,2,2-tetrahydrooctyl)trichlorosilane. Methods are further provided wherein the mixture comprises the second molecule and the third molecule present in a molar ratio of about 100:1 to about 2500:1. Methods are further provided wherein the mixture comprises the second molecule and the third molecule present in a molar ratio of about 2000:1. Methods are further provided wherein the mixture comprises the second molecule and the third molecule present in a molar ratio of 2000:1. Methods are further provided wherein the first molecule lacks a free hydroxyl, amino, or carboxyl group. Methods are further provided wherein the second molecule lacks a free hydroxyl, amino, or carboxyl group. Methods are further provided wherein each of the at least 20,000 non-identical oligonucleic acids is about 50 to about 120 bases in length. Methods are further provided wherein the aggregate deletion error rate is less than about 1 in 1700 bases compared to the predetermined sequences. Methods are further provided wherein the aggregate deletion error rate is achieved without correcting errors. Methods are further provided wherein the assembled at least 200 preselected nucleic acids encode sequences with an aggregate error rate of less than 1 in 1500 bases compared to the predetermined sequences without correcting errors. Methods are further provided wherein the aggregate error rate is less than 1 in 2000 bases compared to the predetermined sequences. Methods are further provided wherein the surface comprises a layer of silicon oxide.

Provided here are devices for oligonucleic acid synthesis, comprising: a structure having a surface, wherein the structure comprises silicon dioxide; a plurality of recesses or posts on the surface, wherein each recess or post comprises: a width length that is 6.8 nm to 500 nm, a pitch length that is about twice the width length, and a depth length that is about 60% to about 125% of the pitch length; a plurality of loci on the surface, wherein each locus has a diameter of 0.5 to 100 µm, wherein each locus comprises at least two of the plurality of recesses or posts; and a plurality of clusters on the surface, wherein each of the clusters comprise 50 to 500 loci and has a cross-section of 0.5 to 2 mm. Devices are further provided wherein each of the clusters comprise 100 to 150 loci. Devices are further provided wherein the structure comprises at least 30,000 loci. Devices are further provided wherein the pitch length is 1 µm or less. Devices are further provided wherein the depth length is 1 µm or less. Devices are further provided wherein each of the loci has a diameter of 0.5 µm. Devices are further provided wherein each of the loci has a diameter of 10 µm. Devices are further provided wherein each of the loci has a diameter of 50 µm. Devices are further provided wherein the cross-section of each of the clusters is about 1.125 mm. Devices are further provided wherein each of the clusters has a pitch of about 1.125 mm. Devices are further provided wherein each locus comprises a molecule that binds to the surface and a nucleoside phosphoramidite. Devices are further provided wherein the molecule that binds to the surface and the nucleoside phosphoramidite is a silane. Devices are further provided wherein the molecule that binds to the surface and the nucleoside phosphoramidite is N-(3-triethoxysilylpropyl)-4-hydroxybutyramide (HAPS), 11-acetoxyundecyltriethoxysilane, n-decyltriethoxysilane, (3-aminopropyl)trimethoxysilane, (3-aminopropyl)triethoxysilane, 3-glycidoxypropyltrimethoxysilane, 3-iodo-propyltrimethoxysilane, or octylchlorosilane. Devices are further provided wherein the silane is 3-glycidoxypropyltrimethoxysilane. Devices are further provided wherein the silane is an aminosilane. Devices are further provided wherein a region surrounding the plurality of loci comprises a molecule that binds to the surface and lacks a nucleoside phosphoramidite. Devices are further provided wherein the molecule that binds to the surface and lacks the nucleoside phosphoramidite is a fluorosilane. Devices are further provided wherein the fluorosilane is (tridecafluoro-1,1,2,2-tetrahydrooctyl)trichlorosilane or perfluorooctyltrichlorosilane. Devices are further provided wherein the surface comprises a layer of silicon oxide.

Provided herein are methods for oligonucleic acid synthesis, comprising: providing predetermined sequences; providing a device for oligonucleic acid synthesis prepared by any one of methods described herein; synthesizing a plurality of non-identical oligonucleic acids at least 10 bases in length, wherein each of the non-identical oligonucleic acids extends from a different locus. Methods are further provided wherein the aggregate deletion error rate is less than about 1 in 1700 bases compared to the predetermined sequences. Methods are further provided wherein the aggregate deletion error rate is achieved without correcting errors. Methods are further provided wherein the plurality of non-identical oligonucleic acids synthesized encode sequences with an aggregate error rate of less than 1 in 1500 bases compared to the predetermined sequences without correcting errors. Methods are further provided wherein the aggregate error rate is less than 1 in 2000 bases compared to the predetermined sequences. Methods are further provided wherein the aggregate error rate is less than 1 in 3000 bases compared to the predetermined sequences.

Provided herein are methods for nucleic acid synthesis, comprising: providing predetermined sequences for at least 200 preselected nucleic acids; providing the device described herein; synthesizing at least 20,000 non-identical oligonucleic acids each at least 50 bases in length, wherein each of the at least 20,000 non-identical oligonucleic acids extends from a different locus; releasing the at least 20,000 non-identical oligonucleic acids from the surface; suspending the at least 20,000 non-identical oligonucleic acids in a solution; and subjecting the solution comprising at least 20,000 non-identical oligonucleic acids to a polymerase chain assembly reaction to assemble at least 200 genes, wherein the assembled at least 200 preselected nucleic acids encode sequences with an aggregate deletion error rate of less than 1 in 1500 bases compared to the predetermined sequences. Methods are further provided wherein the aggregate deletion error rate is less than about 1 in 1700 bases compared to the predetermined sequences. Methods are further provided wherein the aggregate deletion error rate is achieved without correcting errors. Methods are further provided wherein the assembled at least 200 preselected nucleic acids encode sequences with an aggregate error rate of less than 1 in 1500 bases compared to the predetermined sequences without correcting errors. Methods are further provided wherein the aggregate error rate is less than 1 in 2000 bases compared to the predetermined sequences.

Provide herein are devices for oligonucleic acid synthesis, comprising: a structure having a surface, wherein the structure comprises silicon dioxide; a plurality of recesses or posts on the surface, wherein each recess or post comprises (i) a width length that is 6.8 nm to 500 nm, (ii) a pitch length that is about twice the width length, and (iii) a depth length that is about 60% to about 125% of the pitch length; a plurality of loci on the surface, wherein each locus has a diameter of 0.5 to 100 um, wherein each locus comprises at least two of the plurality of recesses or posts; a plurality of clusters on the surface, wherein each of the clusters comprise 50 to 500 loci and has a cross-section of 0.5 to 2 mm, wherein the plurality of loci comprise a less than saturating amount of a molecule that binds the surface and couples to nucleoside phosphoramidite; and a plurality of regions surrounding each loci comprise a molecule that binds the surface and does not couple to nucleoside phosphoramidite, wherein the plurality of loci have a higher surface energy than the plurality of regions surrounding each loci. Devices are further provided wherein the molecule that binds the surface and couples to nucleoside phosphoramidite is a silane disclosed herein. Devices are further provided wherein the molecule that binds the surface and does not couple to nucleoside phosphoramidite is a fluorosilane disclosed herein. Devices are further provided wherein the plurality of loci are coated with a molecule that binds the surface, does not couple to nucleoside phosphoramidite, and has a higher surface energy than the molecule on plurality of regions surrounding each loci. Devices are further provided wherein the surface comprises a layer of silicon oxide.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

FIG. 1A depicts optional cleaning of the surface of a structure. FIG. 1B depicts deposition of a photosensitive lack. FIG. 1C depicts an optical photolithography step. FIG. 1D depicts deposition of chemical layer to be patterned. FIG. 1E depicts removal of the photosensitive lack. FIG. 1F depicts deposition of a second chemical layer.

FIG. 5A illustrates a silicon chip with one side polished. A textured layer is formed via pass printing scheme lithography (FIG. 5B), followed by silicon reactive ion etching and addition of a resist strip (FIG. 5C). Oxidation of the chip (FIG. 5D), printing of a fiducial layer via lithography (FIG. 5E), followed by a final oxide etching results in a textured silicon chip, depicted in FIG. 5F.

FIG. 7A depicts the optional cleaning of the surface of a structure. FIG. 7B depicts deposition of a first chemical layer, an active functional agent to be patterned. FIG. 7C depicts deposition of a photosensitive lack. FIG. 7D depicts an optical photolithography step. FIG. 7E depicts patterning of the chemical layer using the photosensitive lack as mask. FIG. 7F depicts removal of the photosensitive lack. FIG. 7G depicts deposition of a second chemical layer, a passive functionalization agent.

FIG. 19, part B illustrates corresponding BioAnalyzer data for each of the five spots in FIG. 19, part A.

DETAILED DESCRIPTION OF THE INVENTION

The present disclosure provides devices and methods for the rapid parallel synthesis of oligonucleic acids with low error rates. The oligonucleotide synthesis steps described here are "de novo," meaning that oligonucleotides are built one monomer at a time to form a polymer. During de novo synthesis of oligonucleic acids, the crowding of single stranded oligonucleic acids extending from a surface results in an increase in error rates. To reduce the frequency of crowding-related errors, methods are provided herein to reduce the density of nucleoside-coupling agent bound to specific regions of the surface.

Figure 1A:
FIGS. 1A-1F depict a process flow for patterning multiple chemical layers.
Figure 1B:
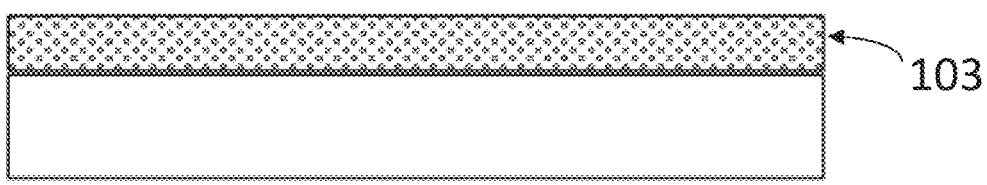
Figure 1C:
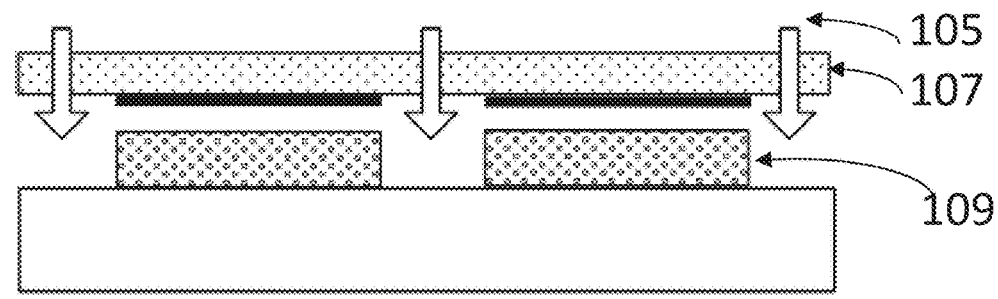
Figure 1D:
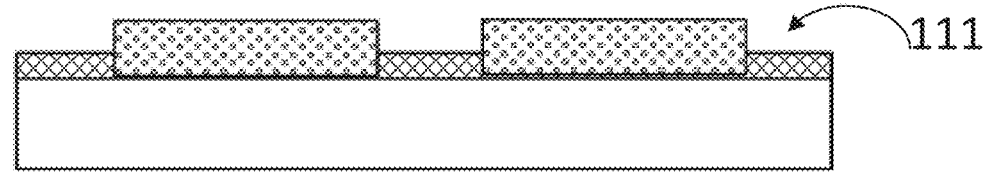
Figure 1E:
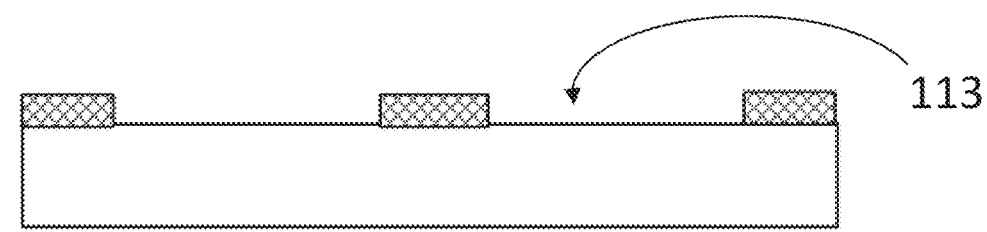
Figure 1F:
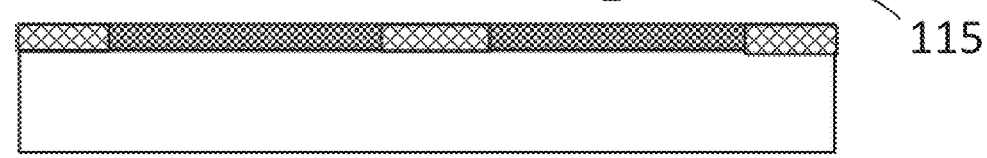
Figure 2A:
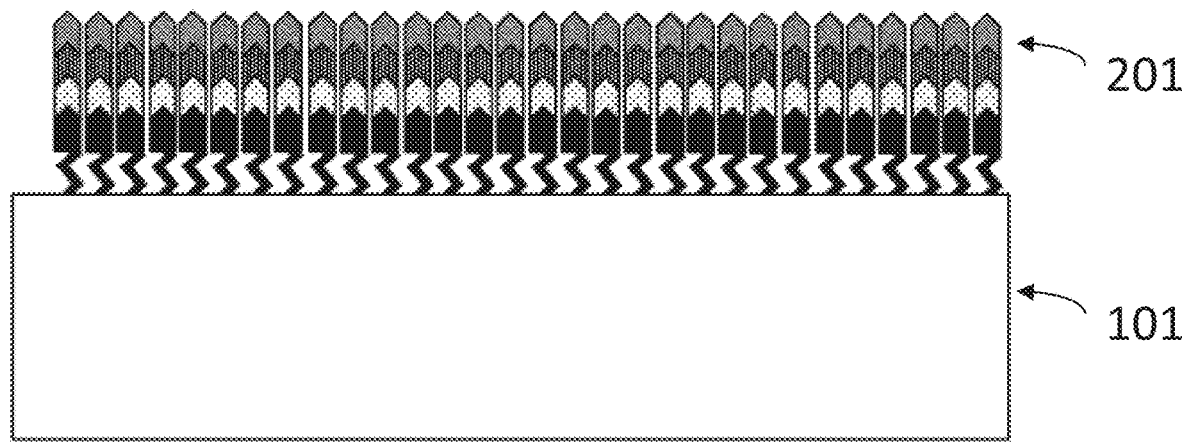
FIG. 2A illustrates a region of a surface for oligonucleic acid synthesis coated with a silane that binds the surface and couples nucleoside.
Figure 2B:
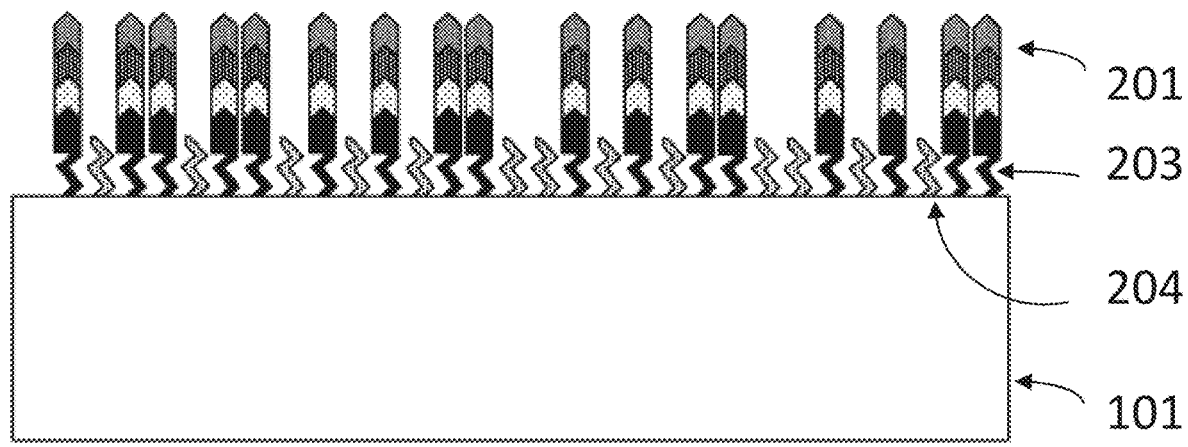
FIG. 2B illustrates a region of a surface for oligonucleic acid synthesis coated with a mixture of silanes, one silane that binds the surface and couples oligonucleic acid, and another silane that binds the surface and does not couple to nucleoside.

An exemplary method for generating a surface having a reduction in nucleoside-coupling agent density is illustrated in FIGS. 1A-1F. As a first step, a structure 101 is optionally cleaned with oxygen plasma, FIG. 1A. Exemplary structures include those made of silicon dioxide or silicon oxide. Directly after cleaning, the structure is coated with a photosensitive lack 103 (e.g., photoresist), FIG. 1B. Optical lithography is then performed, FIG. 1C, where electromagnetic wavelength 105 is projected through a shadow mask 107, resulting in removal of the photosensitive lack at predetermined locations and remaining photosensitive lack 109 at other locations. Next, a first molecule (e.g., a fluorosilane) is deposited on the surface and coats the surface at regions exposed as a result of photolithography 111, FIG. 1D. The first molecule is one that does not couple to nucleoside. The photosensitive lack is then stripped away (FIG. 1E), revealing exposed regions 113. The next step involves a two-part deposition process. First, a second molecule that binds the surface and does not bind nucleoside is deposited on the surface. Next, a mixture is deposited on the surface comprising the second molecule, and a third molecule, where the third molecule binds the surface and is also able to couple nucleoside, FIG. 1F. This two-step deposition process results in predetermined sites 115 on the surface having a low concentration of activating agent. To assist with efficiency of the reactions during the oligonucleic acid synthesis process, the region for oligonucleic acid extension (a locus) has a higher surface energy than the region of the surface surrounding the locus. When oligonucleic acids 201 are extended from a surface having a saturating amount of nucleoside-coupling molecule, they are relatively crowded, FIG. 2A. In contrast, when oligonucleic acids are extended on a surface having a mixture of a nucleoside-coupling molecule 203 and a non-nucleoside-coupling molecule 204, less crowding results, FIG. 2B, and a lower error rate is observed.

Figure 3A:
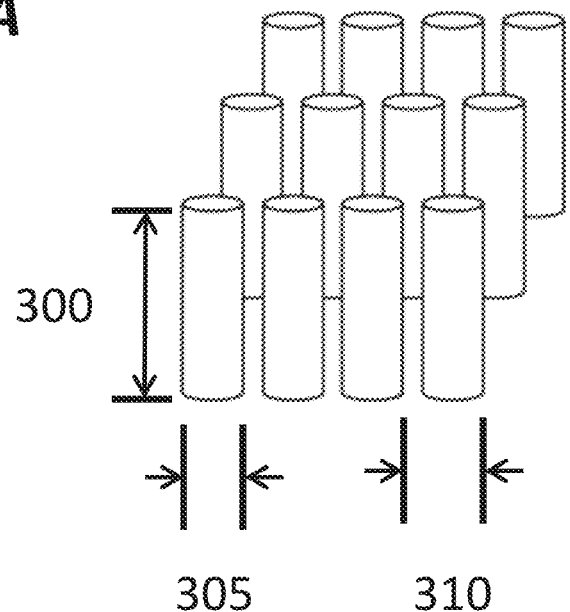
FIG. 3A illustrates an arrangement of an array of posts.
Figure 3B:
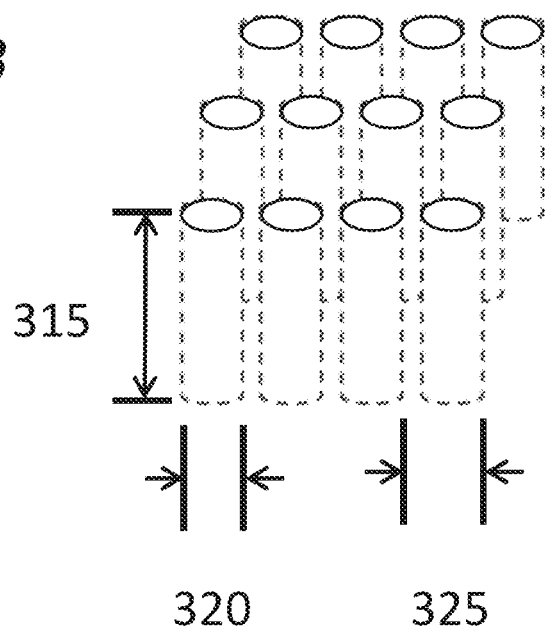
FIG. 3B illustrates an arrangement of an array of wells.

As a consequence of reducing the amount of nucleoside coupling molecules on the surface of a structure, the oligonucleic acid yields are also reduced. If the oligonucleic acid yields are too low, insufficient amounts of material will be produced for subsequent downstream molecular biology processes utilizing oligonucleic acids synthesized, e.g., as gene assembly. In order to increase the oligonucleic acid yields, methods are also provided for increasing the surface area at the site of oligonucleic acid extension by creating textured surface. To increase the surface area, the surface of a device may have a field of protrusions (see, for example, FIG. 3A) or a field of recesses (FIG. 3B), e.g., posts or rivets. To optimize surface area for oligonucleic acid synthesis methods, the height 300, width 305, and pitch 310 of the protrusions or height 315, width 320, and pitch 325 of the recesses are designed such that there is sufficient space for two times the length of the expected oligonucleic acid and sufficient depth for efficient washing. In one example, the width length is at least twice the desired oligonucleic acid length to be synthesized on a surface disclosed herein, the depth length is about 60% to about 125% of the pitch length, and the pitch length is about twice the width length.

Figure 5A:
FIGS. 5A-5C and 5D-5F illustrate the process to manufacture a textured microfluidic device.
Figure 5B:
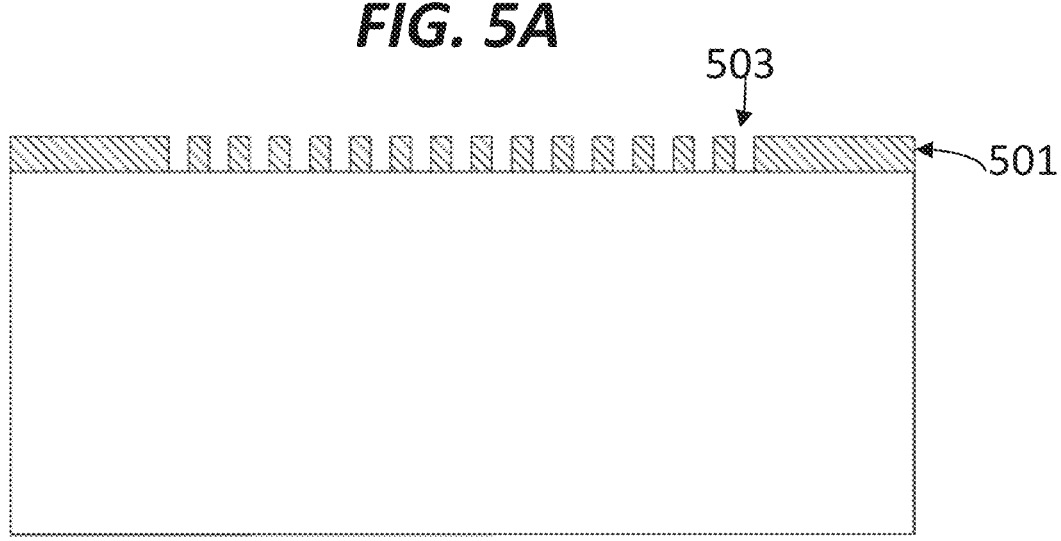
Figure 5C:
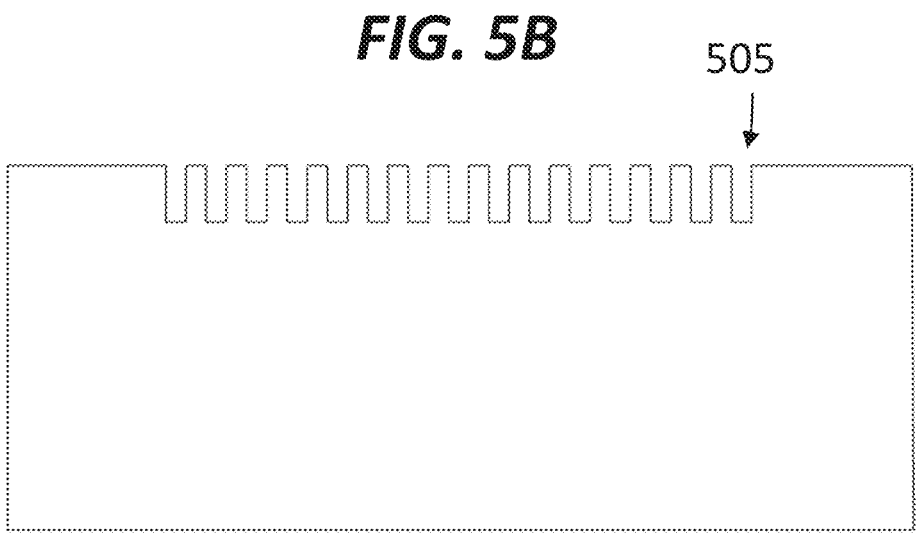
Figure 5D:
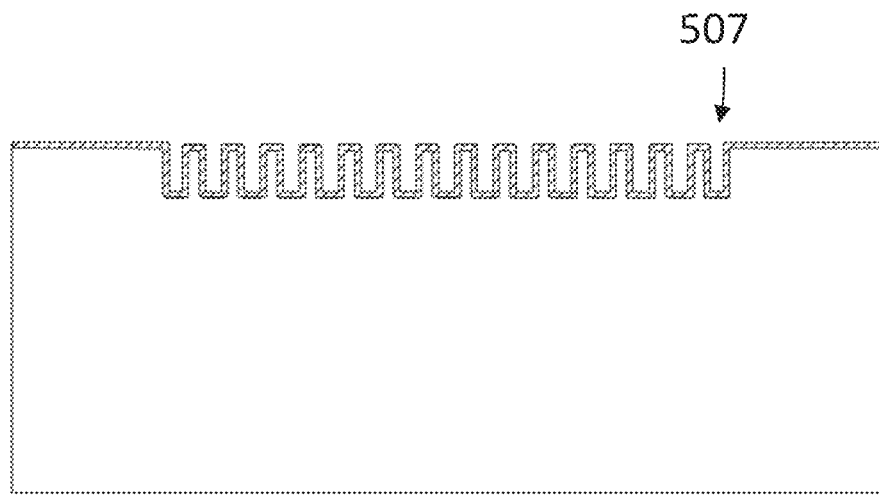
Figure 5E:
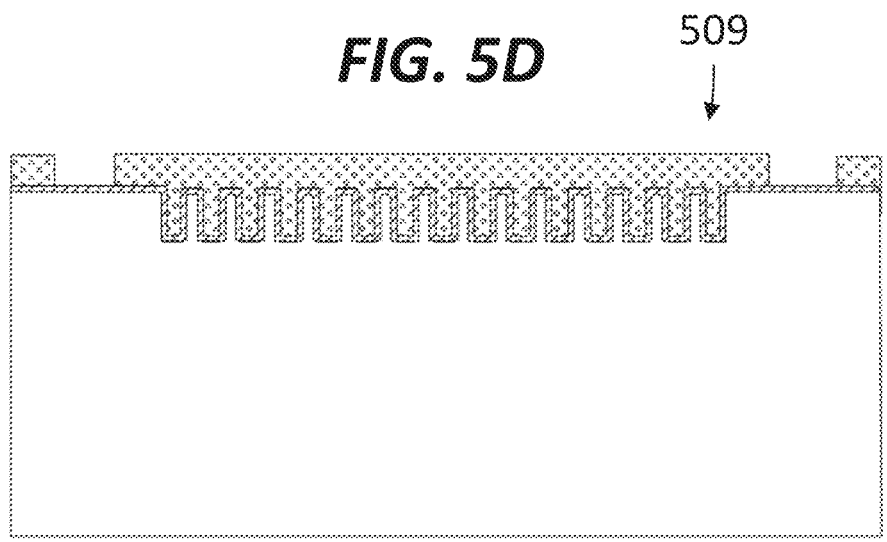
Figure 5F:
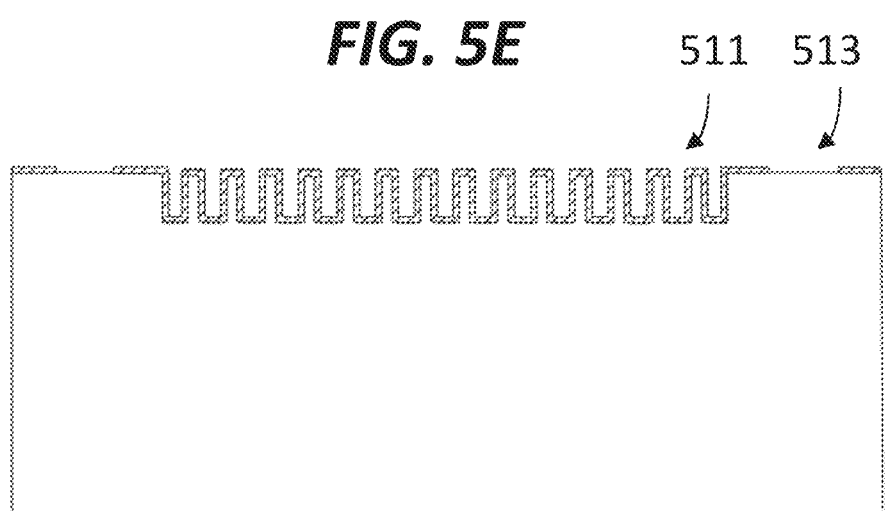
Figure 6:
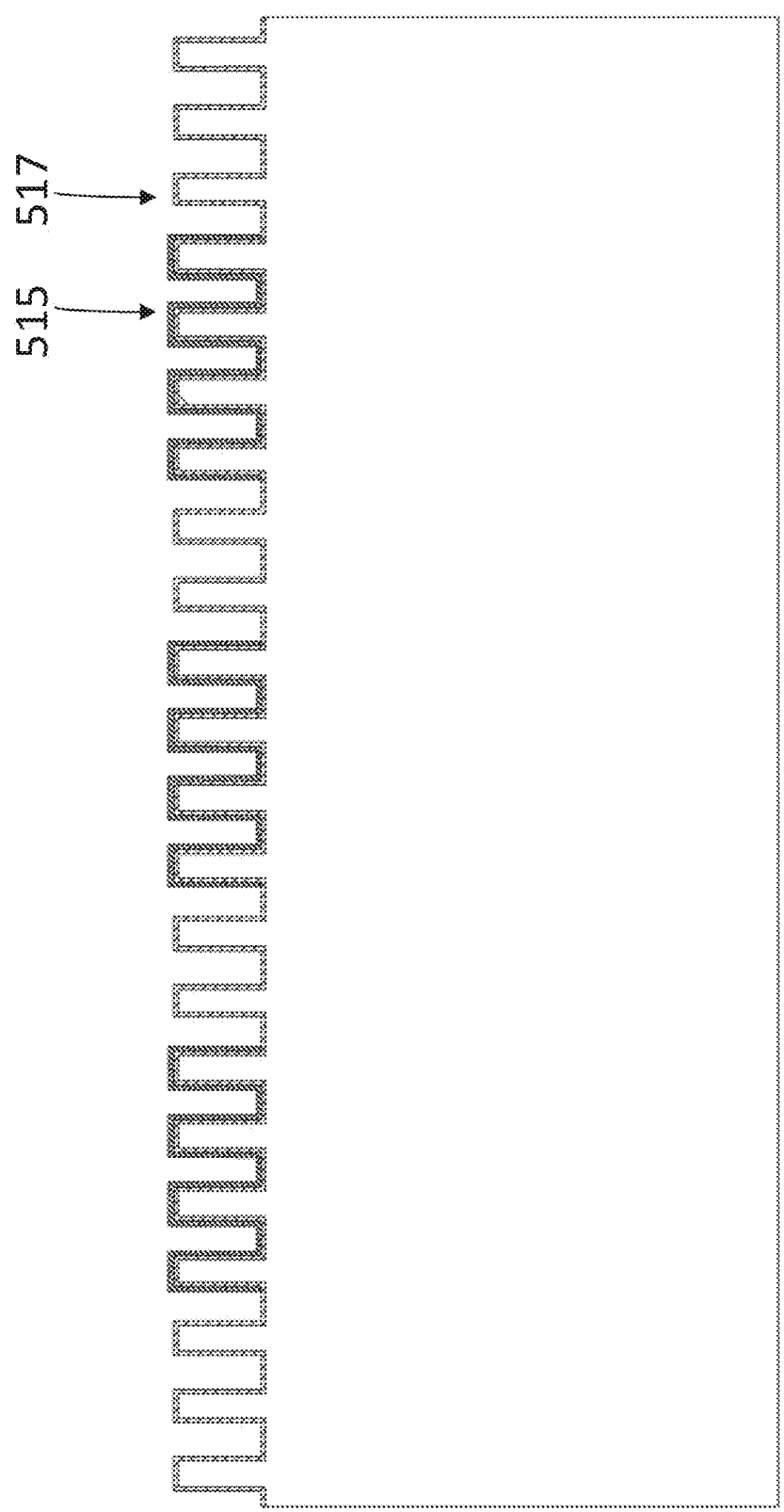
FIG. 6 illustrates a textured surface having small wells.
Figure 7A:
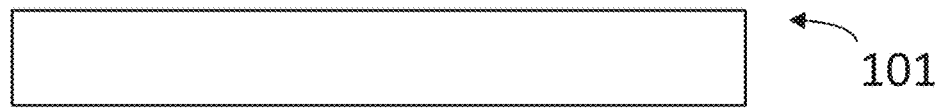
FIGS. 7A-7G illustrate a method for patterning a surface with a chemical layer.
Figure 7B:
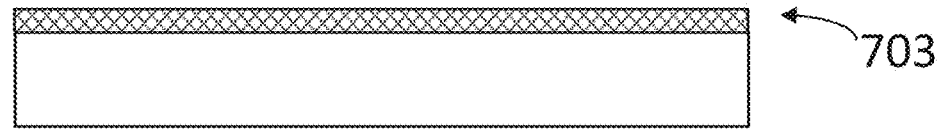
Figure 7C:
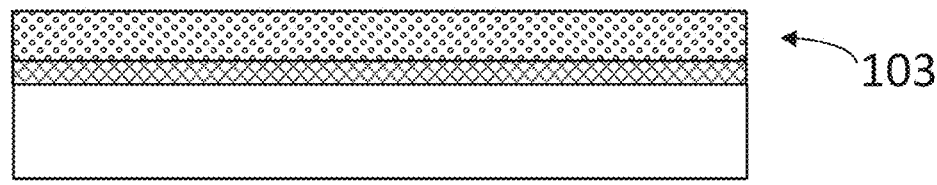
Figure 7D:
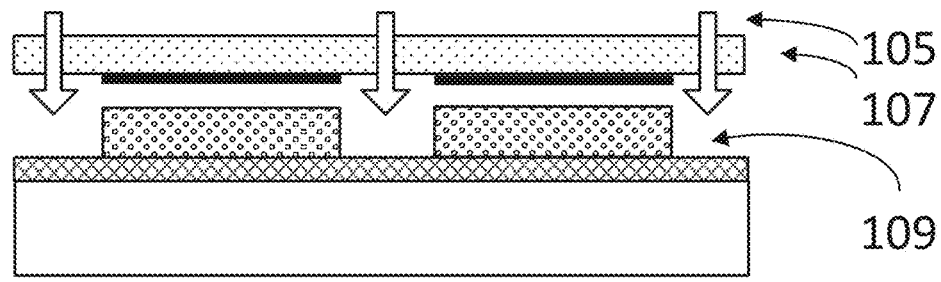
Figure 7E:
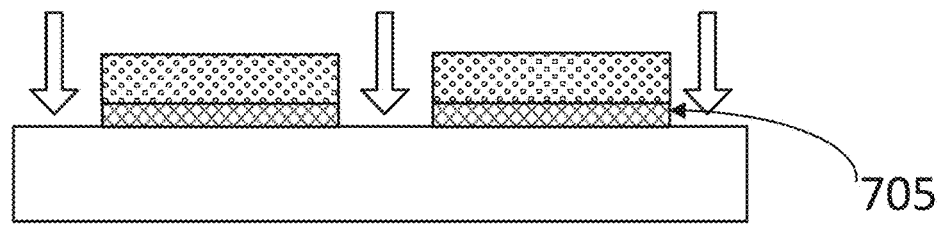
Figure 7F:
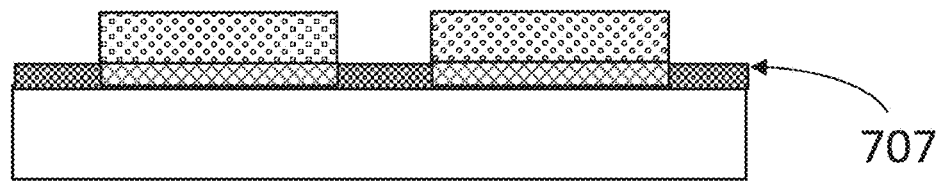
Figure 7G:

A number of steps are performed to make a textured surface. A exemplary structure 101 (e.g., silicon-based) disclosed herein is polished (FIG. 5A), a textured layer pattern 501 is formed via printing lithography (FIG. 5B), a silicon reactive ion etching and resist strip is performed to leave indents 503 in the surface (FIG. 5C), the surface is subject to oxidation 507 (FIG. 5D), a fiducial layer is optionally printed on via lithography using a photosensitive lack 509 (FIG. 5E), after which a final oxide etching results in a textured silicon surface having a fiducial structure 513 (FIG. 5F). The structure may then be additionally exposed to functionalization agents as described above and elsewhere herein, to result in a structure having a patterned surface with loci coated with a molecule for coupling nucleoside 515 (alone or as a mixture depicted in FIG. 2B) surrounding by regions coated with an agent that does not couple nucleoside 517, FIG. 6.

DEFINITIONS

Throughout this disclosure, numerical features are presented in a range format. It should be understood that the description in range format is merely for convenience and brevity and should not be construed as an inflexible limitation on the scope of any embodiments. Accordingly, the description of a range should be considered to have specifically disclosed all the possible subranges as well as individual numerical values within that range to the tenth of the unit of the lower limit unless the context clearly dictates otherwise. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual values within that range, for example, 1.1, 2, 2.3, 5, and 5.9. This applies regardless of the breadth of the range. The upper and lower limits of these intervening ranges may independently be included in the smaller ranges, and are also encompassed within the invention, subject to any specifically excluded limit in the stated range. Where the stated range includes one or both of the limits, ranges excluding either or both of those included limits are also included in the invention, unless the context clearly dictates otherwise.

The terminology used herein is for the purpose of describing particular embodiments only and is not intended to be limiting of any embodiment. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" in reference to a number or range of numbers is understood to mean the stated number and numbers+/−10% thereof, or 10% below the lower listed limit and 10% above the higher listed limit for the values listed for a range.

As used herein, the terms "preselected sequence", "predefined sequence" or "predetermined sequence" are used interchangeably. The terms mean that the sequence of the polymer is known and chosen before synthesis or assembly of the polymer. In particular, various aspects of the invention are described herein primarily with regard to the preparation of nucleic acids molecules, the sequence of the oligonucleotide or polynucleotide being known and chosen before the synthesis or assembly of the nucleic acid molecules.

Surface Materials

Structures for oligonucleic acid synthesis provided herein are fabricated from a variety of materials capable of modification to support a de novo oligonucleic acid synthesis reaction. In some cases, the structures are sufficiently conductive, e.g., are able to form uniform electric fields across all or a portion of the structure. A structure described herein can comprise a flexible material. Exemplary flexible materials include, without limitation, modified nylon, unmodified nylon, nitrocellulose, and polypropylene. A structure described herein can comprise a rigid material. Exemplary rigid materials include, without limitation, glass, fuse silica, silicon, silicon dioxide, silicon nitride, plastics (for example, polytetrafluoroethylene, polypropylene, polystyrene, polycarbonate, and blends thereof, and metals (for example, gold, platinum). Structure disclosed herein can be fabricated from a material comprising silicon, polystyrene, agarose, dextran, cellulosic polymers, polyacrylamides, polydimethylsiloxane (PDMS), glass, or any combination thereof. In some cases, a structure disclosed herein is manufactured with a combination of materials listed herein or any other suitable material known in the art. In some cases, a structure disclosed herein comprises a silicon dioxide base and a surface layer of silicon oxide. Alternatively, the structure can have a base of silicon oxide. Surface of the structure provided here can be textured, resulting in an increase overall surface area for oligonucleic acid synthesis. Structure disclosed herein may comprise at least 5%, 10%, 25%, 50%, 80%, 90%, 95%, or 99% silicon. A device disclosed herein may be fabricated from a silicon on insulator (SOI) wafer.

Patterned Surfaces

Disclosed herein are surfaces for the synthesis of oligonucleic acids at a low error rate. Surfaces disclosed herein comprise predetermined regions having varying wettability characteristics and varying ability to couple nucleoside. For example, a surface disclosed herein comprises high energy regions comprising a molecule that binds to the surface and also couples to nucleoside, and the high energy regions are surrounded by low energy regions comprising a molecule that binds to the surface and does not couple to nucleoside. In some instances, the high energy regions comprise a mixture of molecules having varying ability to couple nucleoside, e.g., a nucleoside phosphoramidite.

To set stage for coupling monomers extending from a structure, surfaces of a structure disclosed herein can be coated with a layer of material comprising an active functionalization agent, such as a nucleoside-coupling agent. An nucleoside-coupling agent is one that binds to the surface and also binds to nucleic acid monomer, thereby supporting a coupling reaction to the surface. Nucleoside-coupling agents are molecules having a reactive group, for example, a hydroxyl, amino or carboxyl group, available for binding to a nucleoside in a coupling reaction. A surface can be additionally coated with a layer of material comprising a passive functionalization agent. A passive functionalization agent or material binds to the surface but does not efficiently bind to nucleic acid, thereby preventing nucleic acid attachment at sites where passive functionalization agent is bound. Passive functionalization agents are molecules lacking an available reactive group (e.g., a hydroxyl, amino or carboxyl group) for binding a nucleoside in a coupling reaction. Surfaces can be configured for both active and passive functionalization agents bound to the surface at within predetermined regions of the surface, generating distinct regions for oligonucleic acid synthesis, wherein the region comprises a less than saturating amount of active functionalization agent, compare FIGS. 2A and 2B.

A first exemplary method of functionalizing a surface is discussed above with reference to FIGS. 1A-1F. In FIG. 1, the active functionalizing agent is deposited as a last step, FIG. 1F. Alternatively, the active functionalization agent may be deposited earlier in the process and function as an adhesion promoter for a photosensitive lack. FIG. 7 provides an illustrative representation of this alternative method. As a first step, a structure 101 is optionally cleaned with oxygen plasma, FIG. 7A. After cleaning, the structure is coated with a first chemical layer, a molecule that binds the surface and binds nucleoside is deposited on the surface 703 (e.g., an aminosilane), FIG. 7B. The surface of the device is then coated with a photosensitive lack 103, FIG. 7C. Optical lithography is then performed, FIG. 7D, where electromagnetic wavelength 105 is projected through a shadow mask 107, resulting in removal of the photosensitive lack 103 at predetermined locations and remaining photosensitive lack 109 (e.g., photoresist) at other locations. The use of a photoresist mask results in patterning of the first chemical layer 705, FIG. 7E. A second chemical layer, a molecule that binds the surface and does not bind nucleoside 707, is deposited on the surface, FIG. 7F. The photosensitive lack is then stripped away (FIG. 7G), revealing patterned regions 709. The resulting surface is patterned with loci comprising nucleoside-coupling molecules for oligonucleic acid extension reactions.

The surface energy of a chemical layer coated on a surface can facilitate localization of droplets on the surface. Depending on the patterning arrangement selected, the proximity of loci and/or area of fluid contact at the loci can be altered. In the context of silicon surfaces, certain aminosilane molecules can bind their silicon atom to the oxygen atom of the surface and also have additional chemical interactions for both binding photoresist or biomolecules. For example, for both (3-aminopropyl)trimethoxysilane (APTMS), or (3-aminopropyl)triethoxysilane (APTES), the silicon atom binds to the oxygen atom of the surface and the amine groups bind to the organic molecules. Exemplary activate functionalizing chemical coating agents include (3-aminopropyl)trimethoxysilane, (3-aminopropyl)triethoxysilane or N-(3-triethoxysilylpropyl)-4-hydroxybutyramide.

Surfaces, or more specifically resolved loci, onto which nucleic acids or other molecules are deposited, e.g., for oligonucleic acid synthesis, can be smooth or substantially planar or are textured, having raised or lowered features (e.g., three-dimensional features). Surfaces disclosed herein can be layered with one or more different layers of compounds. Such modification layers of interest include, without limitation, inorganic and organic layers such as metals, metal oxides, polymers, small organic molecules and the like. Non-limiting polymeric layers include peptides, proteins, nucleic acids or mimetics thereof (e.g., peptide nucleic acids and the like), polysaccharides, phospholipids, polyurethanes, polyesters, polycarbonates, polyureas, polyamides, polyetheyleneamines, polyarylene sulfides, polysiloxanes, polyimides, polyacetates, and any other suitable compounds described herein or otherwise known in the art. In some cases, polymers are heteropolymeric. In some cases, polymers are homopolymeric. In some cases, polymers comprise functional moieties or are conjugated.

Loci disclosed herein can be functionalized with one or more molecules that increase and/or decrease surface energy. The molecule can be chemically inert. The surface energy, or hydrophobicity, of a surface is a factor for determining the affinity of a nucleotide to attach onto the surface. Provided herein is a method for functionalization of a surface disclosed herein comprises: (a) providing a structure having a surface that comprises silicon dioxide; and (b) silanizing the surface using, a suitable silanizing agent described herein or otherwise known in the art, for example, an organofunctional alkoxysilane molecule. In some cases, the organofunctional alkoxysilane molecule comprises dimethylchloro-octodecyl-silane, methyldichloro-octodecyl-silane, trichloro-octodecyl-silane, trimethyl-octodecyl-silane, triethyl-octodecyl-silane, or any combination thereof. In some cases, a surface comprises functionalization with polyethylene/polypropylene (functionalized by gamma irradiation or chromic acid oxidation, and reduction to hydroxyalkyl surface), highly crosslinked polystyrene-divinylbenzene (derivatized by chloromethylation, and aminated to benzylamine functional surface), nylon (the terminal aminohexyl groups are directly reactive), or etched with reduced polytetrafluoroethylene.

A surface disclosed herein can be functionalized by contact with a derivatizing composition that contains a mixture of silanes, under reaction conditions effective to couple the silanes to the surface. Silanization generally can be used to cover a surface through self-assembly with organofunctional alkoxysilane molecules. A variety of siloxane functionalizing reagents can further be used as currently known in the art, e.g., for lowering or increasing surface energy. The organofunctional alkoxysilanes are classified according to their organic functions. Non-limiting examples of siloxane functionalizing reagents include hydroxyalkyl siloxanes (silylate surface, functionalizing with diborane and oxidizing the alcohol by hydrogen peroxide), diol (dihydroxyalkyl) siloxanes (silylate surface, and hydrolyzing to diol), aminoalkyl siloxanes (amines require no intermediate functionalizing step), glycidoxysilanes (3-glycidoxypropyl-dimethyl-ethoxysilane, glycidoxy-trimethoxysilane), mercaptosilanes (3-mercaptopropyl-trimethoxysilane, 3-4 epoxycyclohexyl-ethyltrimethoxysilane or 3-mercaptopropyl-methyl-dimethoxysilane), bicyclohepthenyl-trichlorosilane, butyl-aldehyde-trimethoxysilane, or dimeric secondary aminoalkyl siloxanes. The hydroxyalkyl siloxanes can include 3-(chloro)allyltrichlorosilane turning into 3-hydroxypropyl, or 7-octenyltrichlorosilane turning into 8-hydroxyoctyl. The diol (dihydroxyalkyl) siloxanes include glycidyl trimethoxysilane-derived (3-glycidyloxypropyl) trimethoxysilane (GOPS). The aminoalkyl siloxanes include 3-aminopropyl trimethoxysilane turning into 3-aminopropyl (3-aminopropyl-triethoxysilane, 3-aminopropyl-diethoxy-methylsilane, 3-aminopropyl-dimethyl-ethoxysilane, or 3-aminopropyl-trimethoxysilane). The dimeric secondary aminoalkyl siloxanes can be bis (3-trimethoxysilylpropyl) amine turning into bis(silyloxylpropyl)amine. In some cases, the functionalizing agent comprises 11-acetoxyundecyltriethoxysilane, n-decyltriethoxysilane, (3-aminopropyl) trimethoxysilane, (3-aminopropyl)triethoxysilane, glycidyloxypropyl/trimethoxysilane and N-(3-triethoxysilylpropyl)-4-hydroxybutyramide.

Desired surface tensions, wettabilities, water contact angles, and/or contact angles for other suitable solvents are achieved by providing a surface with a suitable ratio of functionalization agents. A surface disclosed herein can be functionalized to enable covalent binding of molecular moieties that can lower the surface energy so that wettability can be reduced. A portion of a surface disclosed herein may be prepared to have a high surface energy and increased wettability. Surfaces disclosed herein can also be modified to comprise reactive hydrophilic moieties such as hydroxyl groups, carboxyl groups, thiol groups, and/or substituted or unsubstituted amino groups. Suitable materials that can be used for solid phase chemical synthesis, e.g., cross-linked polymeric materials (e.g., divinylbenzene styrene-based polymers), agarose (e.g., Sepharose®), dextran (e.g., Sephadex®), cellulosic polymers, polyacrylamides, silica, glass (particularly controlled pore glass, or "CPG"), ceramics, and the like. The supports may be obtained commercially and used as is, or they may be treated or coated prior to functionalization.

Dilution of Active Functionalization Agent to Form Regions of High Surface Energy To achieve surfaces with low density of nucleoside-coupling agents, a mixture of both active and passive functionalization agents is mixed and deposited at a predetermined region of a surface disclosed herein. Such a mixture provides for a region having a less than saturating amount of active functionalization agent bound to the surface and therefore lowers the density of functionalization agent in a particular region. A mixture of agents that bind to a surface disclosed herein can be deposited on predetermined region of the surface, wherein coated surface provides for a density of synthesized oligonucleic acids that is about 10%, 20%, 30%, 40%, 50%, 60%, 70%, or 80% less than the density of synthesized oligonucleic acids extended from a region of the surface comprising only the active functionalization agent. The mixture can comprise (i) a silane that binds the surface and couples nucleoside and (ii) a silane that binds the surface and does not couple nucleoside is deposited on predetermined region of a surface disclosed herein, wherein coated surface provides for a density of synthesized oligonucleic acids that is about 10%, 20%, 30%, 40%, 50%, 60%, 70%, or 80% less than the density of synthesized oligonucleic acids extended from a region of the surface comprising (i) the silane that binds the surface and couples nucleoside and not (ii) the silane that binds the surface and does not couple nucleoside. A predetermined region of a surface can be treated with a diluted amount of an active functionalization agent disclosed herein provides for a reduction in density of synthesized oligonucleic acids that is about 50% compared to an identical surface coated with a non-diluted amount of the active functionalization agents. One exemplary active functionalization agent is 3-glycidoxypropyltrimethoxysilane, which can optionally be included in a mixture disclosed herein. For example, the mixture can include 3-glycidoxypropyltrimethoxysilane or propyltrimethoxysilane; or 3-glycidoxypropyltrimethoxysilane and propyltrimethoxysilane. Regions surrounding those regions deposited with the mixture can be coated with a passive functionalization agent having a lower surface energy. In some cases, the passive functionalization agent having a lower surface energy is a fluorosilane. Exemplary fluorosilanes include (tridecafluoro-1,1,2,2-tetrahydrooctyl) trichlorosilane and perfluorooctyltrichlorosilane.

More broadly, active functionalization agent can comprise a silane, such as an aminosilane. In some cases, the active functionalization agent comprises a silane that, once activated, couples nucleoside, e.g., a nucleoside phosphoramidite. The active functionalization agent can be a silane that has a higher surface energy than the passive functionalization agent deposited on areas of the surface located outside of predetermined regions where the silane is deposited. In some cases, both molecules types in the mixture comprise silanes, and the mixture is deposited on the surface. For example, one of the molecules in the mixture is a silane that binds the surface and couples to nucleoside, and another one of the molecules in the surface is a silane that binds the surface and does not couple to nucleoside. In such cases, both molecules in the mixture, when deposited on the surface, provide for a region having a higher surface energy than regions surrounding where the mixture is deposited.

Agents in a mixture disclosed here are chosen from suitable reactive and inert moieties, thus diluting the surface density of reactive groups to a desired level for downstream reactions, where both molecules have similar surface energy. In some cases, the density of the fraction of a surface functional group that reacts to form a growing oligonucleotide in an oligonucleotide synthesis reaction is about 0.005, 0.01, 0.05, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 3.0, 3.5, 4.0, 4.5, 5.0, 7.0, 10.0, 15.0, 20.0, 50.0, 75.0, 100.0 µmol/m$^2$.

Mixtures disclosed herein can comprise at least 2, 3, 4, 5 or more different types of functionalization agents. A mixture can comprises 1, 2, 3 or more silanes. The ratio of the at least two types of surface functionalization agents in a mixture deposited on a surface disclosed herein may range from about 1:1 to 1:100 with the active functionalization agent being diluted to a greater amount compared to a functionalization agent that does not couple nucleoside. In some cases, the ratio of the at least two types of surface functionalization agents in a mixture deposited on a surface disclosed herein is about 1:100 to about 1:2500, with the active functionalization agent being diluted to a greater amount compared to a functionalization agent that does not couple nucleoside. Exemplary ratios of the at least two types of surface functionalization agents in a mixture deposited on a surface disclosed herein include at least 1:10, 1:50, 1:100, 1:200, 1:500, 1:1000, 1:2000, 1:2500, 1:3000, or 1:5000, with the active functionalization agent being diluted to a greater amount compared to a functionalization agent that does not couple nucleoside. An exemplary specific ratio of the at least two types of surface functionalization agents in a mixture is about 1:2000, with the active functionalization agent being diluted to a greater amount compared to a functionalization agent that does not couple nucleoside. Another exemplary specific ratio of the at least two types of surface functionalization agents in a mixture is 1:2000, with the active functionalization agent being diluted to a greater amount compared to a functionalization agent that does not couple nucleoside. The passive functionalization agent deposited on the surface can be a fluorosilane molecule. Exemplary fluorosilane molecules are (tridecafluoro-1,1,2, 2-tetrahydrooctyl)trichlorosilane and perfluorooctyltrichlorosilane. The mixture deposited on a surfaced disclosed herein may comprise a silane that binds the surface and nucleoside phosphoramidite and is diluted about 1:100 to about 1:2500 with a silane that bind the surface and does not bind nucleoside phosphoramidite. In some cases, the silane molecule deposited on a surfaced disclosed herein is diluted about 1:2000.

To attain a reduction in active agent density at particular locations on a surface disclosed herein, deposition at regions for nucleic acid extension with the non-nucleoside molecule of the mixture occurs prior to deposition with the mixture itself. In some case, the mixture deposited on a surfaced disclosed herein comprises 3-glycidoxypropyltrimethoxysilane diluted at a ratio of about 1:2000. The mixture deposited on a surfaced disclosed herein may comprise 3-glycidoxypropyltrimethoxysilane diluted at a ratio of about 1:2000 in propyltrimethoxysilane. In one example, a surface disclosed herein is first deposited at regions for nucleic acid extension with propyltrimethoxysilane prior to deposition of a mixture of propyltrimethoxysilane and 3-glycidoxypropyltrimethoxysilane. In some cases, a silane deposited at sites of oligonucleic acid synthesis are selected from the group consisting of 11-acetoxyundecyltriethoxysilane, n-decyltriethoxysilane, (3-aminopropyl)trimethoxysilane, (3-aminopropyl)triethoxysilane, 3-glycidyloxypropyl/trimethoxysilane and N-(3-triethoxysilylpropyl)-4-hydroxybutyramide.

Hydrophilic and Hydrophobic Surfaces

The surface energy, or hydrophobicity of a surface, can be evaluated or measured by measuring a water contact angle. Water contact angle is the angle between the drop surface and a solid surface where a water droplet meets the solid surface. A surface with a water contact angle of smaller than 90°, the solid surface can be considered hydrophilic or polar. A surface with a water contact angle of greater than 90°, the solid surface can be considered hydrophobic or apolar. Highly hydrophobic surfaces with low surface energy can have water contact angle that is greater than 120°.

Surface characteristics of coated surfaces can be adjusted in various ways suitable for oligonucleotide synthesis. A surface described herein is selected to be inert to the conditions of ordinary oligonucleotide synthesis; e.g. the solid surface may be devoid of free hydroxyl, amino, or carboxyl groups to the bulk solvent interface during monomer addition, depending on the selected chemistry. In some cases, the surface may comprise reactive moieties prior to the start of a first cycle, or first few cycles of an oligonucleotide synthesis process, wherein the reactive moieties can be quickly depleted to unmeasurable densities after one, two, three, four, five, or more cycles of the oligonucleotide synthesis reaction. The surface can further be optimized for well or pore wetting, e.g., by common organic solvents such as acetonitrile and the glycol ethers or aqueous solvents, relative to surrounding surfaces.

Without being bound by theory, the wetting phenomenon is understood to be a measure of the surface tension or attractive forces between molecules at a solid-liquid interface, and is expressed in dynes/cm$^2$. For example, fluorocarbons have very low surface tension, which is typically attributed to the unique polarity (electronegativity) of the carbon-fluorine bond. In tightly structured Langmuir- Blodgett type films, surface tension of a layer can be primarily determined by the percent of fluorine in the terminus of the alkyl chains. For tightly ordered films, a single terminal trifluoromethyl group can render a surface nearly as lipophobic as a perfluoroalkyl layer. When fluorocarbons are covalently attached to an underlying derivatized solid (e.g. a highly crosslinked polymeric) support, the density of reactive sites can be lower than Langmuir-Blodgett and group density. For example, surface tension of a methyltrimethoxysilane surface can be about 22.5 mN/m and aminopropyltriethoxysilane surface can be about 35 mN/m. Briefly, hydrophilic behavior of surfaces is generally considered to occur when critical surface tensions are greater than 45 mN/m. As the critical surface tension increases, the expected decrease in contact angle is accompanied with stronger adsorptive behavior. Hydrophobic behavior of surfaces is generally considered to occur when critical surface tensions are less than 35 mN/m. At first, the decrease in critical surface tension is associated with oleophilic behavior, i.e. the wetting of the surfaces by hydrocarbon oils. As the critical surface tensions decrease below 20 mN/m, the surfaces resist wetting by hydrocarbon oils and are considered both oleophobic as well as hydrophobic. For example, silane surface modification can be used to generate a broad range of critical surface tensions. Devices and methods disclosed herein include surface coatings, e.g. those involving silanes, to achieve surface tensions of less than 5, 6, 7, 8, 9, 10, 12, 15, 20, 25, 30, 35, 40, 45, 50, 60, 70, 80, 90, 100, 110, 115, 120 mN/m, or higher. Further, in some cases, the methods and devices disclosed herein use surface coatings, e.g. those involving silanes, to achieve surface tensions of more than 115, 110, 100, 90, 80, 70, 60, 50, 45, 40, 35, 30, 25, 20, 15, 12, 10, 9, 8, 7, 6 mN/m or less. The water contact angle and the surface tension of non-limiting examples of surface coatings, e.g., those involving silanes, are described in Table 1 and Table 2 of Arkles et al. (Silanes and Other Coupling Agents, Vol. 5v: The Role of Polarity in the Structure of Silanes Employed in Surface Modification. 2009), which is incorporated herein by reference in its entirety. The tables are replicated below.

TABLE 1

Contact angles of water (degrees) on smooth surfaces

| | |
|---|---|
| Heptadecafluorodecyltrimethoxysilane | 113-115 |
| Poly(tetrafluoroethylene) | 108-112 |
| Polypropylene | 108 |
| Octadecyldimethylchlorosilane | 110 |
| Octadecyltrichlorosilane | 102-109 |
| Tris(trimethylsiloxy)silylethyldimethylchlorosilane | 103-104 |
| Octyldimethylchlorosilane | 104 |
| Butyldimethylchlorosilane | 100 |
| Trimethylchlorosilane | 90-100 |
| Polyethylene | 88-103 |
| Polystyrene | 94 |
| Poly(chlorotrifluoroethylene) | 90 |
| Human skin | 75-90 |
| Diamond | 87 |
| Graphite | 86 |
| Silicon (etched) | 86-88 |
| Talc | 82-90 |
| Chitosan | 80-81 |
| Steel | 70-75 |
| Methoxyethoxyundecyltrichlorosilane | 73-74 |
| Methacryloxypropyltrimethoxysilane | 70 |
| Gold, typical (see gold, clean) | 66 |
| Intestinal mucosa | 50-60 |
| Kaolin | 42-46 |
| Platinum | 40 |
| Silicon nitride | 28-30 |
| Silver iodide | 17 |

TABLE 1-continued

Contact angles of water (degrees) on smooth surfaces

| | |
|---|---|
| [Methoxy(polyethyleneoxy)propyl]trimethoxysilane | 15-16 |
| Sodalime glass | <15 |
| Gold, clean | <10 |
| Trimethoxysilylpropyl substituted poly(ethyleneimine), hydrochloride | <10 |

TABLE 2

Critical surface tensions (mN/m)

| | |
|---|---|
| Heptadecafluorodecyltrichlorosilane | 12 |
| Poly(tetrafluoroethylene) | 18.5 |
| Octadecyltrichlorosilane | 20-24 |
| Methyltrimethoxysilane | 22.5 |
| Nonafluorohexyltrimethoxysilane | 23 |
| Vinyltriethoxysilane | 25 |
| Paraffin wax | 25.5 |
| Ethyltrimethoxysilane | 27.0 |
| Propyltrimethoxysilane | 28.5 |
| Glass, sodalime (wet) | 30.0 |
| Poly(chlorotrifluoroethylene) | 31.0 |
| Polypropylene | 31.0 |
| Poly(propylene oxide) | 32 |
| Polyethylene | 33.0 |
| Trifluoropropyltrimethoxysilane | 33.5 |
| 3-(2-Aminoethyl)aminopropyltrimethoxysilane | 33.5 |
| Polystyrene | 34 |
| p-Tolyltrimethoxysilane | 34 |
| Cyanoethyltrimethoxysilane | 34 |
| Aminopropyltriethoxysilane | 35 |
| Acetoxypropyltrimethoxysilane | 37.5 |
| Poly(methyl methacrylate) | 39 |
| Poly(vinyl chloride) | 39 |
| Phenyltrimethoxysilane | 40.0 |
| Chloropropyltrimethoxysilane | 40.5 |
| Mercaptopropyltrimethoxysilane | 41 |
| Glycidoxypropyltrimethoxysilane | 42.5 |
| Poly(ethylene terephthalate) | 43 |
| Copper (dry) | 44 |
| Poly(ethylene oxide) | 43-45 |
| Aluminum (dry) | 45 |
| Nylon 6/6 | 45-46 |
| Iron (dry) | 46 |
| Glass, sodalime (dry) | 47 |
| Titanium oxide (anatase) | 91 |
| Ferric oxide | 107 |
| Tin oxide | 111 |

Provided herein are surfaces, or a portion of the surface, functionalized or modified to be more hydrophilic or hydrophobic as compared to the surface or the portion of the surface prior to the functionalization or modification. One or more surfaces may be modified to have a difference in water contact angle of greater than 90°, 85°, 80°, 75°, 70°, 65°, 60°, 55°, 50°, 45°, 40°, 35°, 30°, 25°, 20°, 15° or 10° as measured on one or more uncurved, smooth or planar equivalent surfaces. In some cases, the surface of microstructures, channels, wells, resolved loci, resolved reactor caps or other parts of structure is modified to have a differential hydrophobicity corresponding to a difference in water contact angle that is greater than 90°, 85°, 80°, 75°, 70°, 65°, 60°, 55°, 50°, 45°, 40°, 35°, 30°, 25°, 20°, 15° or 10° as measured on uncurved, smooth or planar equivalent surfaces of such structures.

Provided herein are surfaces have a predetermined first region comprising two or more molecules having different ability to couple nucleoside and have a similarity in water contact angle. In some cases, the similarity is less than 40°, 35°, 30°, 25°, 20°, 15° or 10° as measured on one or more smooth or planar equivalent surfaces. In some cases, the first region is surrounded by a second region, where the first and second region have a difference in water contact angle of greater than 90°, 85°, 80°, 75°, 70°, 65°, 60°, 55°, 50°, 45°, 40°, 35°, 30°, 25°, 20°, 15° or 10° as measured on one or more smooth or planar equivalent surfaces. In some cases, the first region is surrounded by a second region, where the first and second region have a difference in water contact angle of at least 90°, 85°, 80°, 75°, 70°, 65°, 60°, 55°, 50°, 45°, 40°, 35°, 30°, 25°, 20°, 15° or 10° as measured on one or more smooth or planar equivalent surfaces. Unless otherwise stated, water contact angles mentioned herein correspond to measurements that would be taken on uncurved, smooth or planar equivalents of the surfaces in question.

Surface Preparation

Surfaces provided herein comprise or are modified to support oligonucleic acid synthesis at predetermined locations and with a resulting low error rate. A common method for functionalization comprises selective deposition of an organosilane molecule onto a surface of a structure disclosed herein. Selective deposition refers to a process that produces two or more distinct areas on a structure, wherein at least one area has a different surface or chemical property that another area of the same structure. Such properties include, without limitation, surface energy, chemical termination, surface concentration of a chemical molecule, and the like. Any suitable process that changes the chemical properties of the surface described herein or known in the art may be used to functionalize the surface, for example chemical vapor deposition of an organosilane. Typically, this results in the deposition of a self-assembled monolayer (SAM) of the functionalization species.

Provided herein are methods for functionalizing a surface of a structure disclosed herein for oligonucleic acid synthesis which include photolithography. An exemplary photolithographic method comprises 1) applying a photoresist to a surface, 2) exposing the resist to light, e.g., using a binary mask opaque in some areas and clear in others, and 3) developing the resist; wherein the areas that were exposed are patterned. The patterned resist can then serve as a mask for subsequent processing steps, for example, etching, ion implantation, and deposition. After processing, the resist is typically removed, for example, by plasma stripping or wet chemical removal. Oxygen plasma cleaning may optionally be used to facilitate the removal of residual organic contaminants in resist cleared areas, for example, by using a typically short plasma cleaning step (e.g., oxygen plasma). Resist can be stripped by dissolving it in a suitable organic solvent, plasma etching, exposure and development, etc., thereby exposing the areas of the surface that had been covered by the resist. Resist can be removed in a process that does not remove functionalization groups or otherwise damage the functionalized surface.

Provided herein is a method for functionalizing a surface of a structure disclosed herein for oligonucleic acid synthesis comprises a resist or photoresist coat. Photoresist, in many cases, refers to a light-sensitive material useful in photolithography to form patterned coatings. It is applied as a liquid to solidify on a surface as volatile solvents in the mixture evaporate. In some cases, the resist is applied in a spin coating process as a thin film, e.g., 1 µm to 100 µm. The coated resist can be patterned by exposing it to light through a mask or reticle, changing its dissolution rate in a developer. In some cases, the resist coat is used as a sacrificial layer that serves as a blocking layer for subsequent steps that modify the underlying surface, e.g., etching, and then is removed by resist stripping. Surface of a structure can be functionalized while areas covered in resist are protected from active or passive functionalization.

Provide herein are methods where a chemical cleaning is a preliminary step in surface preparation. In some exemplary methods, active functionalization is performed prior to lithography. A structure may be first cleaned, for example, using a piranha solution. An example of a cleaning process includes soaking a structure in a piranha solution (e.g., 90% $H_2SO_4$, 10% $H_2O_2$) at an elevated temperature (e.g., 120° C.) and washing (e.g., water) and drying the structure (e.g., nitrogen gas). The process optionally includes a post piranha treatment comprising soaking the piranha treated structure in a basic solution (e.g., $NH_4OH$) followed by an aqueous wash (e.g., water). Alternatively, a structure can be plasma cleaned, optionally following the piranha soak and optional post piranha treatment. An example of a plasma cleaning process comprises an oxygen plasma etch.

Provided herein are methods for surface preparation where, an active chemical vapor (CVD) deposition step is done after photolithography. An exemplary first step includes optionally cleaning the surface cleaning the surface of a structure using cleaning methods disclosed herein. Cleaning can include oxygen plasma treatment. In some cases, the CVD step is for deposition of a mixture, the mixture having at least two molecules resulting in a high surface energy region and the region coated with the first chemical layer is a lower surface energy region. The mixture may comprise a molecule that binds the surface and couple nucleoside phosphoramidite mixed with a greater amount of a molecule that binds the surface and does not couple nucleoside phosphoramidite. For the two step dilution protocol, prior to depositing the mixture on the surface, a step includes deposition of 100% of the mixture ingredient molecule that binds the surface and does not couple nucleoside phosphoramidite. The first chemical layer can comprise a fluorosilane disclosed herein, for example, tridecafluoro-1,1,2,2-tetrahydrooctyl)-trichlorosilane. The second chemical layer can comprise at least two silanes disclosed herein. In some cases, the two silanes are GOPS and propyltrimethoxysilane. In an exemplary method, the surface is treated with propyltrimethoxysilane prior to treatment with the mixture. The above workflow is an example process and any step or component may be omitted or changed in accordance with properties desired of the final functionalized surface.

A surface of a structure disclosed herein can be coated with a resist, subject to functionalization and/or after lithography, and then treated to remove the resist. In some cases, the resist is removed with a solvent, for example, with a stripping solution comprising N-methyl-2-pyrrolidone. In some cases, resist stripping comprises sonication or ultrasonication. After stripping resist, the surface can be further subjected to deposition of an active functionalization agent binding to exposed areas to create a desired differential functionalization pattern. In some cases, the active functionalization areas comprise one or more different species of silanes, for example, 1, 2, 3, 4, 5, 6, 7, 8, 9, 10 or more silanes. One of the one or more silanes may b present in the functionalization composition in an amount greater than another silane. The composition and density of functionalization agent can contribute to a low error rate of oligonucleic acid synthesis, e.g., an error rate of less than 1 in 1000, less than 1 in 1500, less than 1 in 2000, less than 1 in 3000, less than 1 in 4000, less than 1 in 5000 bases).

Provided herein are methods which include applying an adhesion promoter to the surface. The adhesion promoter is applied in addition to applying the light sensitive lack. In some cases, applying both the adhesion promoter and light sensitive lack is done to surfaces including, without limitation, glass, silicon, silicon dioxide and silicon nitride. Exemplary adhesion promoters include silanes, e.g., aminosilanes. Exemplary aminosilanes include, without limitation, (3-aminopropyl)trimethoxysilane, (3-aminopropyl)triethoxysilane and N-(3-triethoxysilylpropyl)-4-hydroxybutyramide. In addition, a passive layer can be deposited on the surface, which may or may not have reactive oxide groups. The passive layer can comprise silicon nitride ($Si_3N_4$) or polyamide. The photolithographic step can be used to define regions where loci form on the passivation layer.

Provided here are methods for producing a substrate having a plurality of loci starts with a structure. The structure (e.g., silicon) can have any number of layers disposed upon it, including but not limited to a conducting layer such as a metal (e.g., silicon dioxide, silicon oxide, or aluminum). The structure can have a protective layer (e.g., titanium nitride). The layers can be deposited with the aid of various deposition techniques, such as, for example, chemical vapor deposition (CVD), atomic layer deposition (ALD), plasma enhanced CVD (PECVD), plasma enhanced ALD (PEALD), metal organic CVD (MOCVD), hot wire CVD (HWCVD), initiated CVD (iCVD), modified CVD (MCVD), vapor axial deposition (VAD), outside vapor deposition (OVD) and physical vapor deposition (e.g., sputter deposition, evaporative deposition).

An oxide layer can be deposited on the structure. The oxide layer can comprise silicon dioxide. The silicon dioxide can be deposited using tetraethyl orthosilicate (TEOS), high density plasma (HDP), or any combination thereof. The silicon dioxide can be deposited to a thickness suitable for the manufacturing of suitable microstructures described in further detail elsewhere herein. In some cases, silicon dioxide is grown in a conformal way on a silicon substrate. Growth on a silicon substrate can performed in a wet or dry atmosphere. An exemplary wet growth method is provided where wet growth is conducted at high temperatures, e.g., about 1000 degrees Celsius and in water vapor. The dry growth method can be conducted in the presence of oxygen.

Loci can be created using photolithographic techniques such as those used in the semiconductor industry. For example, a photo-resist (e.g., a material that changes properties when exposed to electromagnetic radiation) can be coated onto the silicon dioxide (e.g., by spin coating of a wafer) to any suitable thickness. Exemplary coating thicknesses include about 1, 5, 10, 20, 30, 40, 50, 60, 70, 80, 90, 100, 150, 200, 300, 400, or 500 μm. An exemplary photoresist material is MEGAPOSIT SPR 3612 photoresist (Dow Electronic Material) or a similar product. The substrate including the photo-resist can be exposed to an electromagnetic radiation source. A mask can be used to shield radiation from portions of the photo-resist in order to define the area of the loci. The photo-resist can be a negative resist or a positive resist (e.g., the area of the loci can be exposed to electromagnetic radiation or the areas other than the loci can be exposed to electromagnetic radiation as defined by the mask). The area overlying the location in which the resolved loci are to be created is exposed to electromagnetic radiation to define a pattern that corresponds to the location and distribution of the resolved loci in the silicon dioxide layer. The photoresist can be exposed to electromagnetic radiation through a mask defining a pattern that corresponds to the resolved loci. Next, the exposed portion of the photoresist can be removed, such as, e.g., with the aid of wet chemical etching and a washing operation. The removed portion of the mask can then be exposed to a chemical etchant to etch the substrate and transfer the pattern of resolved loci into the silicon dioxide layer. The etchant can include an acid, such as, for example, buffered HF in the case of silicon dioxide.

Various etching procedures can be used to etch the silicon in the area where the resolved loci are to be formed. The etch can be an isotropic etch (i.e., the etch rate alone one direction substantially equal or equal to the etch rate along an orthogonal direction), or an anisotropic etch (i.e., the etch rate along one direction is less than the etch rate alone an orthogonal direction), or variants thereof. The etching techniques can be both wet silicon etches such as KOH, TMAH, EDP and the like, and dry plasma etches (for example DRIE). Both may be used to etch micro structures wafer through interconnections.

The dry etch can be an anisotropic etch that etches substantially vertically (e.g., toward the substrate) but not laterally or substantially laterally (e.g., parallel to the substrate). In some cases, the dry etch comprises etching with a fluorine based etchant such as $CF_4$, $CHF_3$, $C_2F_6$, $C_3F_6$, or any combination thereof. In some cases, the etching is performed for 400 seconds with an Applied Materials eMax-CT machine having settings of 100 mT, 1000 W, 20 G, and 50 CF4. The substrates described herein can be etched by deep reactive-ion etching (DRIE). DRIE is a highly anisotropic etch process used to create deep penetration, steep-sided holes and trenches in wafers/substrates, typically with high aspect ratios. The substrates can be etched using two main technologies for high-rate DRIE: cryogenic and Bosch. Methods of applying DRIE are described in the U.S. Pat. No. 5,501,893, which is herein incorporated by reference in its entirety.

The wet etch can be an isotropic etch that removes material in all directions. In some cases, the wet oxide etches are performed at room temperature with a hydrofluoric acid base that can be buffered (e.g., with ammonium fluoride) to slow down the etch rate. In some cases, a chemical treatment can be used to etch a thin surface material, e.g., silicon dioxide or silicon nitride. Exemplary chemical treatments include buffered oxide etch (BOE), buffered HF and/or $NH_4F$. The etch time needed to completely remove an oxide layer is typically determined empirically. In one example, the etch is performed at 22° C. with 15:1 BOE (buffered oxide etch).

The silicon dioxide layer can be etched up to an underlying material layer. For example, the silicon dioxide layer can be etched until a titanium nitride layer. In some cases, the silicon dioxide is grown at a temperature of 1000 degrees Celsius and the underlying layer is typically silicon.

An additional surface layer can be added on top of an etched silicon layer subsequent to etching. In an exemplary arrangement, the additional surface layer is one that effectively binds to an adhesion promoter. Exemplary additional surface layers include, without limitation, silicon dioxide and silicon nitride. In the case of silicon dioxide, the additional layer can be added by conformal growth of a thin layer of this material on the silicon.

Clusters and Loci

Provided herein are devices having surfaces which comprises 50 to 10000 clusters 400, each cluster located in a predetermined position. The surface of a device disclosed herein can comprise more than 10000 clusters, each cluster located in a predetermined position. The term "locus" as used herein refers to a discrete region on the surface of a structure which provides support for synthesis of oligonucleotides encoding for a single sequence to extend from the surface. In an exemplary arrangement, each cluster comprises 121 loci 425, each loci being located in a predetermined position. The loci can comprise a molecule that binds the surface and also couples to nucleoside. Moreover, loci can comprise a mixture of (i) a molecule that binds the surface and couples to a nucleoside; and (ii) a molecule that binds the surface and does not couple to nucleoside. In some cases, the regions surrounding the loci comprise a molecule that binds the surface and does not couple to nucleoside, wherein the surface of regions surrounding the loci results a lower surface energy than the surface energy at the loci.

The loci can be located on a substantially planar surface. In some arrangements, a locus is located on a well, microwell, channel, post, or other raised or lowered feature of a surface disclosed herein. A region of a locus can span a plurality of wells, microwells, channels, posts, or other raised or lowered features of a surface disclosed herein.

Provided herein are structures comprising a surface that supports the synthesis of a plurality of oligonucleic acids having different predetermined sequences at addressable locations on a common support. The surface of a structure disclosed herein can support for the synthesis of more than 2,000; 5,000; 10,000; 20,000; 50,000; 100,000; 200,000; 300,000; 400,000; 500,000; 600,000; 700,000; 800,000; 900,000; 1,000,000; 1,200,000; 1,400,000; 1,600,000; 1,800,000; 2,000,000; 2,500,000; 3,000,000; 3,500,000; 4,000,000; 4,500,000; 5,000,000; 10,000,000 or more non-identical oligonucleic acids. In some case, at least a portion of the oligonucleic acids have an identical sequence or are configured to be synthesized with an identical sequence. Structures disclosed herein provides for a surface environment for the growth of oligonucleic acids having at least about 10, 20, 30, 50, 60, 70, 75, 80, 85, 90, 95, 100, 110, 120, 130, 140, 150, 160, 175, 200, 225, 250, 275, 300, 325, 350, 375, 400, 425, 450, 475, 500, 1000, 2000 bases or more in length.

Provided herein are surfaces in which oligonucleic acids are synthesized on distinct loci of a surface disclosed herein, wherein each locus supports the synthesis of a population of oligonucleic acids. In some cases, each locus supports the synthesis of a population of oligonucleic acids having a different sequence than a population of oligonucleic acids grown on another locus. Loci of a surface disclosed herein are each located within a cluster of a plurality of clusters. Provided herein are surfaces which comprise at least 10, 100, 500, 1000, 2000, 3000, 4000, 5000, 6000, 7000, 8000, 9000, 10000, 11000, 12000, 13000, 14000, 15000, 20000, 30000, 40000, 50000 or more clusters. Provided herein are surfaces which comprise more than 2,000; 5,000; 10,000; 100,000; 200,000; 300,000; 400,000; 500,000; 600,000; 700,000; 800,000; 900,000; 1,000,000; 1,100,000; 1,200,000; 1,300,000; 1,400,000; 1,500,000; 1,600,000; 1,700,000; 1,800,000; 1,900,000; 2,000,000; 300,000; 400,000; 500,000; 600,000; 700,000; 800,000; 900,000; 1,000,000; 1,200,000; 1,400,000; 1,600,000; 1,800,000; 2,000,000; 2,500,000; 3,000,000; 3,500,000; 4,000,000; 4,500,000; 5,000,000; or 10,000,000 or more distinct loci. In some cases, each cluster includes 1, 2, 3, 4, 5, 6, 7, 8, 9, 10, 20, 30, 40, 50, 60, 70, 80, 90, 100, 120, 130, 150, 200, 500 or more loci. In some cases, each cluster includes 50 to 500, 50 to 200, 50 to 150, or 100 to 150 loci. In some cases, each cluster includes 100 to 150 loci. In exemplary arrangements, each cluster includes 109, 121, 130 or 137 loci.

The number of distinct oligonucleic acids synthesized on a surface disclosed herein can be dependent on the number of distinct loci available on the surface. Provided herein are structures wherein the density of loci within a cluster of a structure disclosed herein is at least or about 1 locus per mm$^2$, 10 loci per mm$^2$, 25 loci per mm$^2$, 50 loci per mm$^2$, 65 loci per mm$^2$, 75 loci per mm$^2$, 100 loci per mm$^2$, 130 loci per mm$^2$, 150 loci per mm$^2$, 175 loci per mm$^2$, 200 loci per mm$^2$, 300 loci per mm$^2$, 400 loci per mm$^2$, 500 loci per mm$^2$, 1,000 loci per mm$^2$ or more. In some cases, a the surface of a structure disclosed herein comprises from about 10 loci per mm$^2$ to about 500 mm$^2$, from about 25 loci per mm$^2$ to about 400 mm$^2$, or from about 50 loci per mm$^2$ to about 200 mm$^2$.

Provided herein are structures wherein the distance between the centers of two adjacent loci within a cluster is from about 10 μm to about 500 μm, from about 10 μm to about 200 μm, or from about 10 μm to about 100 μm. Provided herein are structures wherein the distance between two centers of adjacent loci is greater than about 10 μm, 20 μm, 30 μm, 40 μm, 50 μm, 60 μm, 70 μm, 80 μm, 90 μm or 100 μm. In some cases, the distance between the centers of two adjacent loci is less than about 200 μm, 150 μm, 100 μm, 80 μm, 70 μm, 60 μm, 50 μm, 40 μm, 30 μm, 20 μm or 10 μm.

Provided herein are structures wherein the number of distinct nucleic acids or genes assembled from a plurality of oligonucleic acids synthesized on the structure is dependent on the number of clusters available in the surface of the structure. In some case, the density of clusters within a region of the surface is at least or about 1 cluster per 100 mm$^2$, 1 cluster per 10 mm$^2$, 1 cluster per 5 mm$^2$, 1 cluster per 4 mm$^2$, 1 cluster per 3 mm$^2$, 1 cluster per 2 mm$^2$, 1 cluster per 1 mm$^2$, 2 clusters per 1 mm$^2$, 3 clusters per 1 mm$^2$, 4 clusters per 1 mm$^2$, 5 clusters per 1 mm$^2$, 10 clusters per 1 mm$^2$, 50 clusters per 1 mm$^2$ or more. In some cases, a region of a surface disclosed herein comprises from about 1 cluster per 10 mm$^2$ to about 10 clusters per 1 mm$^2$. Provided herein are structures wherein the distance between the centers of two adjacent clusters is less than about 50 μm, 100 μm, 200 μm, 500 μm, 1000 μm, or 2000 μm or 5000 μm. Provided herein are structures wherein the distance between the centers of two adjacent clusters is 1.125 mm. In some cases, the distance between the centers of two adjacent clusters is between about 50 μm and about 100 μm, between about 50 μm and about 200 μm, between about 50 μm and about 300 μm, between about 50 μm and about 500 μm, or between about 100 μm to about 2000 μm. In some cases, the distance between the centers of two adjacent clusters is between about 0.05 mm to about 50 mm, between about 0.05 mm to about 10 mm, between about 0.05 mm and about 5 mm, between about 0.05 mm and about 4 mm, between about 0.05 mm and about 3 mm, between about 0.05 mm and about 2 mm, between about 0.1 mm and 10 mm, between about 0.2 mm and 10 mm, between about 0.3 mm and about 10 mm, between about 0.4 mm and about 10 mm, between about 0.5 mm and 10 mm, between about 0.5 mm and about 5 mm, or between about 0.5 mm and about 2 mm. In some cases, the distance between two clusters is about or at least about 0.3 mm, 0.4 mm, 0.5 mm, 0.6 mm, 0.7 mm, 0.8 mm, 0.9 mm, 1 mm, 1.2 mm, 1.4 mm, 1.6 mm, 1.8 mm, 2 mm, 2.2 mm, 2.4 mm, 2.6 mm, 2.8 mm, 3 mm, 3.2 mm, 3.4 mm, 3.6 mm, 3.8 mm, 4 mm, 4.2 mm, 4.4 mm, 4.6 mm, 4.8 mm, 5 mm, 5.2 mm, 5.4 mm, 5.6 mm, 5.8 mm, 6 mm, 6.2 mm, 6.4 mm, 6.6 mm, 6.8 mm, 7 mm, 7.2 mm, 7.4 mm, 7.6 mm, 7.8 mm, 8 mm, 8.2 mm, 8.4 mm, 8.6 mm, 8.8 mm, or 9 mm. The distance between two clusters may range between 0.3-9 mm, 0.4-8 mm, 0.5-7 mm, 0.6-6 mm, 0.7-5 mm, 0.7-4 mm, 0.8-3 mm, or 0.9-2 mm. Those of skill in the art appreciate that the distance may fall within any range bound by any of these values, for example 0.8 mm-2 mm.

Provided herein are structures having a surface wherein one or more loci on the surface comprise a channel or a well. In some cases, the channels or wells are accessible to reagent deposition via a deposition device such as an oligonucleic acid synthesizer. In some cases, reagents and/or fluids may collect in a larger well in fluid communication one or more channels or wells. In some case, a structure disclosed herein comprises a plurality of channels corresponding to a plurality of loci with a cluster, and the plurality of channels or wells are in fluid communication with one well of the cluster. In some cases, a library of oligonucleic acids is synthesized in a plurality of loci of a cluster, followed by the assembly of the oligonucleic acids into a large nucleic acid such as gene, wherein the assembly of the large nucleic acid optionally occurs within a well of the cluster, e.g., by using PCA.

Provided herein are structures wherein a cluster located on a surface disclosed herein has the same or different width, height, and/or volume as another cluster of the surface. A well located on a surface disclosed herein may have the same or different width, height, and/or volume as another well of the surface. Provided herein are structures wherein a channel located on a surface disclosed herein has the same or different width, height, and/or volume as another channel of the surface. Provided herein are structures wherein the diameter of a cluster is between about 0.05 mm to about 50 mm, between about 0.05 mm to about 10 mm, between about 0.05 mm and about 5 mm, between about 0.05 mm and about 4 mm, between about 0.05 mm and about 3 mm, between about 0.05 mm and about 2 mm, between about 0.05 mm and about 1 mm, between about 0.05 mm and about 0.5 mm, between about 0.05 mm and about 0.1 mm, between about 0.1 mm and 10 mm, between about 0.2 mm and 10 mm, between about 0.3 mm and about 10 mm, between about 0.4 mm and about 10 mm, between about 0.5 mm and 10 mm, between about 0.5 mm and about 5 mm, or between about 0.5 mm and about 2 mm. Provided herein are structures wherein the diameter of a cluster is less than or about 5 mm, 4 mm, 3 mm, 2 mm, 1 mm, 0.5 mm, 0.1 mm, 0.09 mm, 0.08 mm, 0.07 mm, 0.06 mm or 0.05 mm. In some cases, the diameter of a cluster is between about 1.0 and about 1.3 mm. In some cases, the diameter of a cluster is between about 0.5 to 2.0 mm. In some cases, the diameter of a cluster is about 1.150 mm. In some cases, the diameter of a cluster or well, or both is about 0.08 mm.

Provided herein are structures wherein the height of a well is from about 20 μm to about 1000 μm, from about 50 μm to about 1000 μm, from about 100 μm to about 1000 μm, from about 200 μm to about 1000 μm, from about 300 μm to about 1000 μm, from about 400 μm to about 1000 μm, or from about 500 μm to about 1000 μm. In some cases, the height of a well is less than about 1000 μm, less than about 900 μm, less than about 800 μm, less than about 700 μm, or less than about 600 μm.

Provided herein are structures wherein the structure disclosed herein comprises a plurality of channels corresponding to a plurality of loci within a cluster, wherein the height or depth of a channel is from about 5 μm to about 500 μm, from about 5 μm to about 400 μm, from about 5 μm to about 300 μm, from about 5 μm to about 200 μm, from about 5 μm to about 100 μm, from about 5 μm to about 50 μm, or from about 10 μm to about 50 μm. In some cases, the height of a channel is less than 100 μm, less than 80 μm, less than 60 μm, less than 40 μm or less than 20 μm.

Provided herein are structures wherein the diameter of a channel, well, or substantially planar locus is from about 0.5 μm to about 1000 μm, from about 0.5 μm to about 500 μm, from about 0.5 μm to about 200 μm, from about 0.5 μm to about 100 μm, from about 1 μm to about 100 μm, from about 5 μm to about 100 μm, or from about 10 μm to about 100 μm. In some cases, the diameter of a locus is about 90 μm, 80 μm, 70 μm, 60 μm, 50 μm, 40 μm, 30 μm, 20 μm, 10 μm, 1 μm, or 0.5 μm. In some cases, the diameter of a channel, well, or substantially planar locus is less than about 100 μm, 90 μm, 80 μm, 70 μm, 60 μm, 50 μm, 40 μm, 30 μm, 20 μm, 10 μm, 1 μm, or 0.5 μm. In some cases, the distance between the center of two adjacent loci is from about 1 μm to about 500 μm, from about 1 μm to about 200 μm, from about 1 μm to about 100 μm, from about 5 μm to about 200 μm, from about 5 μm to about 100 μm, from about 5 μm to about 50 μm, or from about 5 μm to about 30 μm, for example, about 20 μm.

Each of the resolved loci on the substrate can have any shape that is known in the art, or the shapes that can be made by methods known in the art. For example, each of the resolved loci can have an area that is in a circular shape, a rectangular shape, elliptical shape, or irregular shape. In some instances, the resolved loci can be in a shape that allows liquid to easily flow through without creating air bubbles. Resolved loci can have a circular shape, with a diameter that can be about, at least about, or less than about 0.5, 1 micrometers (μm), 2 μm, 3 μm, 4 μm, 5 μm, 6 μm, 7 μm, 8 μm, 9 μm, 10 μm, 11 μm, 12 μm, 13 μm, 14 μm, 15 μm, 16 μm, 17 μm, 18 μm, 19 μm, 20 μm, 25 μm, 30 μm, 35 μm, 40 μm, 45 μm, 50 μm, 55 μm, 60 μm, 65 μm, 70 μm, 75 μm, 80 μm, 85 μm, 90 μm, 95 μm, 100 μm, 110 μm, 120 μm, 130 μm, 140 μm, 150 μm, 160 μm, 170 μm, 180 μm, 190 μm, 200 μm, 250 μm, 300 μm, 350 μm, 400 μm, 450 μm, 500 μm, 550 μm, 600 μm, 650 μm, 700 μm or 750 μm. In some cases, the resolved loci have a diameter of 80 μm. The resolved loci may have a monodisperse size distribution, i.e. all of the microstructures may have approximately the same width, height, and/or length. A resolved loci of may have a limited number of shapes and/or sizes, for example the resolved loci may be represented in 2, 3, 4, 5, 6, 7, 8, 9, 10, 12, 15, 20, or more distinct shapes, each having a monodisperse size. The same shape can be repeated in multiple monodisperse size distributions, for example, 2, 3, 4, 5, 6, 7, 8, 9, 10, 12, 15, 20, or more monodisperse size distributions. A monodisperse distribution may be reflected in a unimodular distribution with a standard deviation of less than 25%, 20%, 15%, 10%, 5%, 3%, 2%, 1%, 0.1%, 0.05%, 0.01%, 0.001% of the mode or smaller.

Textured Surfaces

Structures disclosed herein can be manufactured to increase the surface area such that, at particular regions for oligonucleic acid growth, the yield is increased. For example a textured surface is provided which comprises raised or recessed textured features, such as posts, wells, or other shapes. Texture features of the surfaces (e.g., posts or wells) are measured by the following parameters: S=surface area per unit cell; $S_0$=surface area without texture; d=depth length; w=width length; and p=pitch length. In exemplary arrangements, the ratio of pitch length to width length is about 2. If the ratio of pitch length to width length is 2, then the following equation may be used to calculate the surface area of a chip with texture:

$$S = p^2\left(1 + \frac{\pi d}{2p}\right).$$ Equation 1

If the ratio of pitch length to width length is 2, then the following equation may be used to calculate the surface area of a chip with texture:

$$S = S_0\left(1 + \frac{\pi d}{2p}\right).$$ Equation 2

Provided herein are structures wherein the width length is at least twice the desired oligonucleic acid length to be synthesized on a surface disclosed herein. In some instances, the width length of a textured feature disclosed herein is greater than about 0.68 nm, 1 nm, 2 nm, 3 nm, 4 nm, 5 nm, 6 nm, 7 nm, 8 nm, 9 nm, 10 nm, 15 nm, 20 nm, 50 nm, 100 nm, 200 nm, 300 nm, 400 nm, 500 nm, 600 nm, 700 nm, 800 nm, 900 nm, 1 µm, 2 µm, 3 µm, 4 µm, 5 µm, 6 µm, 7 µm, 8 µm, 9 µm, or 10 µm. In some instances, the width length of a textured feature disclosed herein is about 0.1 nm, 0.5 nm, 1 nm, 2 nm, 3 nm, 4 nm, 5 nm, 6 nm, 7 nm, 8 nm, 9 nm, 10 nm, 15 nm, 20 nm, 50 nm, 100 nm, 200 nm, 300 nm, 400 nm, 500 nm, 600 nm, 700 nm, 800 nm, 900 nm, 1 µm, 2 µm, 3 µm, 4 µm, 5 µm, 6 µm, 7 µm, 8 µm, 9 µm, or 10 µm. Those of skill in the art appreciate that the width length may fall within any range bound by any of these values, for example 10 nm to 400 nm, 100 nm to 800 nm, or 200 nm to 1 µm. In some instances, the width length is 7 nm to 500 nm. In some case, the width length is 6.8 nm to 500 nm.

Provided herein are structures wherein the pitch length of a textured feature disclosed herein is greater than about 0.1 nm, 0.5 nm, 1 nm, 2 nm, 3 nm, 4 nm, 5 nm, 6 nm, 7 nm, 8 nm, 9 nm, 10 nm, 15 nm, 20 nm, 50 nm, 100 nm, 200 nm, 300 nm, 400 nm, 500 nm, 600 nm, 700 nm, 800 nm, 900 nm, 1 µm, 2 µm, 3 µm, 4 µm, 5 µm, 6 µm, 7 µm, 8 µm, 9 µm, or 10 µm. In some instances, the pitch length of a textured feature disclosed herein is about 0.1 nm, 0.5 nm, 1 nm, 2 nm, 3 nm, 4 nm, 5 nm, 6 nm, 7 nm, 8 nm, 9 nm, 10 nm, 15 nm, 20 nm, 50 nm, 100 nm, 200 nm, 300 nm, 400 nm, 500 nm, 600 nm, 700 nm, 800 nm, 900 nm, 1 µm, 2 µm, 3 µm, 4 µm, 5 µm, 6 µm, 7 µm, 8 µm, 9 µm, or 10 µm. Those of skill in the art appreciate that the pitch length may fall within any range bound by any of these values, for example 10 nm to 400 nm, 100 nm to 800 nm, or 200 nm to 1 µm. In some cases, the pitch length is 14 nm to 1 µm. In some cases, the pitch length is 13.6 nm to 1 µm. In some instances, the pitch length is about twice the width length.

Provided herein are structures wherein the depth length of a textured feature disclosed herein is greater than about 0.1 nm, 0.5 nm, 1 nm, 2 nm, 3 nm, 4 nm, 5 nm, 6 nm, 7 nm, 8 nm, 9 nm, 10 nm, 15 nm, 20 nm, 50 nm, 100 nm, 200 nm, 300 nm, 400 nm, 500 nm, 600 nm, 700 nm, 800 nm, 900 nm, 1 µm, 2 µm, 3 µm, 4 µm, 5 µm, 6 µm, 7 µm, 8 µm, 9 µm, or 10 µm. In some cases, the depth length of a textured feature disclosed herein is about 0.1 nm, 0.5 nm, 1 nm, 2 nm, 3 nm, 4 nm, 5 nm, 6 nm, 7 nm, 8 nm, 9 nm, 10 nm, 15 nm, 20 nm, 50 nm, 100 nm, 200 nm, 300 nm, 400 nm, 500 nm, 600 nm, 700 nm, 800 nm, 900 nm, 1 µm, 2 µm, 3 µm, 4 µm, 5 µm, 6 µm, 7 µm, 8 µm, 9 µm, or 10 µm. Those of skill in the art appreciate that the depth length may fall within any range bound by any of these values, for example 10 nm to 400 nm, 100 nm to 800 nm, or 200 nm to 1 µm. In some instances, the depth length is 8 nm to 1 µm. In some cases, the depth length is 13.6 nm to 2 µm. In some instances, the depth length is about 60% to about 125% of the pitch length.

Provided herein are structures wherein the width length and the pitch length are of a predetermined ratio. The ratio of pitch length to width length can be greater than about 0.1, 0.5, 1, 1.5, 2, 2.5, 3, 3.5, 4, 4.5, 5, 6, 7, 8, 9, or 10. The ratio of pitch length to width length can be about 0.1, 0.5, 1, 1.5, 2, 2.5, 3, 3.5, 4, 4.5, 5, 6, 7, 8, 9, or 10. In some instances, the ratio of pitch length to width length is about 1. In some instances, the ratio of pitch length to width length is about 2.

Provided herein are structures wherein the depth length and the pitch length are of a predetermined ratio. In some instances, the ratio of pitch length to width length is greater than about 0.1, 0.5, 1, 1.5, 2, 2.5, 3, 3.5, 4, 4.5, 5, 6, 7, 8, 9, or 10. In some instances, the ratio of pitch length to width length is about 0.1, 0.5, 1, 1.5, 2, 2.5, 3, 3.5, 4, 4.5, 5, 6, 7, 8, 9, or 10. In some instances, the ratio of depth length to pitch length is about 0.5. In some instances, the ratio of depth length to pitch length is about 0.6 to about 1.2. In some instances, the ratio of pitch length to width length is about 1. In some instances, the ratio of depth length to pitch length is about 0.6 to 1.25, or about 0.6 to about 2.5.

Figure 4:
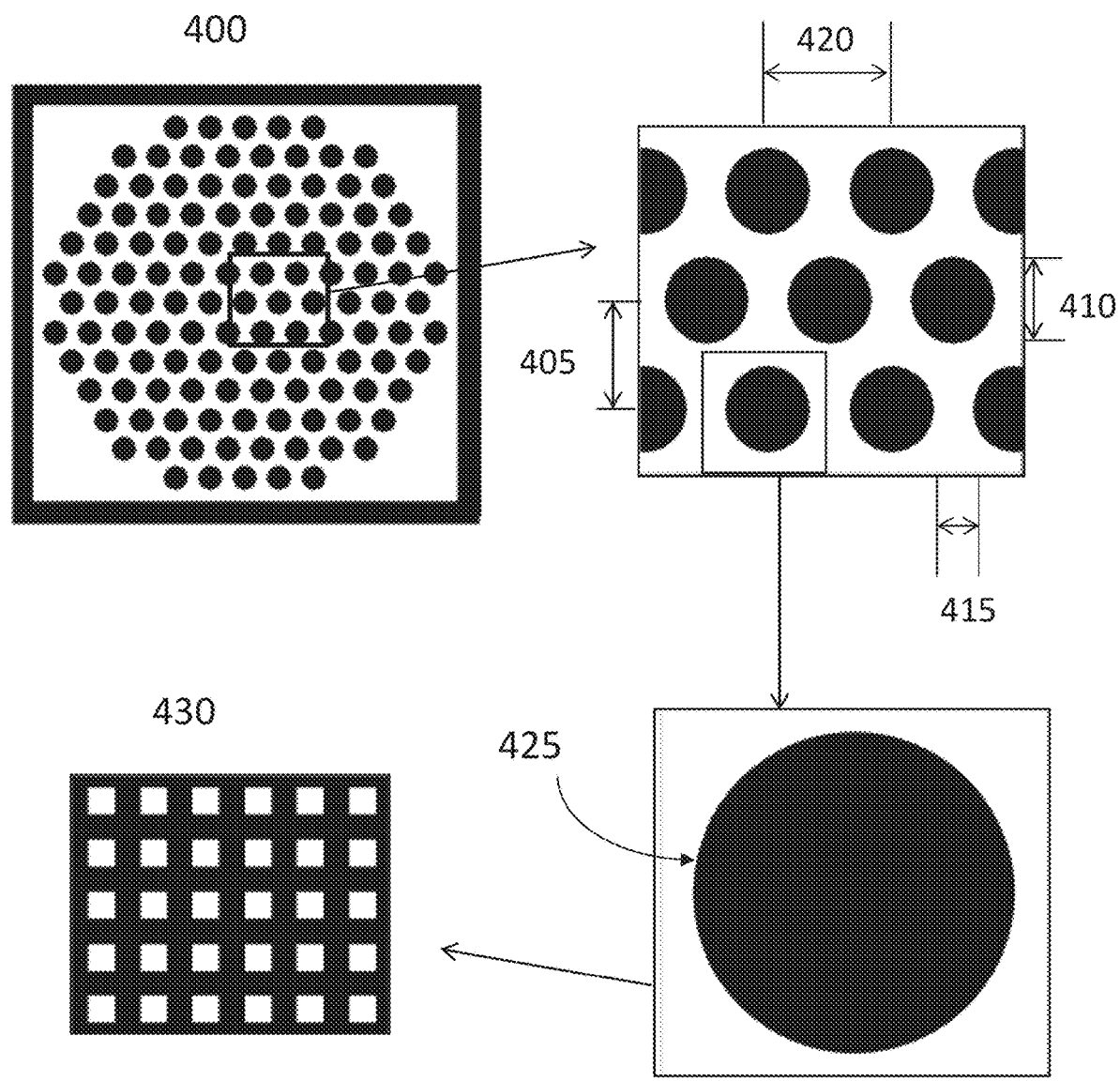
FIG. 4 illustrates loci within a cluster, a section of a cluster, a locus and a textured surface.

Provided herein are structures wherein a surface disclosed herein comprises a plurality of clusters, each cluster comprising a plurality of loci 400, wherein in each loci has a distance apart from each other 415 of about 25.0 µm, a diameter 410 of about 50 µm, a distance from the center of one loci to the center of another loci 405, 420 of 75 µm in X and Y axis directions, FIG. 4, and the surface is optionally textured 430. As exemplary arrangement is illustrated in FIG. 4, where one locus 425 from a cluster of loci 1000 located on a textured surface 403. In some cases, a structure disclosed herein comprises loci having depth to width ratios that greater than about 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, or 20:1. The loci can have a depth to width ratio that is greater than about 5:1. In some cases, the loci have a depth to width ratio that is about 10:1 or greater than 10:1.

Provided herein are structures wherein the surface of a structure described herein is substantially planar or comprises recesses/lowered or protruding/raised features. In some cases, the protrusions comprise wells and/or channels. The raised or lowered features may have sharp or rounded edges and may have cross-sections (widths) of any desired geometric shape, such as rectangular, circular, etc. The lowered features may form channels along the entire substrate surface or a portion of it.

The raised or lowered features may have an aspect ratio of at least or about at least 1:20, 2:20, 3:20, 4:20, 5:20, 6:20, 10:20, 15:20, 20:20, 20:10, 20:5, 20:1, or more. The raised or lowered features may have an aspect ratio of at most or about at most 20:1, 20:5, 20:10, 20:20, 20:15, 20:10, 20:10, 6:20, 5:20, 4:20, 3:20, 2:20, 1:20, or less. The raised or lowered features may have an aspect ratio that falls between 1:20-20:1, 2:20-20:5, 3:20-20:10, 4-20:20:15, 5:20-20:20, 6:20-20:20. Those of skill in the art appreciate that the raised or lowered features may have an aspect ratio that may fall within any range bound by any of these values, for example 3:20-4:20. In some cases, the raised or lowered features have an aspect ratio that falls within any range defined by any of the values serving as endpoints of the range.

Provided herein are structures wherein raised or lowered features have cross-sections of at least or about at least 10 nanometers (nm), 11 nm, 12 nm, 20 nm, 30 nm, 100 nm, 500 nm, 1000 nm, 10000 nm, 100000 nm, 1000000 nm, or more. The raised or lowered features may have cross-sections of at least or most or about at most 1000000 nm, 100000 nm, 10000 nm, 1000 nm, 500 nm, 100 nm, 30 nm, 20 nm, 12 nm, 11 nm, 10 nm, or less. The raised or lowered features may have cross-sections that fall between 10 nm-1000000 nm, 11 nm-100000 nm, 12 nm-10000 nm, 20 nm-1000 nm, 30 nm-500 nm. Those of skill in the art appreciate that the raised or lowered features may have cross-sections that may fall within any range bound by any of these values, for example 10 nm-100 nm. The raised or lowered features may have cross-sections that fall within any range defined by any of the values serving as endpoints of the range.

Provided herein are structures wherein, raised or lowered features have heights of at least or about at least 10 nanometers (nm), 11 nm, 12 nm, 20 nm, 30 nm, 100 nm, 500 nm, 1000 nm, 10000 nm, 100000 nm, 1000000 nm, or more. The raised or lowered features may have heights of at most or about at most 1000000 nanometers (nm), 100000 nm, 10000 nm, 1000 nm, 500 nm, 100 nm, 30 nm, 20 nm, 12 nm, 11 nm, 10 nm, or less. The raised or lowered features may have heights that fall between 10 nm-1000000 nm, 11 nm-100000 nm, 12 nm-10000 nm, 20 nm-1000 nm, 30 nm-500 nm. Those of skill in the art appreciate that the raised or lowered features may have heights that may fall within any range bound by any of these values, for example 100 nm-1000 nm. The raised or lowered features may have heights that fall within any range defined by any of the values serving as endpoints of the range. The individual raised or lowered features may be separated from a neighboring raised or lowered feature by a distance of at least or at least about 5 nanometers (nm), 10 nm, 11 nm, 12 nm, 20 nm, 30 nm, 100 nm, 500 nm, 1000 nm, 10000 nm, 100000 nm, 1000000 nm, or more. The individual raised or lowered features may be separated from a neighboring raised or lowered feature by a distance of at most or about at most 1000000 nanometers (nm), 100000 nm, 10000 nm, 1000 nm, 500 nm, 100 nm, 30 nm, 20 nm, 12 nm, 11 nm, 10 nm, 5 nm, or less. The raised or lowered features may have heights that fall between 5-1000000 nm, 10-100000 nm, 11-10000 nm, 12-1000 nm, 20-500 nm, 30-100 nm. Those of skill in the art appreciate that the individual raised or lowered features may be separated from a neighboring raised or lowered feature by a distance that may fall within any range bound by any of these values, for example 100-1000 nm. The individual raised or lowered features may be separated from a neighboring raised or lowered feature by a distance that falls within any range defined by any of the values serving as endpoints of the range. In some cases, the distance between two raised or lowered features is at least or about at least 0.1, 0.2, 0.5, 1.0, 2.0, 3.0, 5.0, 10.0 times, or more, the cross-section (width) or average cross-section of the raised or lowered features. The distance between the two raised or lowered features is at most or about at most 10.0, 5.0, 3.0, 2.0, 1.0, 0.5, 0.2, 0.1 times, or less, the cross-section (width) or average cross-section of the raised or lowered features. The distance between the two raised or lowered features may be between 0.1-10, 0.2-5.0, 1.0-3.0 times, the cross-section (width) or average cross-section of the raised or lowered features. Those of skill in the art appreciate that the distance between the two raised or lowered features may be between any times the cross-section (width) or average cross-section of the raised or lower features within any range bound by any of these values, for example 5-10 times. The distance between the two raised or lowered features may be within any range defined by any of the values serving as endpoints of the range.

Provided herein are structures wherein groups of raised or lowered features are separated from each other. Perimeters of groups of raised or lowered features may be marked by a different type of structural feature or by differential functionalization. A group of raised or lowered features may be dedicated to the synthesis of a single oligonucleotide. A group of raised or lowered features may span an area that is at least or about at least 10 µm, 11 µm, 12 µm, 13 µm, 14 µm, 15 µm, 20 µm, 50 µm, 70 µm, 90 µm, 100 µm, 150 µm, 200 µm, or wider in cross section. A group of raised or lowered features may span an area that is at most or about at most 200 µm, 150 µm, 100 µm, 90 µm, 70 µm, 50 µm, 20 µm, 15 µm, 14 µm, 13 µm, 12 µm, 11 µm, 10 µm, or narrower in cross section. A group of raised or lowered features may span an area that is between 10-200 µm, 11-150 µm, 12-100 µm, 13-90 µm, 14-70 µm, 15-50 µm, 13-20 µm, wide in cross-section. Those of skill in art appreciate that a group of raised or lowered features may span an area that falls within any range bound by any of these values, for example 12-200 µm. A group of raised or lowered features may span an area that fall within any range defined by any of the values serving as endpoints of the range.

Provided herein are structures wherein a structure comprising a surface is about the size of a standard 96 well plate, for example between about 100 and 200 mm by between about 50 and 150 mm. In some cases, a structure comprising a surface disclosed herein has a diameter less than or equal to about 1000 mm, 500 mm, 450 mm, 400 mm, 300 mm, 250 nm, 200 mm, 150 mm, 100 mm or 50 mm. In some cases, the diameter of a structure comprising a surface disclosed herein is between about 25 mm and 1000 mm, between about 25 mm and about 800 mm, between about 25 mm and about 600 mm, between about 25 mm and about 500 mm, between about 25 mm and about 400 mm, between about 25 mm and about 300 mm, or between about 25 mm and about 200. Non-limiting examples of structure size include about 300 mm, 200 mm, 150 mm, 130 mm, 100 mm, 76 mm, 51 mm and 25 mm. In some cases, a structure comprising a surface disclosed herein has a planar surface area of at least about 100 mm$^2$; 200 mm$^2$; 500 mm$^2$; 1,000 mm$^2$; 2,000 mm$^2$; 5,000 mm$^2$; 10,000 mm$^2$; 12,000 mm$^2$; 15,000 mm$^2$; 20,000 mm$^2$; 30,000 mm$^2$; 40,000 mm$^2$; 50,000 mm$^2$ or more. In some cases, the thickness of a structure comprising a surface disclosed herein is between about 50 um and about 2000 um, between about 50 um and about 1000 um, between about 100 um and about 1000 um, between about 200 um and about 1000 um, or between about 250 um and about 1000 um. Non-limiting examples of structure thickness include 275 um, 375 um, 525 um, 625 um, 675 um, 725 um, 775 um and 925 um. In some cases, the thickness of a structure varies with diameter and depends on the composition of the structure. For example, a structure comprising materials other than silicon has a different thickness than a silicon structure of the same diameter. Structure thickness may be determined by the mechanical strength of the material used and the structure must be thick enough to support its own weight without cracking during handling. Provided herein is a wafer comprises multiple structures (e.g., 1 to 30 or more) disclosed herein.

Provided herein are structures wherein a surface is configured to allow for controlled flow and mass transfer paths for oligonucleic acid synthesis on a surface. The configuration allows for the controlled and even distribution of mass transfer paths, chemical exposure times, and/or wash efficacy during oligonucleic acid synthesis. In some case, the configuration allows for increased sweep efficiency, for example by providing sufficient volume for a growing an oligonucleic acid such that the excluded volume by the growing oligonucleic acid does not take up more than 50, 45, 40, 35, 30, 25, 20, 15, 14, 13, 12, 11, 10, 9, 8, 7, 6, 5, 4, 3, 2, 1%, or less of the initially available volume that is available or suitable for growing the oligonucleic acid.

Provided herein are structures wherein a surface of the structure comprises features with a density of about or greater than about 1, 5, 10, 20, 30, 40, 50, 60, 70, 80, 100, 110, 120, 130, 140, 150, 160, 170, 180, 190, 200, 300, 400 or 500 features per mm². Standard silicon wafer processes can be employed to create a structure surface that will have a high surface area as described above and a managed flow, allowing rapid exchange of chemical exposure. In some cases, the oligonucleotide synthesis surface comprises series of structural features with sufficient separation to allow oligomer chains greater than at least or about at least 20 mer, 25 mer, 30 mer, 50 mer, 100 mer, 200 mer, 250 mer, 300 mer, 400 mer, 500 mer, or more to be synthesized without substantial influence on the overall channel or pore dimension, for example due to excluded volume effects, as the oligonucleotide grows. In some cases, the oligonucleotide synthesis surface comprises a series of structures with sufficient separation to allow oligomer chains greater than at most or about at most 500 mer, 200 mer, 100 mer, 50 mer, 30 mer, 25 mer, 20 mer, or less to be synthesized without substantial influence on the overall channel or pore dimension, for example due to excluded volume effects, as the oligonucleotide grows.

Provided herein are structures wherein the distance between the features is greater than at least or about at least 5 nm, 10 nm, 20 nm, 100 nm, 1000 nm, 10000 nm, 100000 nm, 1000000 nm, or more. In some case, the distance between the features is greater than at most or about at most 1000000 nm, 100000 nm, 10000 nm, 1000 nm, 100 nm, 20 nm, 10 nm, 5 nm, or less. In some case, the distance between the features falls between 5-1000000 nm, 10-100000 nm, 20-10000 nm, or 100-1000 nm. In some case, the distance between the features is greater than 200 nm. The features may be created by any suitable MEMS processes described elsewhere herein or otherwise known in the art, such as a process employing a timed reactive ion etch process. Such semiconductor manufacturing processes can typically create feature sizes smaller than 200 nm, 100 nm, 50 nm, 40 nm, 30 nm, 25 nm, 20 nm, 10 nm, 5 nm, or less. Those of skill in the art appreciate that the feature size smaller than 200 nm can be between any of these values, for example, 20-100 nm. The feature size can fall within any range defined by any of these values serving as endpoints of the range. In some cases, an array of 40 µm wide posts are etched with 30 µm depth, which about doubles the surface area available for synthesis.

Provided herein are devices for oligonucleic acid synthesis, the device comprising a structure having a surface disclosed herein; a plurality of recesses or posts on the surface, wherein each recess or post comprises (i) a width length that is 6.8 nm to 500 nm, (ii) a pitch length that is about twice the width length, and (iii) a depth length that is about 60% to about 125% of the pitch length; a plurality of loci on the surface, wherein each locus has a diameter of 0.5 to 100 um, wherein each locus comprises at least two of the plurality of recesses or posts; a plurality of clusters on the surface, wherein each of the clusters comprise 50 to 500 loci and has a cross-section of 0.5 to 2 mm, wherein the plurality of loci comprise a less than saturating amount of a molecule that binds the surface and couples to nucleoside phosphoramidite; and a plurality of regions surrounding each loci comprise a molecule that binds the surface and does not couple to nucleoside phosphoramidite, wherein the plurality of loci have a higher surface energy than the plurality of regions surrounding each loci. In some cases, the molecule that binds the surface and couples to nucleoside phosphoramidite is a silane disclosed herein. In some cases, the molecule that binds the surface and does not couple to nucleoside phosphoramidite is a fluorosilane disclosed herein. In some cases, the plurality of loci are coated with a molecule that binds the surface, does not couple to nucleoside phosphoramidite, and has a higher surface energy than the molecule on plurality of regions surrounding each loci.

Preparation of Textured Surfaces

As discussed above, FIGS. 5A-5F and FIG. 6 describe a method for generating a textured surface. In some cases, photolithography is applied structure to create a mask of photoresist. In a subsequent step, a deep reactive-ion etching (DRIE) step is used to etch vertical side-walls (e.g., until an insulator layer in a structure comprising an insulator layer) at locations devoid of the photoresist. In a following step, the photoresist is stripped. Photolithography, DRIE and photoresist strip steps may be repeated on the structure handle side. In cases wherein the structure comprises an insulator layer such as silicon dioxide, buried oxide (BOX) is removed using an etching process. Thermal oxidation can then be applied to remove contaminating polymers that may have been deposited on the side walls during the method. In a subsequent step, the thermal oxidation is stripped using a wet etching process.

To resist coat only a small region of the surface (e.g., lowered features such as a well and/or channel), a droplet of resist may be deposited into the lowered feature where it optionally spreads. In some cases, a portion of the resist is removed, for example, by etching (e.g., oxygen plasma etch) to leave a smooth surface covering only a select area.

The surface can be wet cleaned, for example, using a piranha solution. Alternatively, the surface can be plasma cleaned, for example, by dry oxygen plasma exposure. The photoresist may be coated by a process governed by wicking into the device layer channels. The photoresist may be patterned using photolithography to expose areas that are desired to be passive (i.e., areas where oligonucleic acid synthesis is not designed to take place). Patterning by photolithography may occur by exposing the resist to light through a binary mask that has a pattern of interest. After exposure, the resist in the exposed regions may be removed in developer solution.

Alignment Marks

Figure 8:
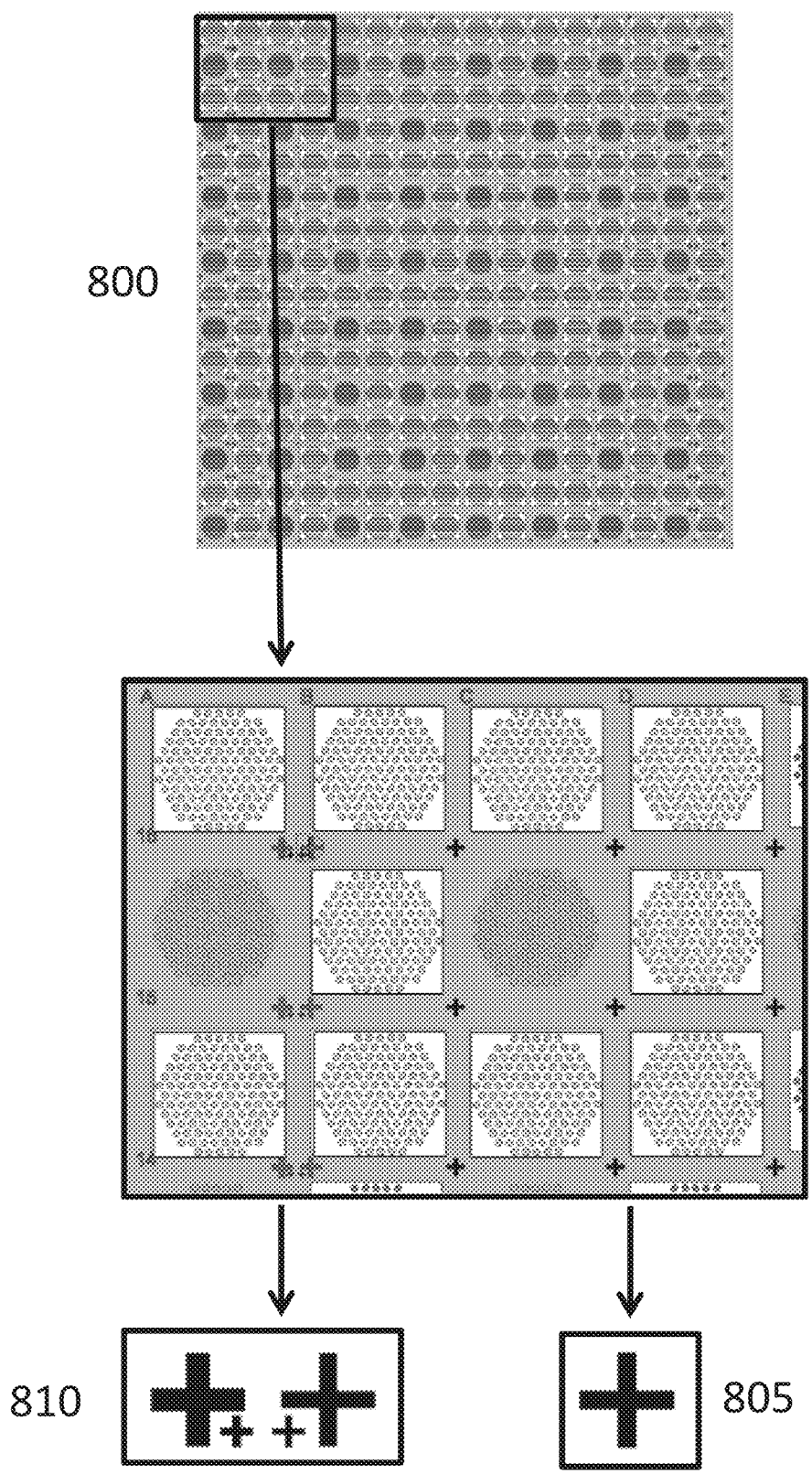
FIG. 8 illustrates a structure having fiducial markings.

During the deposition process, references points on a surface are used by a machine for calibration purposes. Surfaces described herein may comprise fiducial marks, global alignment marks, lithography alignment marks or a combination thereof. Fiducial marks are generally placed on the surface of a structure, such as an array of clusters 800 to facilitate alignment of such devices with other components of a system, FIG. 8 illustrates an exemplary arrangement. The surface of a structure disclosed herein may have one or more fiducial marks, e.g. 2, 3, 4, 5, 6, 7, 8, 9, 10. In some cases, fiducial marks may are used for global alignment of the microfluidic device.

Fiducial marks may have various shapes and sizes. In some cases, a fiducial mark has the shape of a square, circle, triangle, cross, "X", addition or plus sign, subtraction or minus sign, or any combination thereof. In some one example, a fiducial mark is in the shape of an addition or a plus sign 805. In some cases, a fiducial mark comprises a plurality of symbols. Exemplary fiducial mark may comprises one or more plus signs 810, e.g., 2, 3, 4, or more plus signs. In one example, a fiducial mark comprises 4 plus signs.

Fiducial marks may be located on the surface of structures disclosed herein. A fiducial mark may be about 0.5 µm, 1 µm, 2 µm, 3 µm, 4 µm, 5 µm, 6 µm, 7 µm, 8 µm, 9 µm, 10 µm, 100 µm, 1000 µm, 2000 µm, 5000 µm, 7000 µm, 8000 µm, 9000 µm, or 10,000 µm, from the center of the surface.

In some cases, the fiducial mark is located from about 0.1 mm to about 10 mm from the edge of the surface portion, e.g., about 0.5 mm from the edge. In some case, the fiducial is located from about 1 mm to about 10 mm form a cluster, e.g., 1.69 mm. In some instances, a distance from the center of a fiducial mark and a nearest corner of a surface in one dimension is from about 0.5 mm to about 10 mm, e.g., about 1 mm. In some instances, a length of a fiducial mark in one dimension is from about 0.5 mm to about 5 mm, e.g., about 1 mm. In some instances, the width of a fiducial mark is from about 0.01 mm to about 2 mm, e.g., 0.05 mm.

Figure 9:
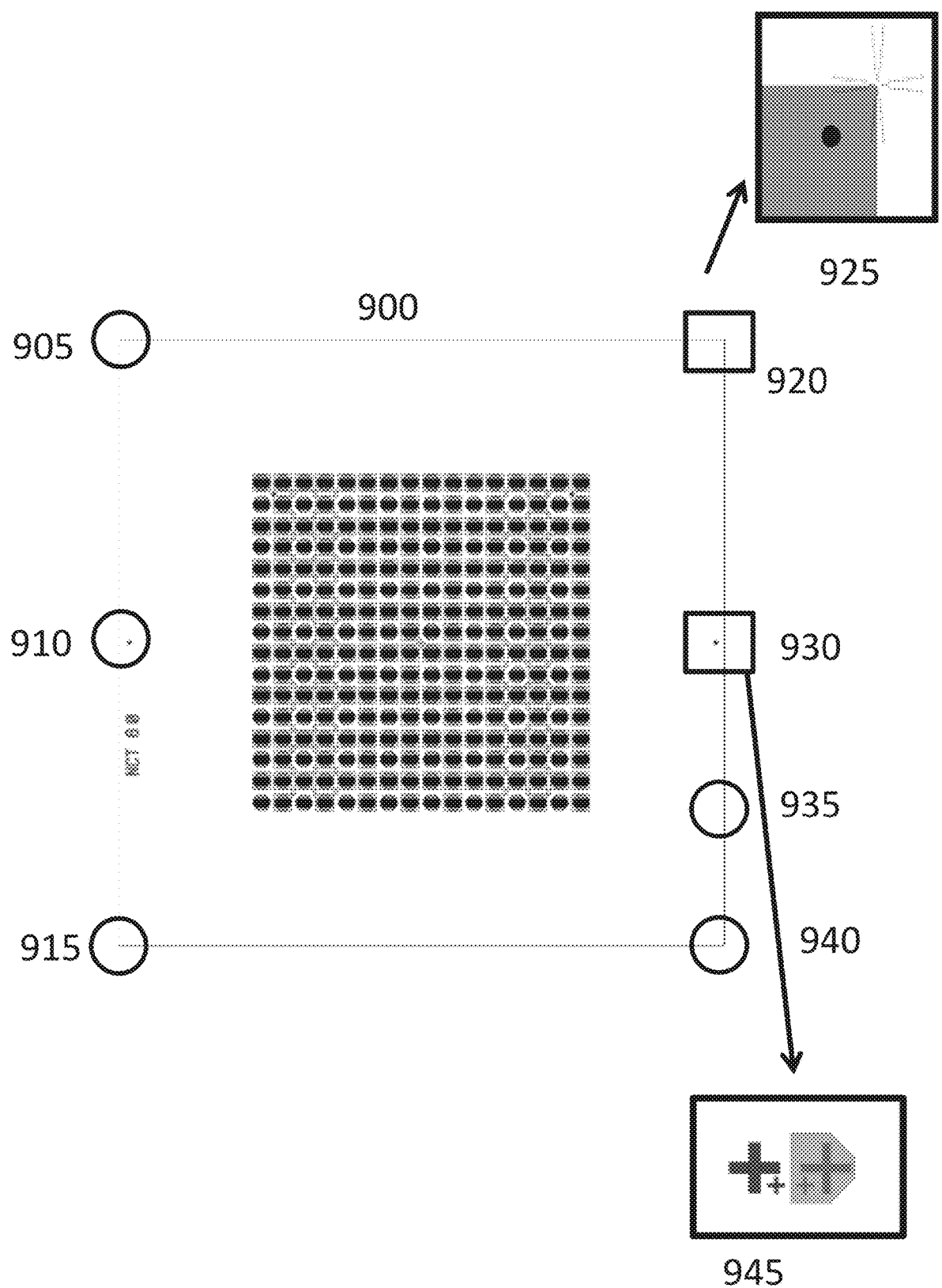
FIG. 9 illustrates another structure having fiducial markings.

Global alignment marks may have various shapes and sizes. Global alignment marks are placed on the surface of a structure described herein to facilitate alignment of such devices with other components of a system, FIG. 9 illustrates an exemplary arrangement. Exemplary global alignment marks have the shape of a square, circle, triangle, cross, "X", addition or plus sign, subtraction or minus sign, or any combination thereof. Exemplary global alignment marks include the shape of a circle 925 or a plus mark 945. In some cases, a global alignment mark is located near an edge of the substrate portion, as shown by the location of marks 905, 910, 915, 920, 930, 935, and 940. A global alignment mark can comprise a plurality of symbols. In some case, a global alignment mark comprises one or more circles, e.g., 2, 3, 4, or more plus signs.

A global alignment mark may be located on the surface of a structure disclosed herein. In some cases, the global alignment mark is about 0.5 µm, 1 µm, 2 µm, 3 µm, 4 µm, 5 µm, 6 µm, 7 µm, 8 µm, 9 µm, 10 µm, 100 µm, 1000 µm, 2000 µm, 5000 µm, 7000 µm, 8000 µm, 9000 µm, or 10,000 µm, from the center of the surface. In some case, the global alignment mark is about 0.5 µm, 1 µm, 2 µm, 3 µm, 4 µm, 5 µm, 6 µm, 7 µm, 8 µm, 9 µm, 10 µm, 100 µm, 1000 µm, 2000 µm, 5000 µm, 7000 µm, 8000 µm, 9000 µm, or 10,000 µm, from the edge of the surface. In some cases, the global alignment mark is about 0.5 µm, 1 µm, 2 µm, 3 µm, 4 µm, 5 µm, 6 µm, 7 µm, 8 µm, 9 µm, 10 µm, 100 µm, 200 µm, 300 µm, 400 µm, 500 µm, 750 µm, or 1000 µm in size. In an example arrangement, the global alignment mark is about 125 µm in diameter and is located about 1000 µm from the edge of the surface of the structure. Surface disclosed herein may comprise one or more global alignment marks, e.g. 2, 3, 4, 5, 6, 7, 8, 9, 10, or more marks. The distance between the global alignment marks may be about 1 µm, 2 µm, 3 µm, 4 µm, 5 µm, 6 µm, 7 µm, 8 µm, 9 µm, 10 µm, 100 µm, 500 µm, 1000 µm, 2000 µm, 5000 µm, 7000 µm, 8000 µm, 9000 µm, or 10,000 µm.

Oligonucleic Acid Synthesis

De Novo Synthesis Workflow

Figure 10:
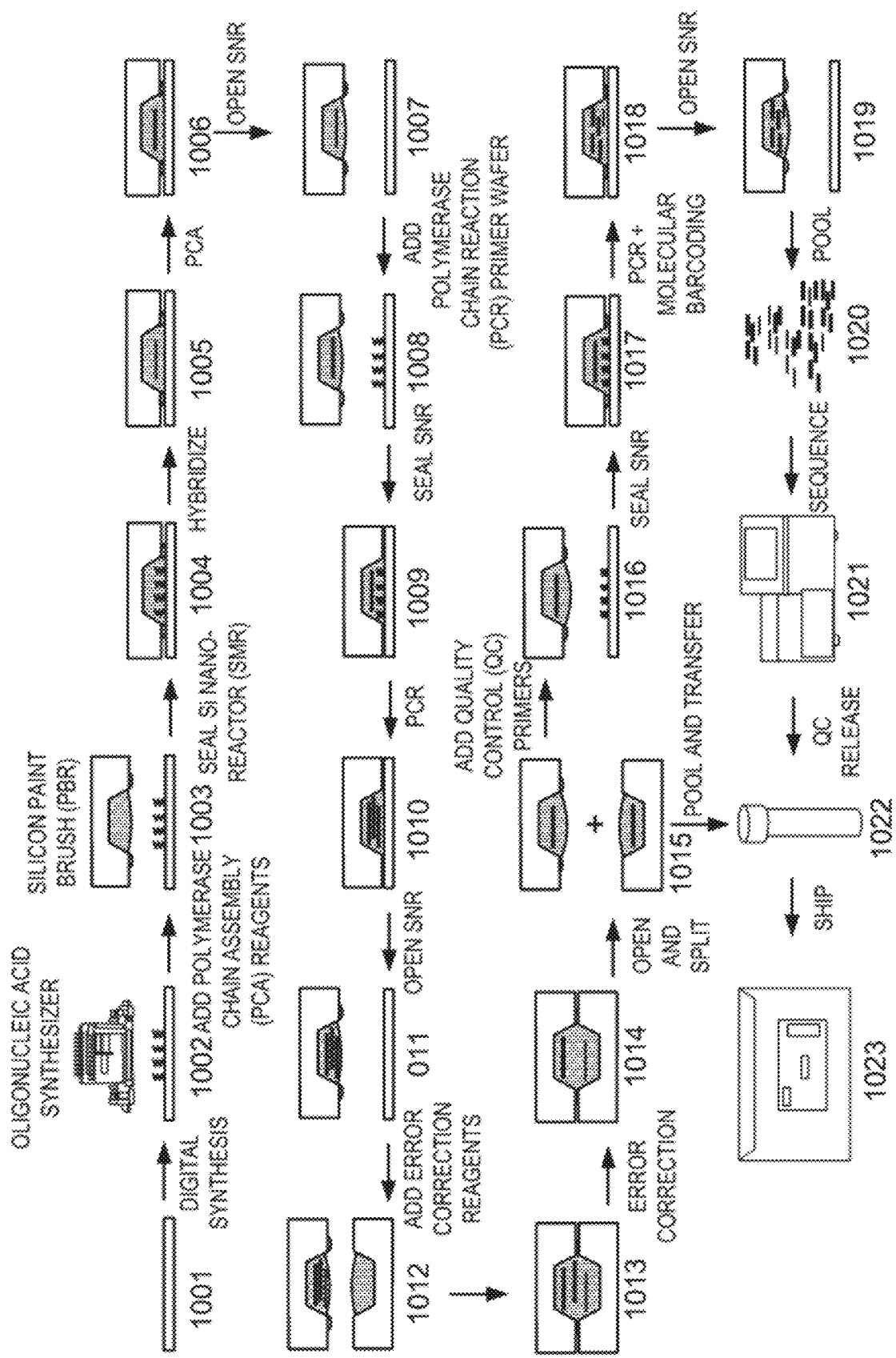
FIG. 10 is a diagram demonstrating a process workflow from oligonucleic synthesis to gene shipment.

Structures having modified surfaces described herein may be used for de novo synthesis processes. An exemplary workflow for one such process is divided generally into phases: (1) de novo synthesis of a single stranded oligonucleic acid library, (2) joining oligonucleic acids to form larger fragments, (3) error correction, (4) quality control, and (5) shipment, FIG. 10. Prior to de novo synthesis, an intended nucleic acid sequence or group of nucleic acid sequences is preselected. For example, a group of genes is preselected for generation.

Once preselected nucleic acids for generation are selected, a predetermined library of oligonucleic acids is designed for de novo synthesis. Various suitable methods are known for generating high density oligonucleic acid arrays. In the workflow example, a surface layer 1001 is provided. In the example, chemistry of the surface is altered in order to improve the oligonucleic acid synthesis process. Areas of low surface energy are generated to repel liquid while areas of high surface energy are generated to attract liquids. The surface itself may be in the form of a planar surface or contain variations in shape, such as protrusions or microwells which increase surface area. In the workflow example, high surface energy molecules selected serve a dual function of supporting DNA chemistry, as disclosed in International Patent Application Publication WO/2015/021080, which is herein incorporated by reference in its entirety.

In situ preparation of oligonucleic acid arrays is generated on a solid support and utilizes single nucleotide extension process to extend multiple oligomers in parallel. A device, such as an oligonucleic acid synthesizer, is designed to release reagents in a step wise fashion such that multiple oligonucleic acids extend, in parallel, one residue at a time to generate oligomers with a predetermined nucleic acid sequence 1002. In some cases, oligonucleic acids are cleaved from the surface at this stage. Cleavage may include gas cleavage, e.g., with ammonia or methylamine.

The generated oligonucleic acid libraries are placed in a reaction chamber. In this exemplary workflow, the reaction chamber (also referred to as "nanoreactor") is a silicon coated well, containing PCR reagents and lowered onto the oligonucleic acid library 1003. Prior to or after the sealing 1004 of the oligonucleic acids, a reagent is added to release the oligonucleic acids from the surface. In the exemplary workflow, the oligonucleic acids are released subsequent to sealing of the nanoreactor 1005. Once released, fragments of single stranded oligonucleic acids hybridize in order to span an entire long range sequence of DNA. Partial hybridization 1005 is possible because each synthesized oligonucleic acid is designed to have a small portion overlapping with at least one other oligonucleic acid in the pool.

After hybridization, a PCA reaction is commenced. During the polymerase cycles, the oligonucleic acids anneal to complementary fragments and gaps are filled in by a polymerase. Each cycle increases the length of various fragments randomly depending on which oligonucleic acids find each other. Complementarity amongst the fragments allows for forming a complete large span of double stranded DNA 1006.

After PCA is complete, the nanoreactor is separated from the surface 1007 and positioned for interaction with a polymerase 1008. After sealing, the nanoreactor is subject to PCR 1009 and the larger nucleic acids are formed. After PCR 1010, the nanochamber is opened 1011, error correction reagents are added 1012, the chamber is sealed 1013 and an error correction reaction occurs to remove mismatched base pairs and/or strands with poor complementarity from the double stranded PCR amplification products 1014. The nanoreactor is opened and separated 1015. Error corrected product is next subject to additional processing steps, such as PCR and molecular bar coding, and then packaged 1022 for shipment 1023.

In some cases, quality control measures are taken. After error correction, quality control steps include for example interaction with a wafer having sequencing primers for amplification of the error corrected product 1016, sealing the wafer to a chamber containing error corrected amplification product 1017, and performing an additional round of amplification 1018. The nanoreactor is opened 1019 and the products are pooled 1020 and sequenced 1021. After an acceptable quality control determination is made, the packaged product 1022 is approved for shipment 1023.

The structures described herein comprise actively functionalized surfaces configured to support the attachment and synthesis of oligonucleic acids. Synthesized oligonucleic acids include oligonucleic acids comprising modified and/or non-canonical bases and/or modified backbones. In various methods, a library of oligonucleic acids having pre-selected sequences is synthesized on a structure disclosed herein. In some cases, one or more of the oligonucleic acids has a different sequence and/or length than another oligonucleic acid in the library. The stoichiometry of each oligonucleic acid synthesized on a surface is controlled and tunable by varying one or more features of the surface (e.g., functionalized surface) and/or oligonucleic acid sequence to be synthesized; one or more methods for surface functionalization and/or oligonucleic acid synthesis; or a combination thereof. In many instances, controlling the density of a growing oligonucleic acid on a resolved locus of a structure disclosed herein allows for oligonucleic acids to be synthesized with a low error rate.

Oligonucleic acids synthesized using the methods and/or devices described herein include at least about 50, 60, 70, 75, 80, 90, 100, 120, 150, 200, 300, 400, 500, 600, 700, 800 or more bases. A library of oligonucleic acids may be synthesized, wherein a population of distinct oligonucleic acids are assembled to generate a larger nucleic acid comprising at least about 500; 1,000; 2,000; 3,000; 4,000; 5,000; 6,000; 7,000; 8,000; 9,000; 10,000; 11,000; 12,000; 13,000; 14,000; 15,000; 16,000; 17,000; 18,000; 19,000; 20,000; 25,000; 30,000; 40,000; or 50,000 bases. Oligonucleic acid synthesis methods described herein are useful for the generation of an oligonucleic acid library comprising at least 500; 1,000; 5,000; 10,000; 20,000; 50,000; 100,000; 200,000; 300,000; 400,000; 500,000; 600,000; 700,000; 800,000; 900,000; 1,000,000; 1,100,000; 1,200,000; 1,300,000; 1,400,000; 1,500,000; 1,600,000; 1,700,000; 1,800,000; 1,900,000; 2,000,000; 2,200,000; 2,400,000; 2,600,000; 2,800,000; 3,000,000; 3,500,000; 4,00,000; or 5,000,000 distinct oligonucleic acids. In some case, at least about 1 pmol, 10 pmol, 20 pmol, 30 pmol, 40 pmol, 50 pmol, 60 pmol, 70 pmol, 80 pmol, 90 pmol, 100 pmol, 150 pmol, 200 pmol, 300 pmol, 400 pmol, 500 pmol, 600 pmol, 700 pmol, 800 pmol, 900 pmol, 1 nmol, 5 nmol, 10 nmol, 100 nmol or more of an oligonucleic acid is synthesized within a locus.

Figure 11:
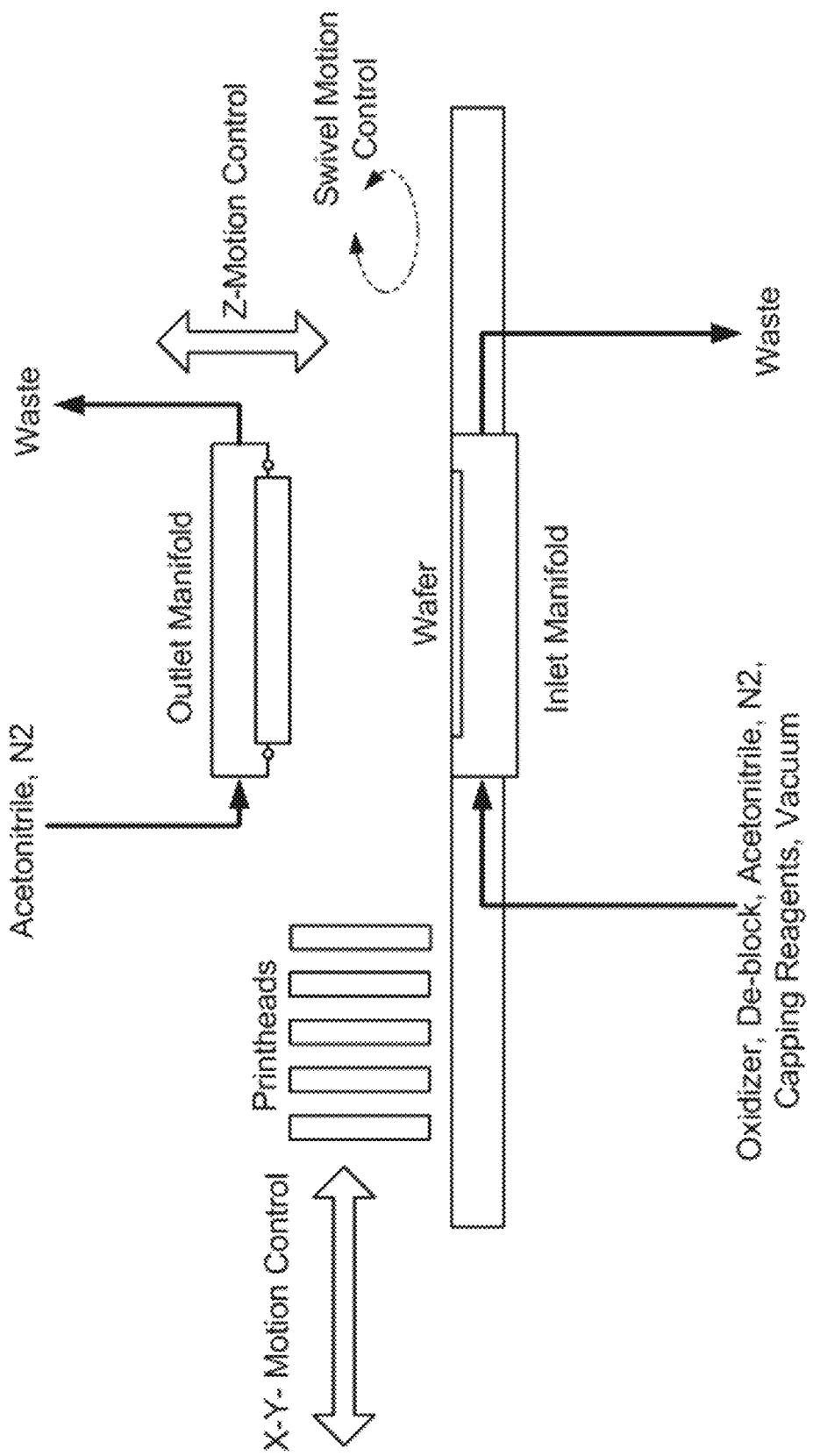
FIG. 11 illustrates an outline of a system for nucleic acid synthesis, including an oligonucleic acid synthesizer, a structure (wafer), schematics outlining the alignment of the system elements in multiple directions, and exemplary set-ups for reagent flow.

Oligonucleic acids are synthesized on a surface described herein using a system comprising an oligonucleic acid synthesizer that deposits reagents necessary for synthesis, FIG. 11. Reagents for oligonucleic acid synthesis include, for example, reagents for oligonucleic acid extension and wash buffers. As non-limiting examples, the oligonucleic acid synthesizer deposits coupling reagents, capping reagents, oxidizers, de-blocking agents, acetonitrile and gases such as nitrogen gas. In addition, the oligonucleic acid synthesizer optionally deposits reagents for the preparation and/or maintenance of structure integrity. The oligonucleic acid synthesizer comprises material deposition devices that can move in the X-Y direction to align with the location of the surface of the structure. The oligonucleic acid synthesizer can also move in the Z direction to seal with the surface of the structure, forming a resolved reactor.

Methods are provided herein where at least or about at least 2, 3, 4, 5, 6, 7, 8, 9, 10, 11, 12, 13, 14, 15, 16, 17, 18, 19, 20, 21, 22, 23, 24, 25, 30, 35, 40, 45, 50, 100, 150, 200, 250, 300, 350, 400, 450, 500, 550, 600, 650, 700, 750, 800, 850, 900, 1000, 10000, 50000, 100000 or more nucleic acids can be synthesized in parallel. Total molar mass of nucleic acids synthesized within the device or the molar mass of each of the nucleic acids may be at least or at least about 10, 20, 30, 40, 50, 100, 250, 500, 750, 1000, 2000, 3000, 4000, 5000, 6000, 7000, 8000, 9000, 10000, 25000, 50000, 75000, 100000 picomoles, or more.

Figure 12:
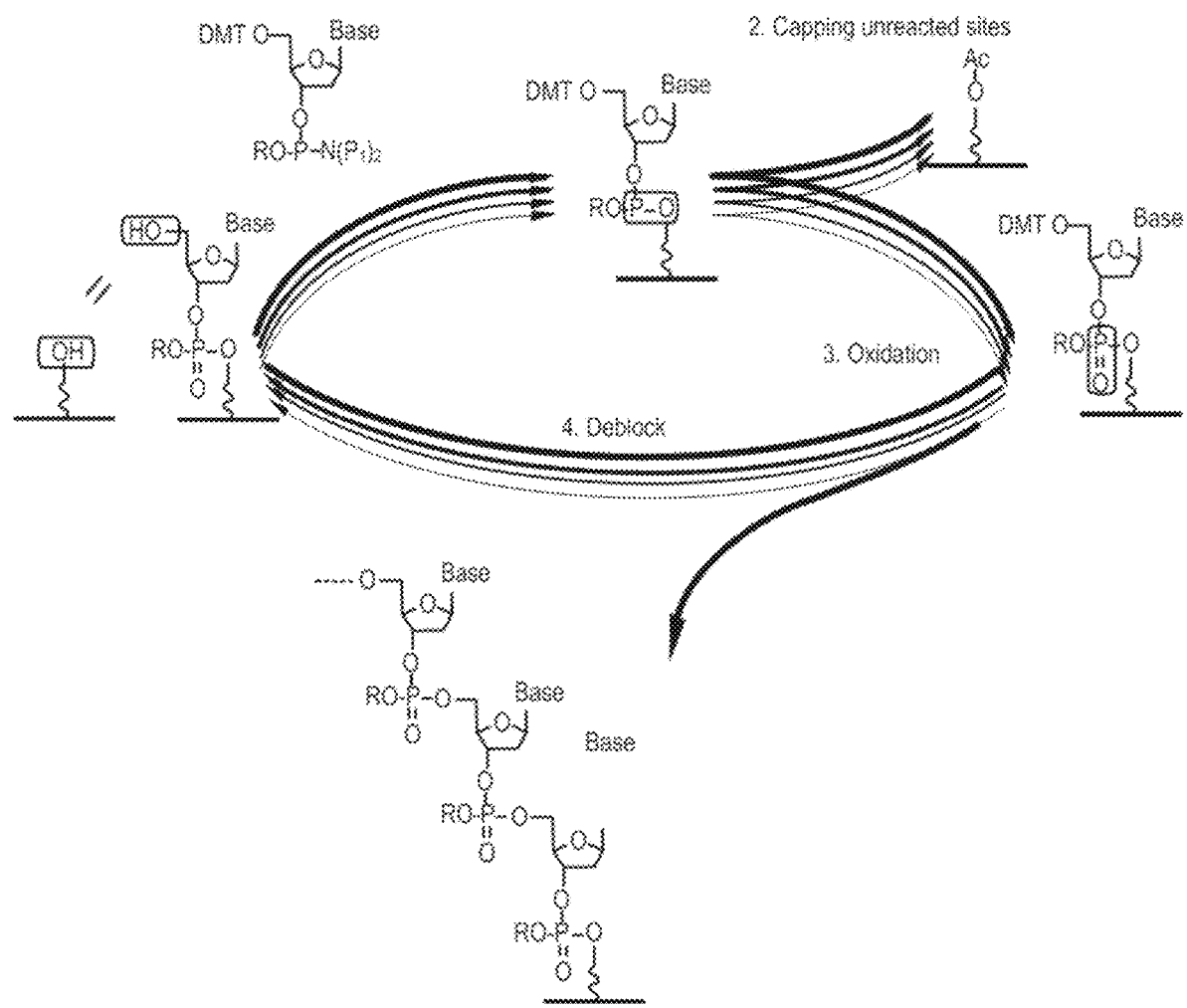
FIG. 12 illustrates phosphoramidite chemistry for oligonucleotide synthesis.

Oligonucleic acid synthesis methods disclosed herein include those which are enzyme independent. An example of a synthesis method that is useful with the devices provided herein is one that incorporates phosphoramidite chemistry, FIG. 12. Typically, after the deposition of a monomer, e.g., a mononucleotide, a dinucleotide, or a longer oligonucleotide with suitable modifications for phosphoramidite chemistry one or more of the following steps may be performed at least once to achieve the step-wise synthesis of high-quality polymers in situ: 1) Coupling, 2) Capping, 3) Oxidation, 4) Sulfurization, and 5) Deblocking (detritylation). Washing steps typically intervene steps 1 to 5.

Provided herein are methods wherein an oligonucleic acid error rate is dependent on the efficiency of one or more chemical steps of oligonucleic acid synthesis. In some cases, oligonucleic acid synthesis comprises a phosphoramidite method, wherein a base of a growing oligonucleic acid chain is coupled to phosphoramidite. Coupling efficiency of the base is related to the error rate. For example, higher coupling efficiency correlates to lower error rates. In some cases, the devices and/or synthesis methods described herein allow for a coupling efficiency greater than 98%, 98.5%, 99%, 99.5%, 99.6%, 99.7%, 99.8%, 99.9%, 99.95%, 99.96%, 99.97%, 99.98%, or 99.99%. In some cases, an oligonucleic acid synthesis method comprises a double coupling process, wherein a base of a growing oligonucleic acid chain is coupled with a phosphoramidite, the oligonucleic acid is washed and dried, and then treated a second time with a phosphoramidite. Efficiency of deblocking in a phosphoramidite oligonucleic acid synthesis method also contributes to error rate. In some cases, the devices and/or synthesis methods described herein allow for removal of 5'-hydroxyl protecting groups at efficiencies greater than 98%, 98.5%, 99%, 99.5%, 99.6%, 99.7%, 99.8%, 99.9%, 99.95%, 99.96%, 99.97%, 99.98%, or 99.99%. Error rate may be reduced by minimization of depurination side reactions.

Methods for the synthesis of oligonucleic acids typically involve an iterating sequence of the following steps: application of a protected monomer to an actively functionalized surface (e.g., locus) to link with either the activated surface, a linker or with a previously deprotected monomer; deprotection of the applied monomer so that it can react with a subsequently applied protected monomer; and application of another protected monomer for linking. One or more intermediate steps include oxidation or sulfurization. In some cases, one or more wash steps precede or follow one or all of the steps.

In an exemplary method, at least 20,000 or more non-identical oligonucleic acids each at least 10, 50, 100 or more bases in length are synthesized, wherein each of the at least 20,000 non-identical oligonucleic acids extends from a different locus of the patterned surface. Methods disclosed herein provides for at least 20,000 non-identical oligonucleic acids collectively encoding for at least 200 preselected nucleic acids, and have an aggregate error rate of less than 1 in 1500 bases compared to predetermined sequences without correcting errors. In some cases, the aggregate error rate is less than 1 in 2000, less than 1 in 3000 bases or less compared to the predetermined sequences. Surfaces provided herein provide for the low error rates.

Oligonucleotide Libraries with Low Error Rates

The term "error rate" may also be referred to herein as a comparison of the collective sequence encoded by oligonucleic acids generated compared to the sequence of one or more predetermined longer nucleic acid, e.g., a gene. An aggregate "error rate" refers to the collective error rate of synthesized nucleic acids compared to the predetermined sequences for which the nucleic acids are intended to encode. Error rates include mismatch error rate, deletion error rate, insertion error rate, insertion/deletion error rate, any combination thereof. Methods and devices herein provide for low error rates are for synthesized oligonucleic acid libraries having at least 20,000; 40,000; 60,000; 80,000; 100,000; 200,000; 300,000; 400,000; 500,000; 600,000; 700,000; 800,000; 1,000,000; or 2,000,000 or more oligonucleic acids. Loci may be configured to comprise a population of oligonucleic acids, wherein the population may be configured to comprise oligonucleic acids having the same or different sequences.

Devices and methods described herein provide for a low overall error rate for the individual types of errors are achieved. Individual types of error rates include deletions, insertions, or substitutions for an oligonucleic acid library synthesized. In some cases, oligonucleic acids synthesized have an average error rate of about 1:500, 1:1000, 1:2000, 1:3000, 1:4000, 1:5000, 1:6000, 1:7000, 1:8000, 1:9000, 1:10000 or less. These error rates may be for at least 50%, 60%, 70%, 80%, 90%, 95%, 98%, 99%, 99.5%, or more of the oligonucleic acids synthesized.

Methods described herein provide synthesis of oligonucleic acids having an average deletion error rate of about 1:500, 1:1000, 1:1700, 1:2000, 1:3000, 1:4000, 1:5000, 1:6000, 1:7000, 1:8000, 1:9000, 1:10000 or less. Methods described herein provide synthesis of oligonucleic acids having an deletion error rate of about 1:500, 1:1000, 1:1700, 1:2000, 1:3000, 1:4000, 1:5000, 1:6000, 1:7000, 1:8000, 1:9000, 1:10000 or less. Methods described herein provide synthesis of oligonucleic acids having an average insertion error rate of about 1:500, 1:1000, 1:2000, 1:3000, 1:4000, 1:5000, 1:6000, 1:7000, 1:8000, 1:9000, 1:10000 or less. Methods described herein provide synthesis of oligonucleic acids having an insertion error rate of about 1:500, 1:1000, 1:2000, 1:3000, 1:4000, 1:5000, 1:6000, 1:7000, 1:8000, 1:9000, 1:10000 or less. Methods described herein provide synthesis of oligonucleic acids having an average substitution error rate of about 1:500, 1:1000, 1:2000, 1:3000, 1:4000, 1:5000, 1:6000, 1:7000, 1:8000, 1:9000, 1:10000 or less. Methods described herein provide synthesis of oligonucleic acids having a substitution error rate of about 1:500, 1:1000, 1:2000, 1:3000, 1:4000, 1:5000, 1:6000, 1:7000, 1:8000, 1:9000, 1:10000 or less. The overall error rate or error rates for individual types of errors such as deletions, insertions, or substitutions for each oligonucleotide synthesized, may be for at least 50%, 60%, 70%, 80%, 90%, 95%, 98%, 99%, 99.5%, or more of the oligonucleotides synthesized.

Oligonucleic Acid Release and Assembly

Oligonucleic acids synthesized using the methods and devices described herein, are optionally released from the surface from which they were synthesized. In some cases, oligonucleic acids are cleaved from the surface at this stage. Cleavage may include gaseous cleavage, e.g., with gaseous ammonia or gaseous methylamine. Loci in a single cluster collectively correspond to sequence encoding for a single gene, and, when cleaved, may remain on the surface of the loci within a cluster. The application of ammonia gas is used to simultaneously deprotect phosphates groups protected during the synthesis steps, i.e. removal of electron-withdrawing cyano group. Once released from the surface, oligonucleic acids may be assembled into larger nucleic acids. Synthesized oligonucleic acids are useful, for example, as components for gene assembly/synthesis, site-directed mutagenesis, nucleic acid amplification, microarrays, and sequencing libraries.

Provided herein are methods where oligonucleic acids of predetermined sequence are designed to collectively span a large region of a target sequence, such as a gene. In some cases, larger oligonucleic acids are generated through ligation reactions to join the synthesized oligonucleic acids. One example of a ligation reaction is polymerase chain assembly (PCA). In some cases, at least of a portion of the oligonucleic acids are designed to include an appended region that is a substrate for universal primer binding. For PCA reactions, the presynthesized oligonucleic acids include overlaps with each other (e.g., 4, 20, 40 or more bases with overlapping sequence). During the polymerase cycles, the oligonucleic acids anneal to complementary fragments and then are filled in by polymerase. Each cycle thus increases the length of various fragments randomly depending on which oligonucleic acids find each other. Complementarity amongst the fragments allows for forming a complete large span of double stranded DNA. In some cases, after the PCA reaction is complete, an error correction step is conducted using mismatch repair detecting enzymes to remove mismatches in the sequence. Once larger fragments of a target sequence are generated, they can be amplified. For example, in some cases, a target sequence comprising 5' and 3' terminal adaptor sequences is amplified in a polymerase chain reaction (PCR) which includes modified primers, e.g., uracil containing primers the hybridize to the adaptor sequences.

Figure 13:
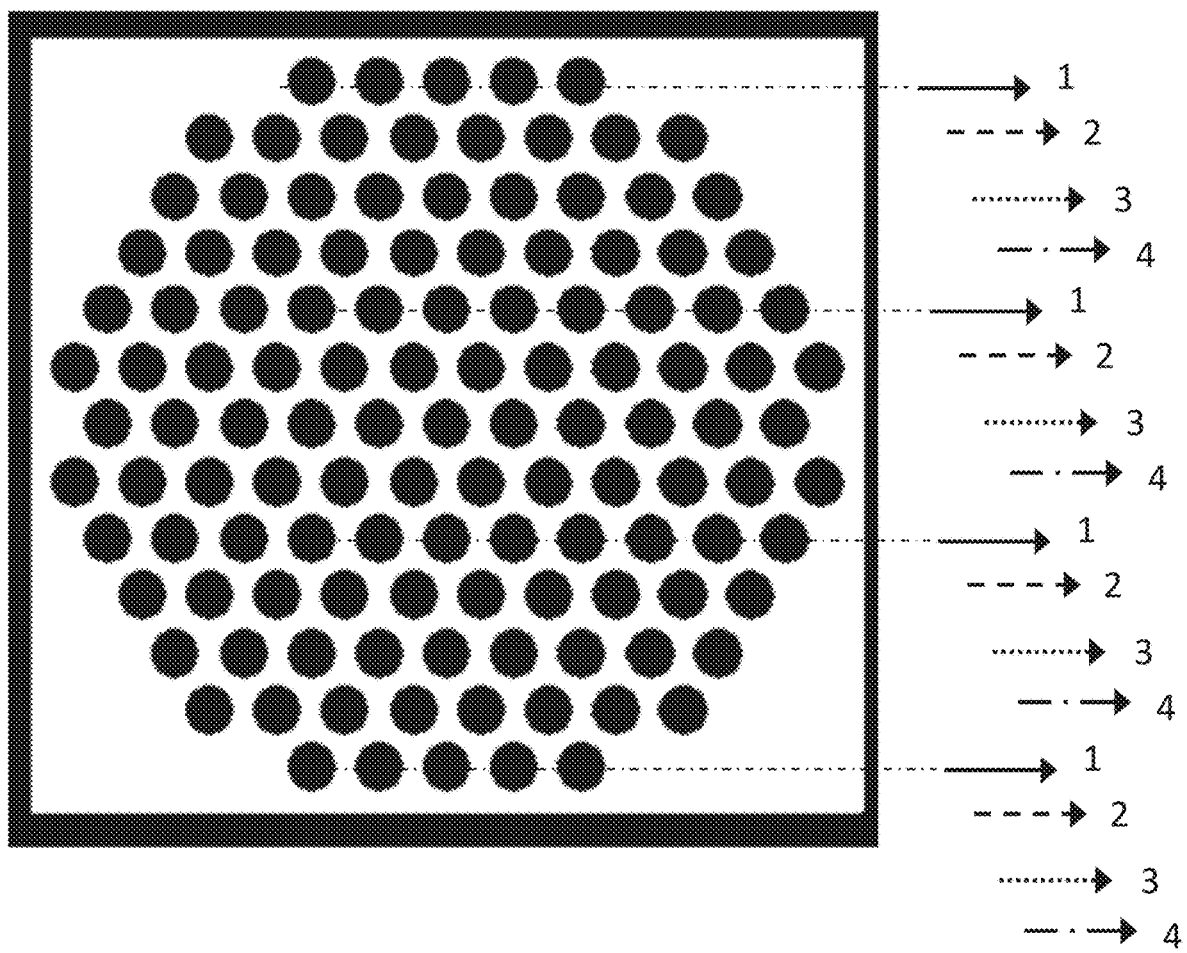
FIG. 13 illustrates a pass-printing scheme.

Provided herein are methods wherein following oligonucleic acid synthesis, oligonucleic acids within one cluster are released from their respective surfaces and pooled into the common area, such as a ell. In some cases, the pooled oligonucleic acids are assembled into a larger nucleic acid, such as a gene, within the well. In some cases, at least about 1, 10, 50, 100, 200, 240, 500, 1000, 10000, 20000, 50000, 100000, 1000000 or more nucleic acids are assembled from oligonucleic acids synthesized on a surface disclosed herein. A pass-printing scheme may be used to deliver reagents to loci in a cluster, as wells as to transfer synthesis reaction products to another location. At least 2, 3, 4, 5, 6, 7, 8, 9, or 10 passes may be used to deliver reagents. For example, four passes of the may be used to deliver reagents to a second structure for assembly or analysis, FIG. 13. In some cases, assembled nucleic acids generated by methods described herein have a low error rate compared to a predetermined sequence without correcting errors. In some cases, assembled nucleic acids generated by methods described herein have an error rate of less than 1:1000, 1:1500, 1:2000, 1:2500, 1:3000 bases compared to a predetermined sequence without correcting errors.

Computer Systems

Methods are provided herein for attachment of pre-synthesized oligonucleotide and/or polynucleotide sequences to a support and in situ synthesis of the same using light-directed methods, flow channel and spotting methods, inkjet methods, pin-based methods and/or bead-based methods are used. In some cases, pre-synthesized oligonucleotides are attached to a support or are synthesized using a spotting methodology wherein monomers solutions are deposited drop wise by a dispenser that moves from region to region. In one example, oligonucleotides are spotted on a support using a mechanical wave actuated dispenser.

The systems described herein can further include a member for providing a droplet to a first spot (or feature) having a plurality of support-bound oligonucleotides. The droplet can include one or more compositions comprising nucleotides or oligonucleotides (also referred herein as nucleotide addition constructs) having a specific or predetermined nucleotide to be added and/or reagents that allow one or more of hybridizing, denaturing, chain extension reaction, ligation, and digestion. In some cases, different compositions or different nucleotide addition constructs may be deposited at different addresses on the support during any one iteration so as to generate an array of predetermined oligonucleotide sequences (the different features of the support having different predetermined oligonucleotide sequences). One particularly useful way of depositing the compositions is by depositing one or more droplet, each droplet containing the desired reagent (e.g. nucleotide addition construct) from a pulse jet device spaced apart from the support surface, onto the support surface or features built into the support surface.

A substrate with resolved features is "addressable" when it has multiple regions of different moieties (e.g., different polynucleotide sequences) such that a region (i.e., a "feature" or "spot" of the substrate) at a particular predetermined location (i.e., an "address") on the substrate will detect a particular target or class of targets (although a feature may incidentally detect non-targets of that location). Substrate features are typically, but need not be, separated by intervening spaces. In some cases, features may be built into a substrate and may create one-, two-, or three-dimensional microfluidic geometries. A "substrate layout" refers to one or more characteristics of the features, such as feature positioning on the substrate, one or more feature dimensions, and an indication of a molecule at a given location.

Any of the systems described herein, may be operably linked to a computer and may be automated through a computer either locally or remotely. Methods and disclosed herein may further comprise software programs on computer systems and use thereof. Accordingly, computerized control for the synchronization of the dispense/vacuum/refill functions such as orchestrating and synchronizing the material deposition device movement, dispense action and vacuum actuation are within the bounds of the invention. The computer systems may be programmed to interface between the user specified base sequence and the position of a material deposition device to deliver the correct reagents to specified regions of the substrate.

Figure 14:
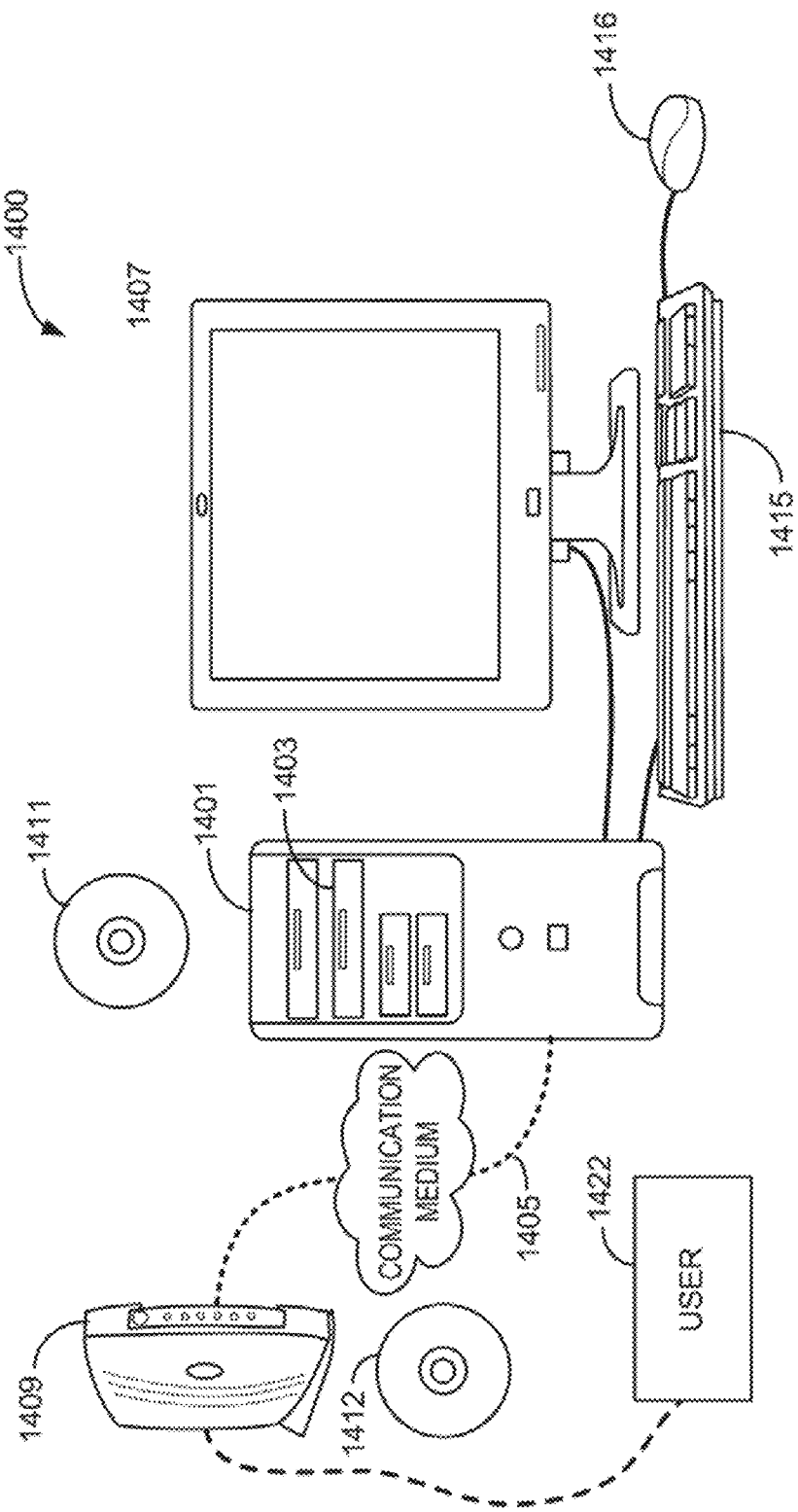
FIG. 14 illustrates a computer system.

The computer system 1400 illustrated in FIG. 14 may be understood as a logical apparatus that can read instructions from media 1411 and/or a network port 1405, which can optionally be connected to server 1409 having fixed media 1412. The system can include a CPU 1401, disk drives 1403, optional input devices such as keyboard 1415 and/or mouse 1416 and optional monitor 1407. Data communication can be achieved through the indicated communication medium to a server at a local or a remote location. The communication medium can include any means of transmitting and/or receiving data. For example, the communication medium can be a network connection, a wireless connection or an internet connection. Such a connection can provide for communication over the World Wide Web. It is envisioned that data relating to the present disclosure can be transmitted over such networks or connections for reception and/or review by a party 1422.

Figure 15:
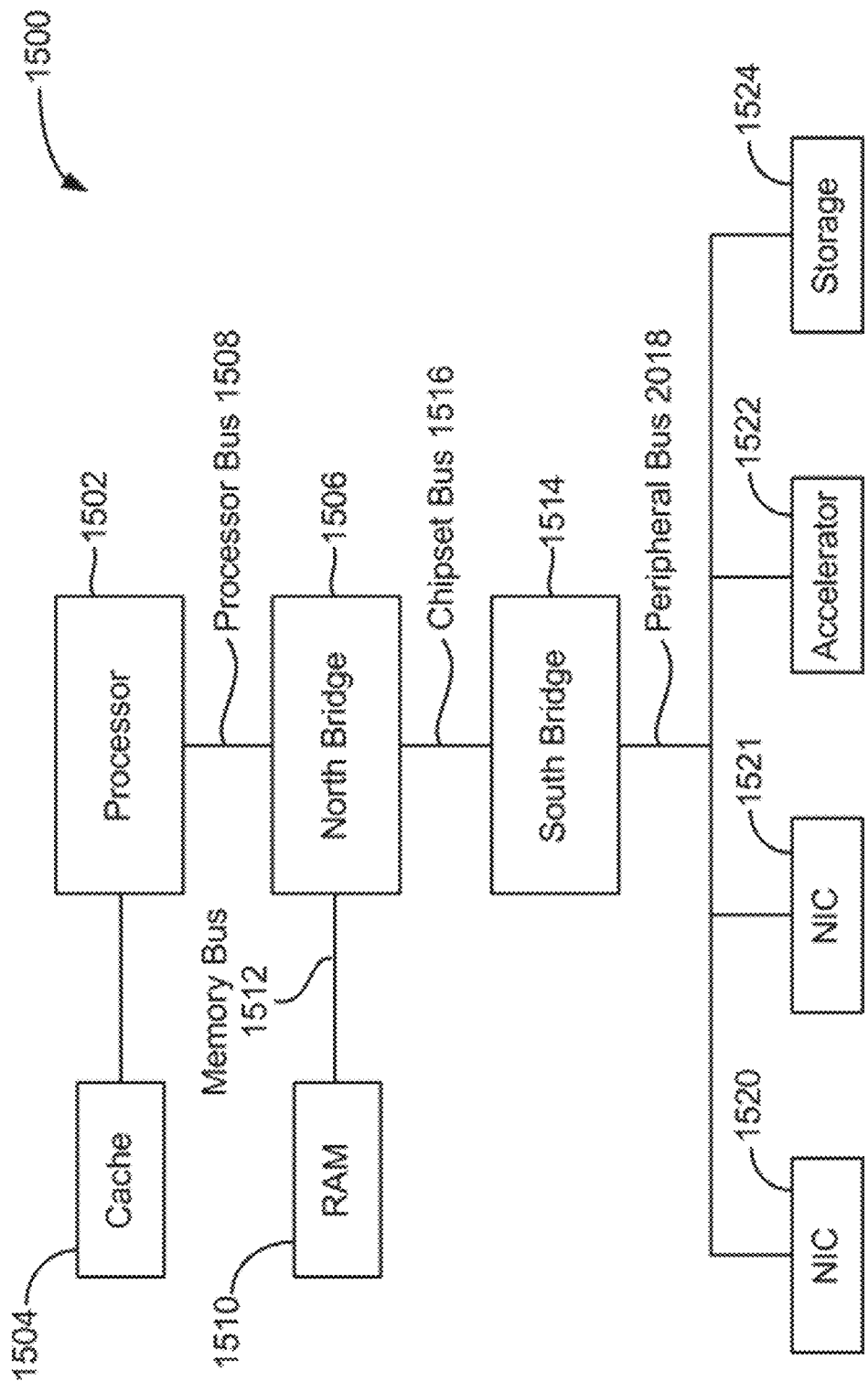
FIG. 15 is a block diagram illustrating a first architecture of a computer system.

FIG. 15 is a block diagram illustrating a first example architecture of a computer system 1500 that can be used in connection with example embodiments of the present invention. An example computer system can include a processor 1502 for processing instructions. Non-limiting examples of processors include: Intel Xeon™ processor, AMD Opteron™ processor, Samsung 32-bit RISC ARM 1176JZ(F)-S v1.0™ processor, ARM Cortex-A8 Samsung S5PC100™ processor, ARM Cortex-A8 Apple A4™ processor, Marvell PXA 930™ processor, or a functionally-equivalent processor. Multiple threads of execution can be used for parallel processing. In some embodiments, multiple processors or processors with multiple cores can also be used, whether in a single computer system, in a cluster, or distributed across systems over a network comprising a plurality of computers, cell phones, and/or personal data assistant devices.

A high speed cache 1504 can be connected to, or incorporated in, the processor 1502 to provide a high speed memory for instructions or data that have been recently, or are frequently, used by processor 1502. The processor 1502 is connected to a north bridge 1506 by a processor bus 1508. The north bridge 1506 is connected to random access memory (RAM) 1510 by a memory bus 1512 and manages access to the RAM 1510 by the processor 1502. The north bridge 1506 is also connected to a south bridge 1514 by a chipset bus 1516. The south bridge 1514 is, in turn, connected to a peripheral bus 1518. The peripheral bus can be, for example, PCI, PCI-X, PCI Express, or other peripheral bus. The north bridge and south bridge are often referred to as a processor chipset and manage data transfer between the processor, RAM, and peripheral components on the peripheral bus 1518. In some alternative architectures, the functionality of the north bridge can be incorporated into the processor instead of using a separate north bridge chip. In some embodiments, system 1500 can include an accelerator card 1522 attached to the peripheral bus 1518. The accelerator can include field programmable gate arrays (FPGAs) or other hardware for accelerating certain processing. For example, an accelerator can be used for adaptive data restructuring or to evaluate algebraic expressions used in extended set processing.

Software and data are stored in external storage 1524 and can be loaded into RAM 1510 and/or cache 1504 for use by the processor. The system 1500 includes an operating system for managing system resources; non-limiting examples of operating systems include: Linux, Windows™, MACOS™, BlackBerry OS™, iOS™, and other functionally-equivalent operating systems, as well as application software running on top of the operating system for managing data storage and optimization in accordance with example embodiments of the present invention. In this example, system 1500 also includes network interface cards (NICs) 1520 and 1521 connected to the peripheral bus for providing network interfaces to external storage, such as Network Attached Storage (NAS) and other computer systems that can be used for distributed parallel processing.

Figure 16:
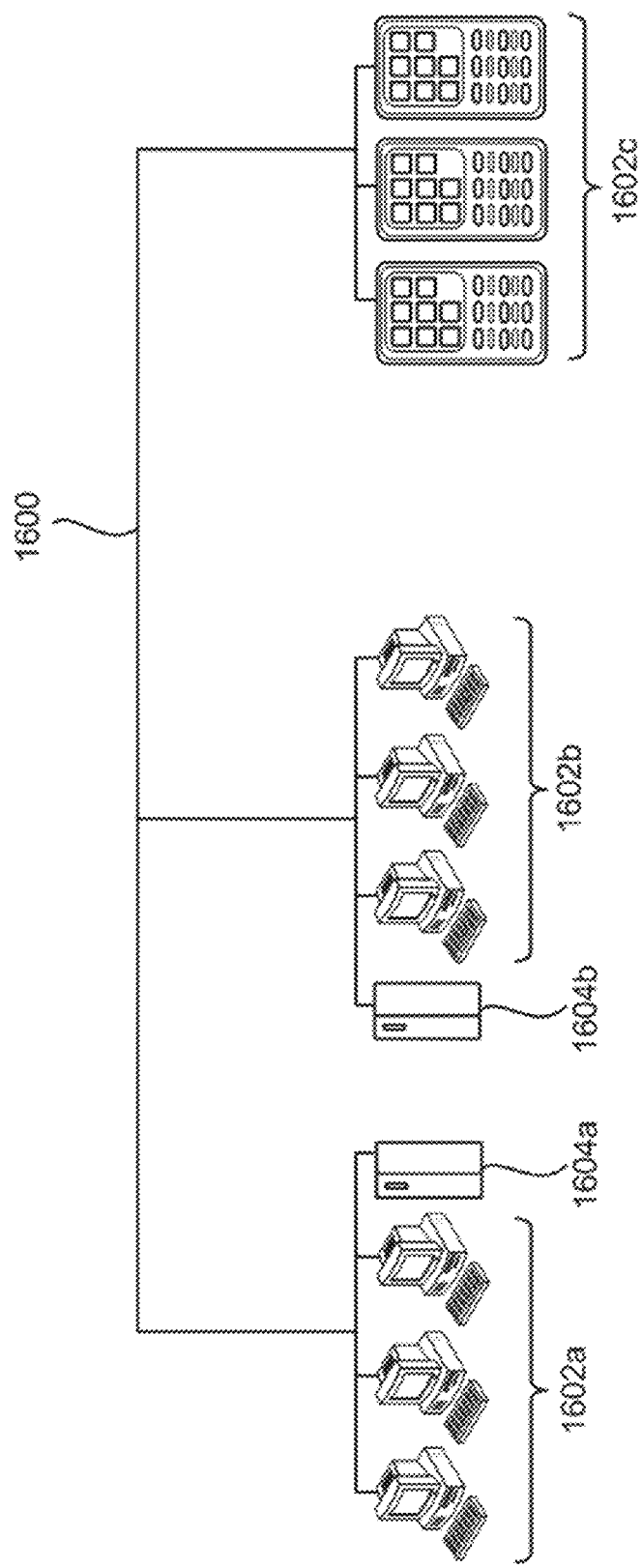
FIG. 16 is a diagram demonstrating a network configured to incorporate a plurality of computer systems, a plurality of cell phones and personal data assistants, and Network Attached Storage (NAS).

FIG. 16 a diagram showing a network 1600 with a plurality of computer systems 1602a, and 1602b, a plurality of cell phones and personal data assistants 1602c, and Network Attached Storage (NAS) 1604a, and 1604b. In example embodiments, systems 1602a, 1602b, and 1602c can manage data storage and optimize data access for data stored in Network Attached Storage (NAS) 1604a and 1604b. A mathematical model can be used for the data and be evaluated using distributed parallel processing across computer systems 1602a, and 1602b, and cell phone and personal data assistant systems 1602c. Computer systems 1602a, and 1602b, and cell phone and personal data assistant systems 1602c can also provide parallel processing for adaptive data restructuring of the data stored in Network Attached Storage (NAS) 1604a and 1604b. FIG. 16 illustrates an example only, and a wide variety of other computer architectures and systems can be used in conjunction with the various embodiments of the present invention. For example, a blade server can be used to provide parallel processing. Processor blades can be connected through a back plane to provide parallel processing. Storage can also be connected to the back plane or as Network Attached Storage (NAS) through a separate network interface. In some cases, processors can maintain separate memory spaces and transmit data through network interfaces, back plane or other connectors for parallel processing by other processors. In other embodiments, some or all of the processors can use a shared virtual address memory space.

Figure 17:
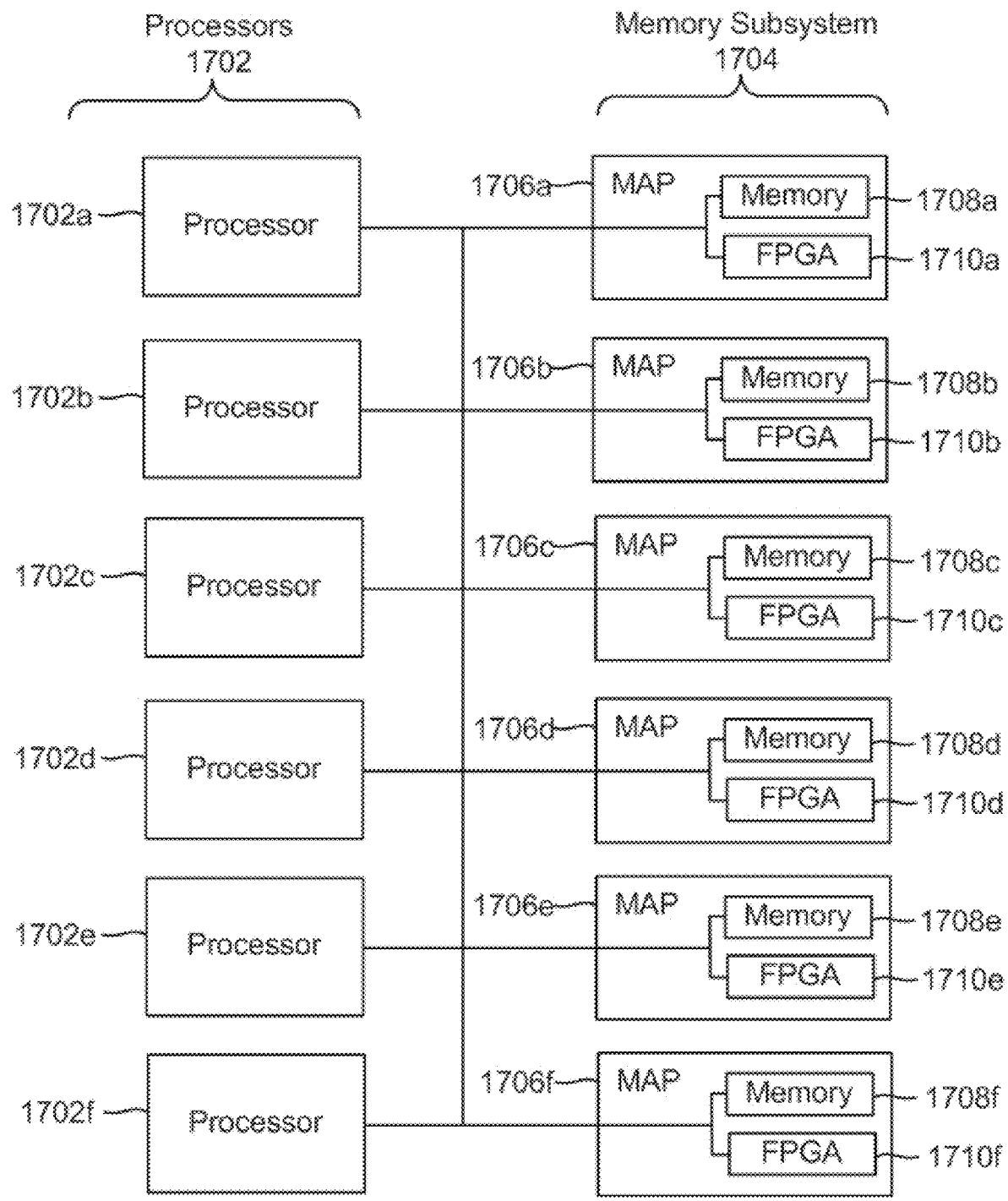
FIG. 17 is a block diagram of a multiprocessor computer system using a shared virtual address memory space.

FIG. 17 is a block diagram of a multiprocessor computer system 1700 using a shared virtual address memory space in accordance with an example embodiment. The system includes a plurality of processors 1702a-f that can access a shared memory subsystem 1704. The system incorporates a plurality of programmable hardware memory algorithm processors (MAPs) 1706a-f in the memory subsystem 1704. Each MAP 1706a-f can comprise a memory 1708a-f and one or more field programmable gate arrays (FPGAs) 1710a-f. The MAP provides a configurable functional unit and particular algorithms or portions of algorithms can be provided to the FPGAs 1710a-f for processing in close coordination with a respective processor. For example, the MAPs can be used to evaluate algebraic expressions regarding the data model and to perform adaptive data restructuring in example embodiments. In this example, each MAP is globally accessible by all of the processors for these purposes. In one configuration, each MAP can use Direct Memory Access (DMA) to access an associated memory 1708a-f, allowing it to execute tasks independently of, and asynchronously from, the respective microprocessor 1702a-f. In this configuration, a MAP can feed results directly to another MAP for pipelining and parallel execution of algorithms.

The above computer architectures and systems are examples only, and a wide variety of other computer, cell phone, and personal data assistant architectures and systems can be used in connection with example embodiments, including systems using any combination of general processors, co-processors, FPGAs and other programmable logic devices, system on chips (SOCs), application specific integrated circuits (ASICs), and other processing and logic elements. In some cases, all or part of the computer system can be implemented in software or hardware. Any variety of data storage media can be used in connection with example embodiments, including random access memory, hard drives, flash memory, tape drives, disk arrays, Network Attached Storage (NAS) and other local or distributed data storage devices and systems.

The computer system can be implemented using software modules executing on any of the above or other computer architectures and systems. In other examples, the functions of the system can be implemented partially or completely in firmware, programmable logic devices such as field programmable gate arrays (FPGAs), system on chips (SOCs), application specific integrated circuits (ASICs), or other processing and logic elements. For example, the Set Processor and Optimizer can be implemented with hardware acceleration through the use of a hardware accelerator card, such as accelerator card 1522.

The following examples are set forth to illustrate more clearly the principle and practice of embodiments disclosed herein to those skilled in the art and are not to be construed as limiting the scope of any claimed embodiments. Unless otherwise stated, all parts and percentages are on a weight basis.

EXAMPLES

Example 1

Patterning of an Wet Deposited Aminosilane on a Silicon Dioxide Surface

In this example, a silicon dioxide wafer was treated with a single organic layer deposited at different locations on the wafer to create loci with a high surface energy and coupling ability to nucleoside. A surface of 1000 Angstroms of silicon dioxide on top of polished silicon was selected. A controlled surface density of hydroxyl groups was achieved on the surface by a wet process using a 1% solution of N-(3-TRIETHOXYSILYLPROPYL-4HYDROXYBUTYR-AMIDE in ethanol and acetic acid deposited on the surface and treated for 4 hours, followed by placing the wafers on a hot plate at 150 degrees C. for 14 hours.

A layer of MEGAPOSIT SPR 3612 photoresist was deposited on top of the aminosilane. In this case, the organic layer was an adhesion promoter for the photoresist. The photoresist layer was patterned by exposure to ultraviolet light through a shadow mask. The photoresist pattern was transferred into the organic layer by oxygen plasma. The photoresist was then stripped, revealing a pattern of regions for biomolecular coupling. Clusters of 80 discs with a diameter of about 80 µm were well resolved.

Figure 18A:
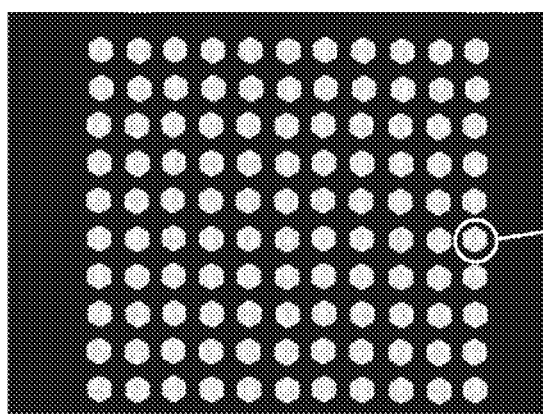
FIG. 18A depicts results from a photolithographic process performed using a chemical layer patterned as an adhesion promoter.
Figure 18B:
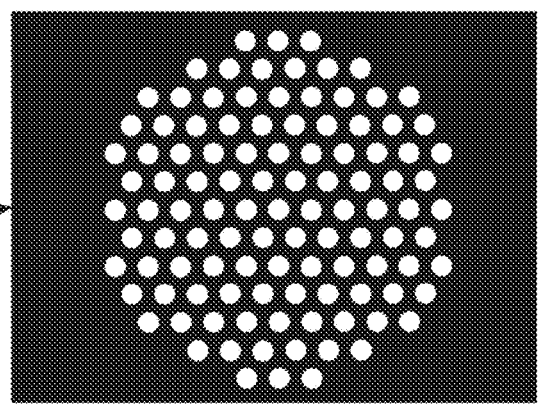
FIG. 18B depicts a close up view of one cluster depicted in FIG. 18A, the cluster having 80 μm discs.

Oligonucleic acids were extended from the surface. The photolithographic process performed without adhesion promoter layer did not result in organized loci having oligonucleic acids extended (data not shown). Oligonucleic acids extension performed a surface treated with the photolithographic process performed using the aminosilane layer resulted in clarified small discs of oligonucleic acids 80 µm in diameter (FIG. 18B) located within a cluster of discs (FIG. 18A).

Example 2

Patterning of a Gaseous Deposited Aminosilane on a Silicon Dioxide Surface

A CVD process was performed by delivering silane to the surface in gaseous state and applying a controlled deposition pressure of about 200 mTor and a controlled temperature of about 150 degrees C. (Data not shown.)

Example 3

Synthesis of a 50-Mer Sequence on an Oligonucleotide Synthesis Device

A oligonucleic acid synthesis device was assembled into a flowcell, which was connected to an Applied Biosystems (ABI394 DNA Synthesizer). The oligonucleic acid synthesis device was uniformly functionalized with N-(3-TRI-ETHOXYSILYLPROPYL)-4-HYDROXYBUTYRAMIDE (Gelest, CAS No. 156214-80-1) and was used to synthesize an exemplary oligonucleotide of 50 bp ("50-mer oligonucleotide") using oligonucleotide synthesis methods described herein. The sequence of the 50-mer was as described in SEQ ID NO.: 1.

5'AGACAATCAACCATTTGGGGTGGACAGCCTT-GACCTCTAGACTTCGGCA T##TTTTTTTTTT3' (SEQ ID NO.: 1), where # denotes Thymidine-succinyl hexamide CED phosphoramidite (CLP-2244 from ChemGenes), which is a cleavable linker enabling the release of oligos from the surface during deprotection. The synthesis was done using standard DNA synthesis chemistry (coupling, capping, oxidation, and deblocking) according to the protocol in Table 3 and an ABI synthesizer.

TABLE 3

| General DNA Synthesis | Table 3 | |
| --- | --- | --- |
| Process Name | Process Step | Time (sec) |
| WASH (Acetonitrile Wash Flow) | Acetonitrile System Flush | 4 |
|  | Acetonitrile to Flowcell | 23 |
|  | N2 System Flush | 4 |
|  | Acetonitrile System Flush | 4 |
| DNA BASE ADDITION (Phosphoramidite + Activator Flow) | Activator Manifold Flush | 2 |
|  | Activator to Flowcell | 6 |
|  | Activator + Phosphoramidite to Flowcell | 6 |
|  | Activator to Flowcell | 0.5 |
|  | Activator + Phosphoramidite to Flowcell | 5 |
|  | Activator to Flowcell | 0.5 |
|  | Activator + Phosphoramidite to Flowcell | 5 |
|  | Activator to Flowcell | 0.5 |
|  | Activator + Phosphoramidite to Flowcell | 5 |
|  | Incubate for 25 sec | 25 |
| WASH (Acetonitrile Wash Flow) | Acetonitrile System Flush | 4 |
|  | Acetonitrile to Flowcell | 15 |
|  | N2 System Flush | 4 |
|  | Acetonitrile System Flush | 4 |
| DNA BASE ADDITION (Phosphoramidite + Activator Flow) | Activator Manifold Flush | 2 |
|  | Activator to Flowcell | 5 |
|  | Activator + Phosphoramidite to Flowcell | 18 |
|  | Incubate for 25 sec | 25 |
| WASH (Acetonitrile Wash Flow) | Acetonitrile System Flush | 4 |
|  | Acetonitrile to Flowcell | 15 |
|  | N2 System Flush | 4 |
|  | Acetonitrile System Flush | 4 |
| CAPPING (Cap A + B, 1:1, Flow) | CapA + B to Flowcell | 15 |
| WASH (Acetonitrile Wash Flow) | Acetonitrile System Flush | 4 |
|  | Acetonitrile to Flowcell | 15 |
|  | Acetonitrile System Flush | 4 |
| OXIDATION (Oxidizer Flow) | Oxidizer to Flowcell | 18 |
| WASH (Acetonitrile Wash Flow) | Acetonitrile System Flush | 4 |
|  | N2 System Flush | 4 |
|  | Acetonitrile System Flush | 4 |
|  | Acetonitrile to Flowcell | 15 |
|  | Acetonitrile System Flush | 4 |
|  | Acetonitrile to Flowcell | 15 |
|  | N2 System Flush | 4 |
|  | Acetonitrile System Flush | 4 |
|  | Acetonitrile to Flowcell | 23 |
|  | N2 System Flush | 4 |
|  | Acetonitrile System Flush | 4 |
| DEBLOCKING (Deblock Flow) | Deblock to Flowcell | 36 |
| WASH (Acetonitrile Wash Flow) | Acetonitrile System Flush | 4 |
|  | N2 System Flush | 4 |
|  | Acetonitrile System Flush | 4 |
|  | Acetonitrile to Flowcell | 18 |
|  | N2 System Flush | 4.13 |
|  | Acetonitrile System Flush | 4.13 |
|  | Acetonitrile to Flowcell | 15 |

Figure 19:
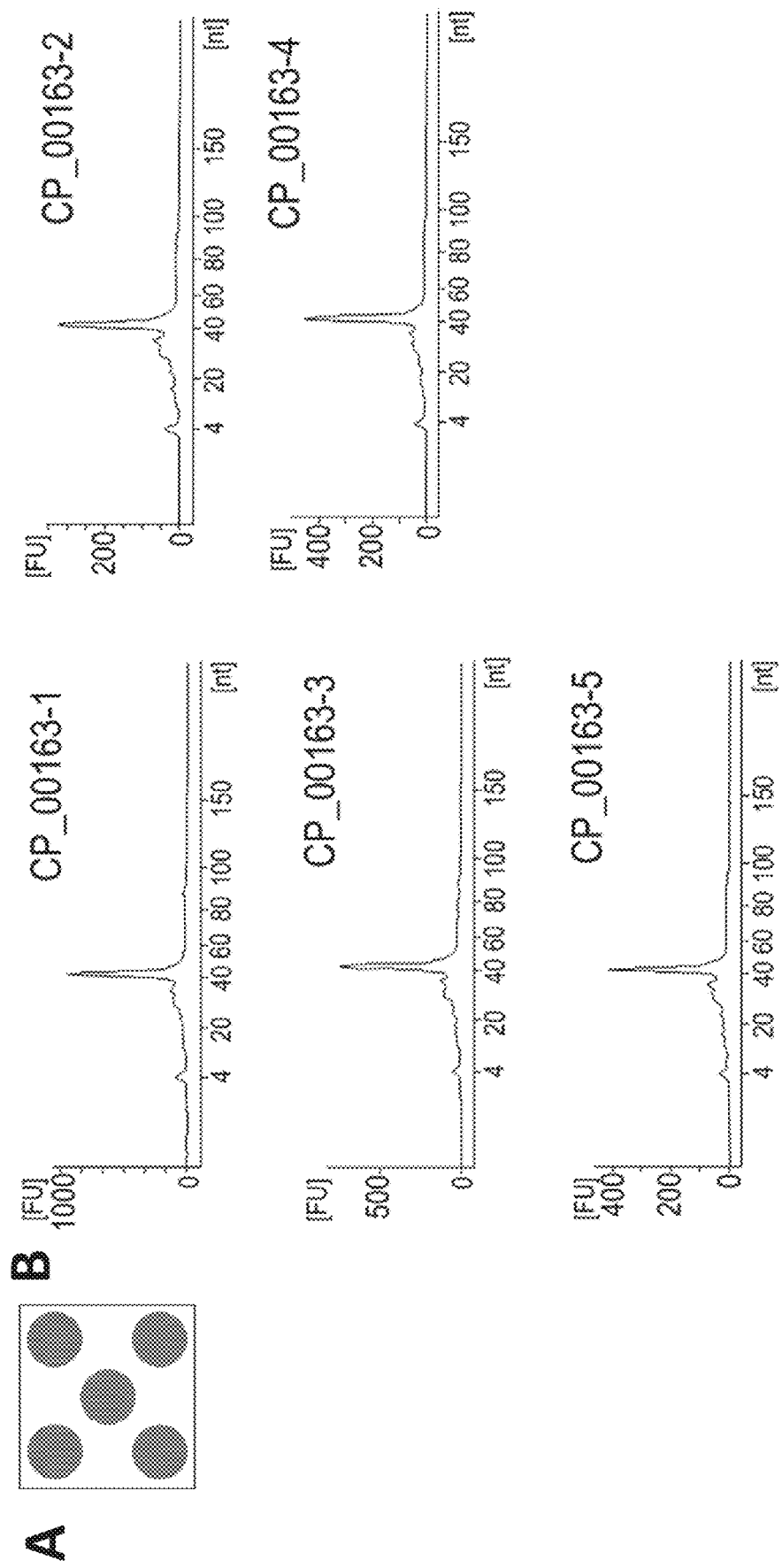
FIG. 19, part A illustrates a functionalized surface.

The phosphoramidite/activator combination was delivered similar to the delivery of bulk reagents through the flowcell. No drying steps were performed as the environment stays "wet" with reagent the entire time. The flow restrictor was removed from the ABI 394 synthesizer to enable faster flow. Without flow restrictor, flow rates for amidites (0.1M in ACN), Activator, (0.25M Benzoylthiotetrazole ("BTT"; 30-3070-xx from GlenResearch) in ACN), and Ox (0.02M 12 in 20% pyridine, 10% water, and 70% THF) were roughly ~100 uL/sec, for acetonitrile ("ACN") and capping reagents (1:1 mix of CapA and CapB, wherein CapA is acetic anhydride in THF/Pyridine and CapB is 16% 1-methylimidizole in THF), roughly ~200 uL/sec, and for Deblock (3% dichloroacetic acid in toluene), roughly ~300 uL/sec (compared to ~50 uL/sec for all reagents with flow restrictor). The time to completely push out Oxidizer was observed, the timing for chemical flow times was adjusted accordingly and an extra ACN wash was introduced between different chemicals. After oligonucleotide synthesis, the chip was deprotected in gaseous ammonia overnight at 75 psi. Five drops of water were applied to the surface to recover oligonucleic acids (FIG. 19A). The recovered oligonucleic acids were then analyzed on a BioAnalyzer small RNA chip (FIG. 19B).

Example 4

Synthesis of a 100-Mer Sequence on an Oligonucleotide Synthesis Device

Figure 20:
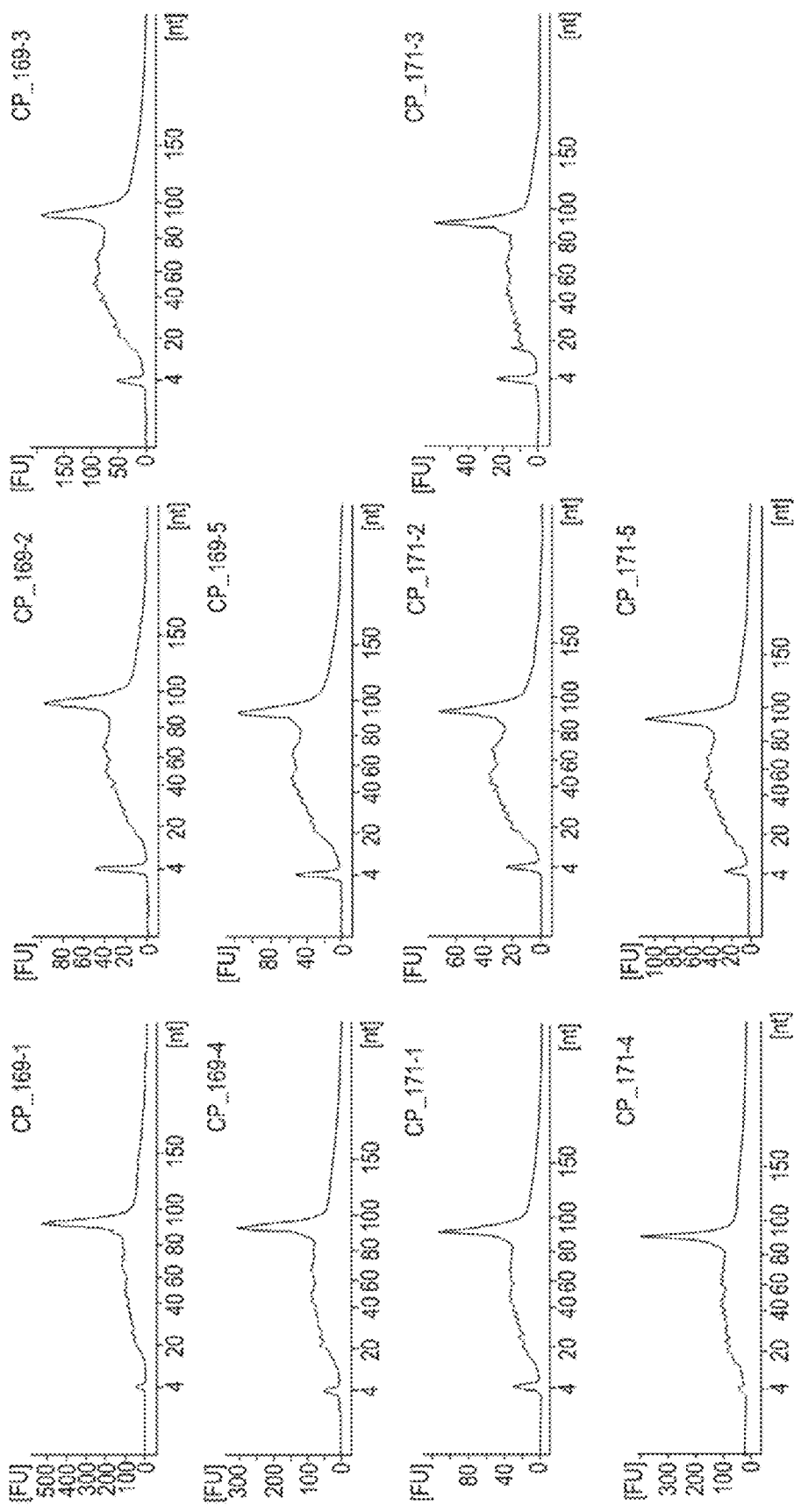
FIG. 20 indicates BioAnalyzer data of surface extracted 100-mer oligonucleotides synthesized on a silicon oligonucleotide synthesis device.

The same process as described in Example 3 for the synthesis of the 50-mer sequence was used for the synthesis of a 100-mer oligonucleotide ("100-mer oligonucleotide"; 5' CGGGATCCTTATCGTCATCGTCGTACAGATCCCGA-CCCATTTGCTGTCCACCAGTCA TGCTAGCCATAC-CATG- ATGATGATGATGATGAGAACC- CCGCAT##TT-TTTTTTTT3', where # denotes Thymidine-succinyl hexamide CED phosphoramidite (CLP-2244 from ChemGenes); SEQ ID NO.: 2) on two different silicon chips, the first one uniformly functionalized with N-(3-TRIETHOXYSILYL-PROPYL)-4-HYDROXYBUTYRAMIDE and the second one functionalized with 5/95 mix of 11-acetoxyundecyltriethoxysilane and n-decyltriethoxysilane, and the oligos extracted from the surface were analyzed on a BioAnalyzer instrument (FIG. 20).

All ten samples from the two chips were further PCR amplified using a forward (5'ATGCGGGGTTCTCAT-CATC3'; SEQ ID NO.: 3) and a reverse (5'CGGGATCCT-TATCGTCATCG3'; SEQ ID NO.: 4) primer in a 50 uL PCR mix (25 uL NEB Q5 mastermix, 2.5 uL 10 uM Forward primer, 2.5 uL 10 uM Reverse primer, 1uL oligo extracted from the surface, and water up to 50 uL) using the following thermalcycling program:

98 C, 30 sec
98 C, 10 sec; 63 C, 10 sec; 72 C, 10 sec; repeat 12 cycles
72 C, 2 min The PCR products were also run on a BioAnalyzer (data not shown), demonstrating sharp peaks at the 100-mer position. Next, the PCR amplified samples were cloned, and Sanger sequenced. Table 4 summarizes the results from the Sanger sequencing for samples taken from spots 1-5 from chip 1 and for samples taken from spots 6-10 from chip 2.

TABLE 4

| Spot | Error rate | Cycle efficiency |
| --- | --- | --- |
| 1 | 1/763 bp | 99.87% |
| 2 | 1/824 bp | 99.88% |
| 3 | 1/780 bp | 99.87% |
| 4 | 1/429 bp | 99.77% |
| 5 | 1/1525 bp | 99.93% |

TABLE 4-continued

| Spot | Error rate | Cycle efficiency |
|---|---|---|
| 6 | 1/1615 bp | 99.94% |
| 7 | 1/531 bp | 99.81% |
| 8 | 1/1769 bp | 99.94% |
| 9 | 1/854 bp | 99.88% |
| 10 | 1/1451 bp | 99.93% |

Thus, the high quality and uniformity of the synthesized oligonucleotides were repeated on two chips with different surface chemistries. Overall, 89%, corresponding to 233 out of 262 of the 100-mers that were sequenced were perfect sequences with no errors.

Figure 21:
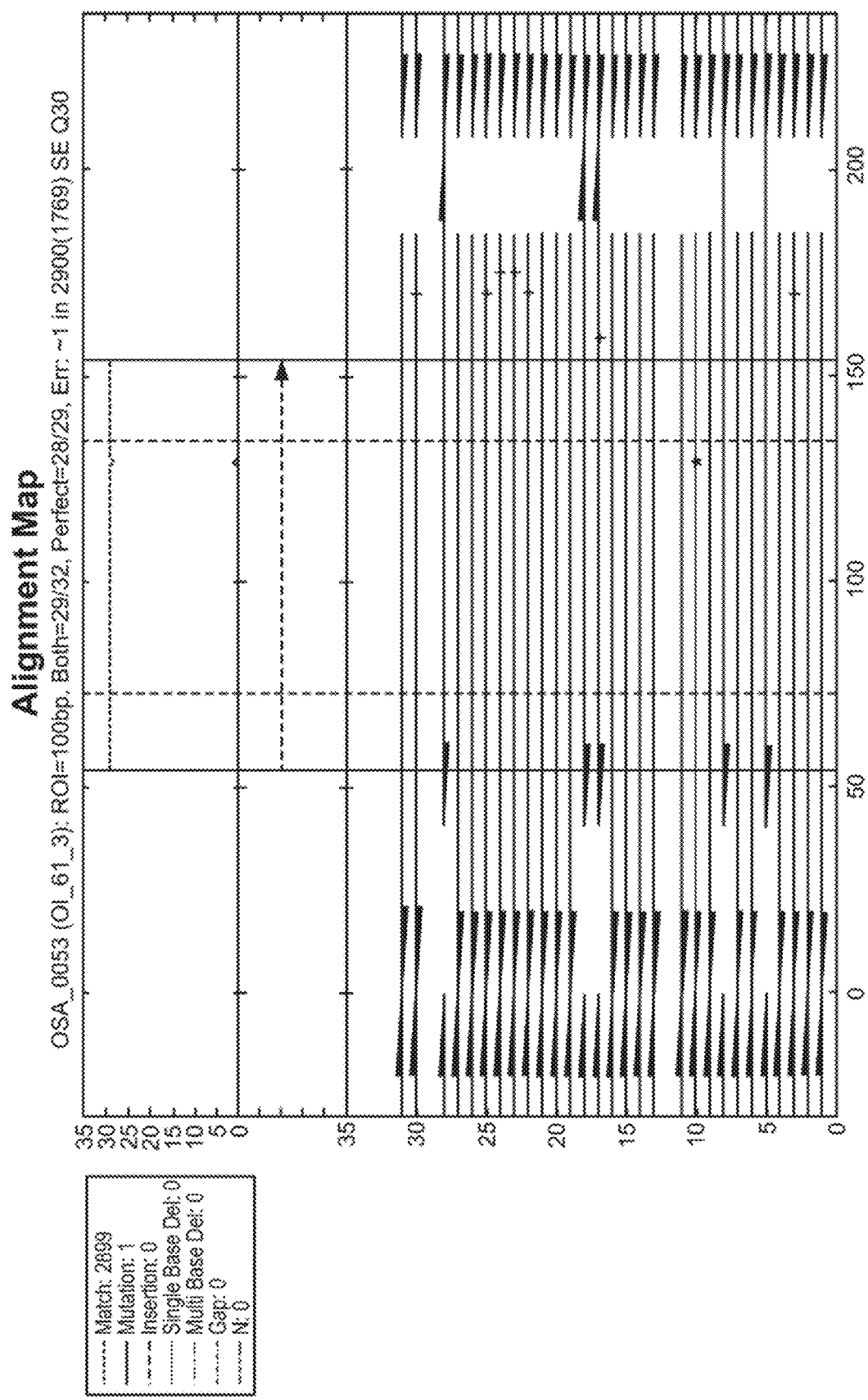
FIG. 21 represents a sequence alignment, where "x" denotes a single base deletion, "star" denotes single base mutation, and "+" denotes low quality spots in Sanger sequencing.
Figure 22:
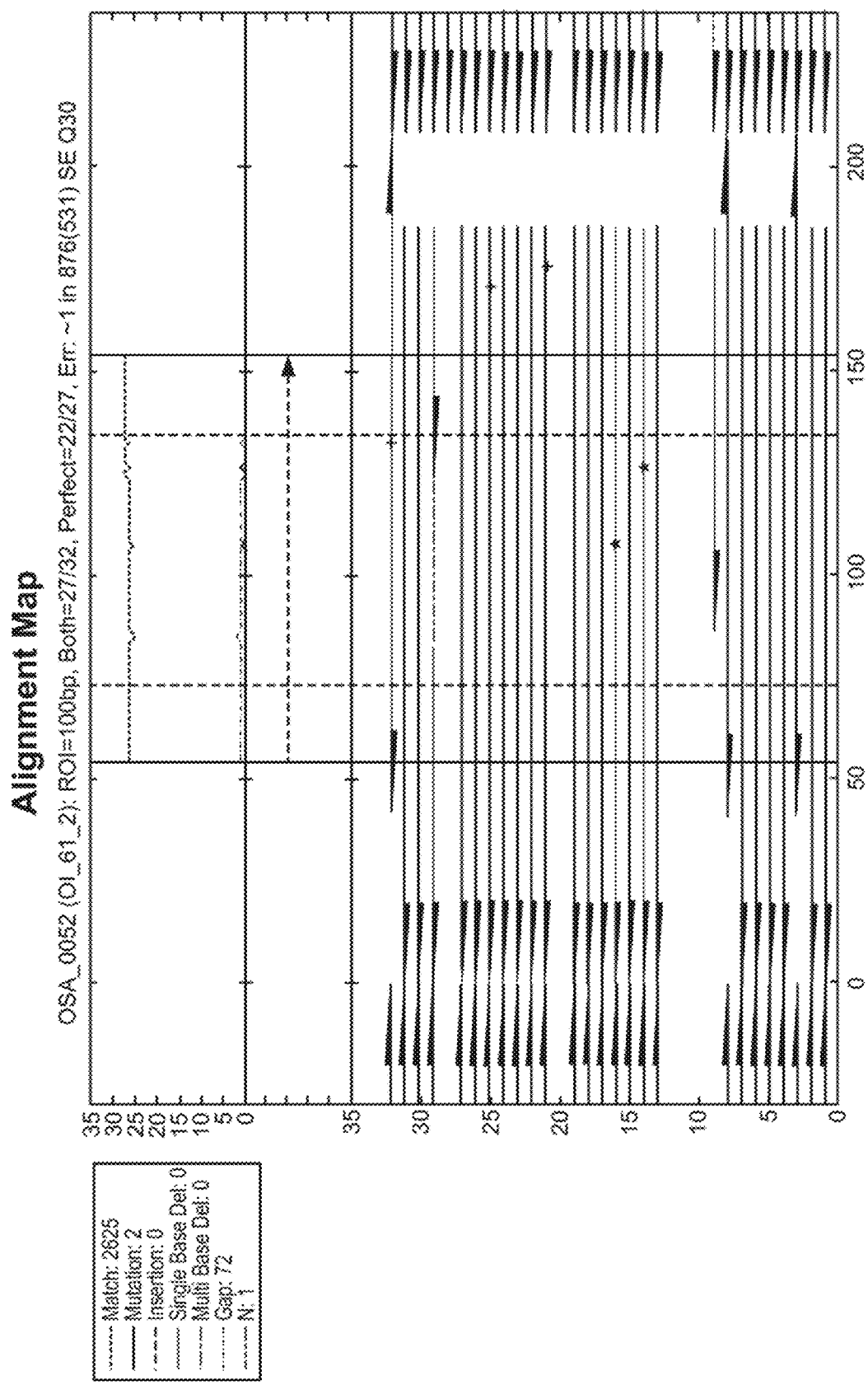
FIG. 22 represents a sequence alignment, where "x" denotes a single base deletion, "star" denotes single base mutation, and "+" denotes low quality spots in Sanger sequencing.

FIGS. 21 and 22 show alignment maps for samples taken from spots 8 and 7, respectively, where "x" denotes a single base deletion, "star" denotes single base mutation, and "+" denotes low quality spots in Sanger sequencing. The aligned sequences in FIG. 21 together represent an error rate of about 97%, where 28 out of 29 reads correspond to perfect sequences. The aligned sequences in FIG. 22 together represent an error rate of about 81%, where 22 out of 27 reads correspond to perfect sequences.

Finally, Table 5 summarizes key error characteristics for the sequences obtained from the oligonucleotides samples from spots 1-10.

TABLE 5

|  | Sample ID/Spot no. | | | | | | | | | |
|---|---|---|---|---|---|---|---|---|---|---|
|  | OSA_0046/1 | OSA_0047/2 | OSA_0048/3 | OSA_0049/4 | OSA_0050/5 | OSA_0051/6 | OSA_0052/7 | OSA_0053/8 | OSA_0054/9 | OSA_0055/10 |
| Total Sequences | 32 | 32 | 32 | 32 | 32 | 32 | 32 | 32 | 32 | 32 |
| Sequencing Quality | 25 of 28 | 27 of 27 | 26 of 30 | 21 of 23 | 25 of 26 | 29 of 30 | 27 of 31 | 29 of 31 | 28 of 29 | 25 of 28 |
| Oligo Quality | 23 of 25 | 25 of 27 | 22 of 26 | 18 of 21 | 24 of 25 | 25 of 29 | 22 of 27 | 28 of 29 | 26 of 28 | 20 of 25 |
| ROI Match Count | 2500 | 2698 | 2561 | 2122 | 2499 | 2666 | 2625 | 2899 | 2798 | 2348 |
| ROI Mutation | 2 | 2 | 1 | 3 | 1 | 0 | 2 | 1 | 2 | 1 |
| ROI Multi Base Deletion | 0 | 0 | 0 | 0 | 0 | 0 | 0 | 0 | 0 | 0 |
| ROI Small Insertion | 1 | 0 | 0 | 0 | 0 | 0 | 0 | 0 | 0 | 0 |
| ROI Single Base Deletion | 0 | 0 | 0 | 0 | 0 | 0 | 0 | 0 | 0 | 0 |
| Large Deletion Count | 0 | 0 | 1 | 0 | 0 | 1 | 1 | 0 | 0 | 0 |
| Mutation: G > A | 2 | 2 | 1 | 2 | 1 | 0 | 2 | 1 | 2 | 1 |
| Mutation: T > C | 0 | 0 | 0 | 1 | 0 | 0 | 0 | 0 | 0 | 0 |
| ROI Error Count | 3 | 2 | 2 | 3 | 1 | 1 | 3 | 1 | 2 | 1 |
| ROI Error Rate | Err: ~1 in 834 | Err: ~1 in 1350 | Err: ~1 in 1282 | Err: ~1 in 708 | Err: ~1 in 2500 | Err: ~1 in 2667 | Err: ~1 in 876 | Err: ~1 in 2900 | Err: ~1 in 1400 | Err: ~1 in 2349 |
| ROI Minus Primer Error Rate | MP Err: ~1 in 763 | MP Err: ~1 in 824 | MP Err: ~1 in 780 | MP Err: ~1 in 429 | MP Err: ~1 in 1525 | MP Err: ~1 in 1615 | MP Err: ~1 in 531 | MP Err: ~1 in 1769 | MP Err: ~1 in 854 | MP Err: ~1 in 1451 |

Example 5

Nanoreactor

A nanoreactor was sealed to a silicon wafer. The wafer contained nucleic acids generated from the DNA synthesis reaction. Gene assembly reagents were added to the reaction chamber. Gene amplification occurred in the resolved enclosure. The reaction chamber included nucleic acids encoding for different predetermined sequences. A series of enzymatic reactions resulted in the linking of amplified nucleic acids into a 2 kilobase gene.

Example 6

Error Correction of Assembled Nucleic Acids

TABLE 6

| Nucleic Acid | Sequence |
|---|---|
| Assembled Gene, SEQ ID NO.: 5 | 5' ATGACCATGATTACGGATTCACT GGCCGTCGTTTTACAACGTCGTGACT GGGAAAACCCTGGCGTTACCCAACTT AATCGCCTTGCAGCACATCCCCCTTT CGCCAGCTGGCGTAATAGCGAAGAGG CCCGCACCGATCGCCCTTCCCAACAG TTGCGCAGCCTGAATGGCGAATGGCG CTTTGCCTGGTTTCCGGCACCAGAAG CGGTGCCGGAAAGCTGGCTGGAGTGC GATCTTCCTGAGGCCGATACTGTCGT CGTCCCCTCAAACTGGCAGATGCACG GTTACGATGCGCCCATCTACACCAAC GTGACCTATCCCATTACGGTCAATCC GCCGTTTGTTCCCACGGAGAATCCGA CGGGTTGTTACTCGCTCACATTTAAT GTTGATGAAAGCTGGCTACAGGAAGG CCAGACGCGAATTATTTTGATGGCG TTAACTCGGCGTTTCATCTGTGGTGC AACGGGCGCTGGGTCGGTTACGGCCA GGACAGTCGTTTGCCGTCTGAATTTG |

TABLE 6-continued

| Nucleic Acid | Sequence |
|---|---|
|  | ACCTGAGCGCATTTTTACGCGCCGGA GAAAACCGCCTCGCGGTGATGGTGCT GCGCTGGAGTGACGGCAGTTATCTGG AAGATCAGGATATGTGGCGGATGAGC GGCATTTTCCGTGACGTCTCGTTGCT GCATAAACCGACTACACAAATCAGCG ATTTCCATGTTGCCACTCGCTTTAAT GATGATTTCAGCCGCGCTGTACTGGA GGCTGAAGTTCAGATGTGCGGCGAGT TGCGTGACTACCTACGGGTAACAGTT TCTTTATGGCAGGGTGAAACGCAGGT |

TABLE 6-continued

| Nucleic Acid | Sequence |
|---|---|
| | CGCCAGCGGCACCGCGCCTTTCGGCG GTGAAATTATCGATGAGCGTGGTGGT TATGCCGATCGCGTCACACTACGTCT GAACGTCGAAAACCCGAAACTGTGGA GCGCCGAAATCCCGAATCTCTAT C 3' |
| Assembly Oligonucleotide 1, SEQ ID NO.: 6 | 5' ATGACCATGATTACGGATTCACT GGCCGTCGTTTTACAACGTCGTGACT GGGAAAACCCTGGCGTTACCCAACTT AATCGCCTTGCAGCACATCCCCCTTT CGCCAGCTGGCGTAATAGCGAAGAGG CCCGCACCGATCGCCCTTCCCAACAG TTGCGCAGCC 3' |
| Assembly Oligonucleotide 2, SEQ ID NO.: 7 | 5' GATAGGTCACGTTGGTGTAGATG GGCGCATCGTAACCGTGCATCTGCCA GTTTGAGGGGACGACGACAGTATCGG CCTCAGGAAGATCGCACTCCAGCCAG CTTTCCGGCACCGCTTCTGGTGCCGG AAACCAGGCAAAGCGCCATTCGCCAT TCAGGCTGCGCAACTGTTGGGA 3' |
| Assembly Oligonucleotide 3, SEQ ID NO.: 8 | 5' CCCATCTACACCAACGTGACCTA TCCCATTACGGTCAATCCGCCGTTTG TTCCCACGGAGAATCCGACGGGTTGT TACTCGCTCACATTTAATGTTGATGA AAGCTGGCTACAGGAAGGCCAGACGC GAATTATTTTTGATGGCGTTAACTCG GCGTTTCATCTGTGGTGCAACGG 3' |
| Assembly Oligonucleotide 4, SEQ ID NO.: 9 | 5' GCCGCTCATCCGCCACATATCCT GATCTTCCAGATAACTGCCGTCACTC CAGCGCAGCACCATCACCGCGAGGCG GTTTTCTCCGGCGCGTAAAAATGCGC TCAGGTCAAATTCAGACGGCAAACGA CTGTCCTGGCCGTAACCGACCCAGCG CCCGTTGCACCACAGATGAAACG 3' |
| Assembly Oligonucleotide 5, SEQ ID NO.: 10 | 5' AGGATATGTGGCGGATGAGCGGC ATTTTCCGTGACGTCTCGTTGCTGCA TAAACCGACTACACAAATCAGCGATT TCCATGTTGCCACTCGCTTTAATGAT GATTTCAGCCGCGCTGTACTGGAGGC TGAAGTTCAGATGTGCGGCGAGTTGC GTGACTACCTACGGGTAACAGTT T 3' |
| Assembly Oligonucleotide 6, SEQ ID NO.: 11 | 5' GATAGAGATTCGGGATTTCGGCG CTCCACAGTTTCGGGTTTTCGACGTT CAGACGTAGTGTGACGCGATCGGCAT AACCACCACGCTCATCGATAATTTCA CCGCCGAAAGGCGCGGTGCCGCTGGC GACCTGCGTTTCACCCTGCCATAAAG AAACTGTTACCCGTAGGTAGTCAC G 3' |

A gene of about 1 kb (SEQ ID NO.: 5; Table 6) was assembled using 6 purchased oligonucleotides (5 nM each during PCA) (Ultramer; SEQ ID NO.: 6-11; Table 6) and assembled in a PCA reaction using a 1×NEB Q5 buffer with 0.02 U/uL Q5 hot-start high-fidelity polymerase and 100 uM dNTP as follows:

1 cycle: 98 C, 30 sec 15 cycles: 98 C, 7 sec; 62 C 30 sec; 72 C, 30 sec 1 cycle: 72 C, 5 min Ultramer oligonucleotides are expected to have error rates of at least 1 in 500 nucleotides, more likely at least 1 in 200 nucleotides or more.

The assembled gene was amplified in a PCR reaction using a forward primer (5' ATGACCATGATTACGGAT-TCACTGGCC3' SEQ ID NO.: 12) and a reverse primer (5'GATAGAGATTCGGGATTTCGGCGCTCC3' SEQ ID NO.: 13), using 1×NEB Q5 buffer with 0.02 U/uL Q5 hot-start high-fidelity polymerase, 200 uM dNTP, and 0.5 uM primers as follows:

1 cycle: 98 C, 30 sec 30 cycles: 98 C, 7 sec; 65 C 30 sec; 72 C, 45 sec 1 cycle: 72 C, 5 min The amplified assembled gene was analyzed in a Bio-Analyzer and cloned. Mini-preps from ~24 colonies were Sanger sequenced. The BioAnalyzer analysis provided a broad peak and a tail for the uncorrected gene, indicated a high error rate. The sequencing indicated an error rate of 1/789 (data not shown). Two rounds of error correction were followed using CorrectASE (Life Technologies, www.lifetechnologies.com/order/catalog/product/A14972) according to the manufacturer's instructions. The resulting gene samples were similarly analyzed in the BioAnalyzer after round one and round two and cloned. (Data not shown.) 24 colonies were picked for sequencing. The sequencing results indicated an error rate of 1/5190 bp and 1/6315 bp after the first and second rounds of error correction, respectively.

Example 7

Figure 23:
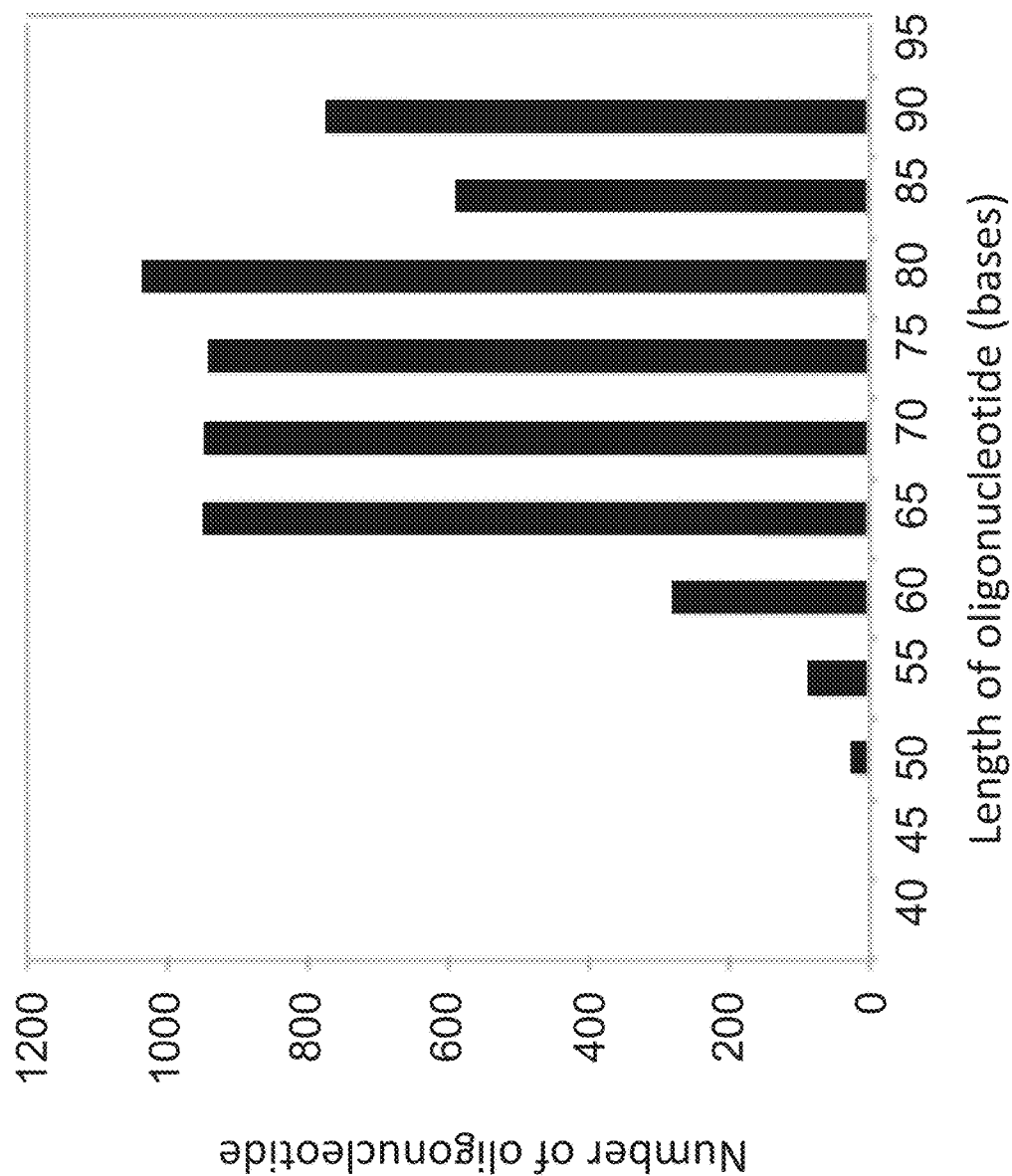
FIG. 23 is a histogram for oligonucleotides encoding for 240 genes, with the length of oligonucleotide as the x-axis and number of oligonucleotide as the y-axis.

Oligonucleic Acid Distribution for Synthesizing Genes Under 1.8 Kb in Length 240 genes were selected for de novo synthesis wherein the genes ranged from 701 to 1796 base pairs in length. The gene sequence for each of the genes was divided into smaller fragments encoding for oligonucleic acids ranging between 50 to 90 nucleotides in length, with each nucleotide having 20 to 25 nucleotides overlapping sequences A distribution chart is depicted in FIG. 23, where the X axis depicts the oligonucleic acid length, and the Y axis depicted the number of oligonucleic acids synthesized. A total of roughly 5,500 oligonucleic acids were synthesized on an aminosilane coated surface using a protocol similar to that of Example 3, and assembled using a polymerase chain assembly reaction to anneal overlapping sequence of each oligonucleotide to a different oligonucleotide to form a gene.

Example 8

Oligonucleic Acid Distribution for Synthesizing a Long Gene Sequence

Figure 24:
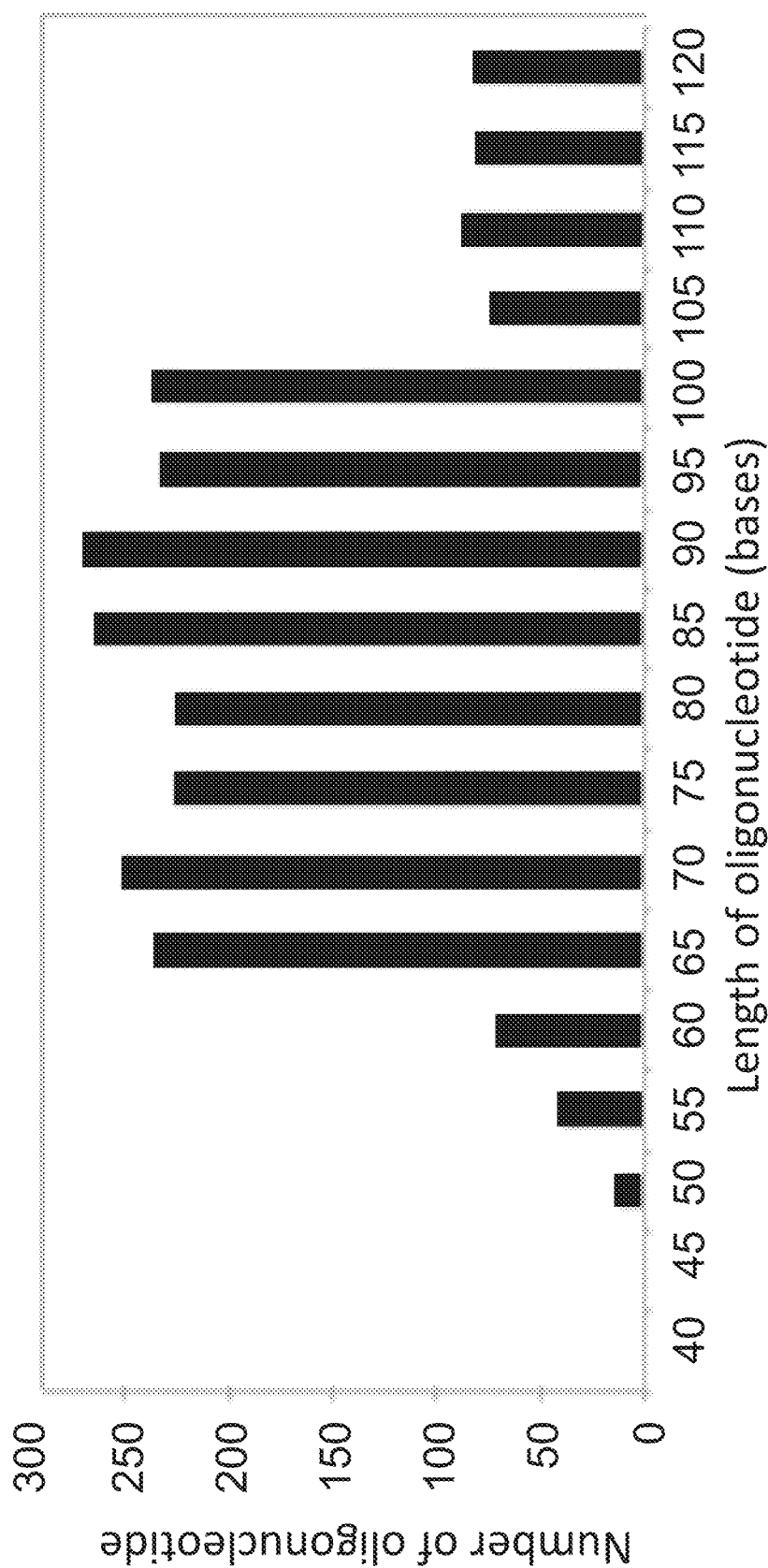
FIG. 24 is a histogram for oligonucleic acids collectively encoding for a gene, with the length of oligonucleotide as the x-axis and number of oligonucleotide as the y-axis.

Gene sequence for a single gene that was larger than 1.8 kb in length was divided into smaller fragments encoding for oligonucleic acids ranging between 50 to 120 nucleotides in length, with each nucleotide having 20 to 25 nucleotides overlapping sequences. A total of 90 different design arrangement were synthesized. A distribution chart is depicted in FIG. 24, where the X axis depicts the oligonucleic acid length, and the Y axis depicted the number of oligonucleic acids synthesized. The oligonucleic acids were synthesized on an aminosilane coated surface using a protocol similar to that of Example 3, and assembled using a polymerase chain assembly reaction to anneal overlapping sequence of each oligonucleotide to a different oligonucleotide to form a gene.

Example 9

Two-Step Deposition Process for Dilution of Nucleoside Coupling Agent

Various methods for surface preparation were preformed, which include: (i) performing an active chemical vapor (CVD) deposition step before photolithography; (ii) performing an active chemical vapor (CVD) deposition step after photolithography; and (i) performing a dilution active chemical vapor (CVD) deposition step after photolithograph.

A first silicon dioxide structure having a silicon oxide layer was individually cleaned in an oxygen plasma (referred to as the "HAPS" chip. An aminosilane, N-(3-TRI-ETHOXYSILYLPROPYL)-4-HYDROXYBUTYR-AMIDE, HAPS), was deposited on the silicon oxide at predetermined locations, referred to as loci. The surface was coated with AZ resist and then baked. The surface was cleaned again in an oxygen plasma, fluorinated (depositing (tridecafluoro-1,1,2,2-tetrahydrooctyl)-trichlorosilane), and then stripped.

A second silicon dioxide structure having a silicon oxide layer was individually cleaned in an oxygen plasma (referred to as the "100% GOPS-1" chip). A silane, 3-glycidoxypropyltrimethoxysilane (GOPS), was deposited on the silicon oxide at predetermined locations, referred to as loci. The surface was coated with AZ resist and then baked. The surface was cleaned again in an oxygen plasma, fluorinated (depositing (tridecafluoro-1,1,2,2-tetrahydrooctyl)-trichlorosilane), and then stripped.

A third silicon dioxide structure having a silicon oxide layer was individually cleaned in an oxygen plasma (referred to as the "100% GOPS-2" chip). Directly after cleaning, the surface was coated with AZ resist and then baked at 90 degrees Celsius for 7 min. The surface was cleaned again in an oxygen plasma, fluorinated in the YES CVD system (depositing (tridecafluoro-1,1,2,2-tetrahydrooctyl)-trichlorosilane), and then stripped. The surface was treated with 100% GOPS at 1 Torr for 1 hour at chamber temperature of 100 degrees Celsius. Lastly, the surface was activated in water for 30 minutes at room temperature.

For the diluted active agent deposition protocol, a fourth silicon dioxide structure having a silicon oxide layer was individually cleaned in an oxygen plasma (referred to as the "GOPS-diluted" chip). Directly after cleaning, the surface was coated with AZ resist and then baked at 90 degrees Celsius for 7 min. The surface was cleaned again in an oxygen plasma, fluorinated in the YES CVD system (depositing (tridecafluoro-1,1,2,2-tetrahydrooctyl)-trichlorosilane), and then stripped. The surface was treated with 100% propyltrimethoxysilane at 3.5 Torr for 15 hours at chamber temperature of 100 C degrees Celsius. The surface was treated with water for 30 minutes, followed by a second deposition step. In the second deposition step, a mixture of 0.05% GOPS and 99.95% propyltrimethoxysilane was deposited on the surface and treated at 3.5 Torr for 1.5 hours at chamber temperature of 100 C. Lastly, the surface was activated in water for 30 minute at room temperature. For each structure prepared, the molecules able to couple nucleoside (HAPS and GOPS) were deposited in described locations on the surfaces, loci, and the loci were arranged in clusters.

Example 10

Characterization of Low Density Oligonucleic Acid Surfaces

Figure 25:
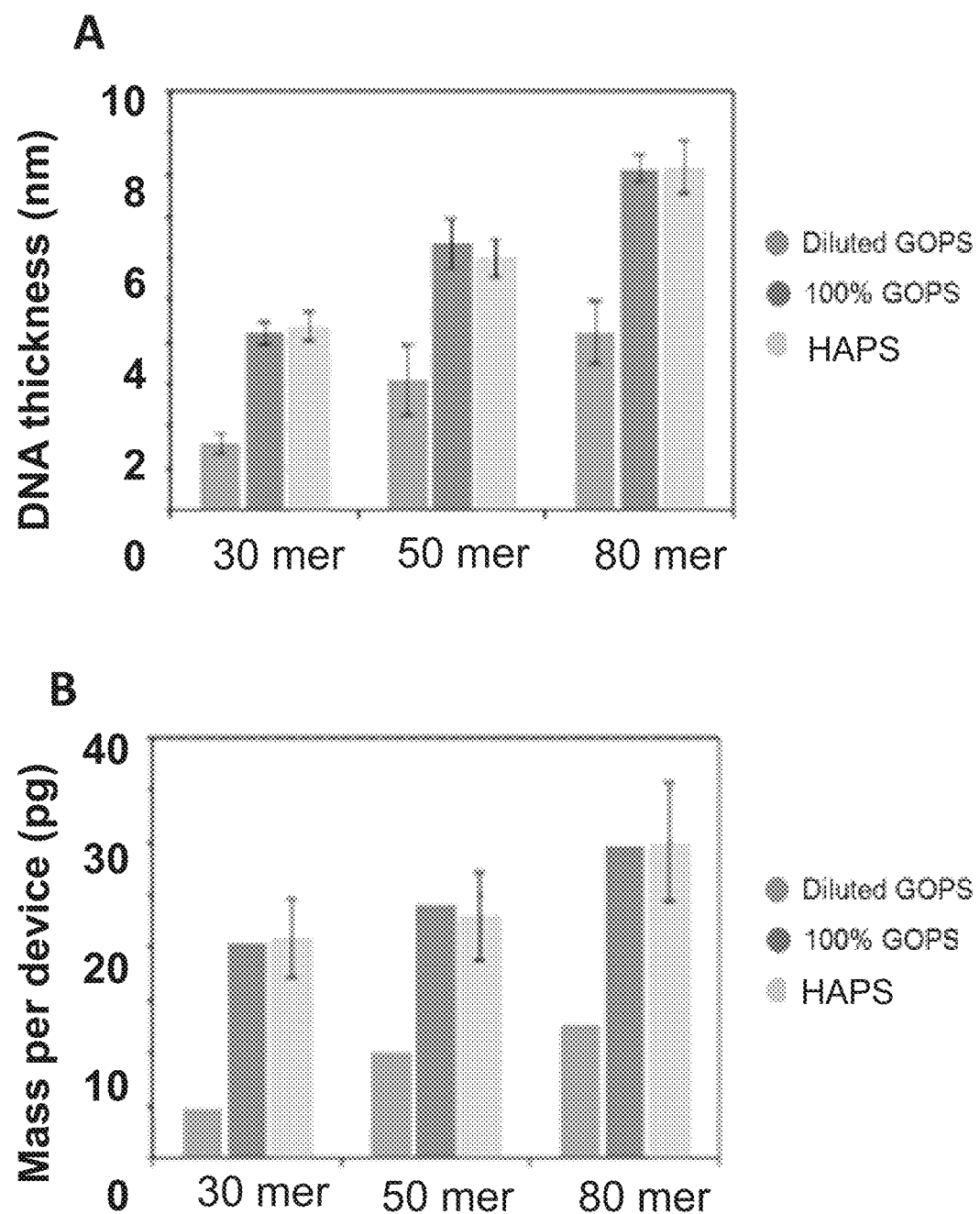
FIG. 25 illustrates plots for DNA thickness per device (part A) and DNA mass per device (part B) for oligonucleic acids of 30, 50, and 80-mers when synthesized a surface.

Oligonucleic acids of 30, 50 and 80 nucleotides in length were synthesized on the surfaces prepared in Example 9. A FRT tool (MicroProf 100, Fries Research and Technology, GmbH, Germany) was used to measure the thickness of DNA post-synthesis. The FRT tool scans across a cluster and measure reflectivity of light, which corresponds to the amount of material on the surface. A summary of the results is shown in FIG. 25A for growth of 30, 50 and 80-mers. In the case of synthesizing 80-mers, the GOPS-diluted surfaces produced a DNA thickness 52% lower than the 100% GOPS-2 and the HAPS chips.

Qubit analysis from fluorometric measurement of the clusters was also performed. A summary of the analysis from growth of 30, 50 and 80-mers is in the chart in FIG. 25B. For 30, 50 and 80-mers, the GOPS-diluted chip resulted in 42% less DNA density than the 100% GOPS-2 or the HAPS chips.

Example 11

Deletion Error Rate Analysis for Low Density Oligonucleic Acid Surfaces

Figure 26:
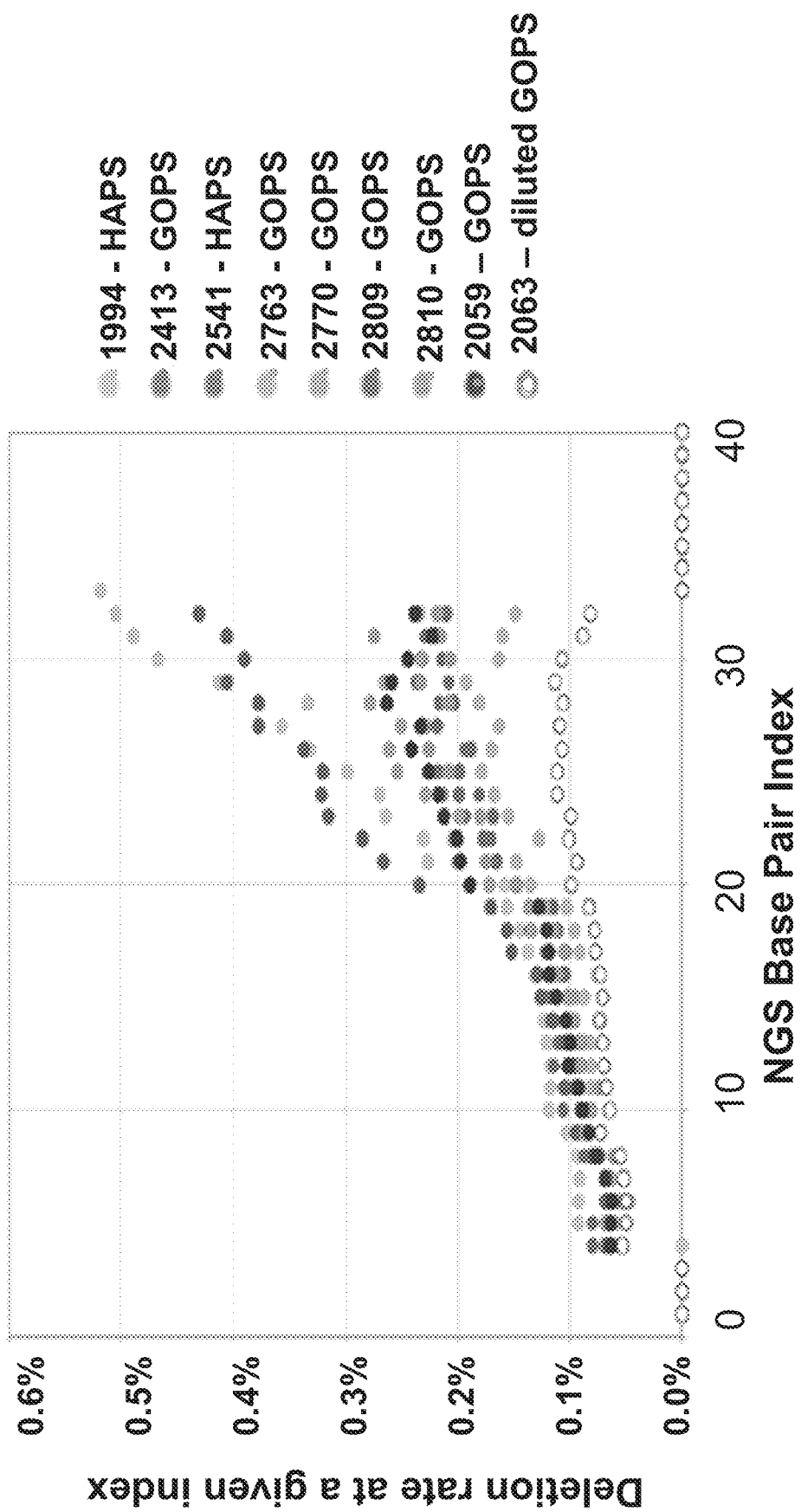
FIG. 26 illustrates the deletion rate at a given index of synthesized oligonucleotides for various silane solutions.

Oligonucleic acids of 30, 50 and 80 nucleotides in length were synthesized on the surfaces prepared in Example 9, gas cleaved from the surface, and subject to sequence analysis using an Illumina MiSeq. Deletion error rates were determined for oligonucleic acids synthesized on the GOPS-diluted surfaces. The total deletion error rate was 0.060%, or 1 in 1674 bases. Sequencing of control oligonucleic acids from the GOPS-diluted chips resulted in a deletion rate of 0.070%. Analysis of the deletion error rate frequency at particular bases in terms of distance from the surface was performed, and results are shown in the plot in FIG. 26. Notably, the GOPS-diluted surfaces resulted in a deletion error rate frequency for bases closer to the surface which is less than twice the error rate frequency for bases further from the surface. In other words, compared to other surfaces analyzed, the GOPS-diluted surfaces reduce the increase in deletion error rate observed at bases closer to the surface. As a whole the GOPS-diluted surfaces resulted in lower average deletion error rate above background error rate levels, Table 7.

TABLE 7

| Surface | Active agent added before or after photoresist | Average deletion error rate above background levels |
|---|---|---|
| GOPS-diluted (no. 2063) | After | 0.03% |
| GOPS-100%-2 (no. 2059) | After | 0.09% |
| GOPS-100%-1 (no. 2413) | Before | 0.07% |
| GOPS-100%-1 (no. 2763) | Before | 0.06% |
| GOPS-100%-1 (no. 2770) | Before | 0.09% |
| GOPS-100%-1 (no. 2809) | Before | 0.15% |
| GOPS-100%-1 (no. 2810) | Before | 0.08% |
| HAPS (no. 1994) | Before | 0.14% |
| HAPS (no. 2541) | Before | 0.07% |

Example 12

Textured Surface

A microfluidic device is manufactured to have increased surface area. An array of recesses or posts is etched into a silicon dioxide wafer to increase surface area by a factor of 2 to 3. A number of steps are performed to make a textured surface. To the starting silicon dioxide wafer, with one side polished, is added a textured layer via a pass printing scheme lithography. A silicon reactive ion etching and resist strip is added to the chip, followed by oxidation of the surface. The fiducial layer is printed on via lithography, after which a final oxide etching results in a textured silicon ship. The surface has a recess or post width that is about 2 times the length of the desired oligonucleic acids to be extended. A chart of exemplary widths is provided in Table 8 based on an approximate length of 0.34 nm/base.

TABLE 8

| No. of bases | Oligo length (nm) | Width of post or recess (nm) |
| --- | --- | --- |
| 1 | 0.34 | 0.68 |
| 10 | 3.4 | 6.8 |
| 100 | 34 | 68 |
| 200 | 68 | 136 |
| 300 | 102 | 204 |

A silicon dioxide structure is prepared having a 16×16 array of clusters. Each cluster includes multiple groups of 4 loci, wherein each loci resides on top of a different design feature, as outlined in Table 9.

TABLE 9

| Locus | Width w (um) | Pitch p (um) | Depth d (um) |
| --- | --- | --- | --- |
| 1 | 0.2 | 0.4 | 0.25-0.5 |
| 2 | 0.3 | 0.6 | 0.4-0.8 |
| 3 | 0.4 | 0.8 | 0.5-1.0 |
| 4 | No texture | No texture | No texture |

Each loci is coated with an silane that binds the surface and couples to nucleoside phosphoramidite. Oligonucleic acid synthesis is perform on the structure and DNA thickness, DNA mass and error rates of the synthesized oligonucleic acids are measured.

Example 13

Array of 256 Clusters

A microfluidic device is manufactured. Each device is 200 mm, double-side polished. A SOI wafer has 21 chips arranged in a 200 mm wafer. Each chip is 32 mm×32 mm in size, and comprised a 16×16 array of clusters. A total of 256 clusters are present in the array. 121 reaction sites are located in a single cluster, providing 30,976 individually addressable oligo sites per chip. Each cluster pitch is 1.125 mm. Each of the reaction sites are about 50 µm.

Example 14

Fiducial Marks

A silicon dioxide structure is prepared having a 16×16 array of clusters. Each cluster includes groups of 4 loci, wherein each loci is in close proximity to a one of three fiducial marks having a plurality of lines, wherein the line weight is listed in Table 10. Each fiducial design is in the shape of a plus 805. One of the test regions includes a plurality of fiducial marks in close proximity 810.

TABLE 10

| Design | Width w (um) | Pitch p (um) |
| --- | --- | --- |
| 1 | 0.2 | 0.4 |
| 2 | 0.3 | 0.6 |
| 3 | 0.4 | 0.8 |

Each loci is coated with an silane that binds the surface and couples to nucleoside phosphoramidite. Oligonucleic acid synthesis is perform on the structure and measurements are taken using the fiducial marks to calibrate align the surface with other components of a system.

Example 15

Global Alignment Marks

A silicon dioxide structure is prepared having a 16×16 array of clusters. Global alignment marks are used to aligning the surface 900 with other components of a system. Global alignment marks 905, 910, 915, 920, 935, and 940 are located at positions on a substantially planar substrate portion of the surface 900 and near an edge of the structure. Detailed circular mark 925 and plus sign mark 945 are shown in an expanded view in FIG. 9.

Example 16

Coating a Textured Surface with Diluted Activating Agent

A structure for oligonucleic acid synthesis is manufactured. Each device is 200 mm, double-side polished. A SOI wafer has 21 chips are arranged in a 200 mm wafer. Each chip is 32 mm×32 mm in size, and comprised a 16×16 array of clusters. A total of 256 clusters are present in the array. 121 reaction sites are located in a single cluster, providing 30,976 individually addressable oligo sites per chip. Each cluster pitch is 1.125 mm. Each of the reaction sites are about 50 µm in diameter. The surface of each chip is textured by methods as describe in Example 12 to include recesses with one of the texture designs listed in Table 9.

The structures for oligonucleic acid synthesis are individually cleaned by treatment with oxygen plasma. Directly after cleaning, the surface is coated with AZ resist and then baked at 90 degrees Celsius for 7 minutes. The surface is cleaned again by treatment with oxygen plasma, fluorinated in a YES CVD system (depositing (tridecafluoro-1,1,2,2-tetrahydrooctyl)-trichlorosilane), and is stripped. The surface is treated with 100% propyltrimethoxysilane at 3.5 Torr for 15 hours at chamber temperature of 100 C degrees Celsius. The surface is treated with water for 30 minutes, followed by a second deposition step. In the second deposition step, a mixture of 0.05% GOPS and 99.95% propyltrimethoxysilane is deposited on the surface and treated at 3.5 Torr for 1.5 hours at chamber temperature of 100 degrees Celsius. Lastly, the surface is activated in water for 30 minute at room temperature. The reaction sites on the surface of each structure comprise diluted GOPS. Each of the reaction sites are surrounded by surface coated with tridecafluoro-1,1,2,2-tetrahydrooctyl)-trichlorosilane.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

What is claimed is:

1. A method for preparing a surface for polynucleotide synthesis, the method comprising:
   depositing a first population of a first plurality of molecules on a surface of a solid support at a first region, wherein the first region comprises a plurality of loci, and wherein the first plurality of molecules comprises a plurality of non-coupling molecules that bind to the surface and lack a reactive group capable of binding to a nucleoside; and
   depositing a mixture on the solid support at the first region, wherein the mixture comprises a second population of the first plurality of molecules and a second plurality of molecules, and wherein the second plurality of molecules comprises a plurality of coupling molecules that bind to the solid support and comprise the reactive group that is capable of binding to the nucleoside, and wherein the first plurality of molecules and the second plurality of molecules are present in the mixture in a molar ratio of 10:1 to 2500:1.

2. The method of claim 1, wherein each of the plurality of coupling molecules is a silane.

3. The method of claim 1, wherein each of the plurality of coupling molecules is N-(3-triethoxysilylpropyl)-4-hydroxybutyramide (HAPS), 11-acetoxyundecyltriethoxysilane, n-decyltriethoxysilane, (3-aminopropyl)trimethoxysilane, (3-aminopropyl)triethoxysilane, 3-glycidoxypropyltrimethoxysilane, 3-iodo-propyltrimethoxysilane, or octylchlorosilane.

4. The method of claim 1, wherein the second molecule each of the plurality of coupling molecules is 3-glycidoxypropyltrimethoxysilane.

5. The method of claim 2, wherein the silane is an aminosilane.

6. The method of claim 1, wherein each of the plurality of non-coupling molecules is propyltrimethoxysilane.

7. The method of claim 1, wherein each of the plurality of non-coupling molecules is a fluorosilane.

8. The method of claim 7, wherein the fluorosilane is (tridecafluoro-1,1,2,2-tetrahydrooctyl)trichlorosilane.

9. The method of claim 1, wherein the mixture comprises the plurality of non-coupling molecules and the plurality of coupling molecules present in a molar ratio of about 100:1 to about 2500:1.

10. The method of claim 1, wherein the mixture comprises the plurality of non-coupling molecules and the plurality of coupling molecules present in a molar ratio of about 2000:1.

11. The method of claim 1, wherein the plurality of coupling molecules lacks a free hydroxyl, amino, or carboxyl group.

12. The method of claim 1, wherein the mixture or the first population is in a gaseous state when deposited on the surface.

13. The method of claim 1, wherein the surface comprises a layer of silicon oxide.

14. The method of claim 1, further comprising synthesizing a plurality of polynucleotides, wherein each polynucleotide of the plurality of polynucleotides comprises at least 10 bases in length.

15. The method of claim 14, wherein the plurality of polynucleotides encode sequences with an aggregate deletion error rate of less than 1 in 1500 bases compared to predetermined sequences.

16. The method of claim 15, wherein the aggregate deletion error rate is achieved without correcting errors.

17. The method of claim 14, wherein the plurality of polynucleotides synthesized encode sequences with an aggregate error rate of less than 1 in 1500 bases compared to predetermined sequences without correcting errors.

18. The method of claim 14, wherein each polynucleotide of the plurality of polynucleotides is 50 to 120 bases in length.

19. The method of claim 14, wherein the plurality of polynucleotides comprises at least 5,000 polynucleotides.

20. The method of claim 14, wherein the plurality of polynucleotides comprises at least 30,000 polynucleotides.

* * * * *

UNITED STATES PATENT AND TRADEMARK OFFICE
CERTIFICATE OF CORRECTION

PATENT NO. : 10,669,304 B2
APPLICATION NO. : 15/015059
DATED : June 2, 2020
INVENTOR(S) : Indermuhle et al.

Page 1 of 1

It is certified that error appears in the above-identified patent and that said Letters Patent is hereby corrected as shown below:

In the Claims

Column 59, Lines 31-32, Claim 4, the portion, "wherein the second molecule each of the plurality of coupling molecules is 3-glycidoxypropyltrimethoxysilane." should read -- wherein each of the plurality of coupling molecules is 3-glycidoxypropyltrimethoxysilane. --

Signed and Sealed this
Second Day of February, 2021

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 13

<210> SEQ ID NO 1
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (51)..(52)
<223> OTHER INFORMATION: Thymidine-succinyl hexamide CED phosphoramidite

<400> SEQUENCE: 1
agacaatcaa ccatttgggg tggacagcct tgacctctag acttcggcat tttttttttt      60
tt                                                                    62

<210> SEQ ID NO 2
<211> LENGTH: 112
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (101)..(102)
<223> OTHER INFORMATION: Thymidine-succinyl hexamide CED phosphoramidite

<400> SEQUENCE: 2
cgggatcctt atcgtcatcg tcgtacagat cccgacccat tgctgtcca ccagtcatgc       60 tagccatacc atgatgatga tgatgatgag aaccccgcat ttttttttt tt              112

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
atgcggggtt ctcatcatc                                                  19

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cgggatcctt atcgtcatcg                                                 20

<210> SEQ ID NO 5
<211> LENGTH: 931
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
atgaccatga ttacggattc actggccgtc gttttacaac gtcgtgactg ggaaaaccct     60

```
ggcgttaccc aacttaatcg ccttgcagca catccccctt tcgccagctg gcgtaatagc        120
gaagaggccc gcaccgatcg cccttcccaa cagttgcgca gcctgaatgg cgaatgcgc         180 tttgcctggt ttccggcacc agaagcggtg ccggaaagct ggctggagtg cgatcttcct        240
gaggccgata ctgtcgtcgt ccctcaaac tggcagatgc acggttacga tgcgcccatc         300
tacaccaacg tgacctatcc cattacggtc aatccgccgt tgttcccac ggagaatccg         360 acgggttgtt actcgctcac atttaatgtt gatgaaagct ggctacagga aggccagacg        420
cgaattattt ttgatggcgt taactcggcg tttcatctgt ggtgcaacgg gcgctgggtc        480
ggttacggcc aggacagtcg tttgccgtct gaatttgacc tgagcgcatt tttacgcgcc        540
ggagaaaacc gcctcgcggt gatggtgctg cgctggagtg acggcagtta tctggaagat        600
caggatatgt ggcggatgag cggcattttc cgtgacgtct cgttgctgca taaaccgact        660
acacaaatca gcgatttcca tgttgccact cgctttaatg atgatttcag ccgcgctgta        720
ctggaggctg aagttcagat gtgcggcgag ttgcgtgact acctacgggt aacagtttct        780
ttatggcagg gtgaaacgca ggtcgccagc ggcaccgcgc ctttcggcgg tgaaattatc        840
gatgagcgtg gtggttatgc cgatcgcgtc acactacgtc tgaacgtcga aaacccgaaa        900
ctgtggagcg ccgaaatccc gaatctctat c                                      931
```

<210> SEQ ID NO 6  
<211> LENGTH: 163  
<212> TYPE: DNA  
<213> ORGANISM: Artificial Sequence  
<220> FEATURE:  
<223> OTHER INFORMATION: Description of Artificial Sequence: Synthetic  
polynucleotide

<400> SEQUENCE: 6

```
atgaccatga ttacggattc actggccgtc gttttacaac gtcgtgactg ggaaaaccct         60
ggcgttaccc aacttaatcg ccttgcagca catccccctt tcgccagctg gcgtaatagc        120
gaagaggccc gcaccgatcg cccttcccaa cagttgcgca gcc                          163
```

<210> SEQ ID NO 7  
<211> LENGTH: 175  
<212> TYPE: DNA  
<213> ORGANISM: Artificial Sequence  
<220> FEATURE:  
<223> OTHER INFORMATION: Description of Artificial Sequence: Synthetic  
polynucleotide

<400> SEQUENCE: 7

```
gataggtcac gttggtgtag atgggcgcat cgtaaccgtg catctgccag tttgagggga         60
cgacgacagt atcggcctca ggaagatcgc actccagcca gctttccggc accgcttctg        120
gtgccggaaa ccaggcaaag cgccattcgc cattcaggct gcgcaactgt tggga             175
```

<210> SEQ ID NO 8  
<211> LENGTH: 176  
<212> TYPE: DNA  
<213> ORGANISM: Artificial Sequence  
<220> FEATURE:  
<223> OTHER INFORMATION: Description of Artificial Sequence: Synthetic  
polynucleotide

<400> SEQUENCE: 8

```
cccatctaca ccaacgtgac ctatcccatt acggtcaatc cgccgtttgt tcccacggag         60
aatccgacgg gttgttactc gctcacattt aatgttgatg aaagctggct acaggaaggc        120
```
cagacgcgaa ttattttga tggcgttaac tcggcgtttc atctgtggtg caacgg    176

<210> SEQ ID NO 9
<211> LENGTH: 176
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
gccgctcatc cgccacatat cctgatcttc cagataactg ccgtcactcc agcgcagcac    60
catcaccgcg aggcggtttt ctccggcgcg taaaaatgcg ctcaggtcaa attcagacgg    120
caaacgactg tcctggccgt aaccgaccca gcgcccgttg caccacagat gaaacg    176

<210> SEQ ID NO 10
<211> LENGTH: 177
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
aggatatgtg gcggatgagc ggcattttcc gtgacgtctc gttgctgcat aaaccgacta    60
cacaaatcag cgatttccat gttgccactc gctttaatga tgatttcagc cgcgctgtac    120
tggaggctga agttcagatg tgcggcgagt tgcgtgacta cctacgggta acagttt    177

<210> SEQ ID NO 11
<211> LENGTH: 178
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
gatagagatt cgggatttcg gcgctccaca gtttcgggtt ttcgacgttc agacgtagtg    60
tgacgcgatc ggcataacca ccacgctcat cgataatttc accgccgaaa ggcgcggtgc    120
cgctggcgac ctgcgtttca ccctgccata agaaactgt tacccgtagg tagtcacg    178

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
atgaccatga ttacggattc actggcc    27

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gatagagatt cgggatttcg gcgctcc    27